US009579319B2

(12) United States Patent
Armer et al.

(10) Patent No.: US 9,579,319 B2
(45) Date of Patent: Feb. 28, 2017

(54) HETEROCYCLIC COMPOUNDS AS HEDGEHOG SIGNALING PATHWAY INHIBITORS

(71) Applicant: Redx Pharma PLC, Cheshire (GB)

(72) Inventors: Richard Armer, Liverpool (GB); Matilda Bingham, Liverpool (GB); Inder Bhamra, Liverpool (GB); Andrew McCarroll, Liverpool (GB)

(73) Assignee: Redx Pharma PLC, Manchester (GB)

( * ) Notice: Subject to any disclaimer, the term of this patent is extended or adjusted under 35 U.S.C. 154(b) by 0 days.

(21) Appl. No.: 14/893,691

(22) PCT Filed: May 28, 2014

(86) PCT No.: PCT/GB2014/051623
§ 371 (c)(1),
(2) Date: Nov. 24, 2015

(87) PCT Pub. No.: WO2014/191737
PCT Pub. Date: Dec. 4, 2014

(65) Prior Publication Data
US 2016/0113928 A1    Apr. 28, 2016

(30) Foreign Application Priority Data

May 28, 2013   (GB) .................................. 1309508.8

(51) Int. Cl.
| | |
|---|---|
| *A61K 31/502* | (2006.01) |
| *C07D 237/30* | (2006.01) |
| *C07D 401/14* | (2006.01) |
| *C07D 471/04* | (2006.01) |
| *A61K 31/501* | (2006.01) |
| *A61K 31/5025* | (2006.01) |
| *A61K 31/506* | (2006.01) |
| *A61K 31/5377* | (2006.01) |
| *C07D 417/14* | (2006.01) |

(52) U.S. Cl.
CPC .......... *A61K 31/502* (2013.01); *A61K 31/501* (2013.01); *A61K 31/506* (2013.01); *A61K 31/5025* (2013.01); *A61K 31/5377* (2013.01); *C07D 237/30* (2013.01); *C07D 401/14* (2013.01); *C07D 417/14* (2013.01); *C07D 471/04* (2013.01)

(58) Field of Classification Search
CPC .. A61K 31/501; A61K 31/502; C07D 401/04; C07D 237/30
USPC .............................. 514/234.5, 248; 544/237
See application file for complete search history.

(56) References Cited

U.S. PATENT DOCUMENTS

| | | | |
|---|---|---|---|
| 3,567,725 A | 3/1971 | Grabowski et al. | |
| 4,022,779 A | 5/1977 | Denzel et al. | |

FOREIGN PATENT DOCUMENTS

| | | | | |
|---|---|---|---|---|
| EP | 2189449 A1 | 5/2010 | | |
| WO | WO-97/26258 A1 | 7/1997 | | |
| WO | WO-98/58929 A1 | 12/1998 | | |
| WO | WO-2006/003147 A1 | 1/2006 | | |
| WO | WO-2008/145681 A2 | 12/2008 | | |
| WO | WO-2009/134574 A2 | 11/2009 | | |
| WO | WO 2009134574 A2 * | 11/2009 | ........... | C07D 401/04 |
| WO | WO-2010/056588 A1 | 5/2010 | | |
| WO | WO-2010/056620 A1 | 5/2010 | | |
| WO | WO 2010056588 A1 * | 5/2010 | ........... | C07D 401/04 |
| WO | WO-2010/147917 A1 | 12/2010 | | |
| WO | WO 2010147917 A1 * | 12/2010 | ........... | C07D 401/14 |

OTHER PUBLICATIONS

Database PubChem Compound [Online], NCBI; Aug. 9, 2005; database accession No. CID6411089.
Database PubChem Compound [Online], NCBI; May 20, 2009; database accession No. CID37104740.
Database PubChem Compound [Online], NCBI; Jul. 21, 2009; database accession No. CID43599651.
Database PubChem Compound [Online], NCBI; Jun. 21, 2011; database accession No. CID53182314.
Database PubChem Compound [Online], NCBI; Jun. 21, 2011; database accession No. CID53182466.
Database PubChem Compound [Online], NCBI; Oct. 22, 2012; database accession No. CID62593553.
Database PubChem Compound [Online], NCBI; Oct. 22, 2012; database accession No. CID62592854.
Davidson, M. W. et al., "Synthesis of as-Triazines as Potential Antiviral Agents", *Journal of Pharmaceutical Sciences*, 67(5):737-739 (1978).
Holava, H. M. et al., "1-Substituted 4-Aryl-(or 4-Aralkyl-)phthalazines", *Journal of Medicinal Chemistry*, 12:555-556 (May 1969).
Werbel, L. M. et al., "Synthesis and Antimalarial Effects of N, N-Dialkyl-6(substituted phenyl)-1,2,4,5-tetrazin-3-amines (1,2)", *Journal of Heterocyclic Chemistry*, 16(5):881-894 (Jul. 1979).
International Preliminary Report on Patentability (IPRP) from parent application PCT/GB2014/051623, dated Aug. 13, 2015.
Rimkus, T. K., et al., "Targeting the Sonic Hedgehog Signaling Pathway: Review of Smoothened and GLI Inhibitors," *Cancers* 2016, 8, 22, pp. 1-23.
Irvine, D. A., et al., "Targeting hedgehog in hematologic malignancy," *Blood*, Mar. 8, 2012, vol. 119, No. 10, pp. 2196-2204.

* cited by examiner

*Primary Examiner* — Kamal Saeed
*Assistant Examiner* — Janet L Coppins
(74) *Attorney, Agent, or Firm* — Dana M. Gordon; Foley Hoag LLP

(57) ABSTRACT

This invention relates to novel compounds of formula (I). The compounds of the invention are hedgehog pathway antagonists. Specifically, the compounds of the invention are useful as Smoothened (SMO) inhibitors. The invention also contemplates the use of the compounds for treating conditions treatable by the inhibition of the Hedgehog pathway and SMO, for example cancer.

37 Claims, No Drawings

HETEROCYCLIC COMPOUNDS AS HEDGEHOG SIGNALING PATHWAY INHIBITORS

RELATED APPLICATIONS

This application is the U.S. national phase of International Patent Application No. PCT/GB2014/051623, filed May 28, 2014, which claims priority to United Kingdom Patent Application serial number GB 1309508.8, filed May 28, 2013.

This invention relates to compounds. More specifically, the invention relates to compounds useful as inhibitors of the Hedgehog signalling pathway. Specifically, inhibitors of Smoothened (Smo) are contemplated by the invention. In addition the invention contemplates processes to prepare the compounds and uses of the compounds.

The Hedgehog signalling pathway plays a key role in embryonic cells and is one of the key regulators of animal development. Malfunction of the Hedgehog signalling pathway during embryonic development can lead to abnormalities in the structure of bodily organs and the structure of the skeleton. Later in life, the Hedgehog signalling pathway has a role in regulating adult stem cells in the maintenance and the regeneration of tissue by directing cell differentiation and proliferation. Abnormalities in the Hedgehog signalling pathway have been shown to result in certain conditions, for example cancer.

There are three Hedgehog proteins (Hh) associated with the Hedgehog signalling pathway, Sonic Hedgehog (Shh), Indian Hedgehog (Ihh) and Desert Hedgehog (Dhh). The Hedgehog proteins bind to the Patched-1 receptor. The Patched-1 receptor inhibits Smo activity and upon binding of a Hedgehog protein with Patched-1 this inhibition is alleviated, leading to activation of the GLI transcription factors Gli1, Gli2 and Gli3 which are involved in cell fate determination and proliferation.

Aberrant activation of the hedgehog pathway has been implicated in patients suffering from a range of cancers, for example Basal cell carcinoma, pancreatic cancer, medulloblastoma, small cell lung cancer and prostate cancer. Moreover, it has been suggested that aberrant hedgehog signalling may contribute to the regulation of cancer stem cells.

In January 2012 Genentech was given FDA approval for Vismodegib for the treatment of basal-cell carcinoma. This was approval of the first Hedgehog signalling pathway inhibitor. Vismodegib is being studied in the clinic for the treatment of a range of other cancers including colorectal cancer, small-cell lung cancer, stomach cancer, pancreatic cancer, medulloblastoma and chondrosarcoma. Recently, WO 2010/147917 disclosed Hedgehog pathway inhibitors for the treatment of various cancers. In addition Novartis Oncology have completed Phase II clinical trials for the treatment of Basal Cell Carcinomas on LDE225, a Smo receptor inhibitor. Thus, it is clear that inhibition of aberrant Hedgehog pathway signalling and Smo expression has emerged as an attractive target for anticancer therapy.

Inhibiting the Hedgehog signalling pathway with small molecules has become an important target for clinicians to treat clinically significant cancers, such as solid tumours, through the reversal or control of aberrant cell growth. However, there is still a need to possess effective Hedgehog signalling pathway inhibitors and Smo inhibitors as effective treatments for various cancer types.

It is an aim of certain embodiments of this invention to provide new cancer treatments. In particular, it is an aim of certain embodiments of this invention to provide compounds which have comparable activity to existing cancer treatments, ideally better activity. Certain embodiments of the invention also aim to provide improved solubility compared to prior art compounds and existing therapies. It is particularly attractive for certain compounds of the invention to provide better activity and better solubility over known compounds.

It is an aim of certain embodiments of this invention to provide compounds which exhibit reduced cytotoxicity relative to prior art compounds and existing therapies.

Another aim of certain embodiments of this invention is to provide compounds having a convenient pharmacokinetic profile and a suitable duration of action following dosing. A further aim of certain embodiments of this invention is to provide compounds in which the metabolised fragment or fragments of the drug after absorption are GRAS (Generally Regarded As Safe).

Certain embodiments of the present invention satisfy some or all of the above aims.

In accordance with the present invention there is provided compounds as disclosed below. Furthermore, the invention provides compounds capable of inhibiting the Hedgehog signalling pathway, specifically Smoothened (Smo) and the use of these compounds in inhibiting the Hedgehog signalling pathway and Smo. In accordance with the invention there is provided a method of treating conditions modulated by Smo. The invention provides compounds for use in treating a condition which is modulated by Smo.

In a first aspect of the invention there is provided a compound according to formula (I) and pharmaceutically acceptable salts and solvates thereof:

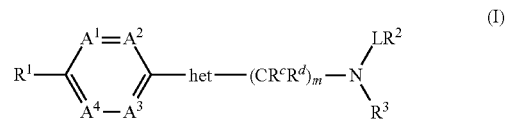

wherein
"het" is selected from substituted or unsubstituted: aziridinylene, azetidinylene, pyrolidinylene, piperidinylene and azepanylene;
or "het" represents a substituted or unsubstituted heteroalkylene chain in which the heteroatom present in a $C_{1-6}$ alkylene chain is nitrogen and wherein the nitrogen atom is substituted by hydrogen or $C_{1-4}$ alkyl;
at least one of $A^1$, $A^2$, $A^3$ and $A^4$ is N and the remaining $A^1$, $A^2$, $A^3$ and $A^4$ are each independently selected from $CR^4$ or N;
wherein $R^4$ is selected from H, halo, $C_{1-6}$ alkyl, $C_{1-6}$ haloalkyl, —$OR^a$, —SH, $C_{2-6}$ alkenyl, $C_{2-6}$ alkynyl, $C_{3-8}$ cycloalkyl, $C_{3-8}$ cycloalkenyl, aryl, heterocyclic, —$NR^aR^b$, —CN, acyl, —C(O)$R^a$, —C(O)O$R^a$, —SO$_2R^a$, and —SO$_3R^a$, and two adjacent $R^4$ groups may form a ring with the carbon atom to which they are attached forming a fused bicyclic ring system of 8 to 12 atoms, wherein the ring formed by the two $R^4$ groups is a saturated or unsaturated carbocyclic ring with 4, 5, 6, 7, or 8 carbon atoms or a saturated or unsaturated heterocyclic ring with 4, 5, 6, 7, or 8 atoms containing 1, 2 or 3 heteroatoms;
L is selected from either a substituted or unsubstituted $C_{1-6}$ alkylene chain which is saturated or unsaturated and which may also optionally contain, where chemically possible, 1, 2 or 3 N, O, or S atoms in the chain which are independently chosen at each occurrence;

or L is selected from a bond, —C(NR$^a$)—, —C(O)O—, —C(O)NR$^3$—, —C(NR$^a$)NR$^3$—, and —SO$_2$—;

R$^1$ is selected from —OR$^5$, —NR$^5$R$^a$, —NR$^a$C(O)R$^a$, —CN, —C$_{1-4}$ acyl, —C(O)R$^a$, —C(O)NR$^a$, —O(O)OR$^a$, —SO$_2$R$^a$, —SO$_3$R$^a$, substituted or unsubstituted C$_{1-6}$ alkyl, C$_{1-6}$ haloalkyl, substituted or unsubstituted C$_{2-6}$ alkenyl, substituted or unsubstituted C$_{2-6}$ alkynyl, substituted or unsubstituted C$_{3-8}$ cycloalkyl, substituted or unsubstituted C$_{3-8}$ cycloalkenyl, substituted or unsubstituted aryl, and substituted or unsubstituted heterocyclic;

wherein R$^5$ is H, —SO$_2$R$^a$, —SO$_2$NR$^a$R$^b$, substituted or unsubstituted C$_{1-4}$ alkyl, C$_{1-4}$ haloalkyl, substituted or unsubstituted C$_{3-8}$ cycloalkyl, substituted or unsubstituted C$_{3-8}$ cycloalkenyl, substituted or unsubstituted aryl, and substituted or unsubstituted heterocyclic;

R$^2$ is represented by —CR$^6$R$^7$R$^8$, wherein R$^6$, R$^7$ and R$^8$ are independently selected at each occurrence from H and substituted or unsubstituted: C$_{1-14}$ alkyl, C$_{1-14}$ haloalkyl, carbocyclic, and heterocyclic, or R$^2$ is selected from substituted or unsubstituted: C$_{1-14}$ alkyl, C$_{1-14}$ haloalkyl, carbocyclic, and heterocyclic;

R$^3$ is selected from H, —SO$_2$R$^a$, —SO$_2$NR$^a$R$^b$, substituted or unsubstituted C$_{1-4}$ alkyl, C$_{1-4}$ haloalkyl, substituted or unsubstituted C$_{3-8}$ cycloalkyl, substituted or unsubstituted C$_{3-8}$ cycloalkenyl, substituted or unsubstituted aryl, and substituted or unsubstituted heterocyclic;

R$^a$ and R$^b$ are independently selected at each occurrence from: H, C$_{1-4}$ alkyl, C$_{1-4}$ haloalkyl, C$_{1-4}$ acyl, C$_{3-7}$ cycloalkyl, and C$_{3-7}$ halocycloalkyl;

R$^c$ and R$^d$ are independently selected from H, halo, —OR$^a$, C$_{1-4}$ alkyl, C$_{1-4}$ haloalkyl, C$_{1-4}$ acyl, C$_{3-7}$ cycloalkyl, and C$_{3-7}$ halocycloalkyl;

m is 0, 1 or 2; and when a group is substituted, the group contains 1 to 5 substituents independently selected at each occurrence from the group comprising: halo, —OR$^a$, —SR$^a$, —NR$^a$R$^b$, NO$_2$, =O, —CN, acyl, C$_{1-6}$ alkyl, C$_{1-6}$ haloalkyl, C$_{3-8}$ cycloalkyl, —SO$_2$R$^a$, and SO$_3$R$^a$, —C(OR$^a$)R$^a$R$^b$, —C(O)R$^a$ and C(O)OR$^a$.

There is provided a compound according to formula (I) with the proviso that R$^1$ is not substituted or unsubstituted thiadiazolinyl when

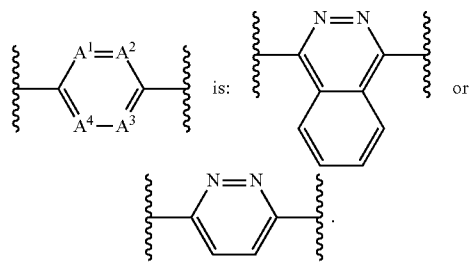

There is provided a compound according to formula (I), wherein L is not —C(O)O—.

There is also provided a compound of formula (I), wherein the compound of formula (I) is a compound according to formula (Ia) and pharmaceutically acceptable salts and solvates thereof:

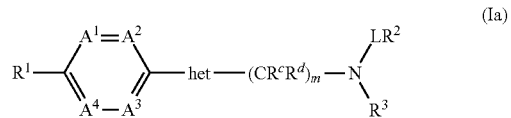

wherein

"het" is selected from substituted or unsubstituted: aziridinylene, azetidinylene, pyrolidinylene, piperidinylene and azepanylene;

or "het" represents a substituted or unsubstituted heteroalkylene chain in which the heteroatom present in a C$_{1-6}$ alkylene chain is nitrogen and wherein the nitrogen atom is substituted by hydrogen or C$_{1-4}$ alkyl;

at least one of A$^1$, A$^2$, A$^3$ and A$^4$ is N and the remaining A$^1$, A$^2$, A$^3$ and A$^4$ are each independently selected from CR$^4$ or N;

wherein R$^4$ is selected from H, halo, C$_{1-6}$ alkyl, C$_{1-6}$ haloalkyl, —OR$^a$, —SH, C$_{2-6}$ alkenyl, C$_{2-6}$ alkynyl, C$_{3-8}$ cycloalkyl, C$_{3-8}$ cycloalkenyl, aryl, heterocyclic, —NR$^a$R$^b$, —CN, acyl, —C(O)R$^a$, —C(O)OR$^a$, —SO$_2$R$^a$, and —SO$_3$R$^a$, and two adjacent R$^4$ groups may form a ring with the carbon atom to which they are attached forming a fused bicyclic ring system of 8 to 12 atoms, wherein the ring formed by the two R$^4$ groups is a saturated or unsaturated carbocyclic ring with 4, 5, 6, 7, or 8 carbon atoms or a saturated or unsaturated heterocyclic ring with 4, 5, 6, 7, or 8 atoms containing 1, 2 or 3 heteroatoms;

L is selected from either a substituted or unsubstituted C$_{1-6}$ alkylene chain which is saturated or unsaturated and which may also optionally contain, where chemically possible, 1, 2 or 3 N, O, or S atoms in the chain which are independently chosen at each occurrence;

or L is selected from a bond, —C(NR$^a$)—, —C(O)O—, —C(O)NR$^3$—, —C(NR$^a$)NR$^3$—, and —SO$_2$—;

R$^1$ is selected from —OR$^5$, —NR$^5$R$^a$, —NR$^a$C(O)R$^a$, —CN, —C$_{1-4}$ acyl, —C(O)R$^a$, —C(O)NR$^a$, —O(O)OR$^a$, —SO$_2$R$^a$, —SO$_3$R$^a$, substituted or unsubstituted C$_{1-6}$ alkyl, C$_{1-6}$ haloalkyl, substituted or unsubstituted C$_{2-6}$ alkenyl, substituted or unsubstituted C$_{2-6}$ alkynyl, substituted or unsubstituted C$_{3-8}$ cycloalkyl, substituted or unsubstituted C$_{3-8}$ cycloalkenyl, substituted or unsubstituted aryl, and substituted or unsubstituted heterocyclic, wherein R$^5$ is H, —SO$_2$R$^a$, —SO$_2$NR$^a$R$^b$, substituted or unsubstituted C$_{1-4}$ alkyl, C$_{1-4}$ haloalkyl, substituted or unsubstituted C$_{3-8}$ cycloalkyl, substituted or unsubstituted C$_{3-8}$ cycloalkenyl, substituted or unsubstituted aryl, and substituted or unsubstituted heterocyclic;

R$^2$ is represented by —CR$^6$R$^7$R$^8$, wherein R$^6$, R$^7$ and R$^8$ are independently selected at each occurrence from H and substituted or unsubstituted: C$_{1-14}$ alkyl, C$_{1-14}$ haloalkyl, carbocyclic, and heterocyclic, or R$^2$ is selected from substituted or unsubstituted: C$_{1-14}$ alkyl, C$_{1-14}$ haloalkyl, carbocyclic, and heterocyclic;

R$^3$ is selected from H, —SO$_2$R$^a$, —SO$_2$NR$^a$R$^b$, substituted or unsubstituted C$_{1-4}$ alkyl, C$_{1-4}$ haloalkyl, substituted or unsubstituted C$_{3-8}$ cycloalkyl, substituted or unsubstituted C$_{3-8}$ cycloalkenyl, substituted or unsubstituted aryl, and substituted or unsubstituted heterocyclic;

R$^a$ and R$^b$ are independently selected at each occurrence from: H, C$_{1-4}$ alkyl, C$_{1-4}$ haloalkyl, C$_{1-4}$ acyl, C$_{3-7}$ cycloalkyl, and C$_{3-7}$ halocycloalkyl;

R$^c$ and R$^d$ are independently selected from H, halo, —OR$^a$, C$_{1-4}$ alkyl, C$_{1-4}$ haloalkyl, C$_{1-4}$ acyl, C$_{3-7}$ cycloalkyl, and C$_{3-7}$ halocycloalkyl;

m is 0, 1 or 2; and when a group is substituted, the group contains 1 to 5 substituents independently selected at each occurrence from the group comprising: halo, —OR$^a$, —SR$^a$, —NR$^a$R$^b$, NO$_2$, =O, —CN, acyl, C$_{1-6}$ alkyl, C$_{1-6}$ haloalkyl, C$_{3-8}$ cycloalkyl, —SO$_2$R$^a$, and SO$_3$R$^a$, —C(OR$^a$)R$^a$R$^b$, —C(O)R$^a$ and C(O)OR$^a$;

provided that:
(1) LR$^2$ is not —CO(O)tBu; and
(2) R$^1$ is not a substituted or unsubstituted thiadiazolinyl group when

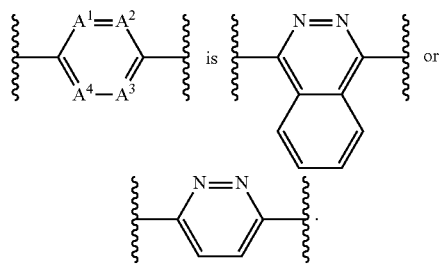

There is provided a compound according to formula (Ib) and pharmaceutically acceptable salts and solvates thereof:

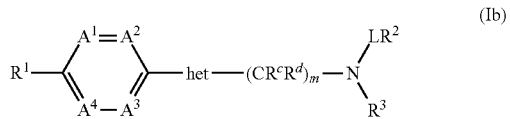

(Ib)

wherein
"het" is selected from substituted or unsubstituted: aziridinylene, azetidinylene, pyrolidinylene, piperidinylene and azepanylene;
or "het" represents a substituted or unsubstituted heteroalkylene chain in which the heteroatom present in a C$_{1-6}$ alkylene chain is nitrogen and wherein the nitrogen atom is substituted by hydrogen or C$_{1-4}$ alkyl;
at least one of A$^1$, A$^2$, A$^3$ and A$^4$ is N and the remaining A$^1$, A$^2$, A$^3$ and A$^4$ are each independently selected from CR$^4$ or N;
wherein R$^4$ is selected from H, halo, C$_{1-6}$ alkyl, C$_{1-6}$ haloalkyl, —OR$^a$, —SH, C$_{2-6}$ alkenyl, C$_{2-6}$ alkynyl, C$_{3-8}$ cycloalkyl, C$_{3-8}$ cycloalkenyl, aryl, heterocyclic, —NR$^a$R$^b$, —CN, acyl, —C(O)R$^a$, —C(O)OR$^a$, —SO$_2$R$^a$, and —SO$_3$R$^a$, and two adjacent R$^4$ groups may form a ring with the carbon atom to which they are attached forming a fused bicyclic ring system of 8 to 12 atoms, wherein the ring formed by the two R$^4$ groups is a saturated or unsaturated carbocyclic ring with 4, 5, 6, 7, or 8 carbon atoms or a saturated or unsaturated heterocyclic ring with 4, 5, 6, 7, or 8 atoms containing 1, 2 or 3 heteroatoms;
L is selected from either a substituted or unsubstituted C$_{1-6}$ alkylene chain which is saturated or unsaturated and which may also optionally contain, where chemically possible, 1, 2 or 3 N, O, or S atoms in the chain which are independently chosen at each occurrence;
or L is selected from a bond, —C(NR$^a$)—, —C(O)NR$^3$—, —C(NR$^a$)NR$^3$—, and —SO$_2$—;
R$^1$ is selected from substituted or unsubstituted: pyrrolyl, imidazolyl, pyrazolyl, oxazolyl, oxadiazolyl, isoxazolyl, triazolyl, tetrazolyl, thiazolyl, isothiazolyl, furanyl, pyridinyl, pyridazinyl, pyrazinyl, pyrimidinyl, substituted or unsubstituted C$_{4-8}$ heterocycloalkyl, —OR$^5$ and —NR$^5$R$^a$;
wherein R$^5$ is H, —SO$_2$R$^a$, —SO$_2$NR$^a$R$^b$, substituted or unsubstituted C$_{1-4}$ alkyl, C$_{1-4}$ haloalkyl, substituted or unsubstituted C$_{3-8}$ cycloalkyl, substituted or unsubstituted C$_{3-8}$ cycloalkenyl, substituted or unsubstituted aryl, and substituted or unsubstituted heterocyclic;
R$^2$ is represented by —CR$^6$R$^7$R$^8$, wherein R$^6$, R$^7$ and R$^8$ are independently selected at each occurrence from H and substituted or unsubstituted: C$_{1-14}$ alkyl, C$_{1-14}$ haloalkyl, carbocyclic, and heterocyclic,
or R$^2$ is selected from substituted or unsubstituted: C$_{1-14}$ alkyl, C$_{1-14}$ haloalkyl, carbocyclic, and heterocyclic;
R$^3$ is selected from H, —SO$_2$R$^a$, —SO$_2$NR$^a$R$^b$, substituted or unsubstituted C$_{1-4}$ alkyl, C$_{1-4}$ haloalkyl, substituted or unsubstituted C$_{3-8}$ cycloalkyl, substituted or unsubstituted C$_{3-8}$ cycloalkenyl, substituted or unsubstituted aryl, and substituted or unsubstituted heterocyclic;
R$^a$ and R$^b$ are independently selected at each occurrence from: H, C$_{1-4}$ alkyl, C$_{1-4}$ haloalkyl, C$_{1-4}$ acyl, C$_{3-7}$ cycloalkyl, and C$_{3-7}$ halocycloalkyl;
R$^c$ and R$^d$ are independently selected from H, halo, —OR$^a$, C$_{1-4}$ alkyl, C$_{1-4}$ haloalkyl, C$_{1-4}$ acyl, C$_{3-7}$ cycloalkyl, and C$_{3-7}$ halocycloalkyl;
m is 0, 1 or 2; and
when a group is substituted, the group contains 1 to 5 substituents independently selected at each occurrence from the group comprising: halo, —OR$^a$, —SR$^a$, —NR$^a$R$^b$, NO$_2$, =O, —CN, acyl, C$_{1-6}$ alkyl, C$_{1-6}$ haloalkyl, C$_{3-8}$ cycloalkyl, —SO$_2$R$^a$, and SO$_3$R$^a$, —C(OR$^a$)R$^a$R$^b$, —C(O)R$^a$ and C(O)OR$^a$.

In all embodiments "het" may be selected from substituted or unsubstituted aziridinylene, substituted or unsubstituted azetidinylene, substituted or unsubstituted pyrolidinylene, substituted or unsubstituted piperidinylene, and substituted or unsubstituted azepanylene.

In an embodiment "het" is selected from substituted or unsubstituted: aziridinylene, azetidinylene, pyrolidinylene, piperidinylene and azepanylene. Preferably, pyrolidinylene, piperidinylene and azepanylene. In an alternative embodiment "het" represents a substituted or unsubstituted heteroalkylene chain in which the heteroatom present in a C$_{1-6}$ alkylene chain is nitrogen and wherein the nitrogen atom is substituted by hydrogen or C$_{1-4}$ alkyl.

Optionally, "het" is piperidinylene or pyrolidinylene.

In an embodiment "het" is selected from substituted or unsubstituted: pyrolidinylene, piperidinylene and azepanylene;
or "het" represents a substituted or unsubstituted heteroalkylene chain in which the heteroatom present in a C$_{1-6}$ alkylene chain is nitrogen and wherein the nitrogen atom is substituted by hydrogen or C$_{1-4}$ alkyl.

In an embodiment "het" is represented by groups selected from substituted or unsubstituted:

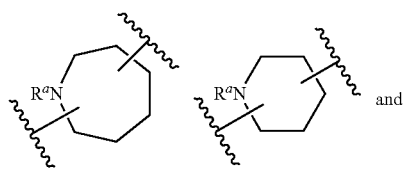

and

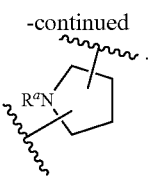

In an alternative embodiment "het" is selected from substituted or unsubstituted:

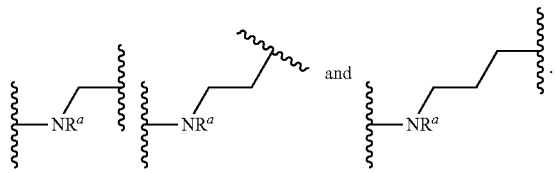

In embodiments "het" is bonded to —(CR$^c$R$^d$)— via a carbon atom. In embodiments "het" is bonded to the A ring via a nitrogen atom. In embodiments "het" is bonded to —(CR$^c$R$^d$)— via a carbon atom and to the A ring via a nitrogen atom.

In embodiments "het" is selected from substituted or unsubstituted:

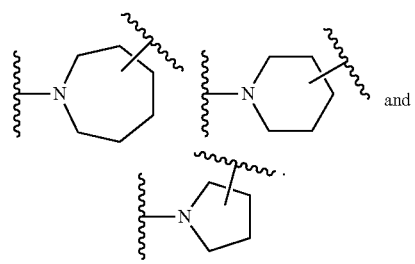

In an embodiment "het" is selected from substituted or unsubstituted:

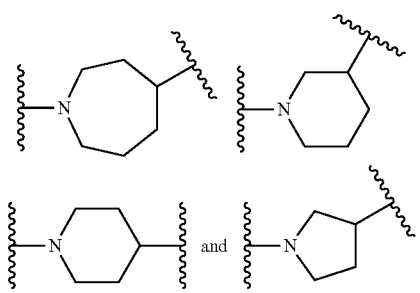

Preferably "het" is substituted or unsubstituted:

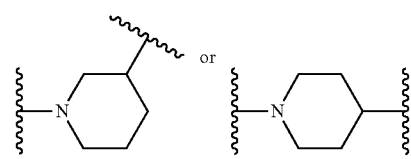 [SMILES: *C1CCCN(*)C1 ; "or" ; *C1CCN(*)CC1]

In embodiments "het" is unsubstituted. In alternative embodiments "het" is substituted with 1 to 5 substituents independently selected at each occurrence from the group comprising: halo, —OR$^a$, —SR$^a$, —NR$^a$R$^b$, NO$_2$, =O, —CN, acyl, C$_{1-6}$ alkyl, C$_{1-6}$ haloalkyl, C$_{3-8}$ cycloalkyl, —SO$_2$R$^a$, and SO$_3$R$^a$, —C(O)R$^a$ and C(O)OR$^a$.

In an embodiment the compound of formula (I) is a compound according to formula (II), (IIa) or (IIb) and pharmaceutically acceptable salts and solvates thereof:

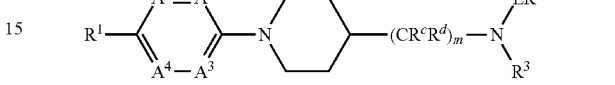

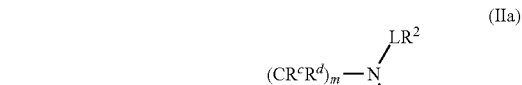

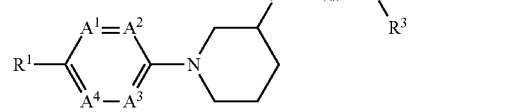

In embodiments one of A$^1$, A$^2$, A$^3$ and A$^4$ is N and the remaining A$^1$, A$^2$, A$^3$ and A$^4$ are each independently selected from N or CR$^4$. Optionally, one of A$^1$, A$^2$, A$^3$ and A$^4$ is N, two of the remaining A$^1$, A$^2$, A$^3$ and A$^4$ are each CR$^4$ and the remaining A$^1$, A$^2$, A$^3$ and A$^4$ is selected from N or CR$^4$. In embodiments at least two of A$^1$, A$^2$, A$^3$ and A$^4$ are N and the remaining A$^1$, A$^2$, A$^3$ and A$^4$ are each independently selected from N or CR$^4$. Optionally, two of A$^1$, A$^2$, A$^3$ and A$^4$ are N and two of A$^1$, A$^2$, A$^3$ and A$^4$ are CR$^4$.

In embodiments

is selected from:

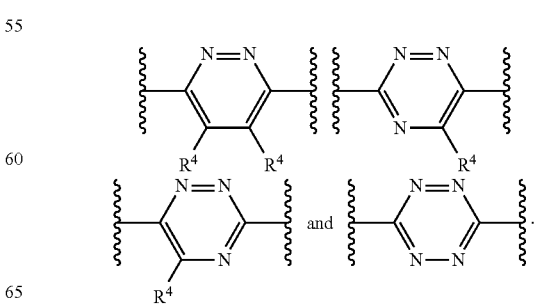

In an embodiment

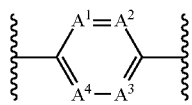

is:

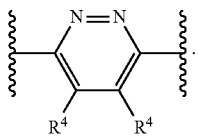

In an embodiment the compound of formula (I) is a compound according to formula (III) and pharmaceutically acceptable salts and solvates thereof:

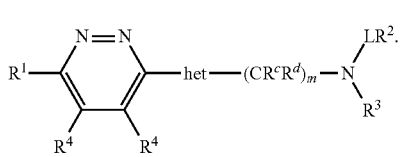

In an embodiment the compound of formula (I) is a compound according to formula (IV) or (IVa) and pharmaceutically acceptable salts and solvates thereof:

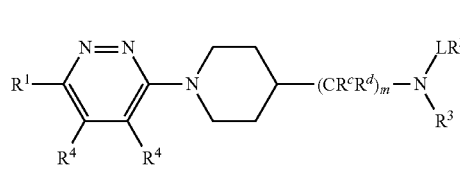

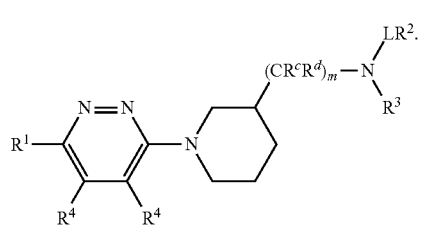

In embodiments $R^4$ is selected from: $C_{1-6}$ alkyl, $C_{1-6}$ haloalkyl, aryl and heterocyclic, and two adjacent $R^4$ groups may form a ring with the atom to which the $R^4$ groups are attached forming a fused bicyclic ring system of 8 to 12 atoms, wherein the ring formed by the two $R^4$ groups is a saturated or unsaturated carbocyclic ring with 4, 5, 6, 7 or 8 carbon atoms or a saturated or unsaturated heterocyclic ring with 4, 5, 6, 7 or 8 atoms containing 1, 2 or 3 heteroatoms.

In embodiments two adjacent $R^4$ groups are both $C_{1-6}$ alkyl or both form a ring with the atom to which the $R^4$ groups are attached forming a fused bicyclic ring system of 8 to 12 atoms, wherein the ring formed by the two $R^4$ groups is a saturated or unsaturated carbocyclic ring with 4, 5, 6, 7 or 8 carbon atoms or a saturated or unsaturated heterocyclic ring with 4, 5, 6, 7 or 8 atoms containing 1, 2 or 3 heteroatoms.

In embodiments two adjacent $R^4$ groups are both methyl or hydrogen or two adjacent $R^4$ groups both form a ring with the atom to which the $R^4$ groups are attached forming a fused bicyclic ring system of 9 or 10 atoms, wherein the ring formed by the two $R^4$ groups is a saturated or unsaturated carbocyclic ring with 5 or 6 carbon atoms or a saturated or unsaturated heterocyclic ring with 5 or 6 atoms containing 1 or 2 heteroatoms.

In embodiments two adjacent $R^4$ groups are both methyl.

In embodiments two adjacent $R^4$ groups are both hydrogen.

Alternatively, two adjacent $R^4$ groups both form a ring with the atom to which the $R^4$ groups are attached forming a fused bicyclic ring system of 9 or 10 atoms, wherein the ring formed by the two $R^4$ groups is a saturated or unsaturated carbocyclic ring with 5 or 6 carbon atoms or a saturated or unsaturated heterocyclic ring with 5 or 6 atoms containing 1 or 2 heteroatoms.

In embodiments two adjacent $R^4$ groups are both methyl or hydrogen or two adjacent $R^4$ groups may both form a ring with the atom to which the $R^4$ groups are attached, wherein the ring formed by the two $R^4$ groups is phenyl, pyridyl, pyridazinylpyrimidinyl, pyrazinyl, pyrazolyl, cyclopentyl or tetrahydrofuranyl. Preferably, the ring formed by the two $R^4$ groups is cyclopentyl, phenyl or pyridyl.

In an embodiment $R^4$ is not hydrogen.

In embodiments

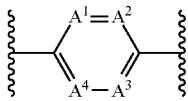

is selected from:

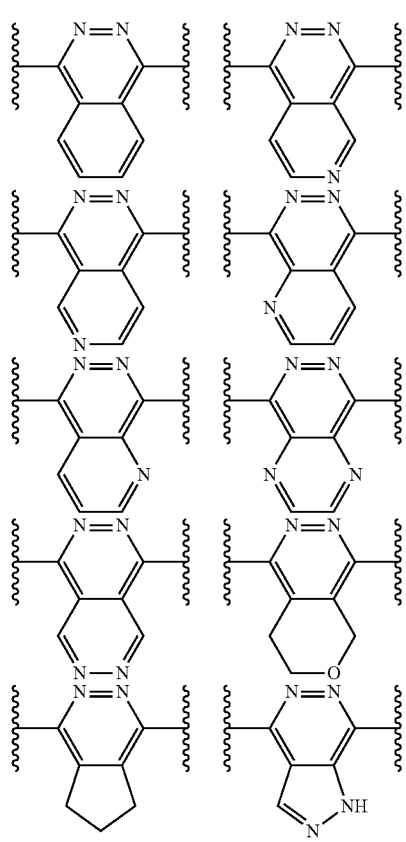

-continued
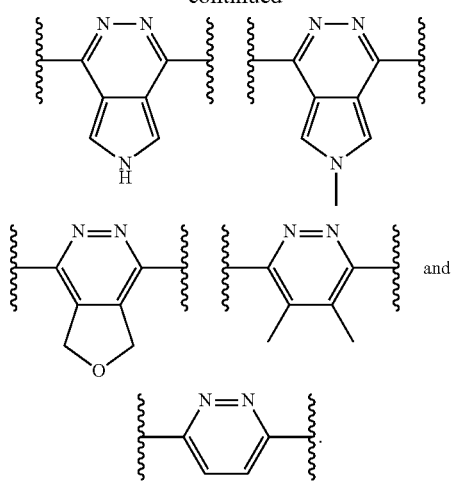
In embodiments
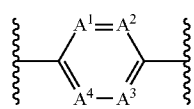
is selected from:
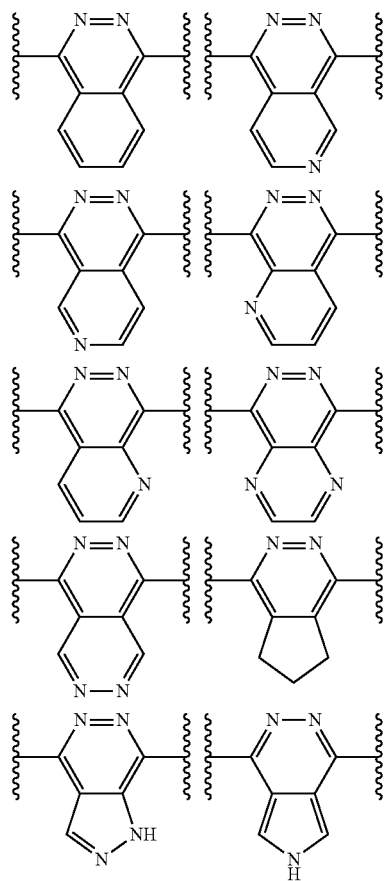
-continued
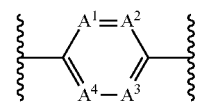
In an embodiment
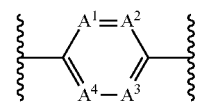
is selected from:
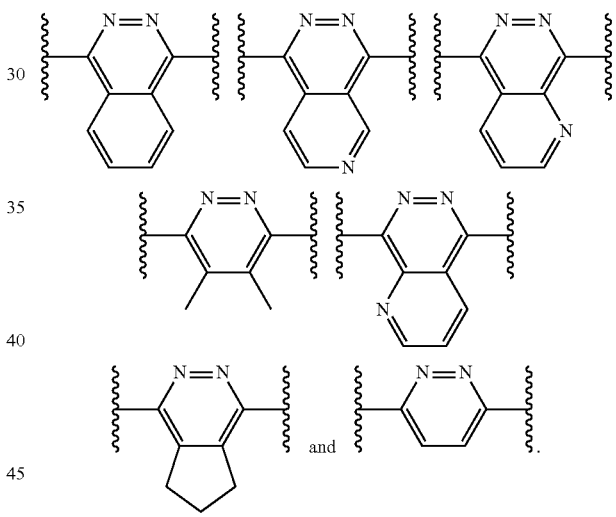
In an embodiment
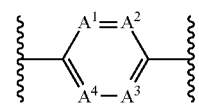
is selected from:
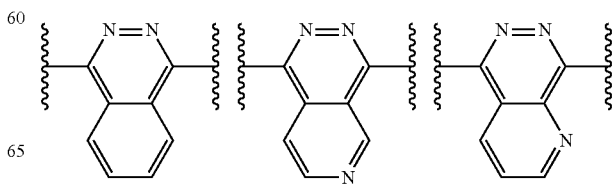

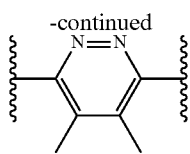

In an embodiment

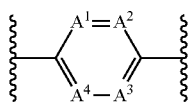

is selected from:

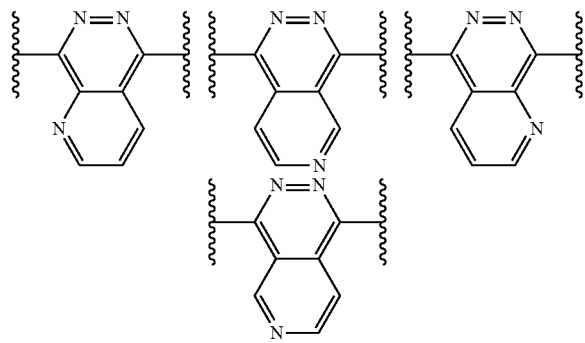

In an embodiment

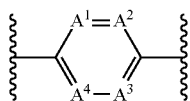

is selected from:

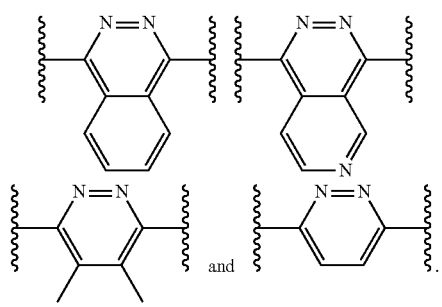

In an embodiment

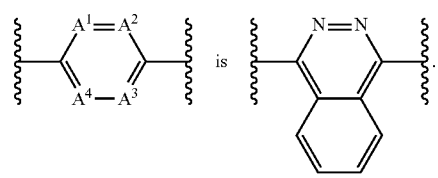

In an embodiment

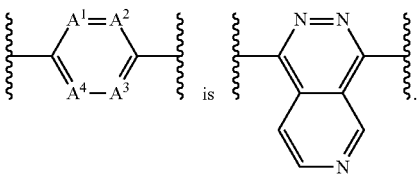

In an embodiment

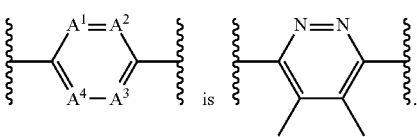

In an embodiment the compound of formula (I) is a compound according to formula (V) and pharmaceutically acceptable salts and solvates thereof:

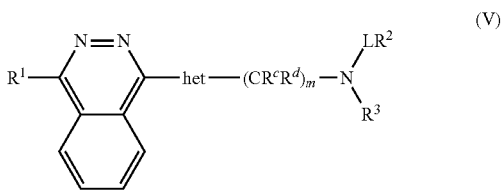

(V)

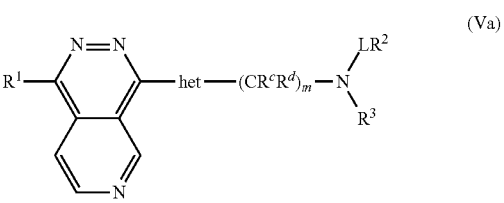

(Va)

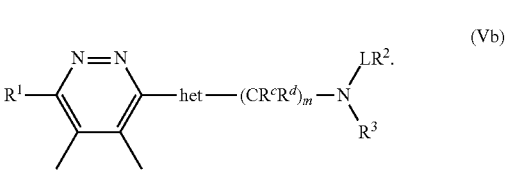

(Vb)

In an embodiment the compound of formula (I) is a compound according to formula (VI) or (VIa) and pharmaceutically acceptable salts and solvates thereof:

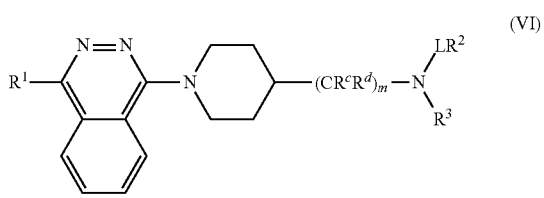

(VI)

(VIa)

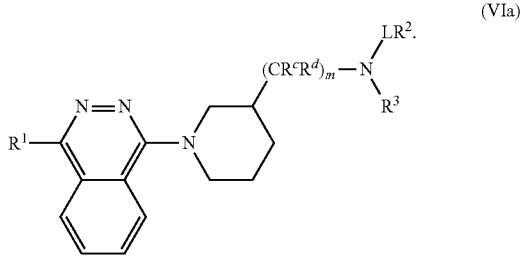

In embodiments L is selected from a substituted or unsubstituted saturated $C_{1-6}$ alkylene chain which may also contain where chemically possible 1, 2 or 3 N, O or S atoms in the chain which are independently chosen at each occurrence, or L is selected from a bond, —C(NR$^a$)—, —C(O)O—, —C(O)NR$^3$—, C(NR$^a$)NR$^3$— and —SO$_2$—.

In an embodiment L is not —C(O)O—.

In embodiments L is selected from a substituted or unsubstituted saturated $C_{1-6}$ alkylene chain which may also contain where chemically possible 1, 2 or 3 N, O or S atoms in the chain which are independently chosen at each occurrence, or L is selected from a bond, —C(NR$^a$)—, —C(O)NR$^3$—, C(NR$^a$)NR$^3$— and —SO$_2$—.

In embodiments L is selected from a bond, —CR$^c$R$^d$—, —CR$^c$R$^d$CR$^c$R$^d$—, —C(NR$^a$)—, —C(O)NR$^3$— and —SO$_2$—. Optionally, R$^a$, R$^c$ and R$^d$ are independently selected at each occurrence from H and $C_{1-4}$ alkyl and R$^3$ is selected from H and $C_{1-4}$ alkyl. Optionally, L may be a bond, —CR$^c$R$^d$—, —C(O)NR$^3$— or —SO$_2$—. Preferably, L may be —C(O)NR$^3$— or —CR$^c$R$^d$—.

In embodiments L is selected from a bond —CH$_2$—, —CH$_2$CH$_2$—, —CH(CH$_3$)—, —C(NH)—, —C(O)NH—, —C(O)N(CH$_3$)— and —SO$_2$—. In an embodiment L is —CH$_2$— or —C(O)NH—.

In embodiments R$^1$ is selected from —OR$^5$, —NR$^5$R$^a$, —NR$^a$C(O)R$^a$ substituted or unsubstituted $C_{1-6}$ alkyl, —CN, substituted or unsubstituted aryl and substituted or unsubstituted heterocyclic.

In embodiments R$^1$ is selected from —OR$^5$, —NR$^5$R$^a$, —NR$^a$C(O)R$^a$ substituted or unsubstituted $C_{1-6}$ alkyl, —CN and substituted or unsubstituted heterocyclic wherein nitrogen is the sole heteroatom of the heterocyclic group.

In embodiments the heterocyclic moiety is selected from substituted or unsubstituted $C_{4-8}$ heterocycloalkyl and substituted or unsubstituted $C_{5-6}$ heteroaryl and the carbocyclic moiety is selected from substituted or unsubstituted $C_{4-8}$ cycloalkyl and substituted or unsubstituted $C_{5-6}$ aryl. In an embodiment R$^1$ is substituted or unsubstituted heterocyclic and the heterocyclic moiety is selected from substituted or unsubstituted $C_{4-8}$ heterocycloalkyl and substituted or unsubstituted $C_{5-6}$ heteroaryl. Preferably, R$^1$ is substituted or unsubstituted $C_{5-6}$ heteroaryl. Optionally, the heteroatom is nitrogen. In embodiments nitrogen is the sole heteroatom of R$^1$, such that R$^1$ consists of carbon, hydrogen and nitrogen atoms.

In an embodiment R$^1$ is substituted or unsubstituted: pyrrolyl, imidazolyl, pyrazolyl, oxazolyl, oxadiazolyl, isoxazolyl, triazolyl, tetrazolyl, thiazolyl, isothiazolyl, furanyl, pyridinyl, pyridazinyl, pyrazinyl and pyrimidinyl. In an embodiment the substituted or unsubstituted $C_{5-6}$ heteroaryl of R$^1$ may be substituted or unsubstituted: pyrazolyl, pyridinyl, pyridazinyl, pyrimidinyl, pyrazinyl, imidazolyl or tetrazolyl. Preferably, R$^1$ is substituted or unsubstituted pyrimidinyl, pyrazolyl, isoxazolyl and triazolyl. Preferably, R$^1$ is substituted or unsubstituted pyrazolyl.

In an embodiment R$^1$ is substituted or unsubstituted $C_{4-8}$ heterocycloalkyl. The substituted or unsubstituted $C_{4-8}$ heterocycloalkyl may be substituted or unsubstituted: piperidinyl, piperazinyl, morpholinyl, thiomorpholinyl, pyrrolidinyl, azetidinyl, imidazolidinyl or succinimidyl.

In an alternative embodiment R$^1$ is —OR$^5$ or —NR$^5$R$^a$ wherein R$^5$ is independently selected from: H, —SO$_2$R$^a$, —SO$_2$NR$^a$R$^b$, substituted or unsubstituted $C_{1-4}$ alkyl, $C_{1-4}$ haloalkyl, substituted or unsubstituted $C_{5-6}$ aryl, and substituted or unsubstituted $C_{4-8}$ heterocycloalkyl and substituted or unsubstituted $C_{5-6}$ heteroaryl.

In an embodiment R$^1$ may be selected from —OMe, —OPh, —OC$_{1-4}$ alkyl, —N(CH$_3$)CH$_3$, —NHCH$_2$CH$_2$N(CH$_3$)$_2$, —NHSO$_2$CH$_3$, —N(CH$_3$)SO$_2$CH$_3$, —NHSO$_2$NCH$_3$, —N(CH$_3$)SO$_2$CH$_3$, —NC(O)R$^a$, methyl, ethyl, propyl, butyl, and —CN.

In an embodiment R$^1$ may be selected from hydroxyl, methoxy, methyl, N-methylamino, Me$_2$N(CH$_2$)NH—, nitrile, phenyloxy and substituted or unsubstituted: pyrazolyl, pyridyl, morpholinyl, pyrazinyl, pyrimidinyl, piperazinyl, pyridazinyl, pyrolidin-yl-one, imidazolin-yl-one, or pyridazinyl.

In an embodiment R$^1$ may be selected from hydroxyl, methoxy, methyl, N-methylamino, Me$_2$N(CH$_2$)NH—, nitrile, phenyloxy, pyrazolyl, methylpyrazolyl, pyridyl, methoxypyridyl, methylpyridyl, morpholinyl, pyrazinyl, aminopyrimidinyl, piperazinyl, methylpiperazinyl, pyridazinyl, pyrolidin-yl-one, imidazolin-yl-one, or pyridazinyl.

In an embodiment R$^1$ may be selected from:

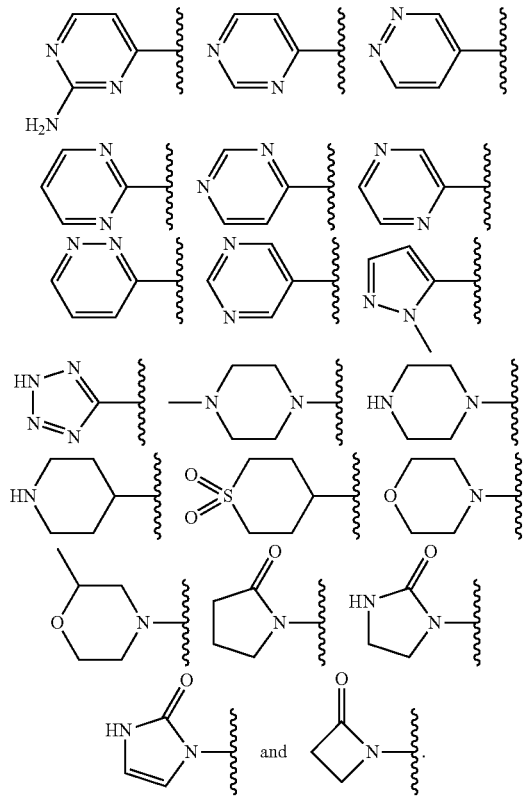

In an embodiment R¹ may be selected from:

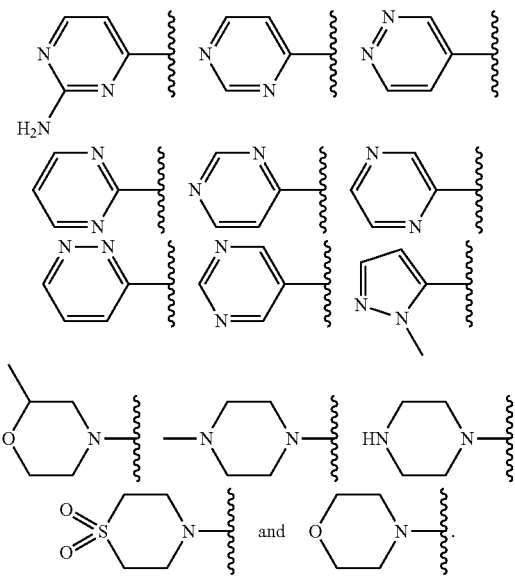

In an embodiment R¹ is:

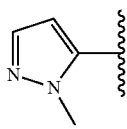

In an embodiment R¹ is not substituted or unsubstituted phenyl. In an embodiment R¹ is not substituted or unsubstituted thiadiazolyl, specifically 1,2,4-thiadiazolyl.

In an embodiment R² is represented by —CR⁶R⁷R⁸, wherein R⁶, R⁷ and R⁸ are independently selected at each occurrence from H and substituted or unsubstituted: $C_{1-14}$ alkyl, $C_{1-14}$ haloalkyl, carbocyclic, and heterocyclic. The carbocyclic and heterocyclic moieties may be monocyclic or fused polycyclic ring systems, for example bicyclic fused ring systems. Optionally, carbocyclic may be cycloalkyl and aryl and heterocyclic may be heterocycloalkyl and heteroaryl. Further optionally carbocyclic may be $C_{3-8}$ cycloalkyl and $C_{5-6}$ aryl and heterocyclic may be $C_{3-8}$ heterocycloalkyl and $C_{5-6}$ heteroaryl.

In an embodiment R² is represented by —CR⁶R⁷R⁸, wherein R⁶, R⁷ and R⁸ are independently selected at each occurrence from H and substituted or unsubstituted: $C_{1-14}$ alkyl, $C_{1-14}$ haloalkyl, $C_{3-8}$ cycloalkyl, $C_{3-8}$ heterocycloalkyl, phenyl, toluenyl, pyridinyl, pyridazinyl, pyrimidinyl, pyrazinyl, pyrrolyl, pyrazolyl, triazolyl, tetrazolyl, oxazolyl, isoxazolyl, oxadiazolyl, thiazolyl, and isothiazolyl.

In an embodiment R⁶, R⁷ and R⁸ are independently selected at each occurrence from H and substituted or unsubstituted: $C_{1-6}$ alkyl, $C_{1-6}$ haloalkyl, $C_{3-8}$ cycloalkyl, $C_{3-8}$ heterocycloalkyl, phenyl, toluenyl, pyridinyl, pyridazinyl, pyrimidinyl, pyrazinyl, pyrrolyl, pyrazolyl, triazolyl, tetrazolyl, oxazolyl, isoxazolyl, oxadiazolyl, thiazolyl, and isothiazolyl.

In an embodiment R⁶, R⁷ and R⁸ are independently selected at each occurrence from H and substituted or unsubstituted: $C_{1-14}$ alkyl (optionally $C_{1-6}$ alkyl), $C_{1-14}$ haloalkyl (optionally $C_{1-6}$ haloalkyl), $C_{3-8}$ cycloalkyl, phenyl, toluenyl, pyridinyl, pyridazinyl, pyrimidinyl, pyrazinyl, pyrrolyl, pyrazolyl, triazolyl, tetrazolyl, oxazolyl, isoxazolyl, oxadiazolyl, thiazolyl, and isothiazolyl.

In an embodiment two of R⁶, R⁷ and R⁸ are the same and the third is selected independently. In an alternative embodiment R⁶, R⁷ and R⁸ are all the same.

In an embodiment R⁶, R⁷ and R⁸ are all one of the groups selected from: methyl, trifluoromethyl, cyclohexanyl and phenyl.

In an embodiment R² is not tert-butyl. In an embodiment R⁶, R⁷ and R⁸ are not methyl. In an embodiment R¹ is not substituted or unsubstituted phenyl. In an embodiment R¹ is not substituted or unsubstituted phenyl when L is —C(O)O— and R² is —CR⁶R⁷R⁸, wherein R⁶, R⁷ and R⁸ are each methyl.

In an embodiment R² is selected from substituted or unsubstituted: $C_{1-14}$ alkyl, $C_{1-14}$ haloalkyl, carbocyclic, and heterocyclic. The carbocyclic and heterocyclic moieties may be monocyclic or fused polycyclic ring systems, for example bicyclic fused ring systems. Optionally, carbocyclic may be cycloalkyl and aryl and heterocyclic may be heterocycloalkyl and heteroaryl. Further optionally carbocyclic may be $C_{3-8}$ cycloalkyl and $C_{5-6}$ aryl and heterocyclic may be $C_{3-8}$ heterocycloalkyl and $C_{5-6}$ heteroaryl. In an embodiment carbocyclic may be $C_{3-8}$ cycloalkyl and $C_6$ aryl and heterocyclic may be $C_{3-8}$ heterocycloalkyl and $C_6$ heteroaryl.

In embodiments where R² is $C_{5-6}$ aryl and $C_{5-6}$ heteroaryl the ring of the $C_{5-6}$ aryl and $C_{5-6}$ heteroaryl may be ortho and/or meta and/or para substituted. In embodiments where R² is $C_{5-6}$ aryl and $C_{5-6}$ heteroaryl the ring may be ortho substituted. In embodiments where R² is $C_{5-6}$ aryl and $C_{5-6}$ heteroaryl the ring may be meta substituted. In embodiments where R² is $C_6$ aryl and $C_6$ heteroaryl the 6 membered ring may be para substituted. In embodiments where R² is $C_6$ aryl and $C_6$ heteroaryl the 6 membered ring may be ortho and para substituted. In embodiments where R² is $C_{5-6}$ aryl and $C_{5-6}$ heteroaryl the 6 membered ring may be di-meta substituted.

In an embodiment R² is selected from substituted or unsubstituted: $C_{1-14}$ alkyl, $C_{1-14}$ haloalkyl, $C_{3-8}$ cycloalkyl, $C_{3-8}$ heterocycloalkyl, phenyl, toluenyl, pyridinyl, pyridazinyl, pyrimidinyl, pyrazinyl, pyrrolyl, pyrazolyl, triazolyl, tetrazolyl, oxazolyl, isoxazolyl, oxadiazolyl, thiazolyl, and isothiazolyl.

In an embodiment R² may be selected from tert-butyl or substituted or unsubstituted: cyclopropyl, phenyl, toluenyl, pyridinyl, pyridazinyl, pyrimidinyl, pyrazinyl, pyrrolyl, pyrazolyl, triazolyl, tetrazolyl, oxazolyl, isoxazolyl, oxadiazolyl, thiazolyl, and isothiazolyl. Preferably, R² is substituted or unsubstituted phenyl, toluenyl and pyridinyl.

In an embodiment R² may be selected from substituted or unsubstituted: phenyl, toluenyl, pyridinyl, pyridazinyl, pyrimidinyl, pyrazinyl, pyrrolyl, pyrazolyl, triazolyl, tetrazolyl, oxazolyl, isoxazolyl, oxadiazolyl, thiazolyl, and isothiazolyl. Preferably, R² is substituted or unsubstituted phenyl, toluenyl and pyridinyl.

In embodiments where R² is substituted and R² may be substituted by 1 to 5 substituents, optionally 1, 2 or 3 substituents, independently selected at each occurrence from the group comprising halo, —ORᵃ, —NO₂, $C_{1-6}$ alkyl, $C_{1-6}$ haloalkyl, —C(ORᵃ)RᵃR^b, —SC$_{1-4}$ alkyl, —C(O)RₐR_b, —N(CO)Rₐ, and —CN.

In embodiments where R² is substituted, R² may be substituted by 1 or 2 substituents independently selected at each occurrence from the group comprising halo (optionally fluoro or chloro), —NO₂, —OC$_{1-4}$ haloalkyl (optionally —OCF₃), $C_{1-6}$ alkyl (optionally methyl, ethyl, iso-propyl or tert-butyl), $C_{1-6}$ haloalkyl (optionally trifluormethyl), —C(OH)(C$_{1-6}$ alkyl)C$_{1-6}$ alkyl, —SC$_{1-4}$ alkyl (optionally —SMe), —SO$_2$C$_{1-4}$ alkyl (optionally —SO$_2$Me), acyl (optionally —C(O)OMe) and —CN. For example, the substituents may be selected from fluoro, chloro, —NO$_2$, —OCF$_3$, —OCF$_2$H, —OMe, —OEt, —SMe, —SEt, —SO$_2$Me, methyl, ethyl, iso-propyl, tert-butyl, trifluoromethyl, —C(O)OMe, —C(OH)(CH$_3$)CH$_3$, —C(OH)(CH$_3$)CH$_2$CH$_3$ and —CN.

In embodiments where R$^2$ is substituted, R$^2$ may be substituted by 1 or 2 substituents independently selected at each occurrence from the group comprising halo, —NO$_2$, —OC$_{1-4}$ haloalkyl, C$_{1-6}$ alkyl, C$_{1-6}$ haloalkyl, —C(OH)(C$_{1-6}$ alkyl)C$_{1-6}$ alkyl, —SC$_{1-4}$ alkyl and —CN. For example, the substituents may be selected from fluoro, chloro, —NO$_2$, —OCF$_3$, —OCF$_2$H, —OMe, —OEt, —SMe, —SEt, methyl, ethyl, trifluoromethyl, —C(OH)(CH$_3$)CH$_3$, —C(OH)(CH$_3$)CH$_2$CH$_3$ and —CN.

In an embodiment R$^2$ is substituted by trifluoromethyl. In an alternative embodiment R$^2$ is substituted by —OCF$_3$. In an embodiment R$^2$ is substituted by —C(OH)(CH$_3$)CH$_3$. In an embodiment R$^2$ is substituted by methyl. In an embodiment R$^2$ is substituted by fluoro. In an embodiment R$^2$ is substituted by chloro. In an embodiment R$^2$ is substituted by —CN. In an embodiment R$^2$ is substituted by fluoro and trifluoromethyl. In an embodiment R$^2$ is substituted by fluoro and —OCF$_3$. In an embodiment R$^2$ is substituted by fluoro and methyl.

R$^2$ may be represented by:

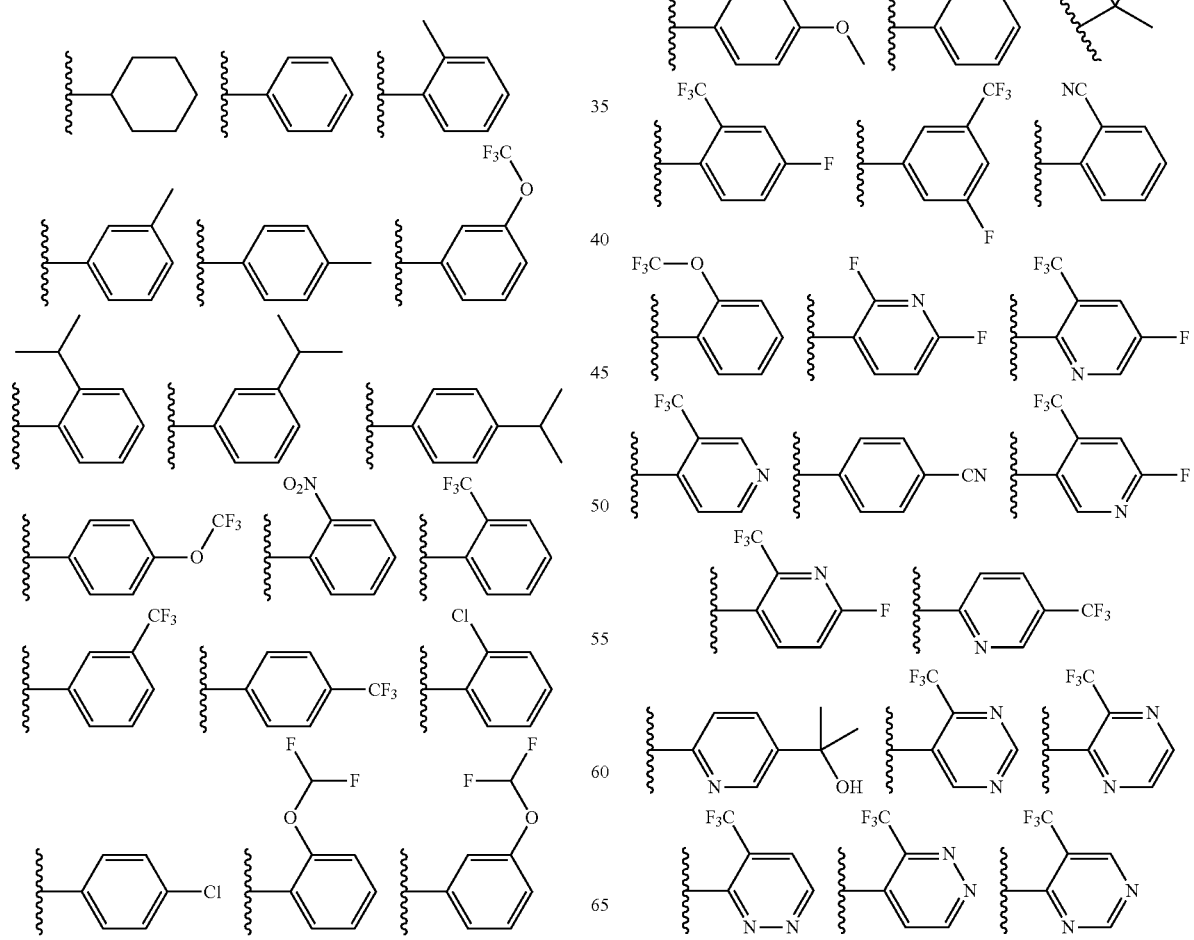

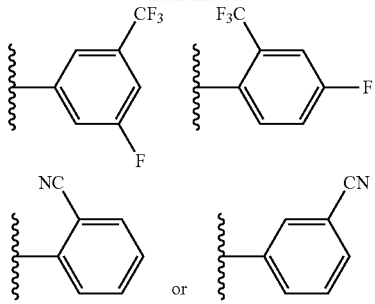

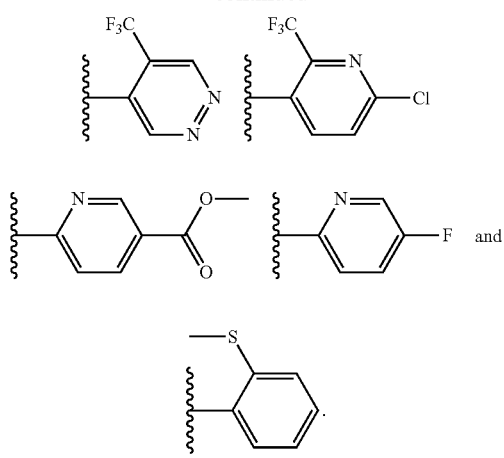

In addition R² may be represented by:

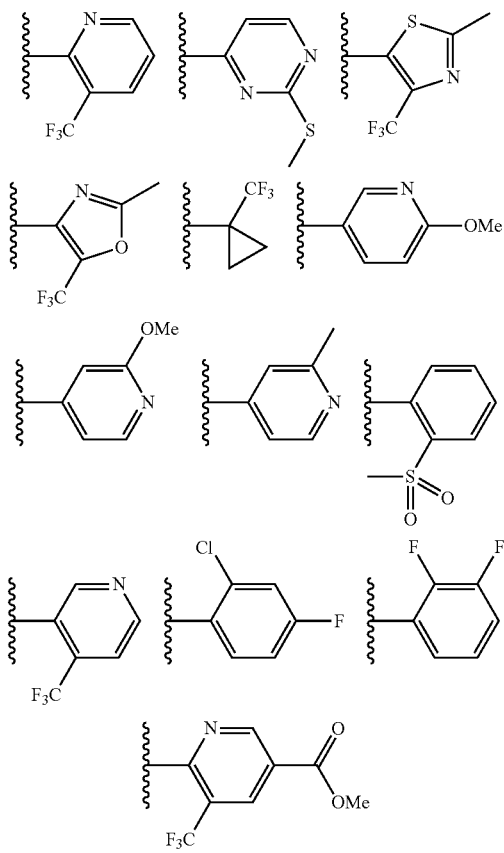

In a preferred embodiment R² is

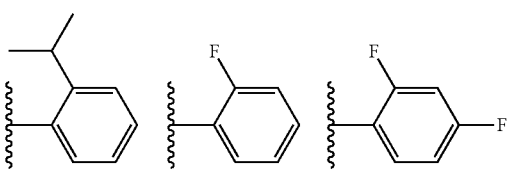

In an embodiment, R³ is selected from H, substituted or unsubstituted $C_{1-4}$ alkyl, substituted or unsubstituted $C_{1-4}$ haloalkyl, substituted or unsubstituted $C_{3-8}$ cycloalkyl. Preferably, R³ is H, methyl, cyclopropyl or —C(O)CF₃.

In an embodiment R³ is H or substituted or unsubstituted $C_{1-4}$ alkyl or substituted or unsubstituted $C_{1-4}$ haloalkyl. Preferably, R³ is H, methyl or —C(O)CF₃.

In an embodiment all occurrences of $R^a$ and $R^b$ are hydrogen.

In an embodiment all occurrences of $R^c$ and $R^d$ are hydrogen.

In an embodiment m is 0 or 1. Optionally, m is 0. Optionally, m is 1. In particular, m may be 0 when het is piperidinylene. Thus, m may be 0 in compounds of formula (II) or (IIa). Also, m may be 0 or 1 when het is pyrrolidinylene. Thus, m may be 0 or 1 in compounds of formula (IIb).

Optionally, the compounds of the invention may be compounds of formula (I), as described above, provided that R¹ is not substituted phenyl. Optionally, the compounds of the invention may be compounds of formula (I), as described above, provided that R¹ is not unsubstituted phenyl. Optionally, R¹ is not substituted or unsubstituted phenyl Optionally, the compounds of the invention may be compounds of formula (I), as described above, provided that R¹ is not substituted or unsubstituted 1,2,4-thiadiazolyl, optionally thiadiazolyl generally.

The compounds of the invention may be compounds of formula (I) provided that L is not —C(O)O— when R² is —CR⁶R⁷R⁸, wherein R⁶, R⁷ and R⁸ are each methyl and provided that R¹ is not substituted or unsubstituted thiadiazolyl, specifically 1,2,4-thiadiazolyl.

In embodiments R¹ is not substituted or unsubstituted phenyl when L is —C(O)O— and R² is tert-butyl. Optionally, R¹ is not substituted or unsubstituted phenyl when L is —C(O)O—. Optionally, R¹ is not substituted or unsubstituted phenyl when R² is tert-butyl. In embodiments R¹ is not substituted or unsubstituted phenyl, optionally provided that L is not —C(O)O—, optionally provided that R² is not tert-butyl and further optionally provided that R³ is not hydrogen or methyl.

In embodiments R¹ is not pyrazolyl or methyl pyrazolyl when L is —C(O)O— and R² is tert-butyl. Optionally, R¹ is not substituted or unsubstituted phenyl when L is —C(O)O—. Optionally, R¹ is not pyrazolyl or methyl pyrazolyl when R² is tert-butyl. In embodiments R¹ is not pyrazolyl or methyl pyrazolyl, optionally provided that L is not —C(O)O—, optionally provided that R² is not tert-butyl and further optionally provided that R³ is not hydrogen or methyl.

In embodiments, the compound of formula (I) is a compound according to formula (VII) and pharmaceutically acceptable salts and solvates thereof:

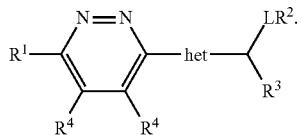
(VII)

In embodiments, the compound of formula (I) is a compound according to formula (VIII) or formula (VIIIa) and pharmaceutically acceptable salts and solvates thereof:

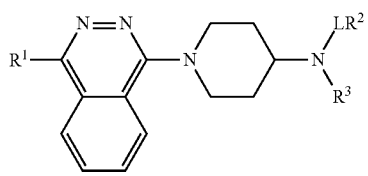
(VIII)

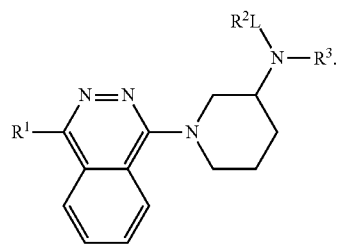
(VIIIa)

In an embodiment, the compound of formula (I) is a compound according to formula (IX) and pharmaceutically acceptable salts and solvates thereof:

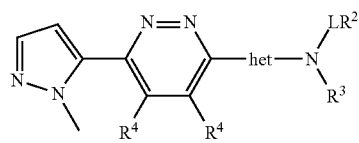
(IX)

In an embodiment, the compound of formula (I) is a compound according to formula (X) or formula (Xa) and pharmaceutically acceptable salts and solvates thereof:

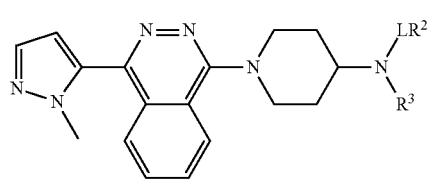
(X)

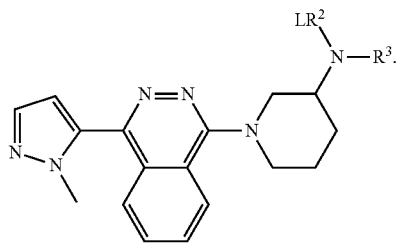
(Xa)

In an embodiment the compound of formula (I) is a compound according to formula (X) provided that L is not —C(O)O— when $R^2$ is tert-butyl. In an embodiment the compound of formula (I) is a compound according to formula (X) provided that L is not —C(O)O— and optionally provided that $R^2$ is not tert-butyl.

In an embodiment, the compound of formula (I) is a compound according to formula (XI) and pharmaceutically acceptable salts and solvates thereof:

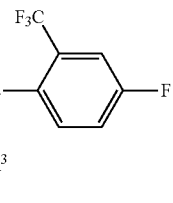
(XI)

In an embodiment, the compound of formula (I) is a compound according to formula (XII) or formula (XIIa) and pharmaceutically acceptable salts and solvates thereof:

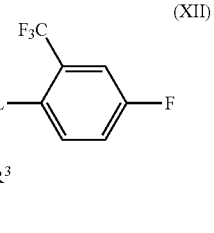
(XII)

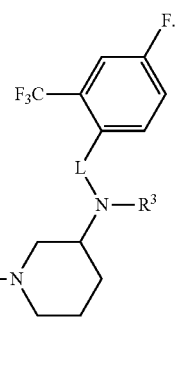
(XIIa)

The compound of formula (I) may be a compound of formula (XIII) and in particular a compound of formula (XIIIa) and pharmaceutically acceptable salts and solvates thereof:

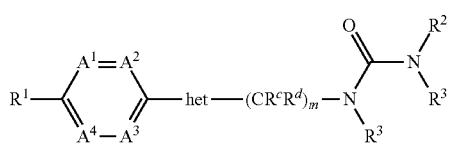

(XIII)

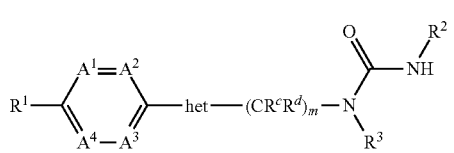

(XIIIa)

There are provided compounds of formulae (XIII) or (XIIIa), wherein R¹ is substituted or unsubstituted pyrazolyl. The compounds of formulae (XIII) or (XIIIa) may have R² represented by substituted or unsubstituted phenyl, toluenyl and pyridinyl. In addition there is provided compounds of formulae (XIII) or (XIIIa), wherein het is:

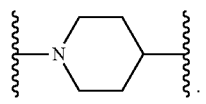

There are provided compounds of formulae (XIII) or (XIIIa), wherein

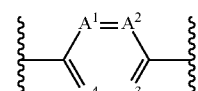

may be selected from:

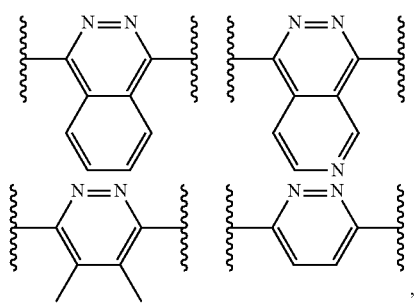

Preferably,

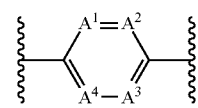

may be selected from:

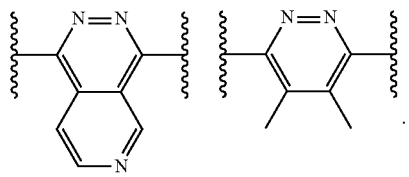

In an embodiment the compound of formula (I) may be a compound according to formulae (XIII) or (XIIIa), wherein R¹ is substituted or unsubstituted pyrazolyl, R² is substituted or unsubstituted phenyl, toluenyl and pyridinyl and het is:

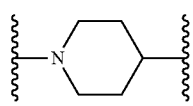

There are provided, compounds of formula (XIII) and in particular compounds of formula (XIIIa), wherein:

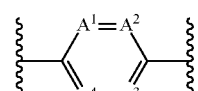

may be selected from:

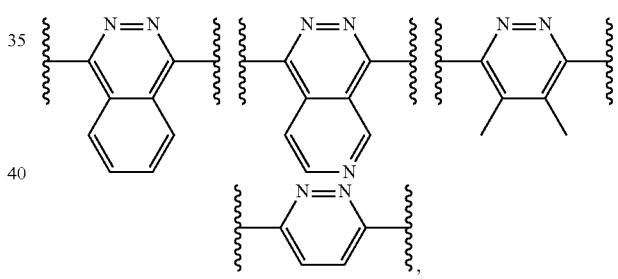

het may be:

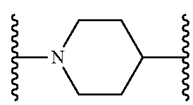

R¹ may be substituted or unsubstituted pyrazolyl,
R² may be substituted or unsubstituted phenyl, toluenyl and pyridinyl,
R³ may be H, methyl or —C(O)CF₃, preferably H or methyl, and
m may be 0 or 1, preferably 0.
wherein when a group is substituted, the group contains 1 to 5 substituents independently selected at each occurrence from the group comprising: halo, —OR$^a$, —SR$^a$, —NR$^a$R$^b$, NO₂, =O, —CN, acyl, C$_{1-6}$ alkyl, C$_{1-6}$ haloalkyl, C$_{3-8}$ cycloalkyl, —SO₂R$^a$, and SO₃R$^a$, —C(OR$^a$)R$^a$R$^b$, —C(O)R$^a$ and C(O)OR$^a$.
optionally wherein R² may be substituted by 1 or 2 substituents independently selected at each occurrence from the group comprising halo, —NO$_2$, —OC$_{1-4}$ haloalkyl, C$_{1-6}$ alkyl, C$_{1-6}$ haloalkyl, —C(OH)(C$_{1-6}$ alkyl)C$_{1-6}$ alkyl, —SC$_{1-4}$ alkyl and —CN;

preferably wherein

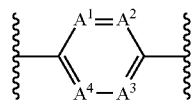

may be selected from:

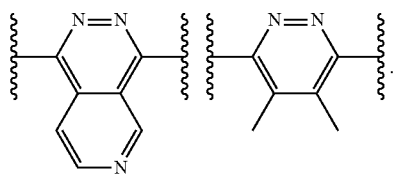

The compound of formula (I) may be a compound of formula (VII) where L is —C(O)NR$^3$— or in particular —C(O)NH—, as represented by the compounds of formula (XIV) and (XIVa):

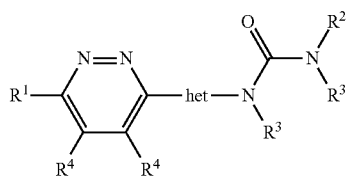

(XIV)

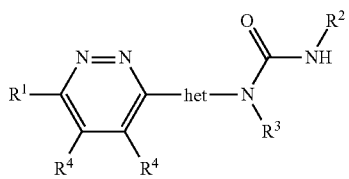

(XIVa)

There are provided compounds of formulae (XIV) or (XIVa), wherein R$^1$ may be substituted or unsubstituted pyrazolyl. There are provided compounds of formulae (XIV) or (XIVa), wherein R$^2$ may be substituted or unsubstituted phenyl, toluenyl and pyridinyl. In addition there are provided compounds of formulae (XIV) or (XIVa), wherein R$^1$ is substituted or unsubstituted pyrazolyl, R$^2$ is substituted or unsubstituted phenyl, toluenyl and pyridinyl, and het is:

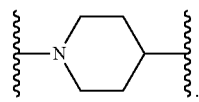 [SMILES: *C1CCN(*)CC1]

The compound of formula (I) may be a compound of formula (IX) where L is —C(O)NR$^3$— or in particular —C(O)NH—, as represented by the compounds of formulae (XV) and (XVa):

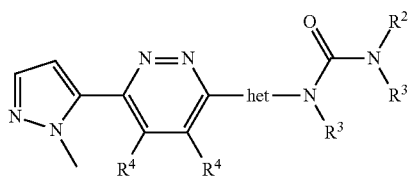

(XV)

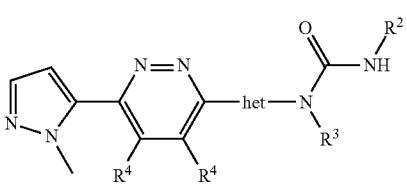

(XVa)

The compounds of formulae (XV) or (XVa) may have an R$^2$ selected from substituted or unsubstituted phenyl, toluenyl and pyridinyl;
wherein when a group is substituted, the group contains 1 to 5 substituents independently selected at each occurrence from the group comprising: halo, —OR$^a$, —SR$^a$, —NR$^a$R$^b$, NO$_2$, =O, —CN, acyl, C$_{1-6}$ alkyl, C$_{1-6}$ haloalkyl, C$_{3-8}$ cycloalkyl, —SO$_2$R$^a$, and SO$_3$R$^a$, —C(OR$^a$)R$^a$R$^b$, —C(O)R$^a$ and C(O)OR$^a$.

optionally wherein R$^2$ may be substituted by 1 or 2 substituents independently selected at each occurrence from the group comprising halo, —NO$_2$, —OC$_{1-4}$ haloalkyl, C$_{1-6}$ alkyl, C$_{1-6}$ haloalkyl, —C(OH)(C$_{1-6}$ alkyl)C$_{1-6}$ alkyl, —SC$_{1-4}$ alkyl and —CN.

In compounds of formulae (XV) or (XVa) "het" may be unsubstituted:

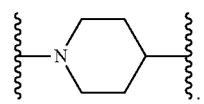

The compounds of formulae (XV) or (XVa) may have an R$^2$ selected from substituted or unsubstituted phenyl, toluenyl and pyridinyl,
wherein when R$^2$ is substituted, the group contains 1 to 5 substituents independently selected at each occurrence from the group comprising: halo, —OR$^a$, —SR$^a$, —NR$^a$R$^b$, NO$_2$, =O, —CN, acyl, C$_{1-6}$ alkyl, C$_{1-6}$ haloalkyl, C$_{3-8}$ cycloalkyl, —SO$_2$R$^a$, and SO$_3$R$^a$, —C(OR$^a$)R$^a$R$^b$, —C(O)R$^a$ and C(O)OR$^a$.

optionally wherein R$^2$ may be substituted by 1 or 2 substituents independently selected at each occurrence from the group comprising halo, —NO$_2$, —OC$_{1-4}$ haloalkyl, C$_{1-6}$ alkyl, C$_{1-6}$ haloalkyl, —C(OH)(C$_{1-6}$ alkyl)C$_{1-6}$ alkyl, —SC$_{1-4}$ alkyl and —CN;
R$^3$ may be H, methyl or —C(O)CF$_3$, preferably H or methyl; and
"het" may be unsubstituted:

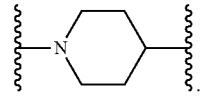

The invention provides compounds of formula (I), optionally provided that the compounds of formula (I) are not compounds of formula (XIII) and in particular compounds of formula (XIIIa).

The invention provides compounds of formula (I), optionally provided that the compounds of formula (I) are not compounds of formula (XIII) and in particular compounds of formula (XIIIa), wherein:

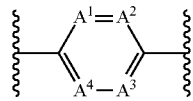

Is selected from:

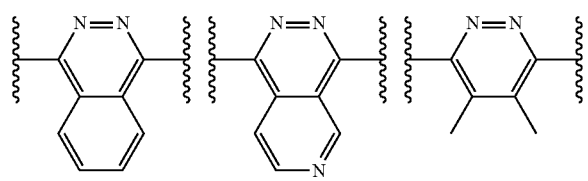

het is:

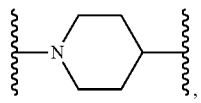

R¹ is substituted or unsubstituted pyrazolyl,

R² is substituted or unsubstituted phenyl, toluenyl and pyridinyl,

R³ is H, methyl or —C(O)CF₃, preferably H or methyl, and m is 0 or 1, preferably 0, wherein when a group is substituted, the group contains 1 to 5 substituents independently selected at each occurrence from the group comprising: halo, —OR$^a$, —SR$^a$, —NR$^a$R$^b$, NO₂, =O, —CN, acyl, C$_{1-6}$ alkyl, C$_{1-6}$ haloalkyl, C$_{3-8}$ cycloalkyl, —SO₂R$^a$, and SO₃R$^a$, —C(OR$^a$)R$^a$R$^b$, —C(O)R$^a$ and C(O)OR$^a$.

optionally wherein R² may be substituted by 1 or 2 substituents independently selected at each occurrence from the group comprising halo, —NO₂, —OC$_{1-4}$ haloalkyl, C$_{1-6}$ alkyl, C$_{1-6}$ haloalkyl, —C(OH)(C$_{1-6}$ alkyl)C$_{1-6}$ alkyl, —SC$_{1-4}$ alkyl and —CN, preferably where

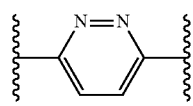

is selected from:

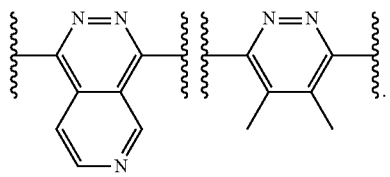

Furthermore, there are provided compounds of formula (I) optionally wherein L is not —C(O)NR³—, and

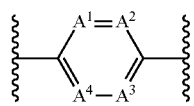

is not selected from:

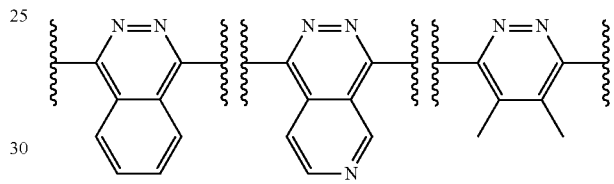

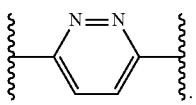

Compounds of formula (I) may have L selected from either a substituted or unsubstituted C$_{1-6}$ alkylene chain which is saturated or unsaturated and which may also optionally contain, where chemically possible, 1, 2 or 3 N, O, or S atoms in the chain which are independently chosen at each occurrence;

or L selected from a bond, —C(NR$^a$)—, —C(O)O—, —C(NR$^a$)NR³—, and —SO₂—.

In an embodiment the compound of formula (I) is not a compound shown below:

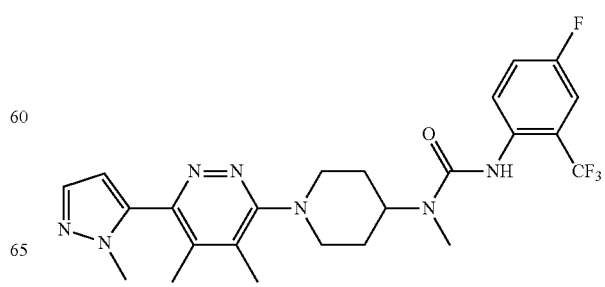

-continued

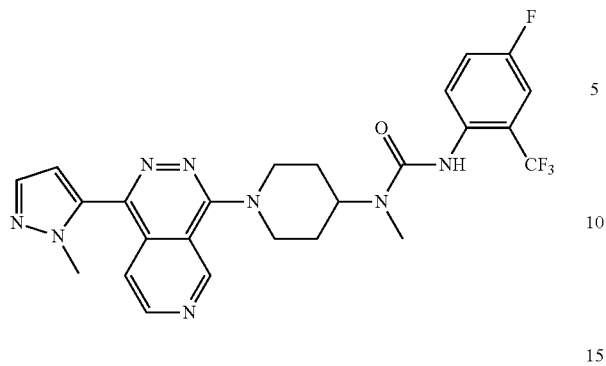

The compound of formula (I) may be a compound of formula (XVI), wherein the compound of formula (XVI) is a compound of formula (Ib) and L is selected from either a substituted or unsubstituted $C_{1-6}$ alkylene chain (optionally $C_{1-2}$ alkylene chain) which is saturated or unsaturated and which may also optionally contain, where chemically possible, 1, 2 or 3 N, O, or S atoms in the chain which are independently chosen at each occurrence. Preferably, the compound of the invention is a compound of formula (XVI) wherein L is selected from either a substituted or unsubstituted $C_{1-2}$ alkylene chain which is saturated. In particular, the compound of formula (I) may be a compound of formula (XVIa) and pharmaceutically acceptable salts and solvates thereof:

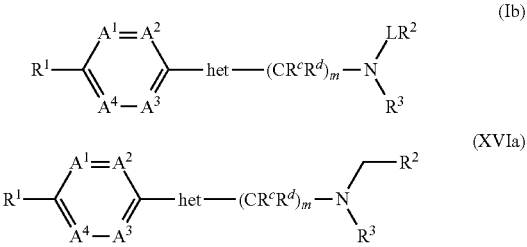

There are provided compounds of formulae (XVI) or (XVIa), wherein $R^1$ is substituted or unsubstituted pyrazolyl. The compounds of formulae (XIII) or (XIIIa) may have $R^2$ represented by substituted or unsubstituted phenyl, toluenyl and pyridinyl. In addition there is provided compounds of formulae (XIII) or (XIIIa), wherein het is:

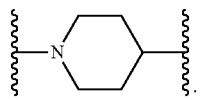

There are provided compounds of formulae (XVI) or (XVIa), wherein

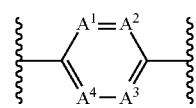

may be selected from:

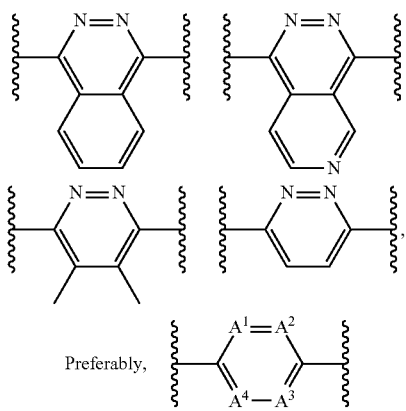

may be selected from:

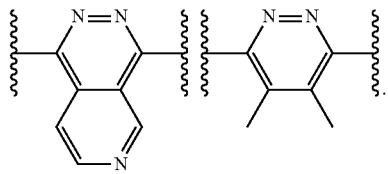

In an embodiment the compound of formula (I) may be a compound according to formulae (XVI) or (XVIa), wherein $R^1$ is substituted or unsubstituted pyrazolyl, $R^2$ is substituted or unsubstituted phenyl, toluenyl and pyridinyl and het is:

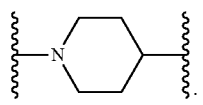

There are provided, compounds of formula (XVI) and in particular compounds of formula (XVIa), wherein:

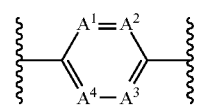

may be selected from:

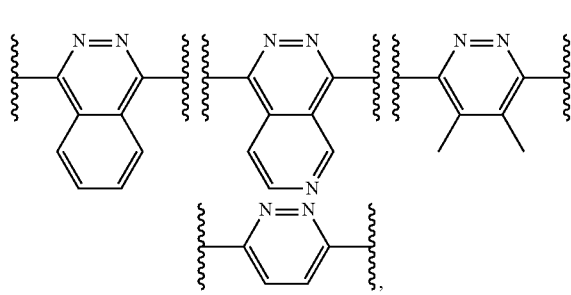

het may be:

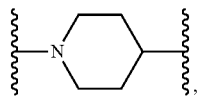

R¹ may be substituted or unsubstituted pyrazolyl,
R² may be substituted or unsubstituted phenyl, toluenyl and pyridinyl,
R³ may be H, methyl, cyclopropyl or —C(O)CF₃, preferably H or methyl, and
m may be 0 or 1, preferably 0;
wherein when a group is substituted, the group contains 1 to 5 substituents independently selected at each occurrence from the group comprising: halo, —OR$^a$, —SR$^a$, —NR$^a$R$^b$, NO₂, =O, —CN, acyl, C$_{1-6}$ alkyl, C$_{1-6}$ haloalkyl, C$_{3-8}$ cycloalkyl, —SO₂R$^a$, and SO₃R$^a$, —C(OR$^a$)R$^a$R$^b$, —C(O)R$^a$ and C(O)OR$^a$.
optionally wherein R² may be substituted by 1 or 2 substituents independently selected at each occurrence from the group comprising halo, —NO₂, —OC$_{1-4}$ haloalkyl, C$_{1-6}$ alkyl, C$_{1-6}$ haloalkyl, —C(OH)(C$_{1-6}$ alkyl)C$_{1-6}$ alkyl, —SC$_{1-4}$ alkyl and —CN;
preferably wherein

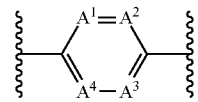

may be selected from:

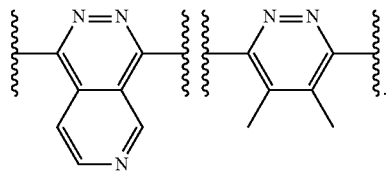

The compound of formula (I) may be a compound of formula (XVII), wherein the compound of formula (XVII) is a compound of formula (VII) and L is selected from either a substituted or unsubstituted C$_{1-6}$ alkylene chain (optionally C$_{1-2}$ alkylene chain) which is saturated or unsaturated and which may also optionally contain, where chemically possible, 1, 2 or 3 N, O, or S atoms in the chain which are independently chosen at each occurrence. Preferably, the compound of the invention is a compound of formula (XVII) wherein L is selected from either a substituted or unsubstituted C$_{1-2}$ alkylene chain which is saturated. In particular, the compound of formula (I) may be a compound of formula (XVIIa) and pharmaceutically acceptable salts and solvates thereof.

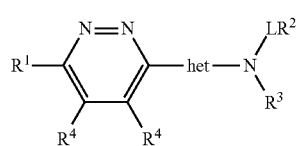
(VII)

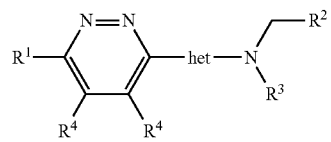
(XVIIa)

There are provided compounds of formulae (XVII) or (XVIIa), wherein R¹ may be substituted or unsubstituted pyrazolyl. There are provided compounds of formulae (XVII) or (XVIIa), wherein R² may be substituted or unsubstituted phenyl, toluenyl and pyridinyl. In addition there are provided compounds of formulae (XVII) or (XVIIa), wherein R¹ is substituted or unsubstituted pyrazolyl, R² is substituted or unsubstituted phenyl, toluenyl and pyridinyl, and het is:

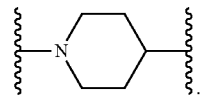

The compound of formula (I) may be a compound of formula (XVIII), wherein the compound of formula (XVIII) is a compound of formula (IX) and L is selected from either a substituted or unsubstituted C$_{1-6}$ alkylene chain (optionally C$_{1-2}$ alkylene chain) which is saturated or unsaturated and which may also optionally contain, where chemically possible, 1, 2 or 3 N, O, or S atoms in the chain which are independently chosen at each occurrence. Preferably, the compound of the invention is a compound of formula (XVIII) wherein L is selected from either a substituted or unsubstituted C$_{1-2}$ alkylene chain which is saturated. In particular, the compound of formula (I) may be a compound of formula (XVIIIa) and pharmaceutically acceptable salts and solvates thereof.

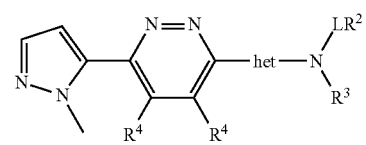
(IX)

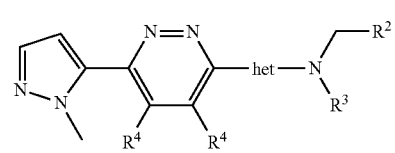
(XVIIIa)

The compounds of formulae (XVIII) or (XVIIIa) may have an R² selected from substituted or unsubstituted phenyl, toluenyl and pyridinyl;
wherein when a group is substituted, the group contains 1 to 5 substituents independently selected at each occurrence from the group comprising: halo, —OR$^a$, —SR$^a$, —NR$^a$R$^b$, NO₂, =O, —CN, acyl, C$_{1-6}$ alkyl, C$_{1-6}$ haloalkyl, C$_{3-8}$ cycloalkyl, —SO₂R$^a$, and SO₃R$^a$, —C(OR$^a$)R$^a$R$^b$, —C(O)R$^a$ and C(O)OR$^a$.
optionally wherein R² may be substituted by 1 or 2 substituents independently selected at each occurrence from the group comprising halo, —NO₂, —OC$_{1-4}$ haloalkyl, C$_{1-6}$ alkyl, C$_{1-6}$ haloalkyl, —C(OH)(C$_{1-6}$ alkyl)C$_{1-6}$ alkyl, —SC$_{1-4}$ alkyl and —CN.

In compounds of formulae (XVIII) or (XVIIIa) "het" may be unsubstituted:

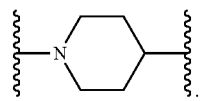

The compounds of formulae (XVIII) or (XVIIIa) may have an $R^2$ selected from substituted or unsubstituted phenyl, toluenyl and pyridinyl,
wherein when $R^2$ is substituted, the group contains 1 to 5 substituents independently selected at each occurrence from the group comprising: halo, —$OR^a$, —$SR^a$, —$NR^aR^b$, $NO_2$, =O, —CN, acyl, $C_{1-6}$ alkyl, $C_{1-6}$ haloalkyl, $C_{3-8}$ cycloalkyl, —$SO_2R^a$, and $SO_3R^a$, —$C(OR^a)R^aR^b$, —$C(O)R^a$ and $C(O)OR^a$.
optionally wherein $R^2$ may be substituted by 1 or 2 substituents independently selected at each occurrence from the group comprising halo, —$NO_2$, —$OC_{1-4}$ haloalkyl, $C_{1-6}$ alkyl, $C_{1-6}$ haloalkyl, —$C(OH)(C_{1-6}$ alkyl)$C_{1-6}$ alkyl, —$SC_{1-4}$ alkyl and —CN;
$R^3$ may be H, methyl or —$C(O)CF_3$, preferably H or methyl; and
"het" may be unsubstituted:

Compounds of the invention include:

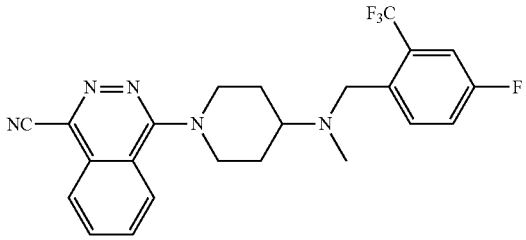

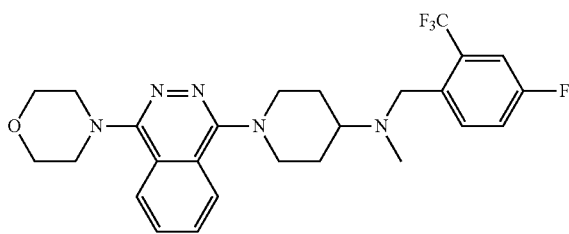

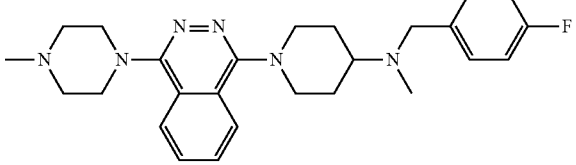

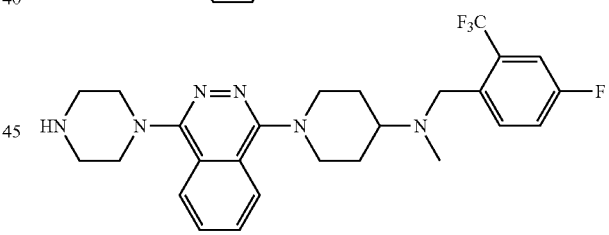

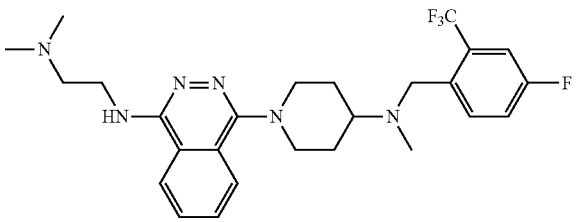

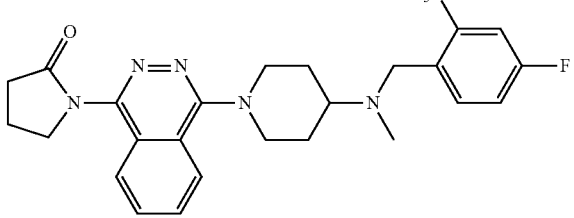

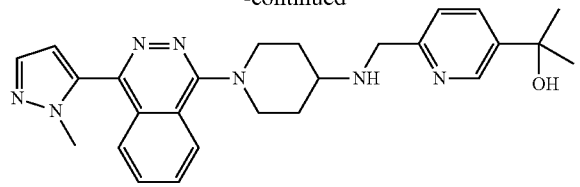
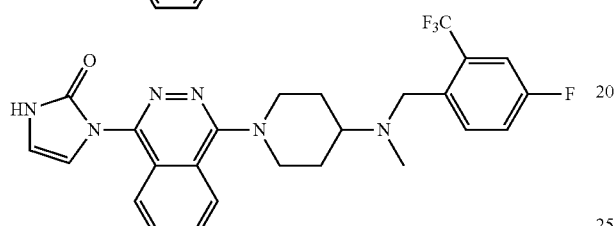
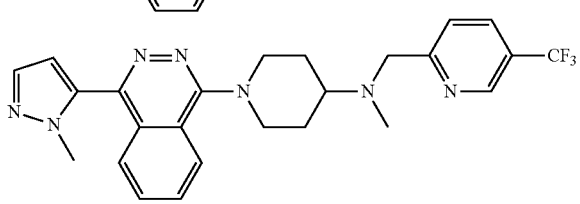
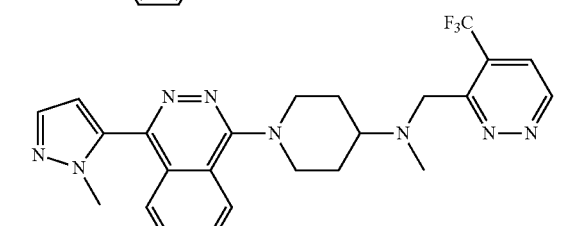
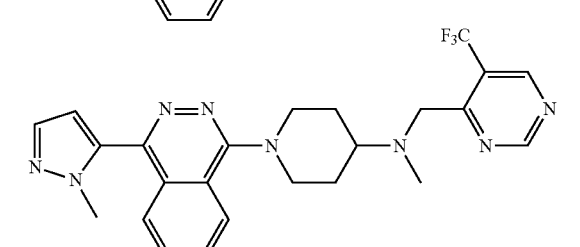
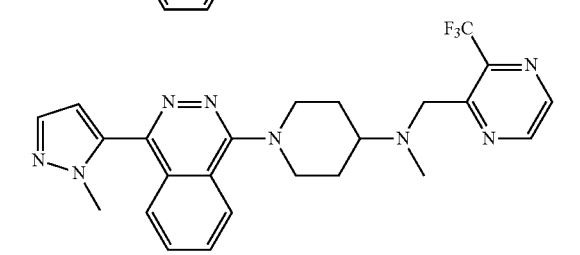
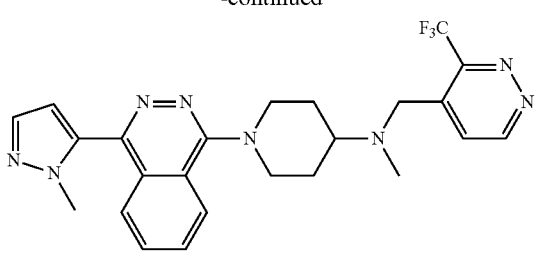
In addition, compounds of the invention include:
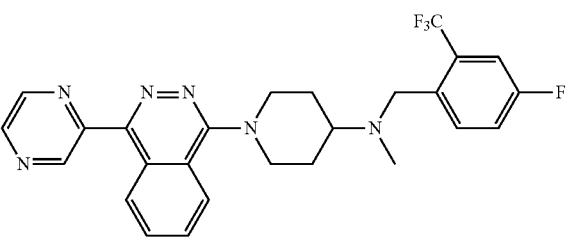
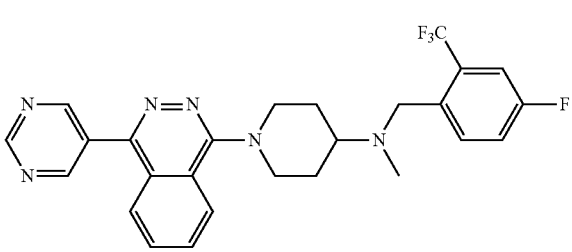
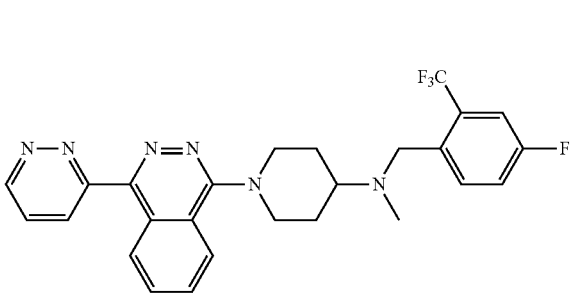

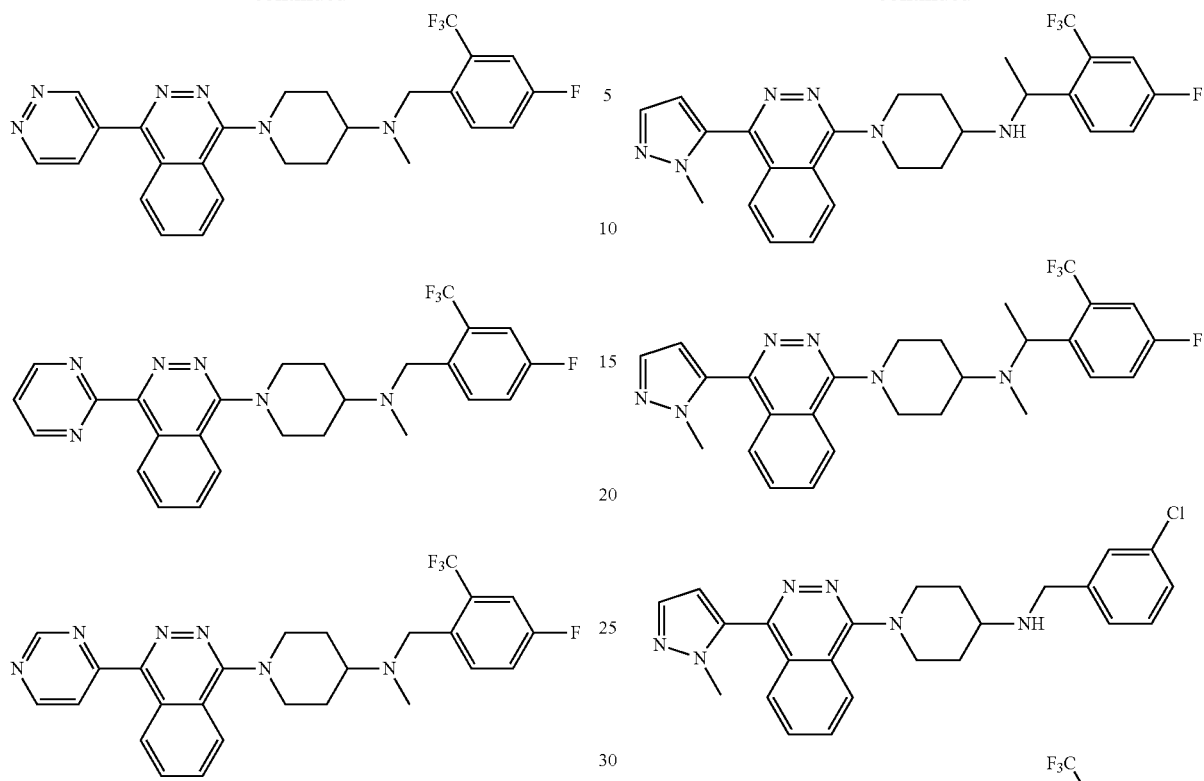
Preferred compounds of the invention include:
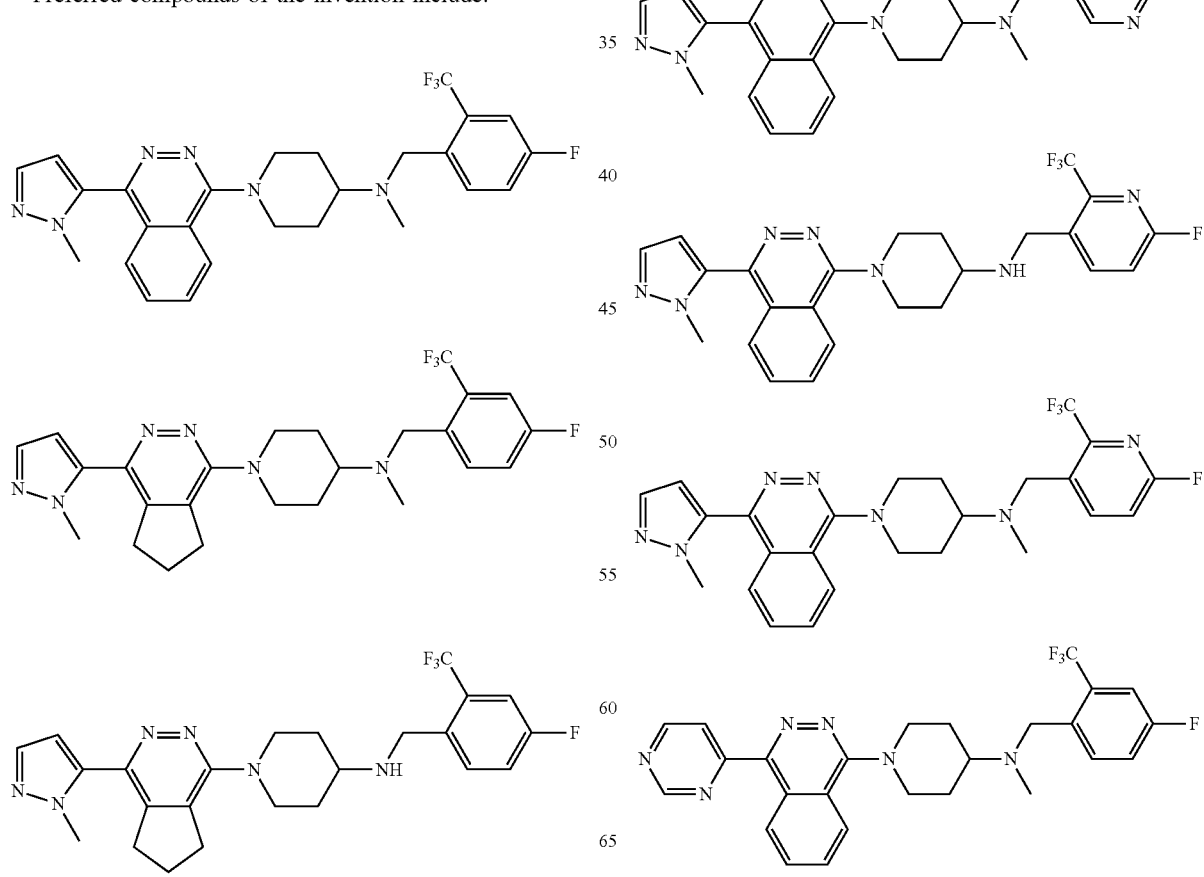

41
-continued
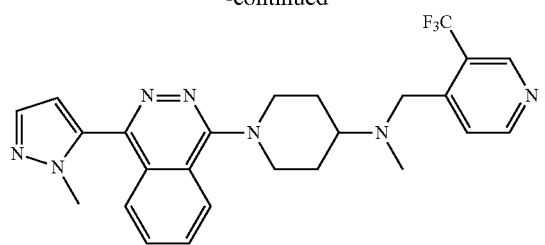
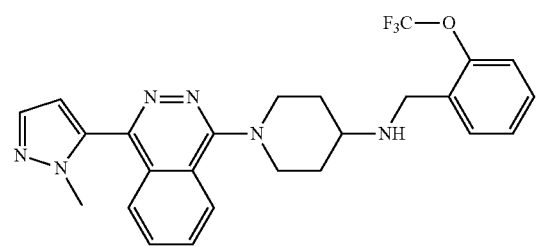
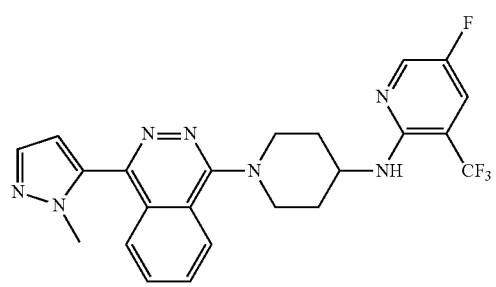
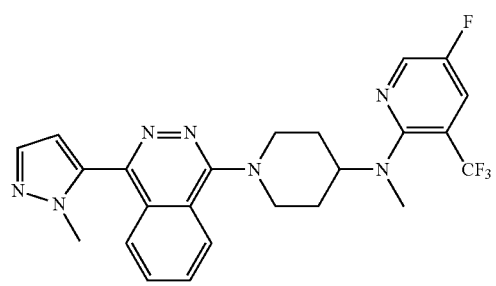
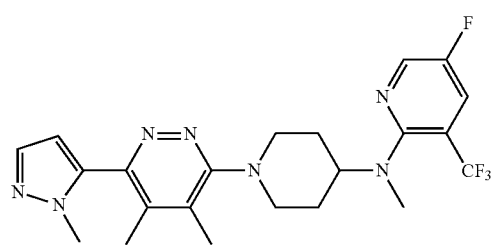
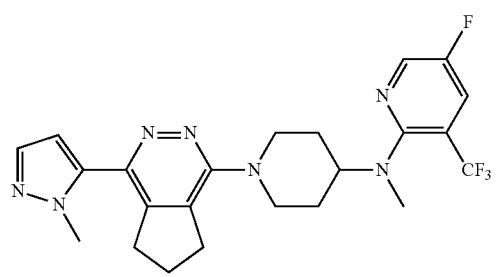
42
-continued
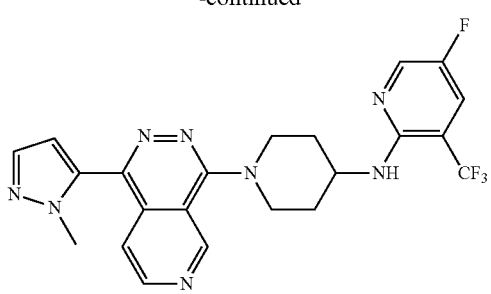
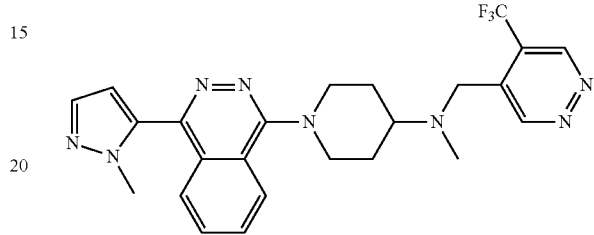
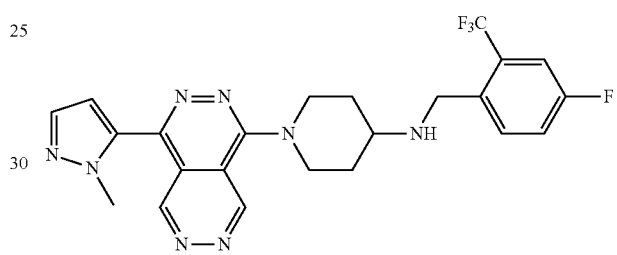
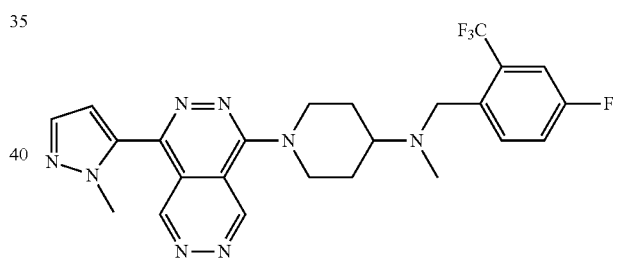
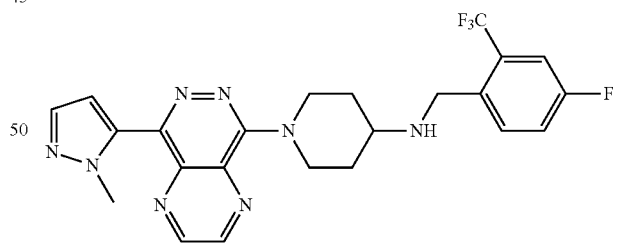
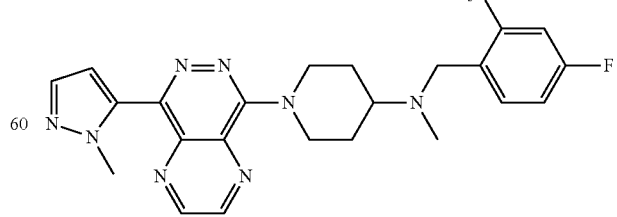
Compounds also contemplated by the invention that are particularly preferred are:

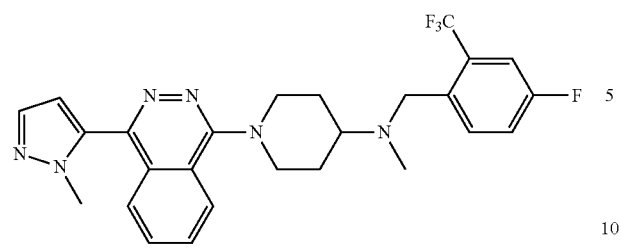
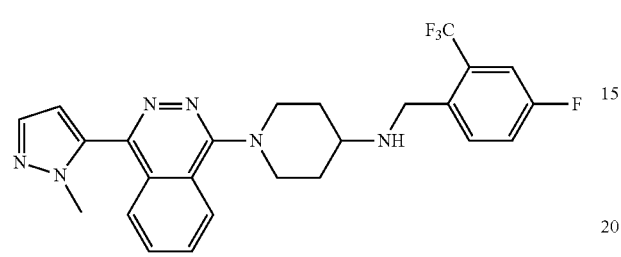
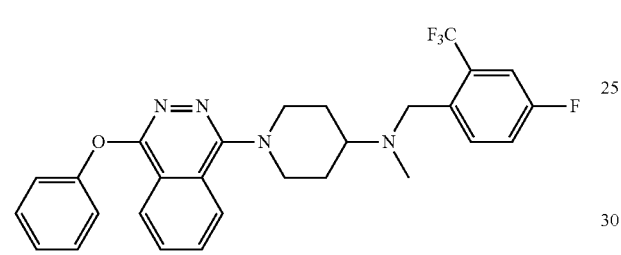
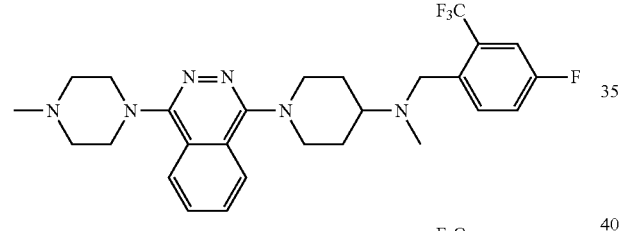
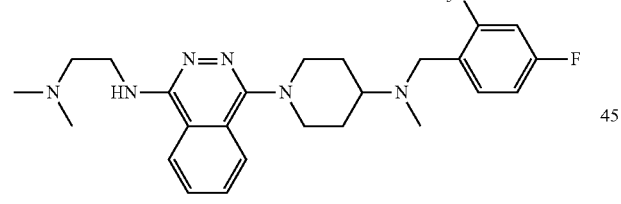
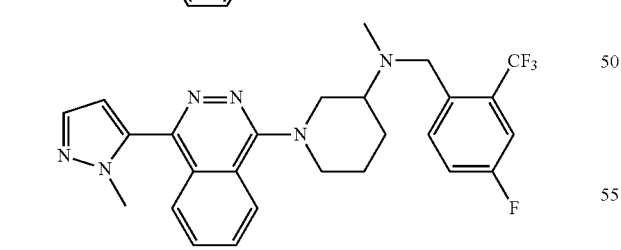
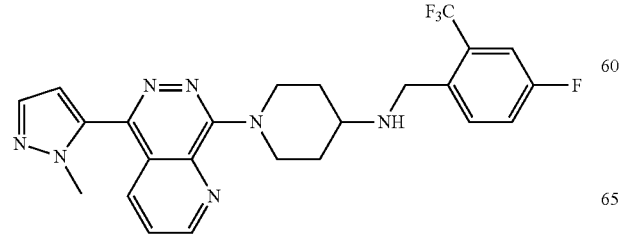

45
-continued
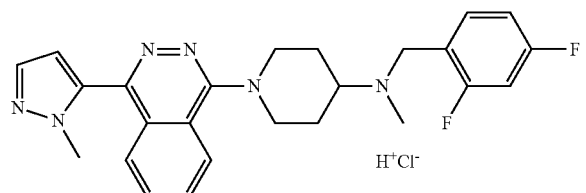
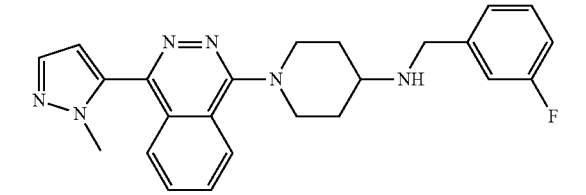
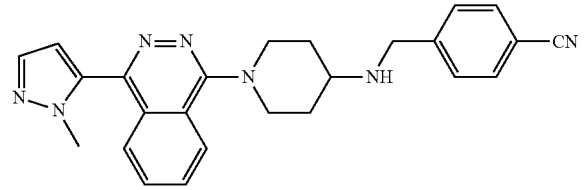
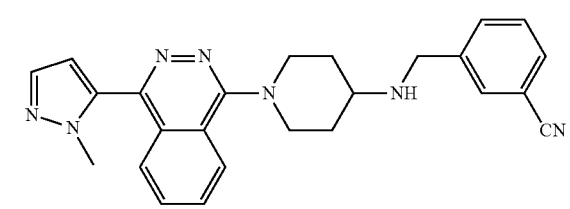
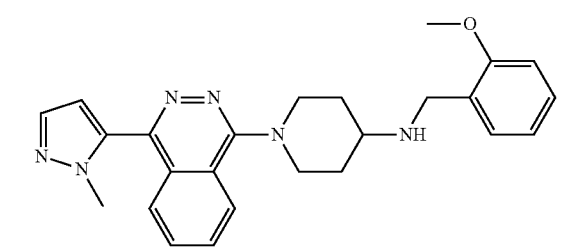
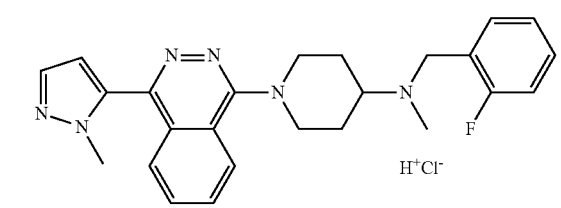
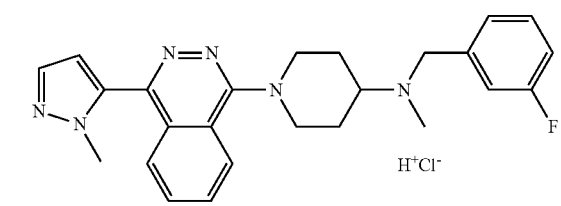
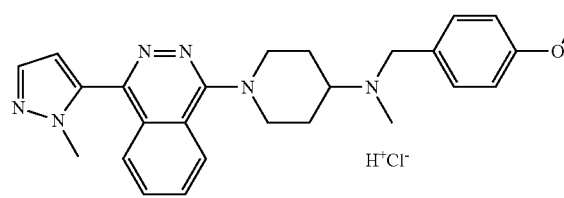
46
-continued
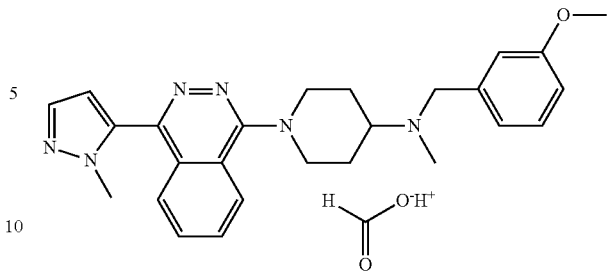
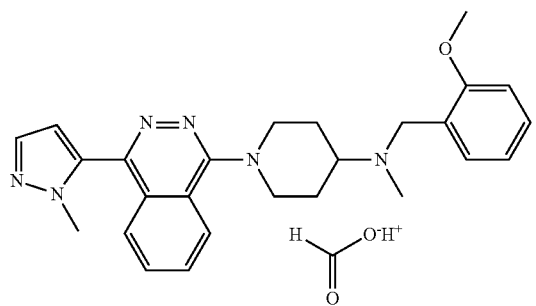
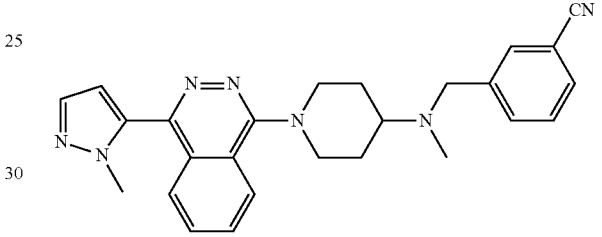
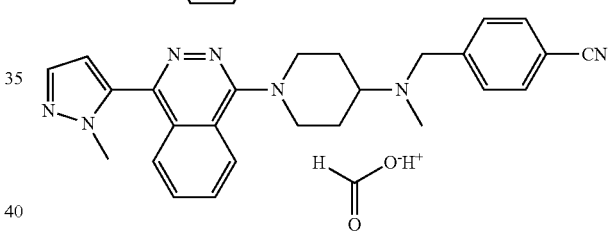
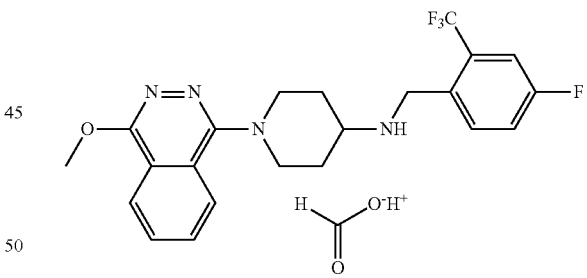
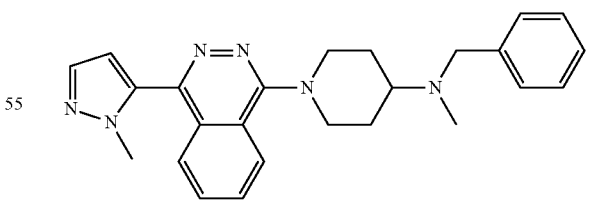
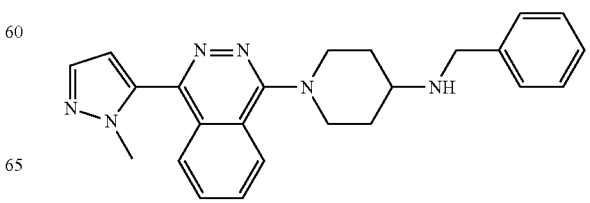

47
-continued
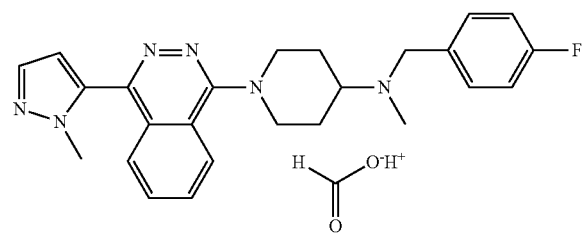
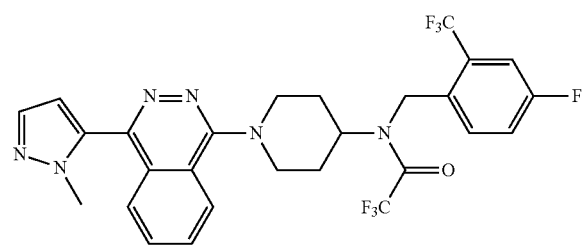
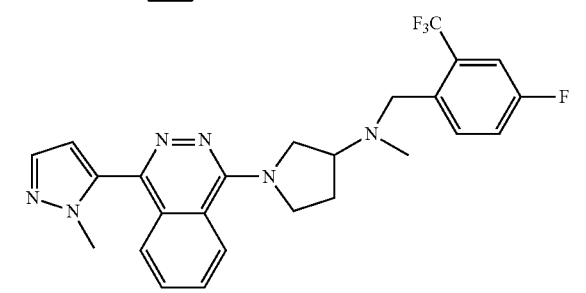
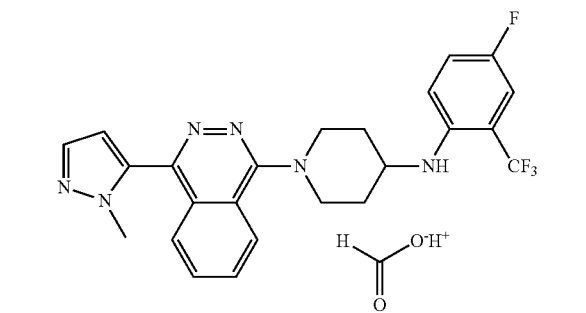
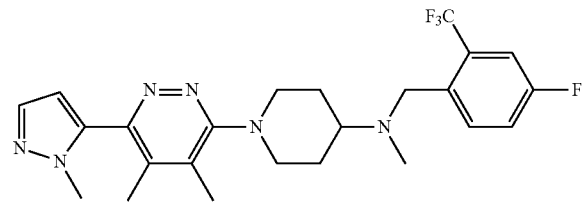
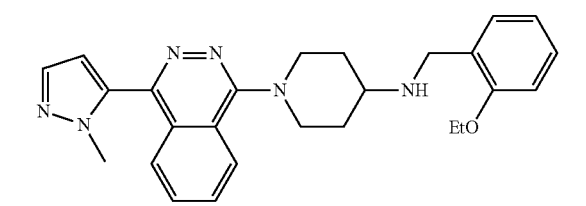
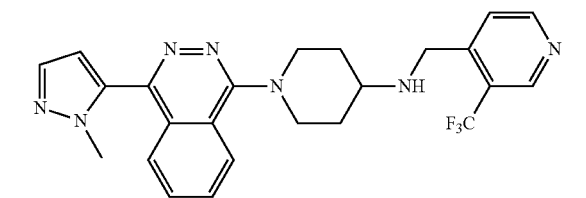
48
-continued
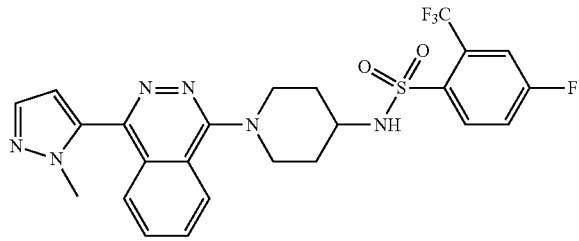
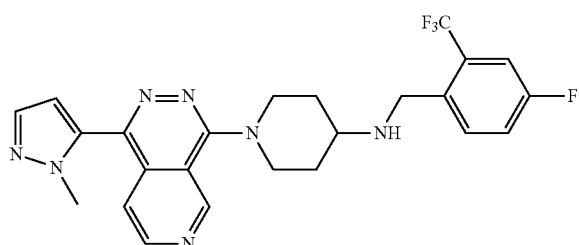
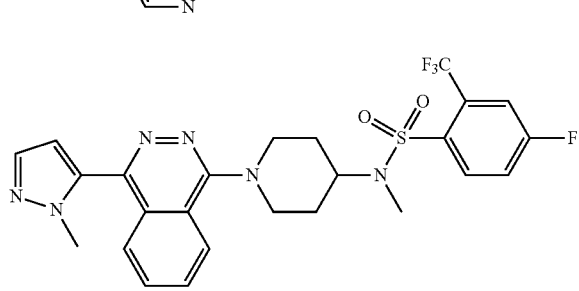
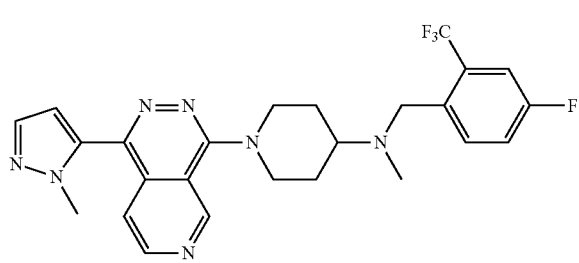
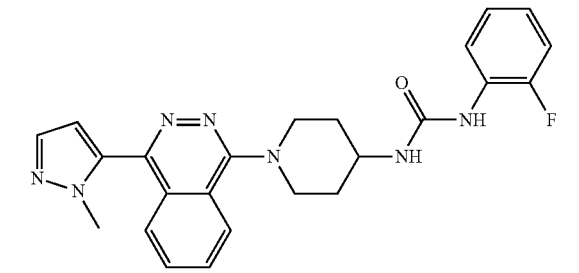
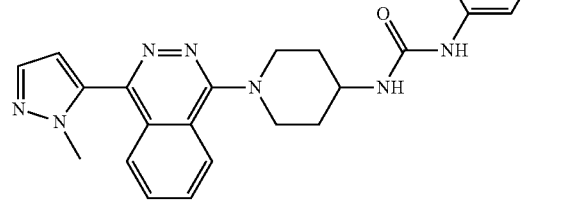

49
-continued
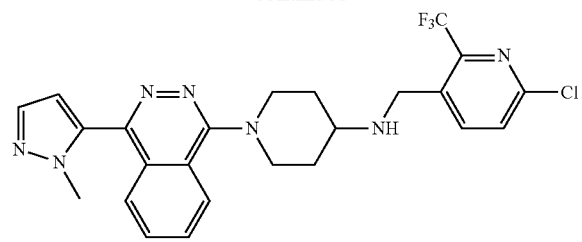
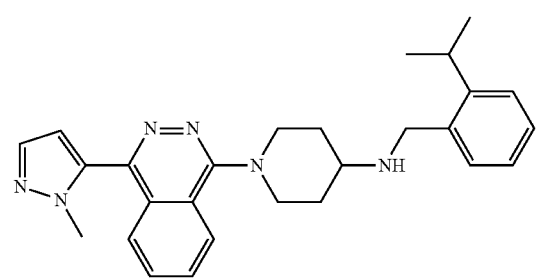
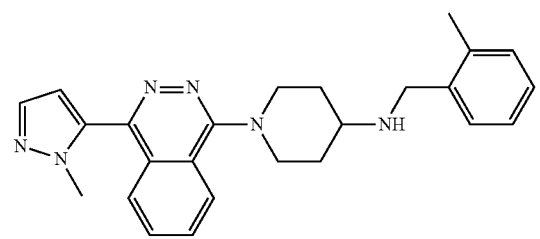
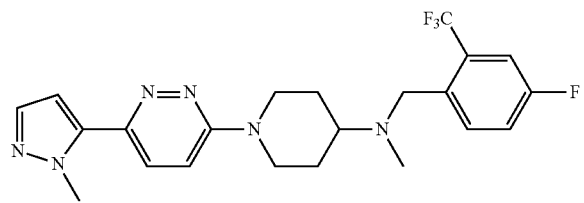
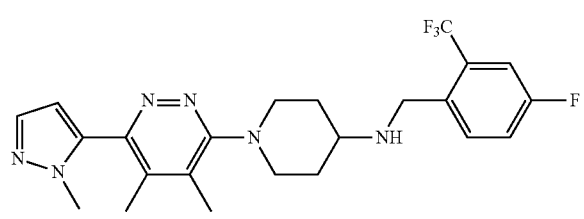
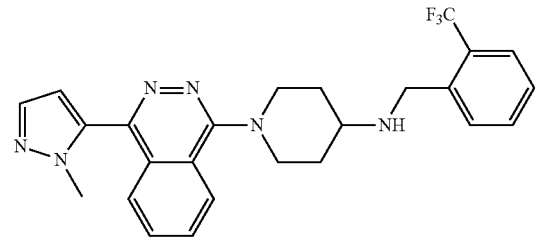
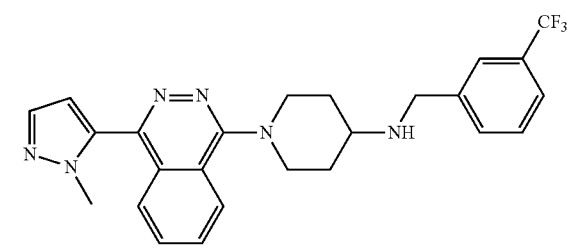
50
-continued
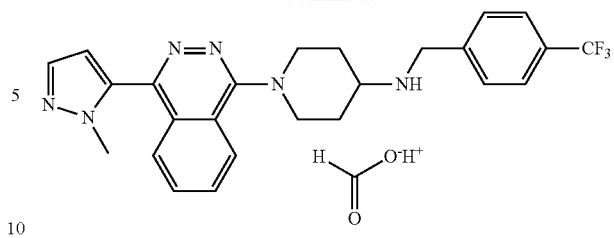
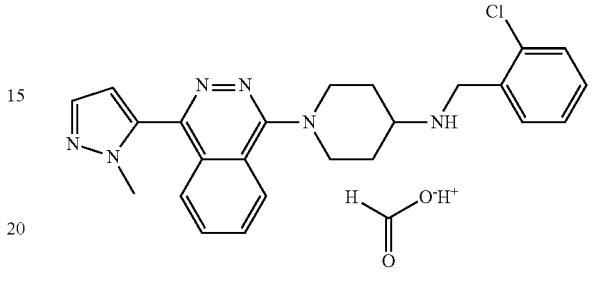
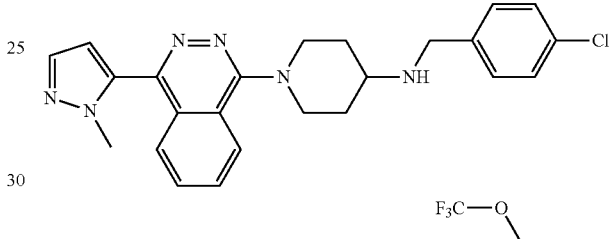
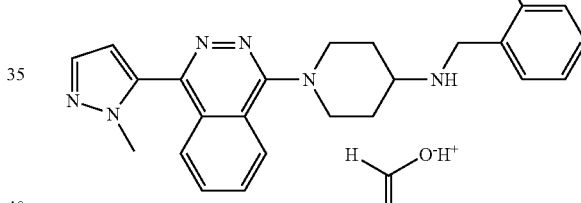
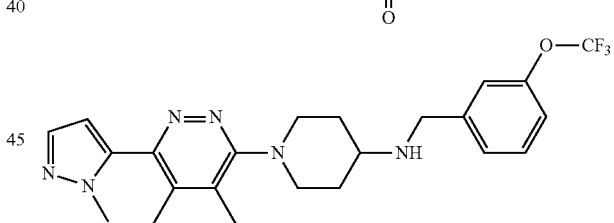
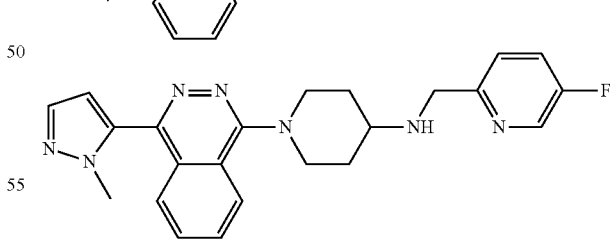
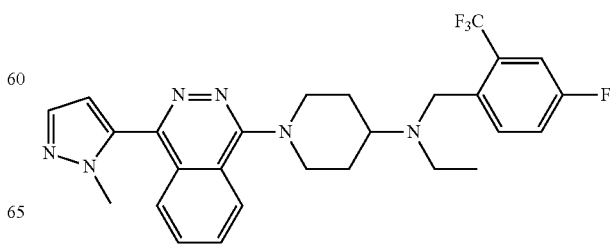

51
-continued
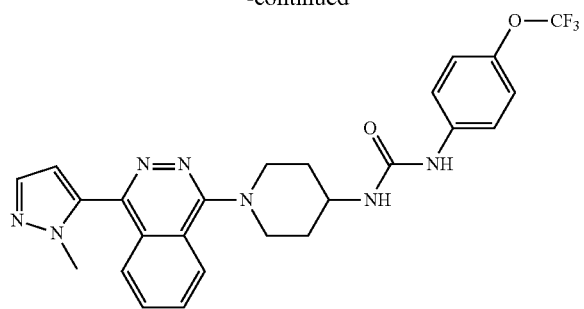
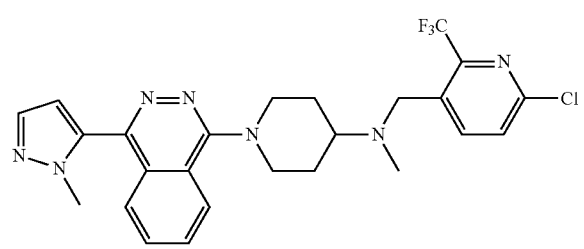
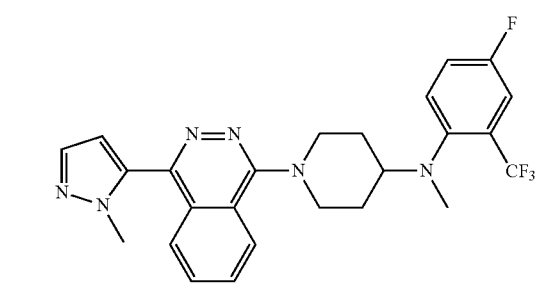
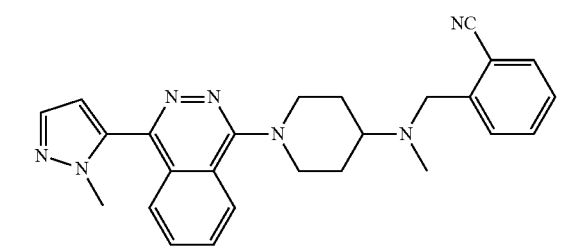
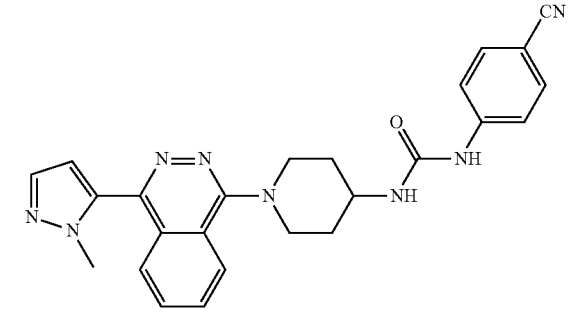
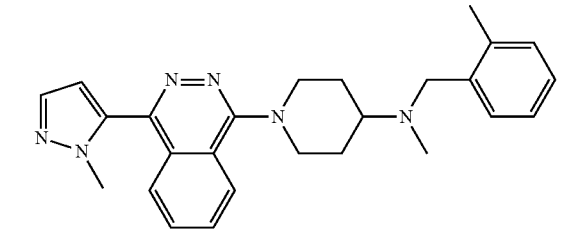
52
-continued
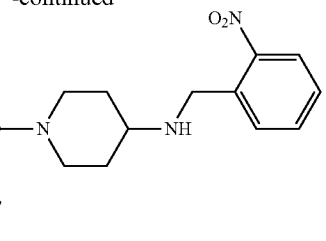
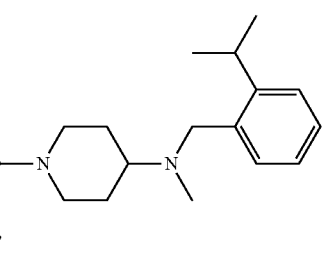
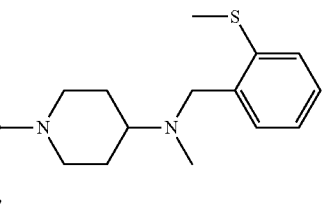
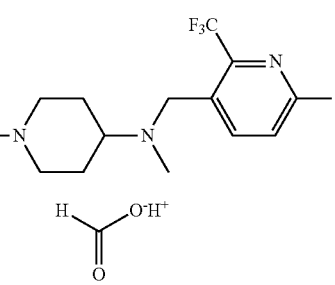
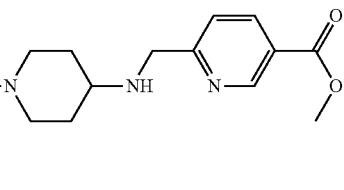

53
-continued
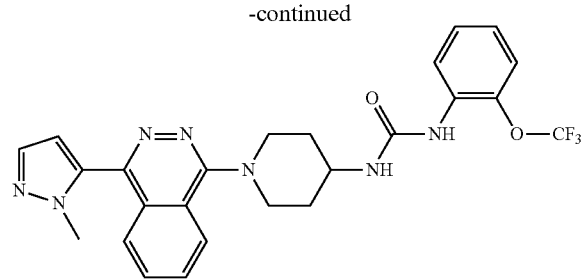
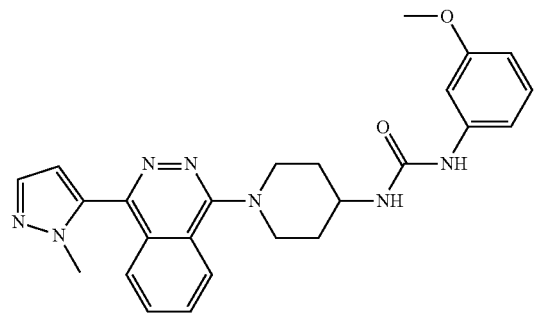
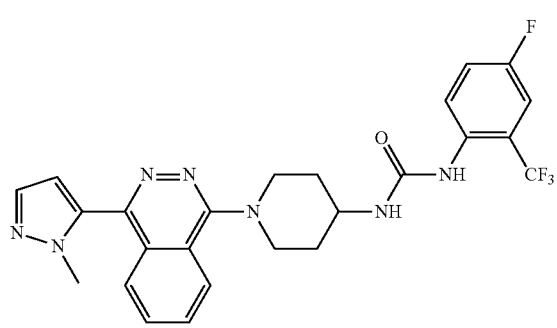
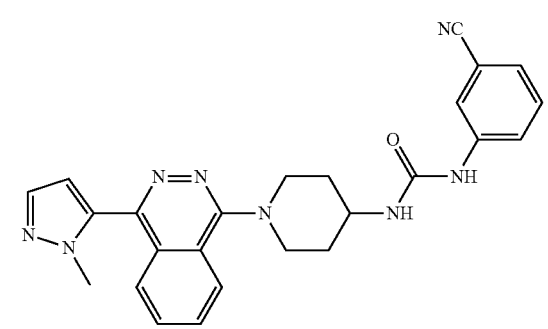
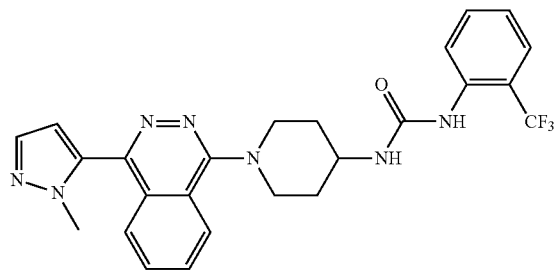
54
-continued
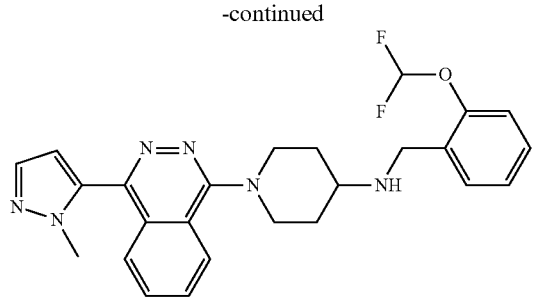
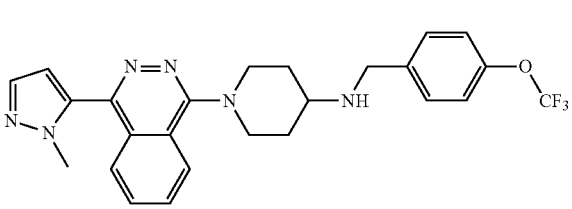
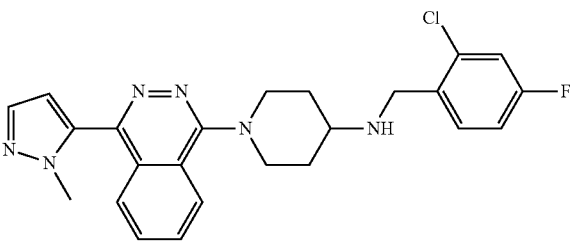
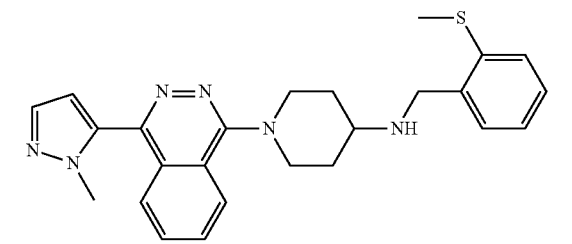
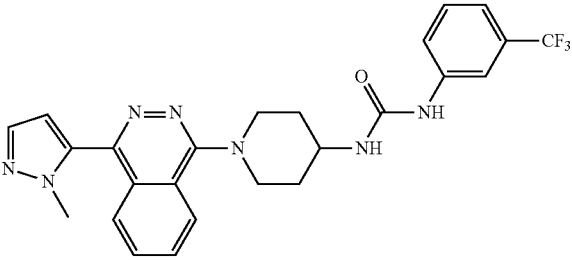
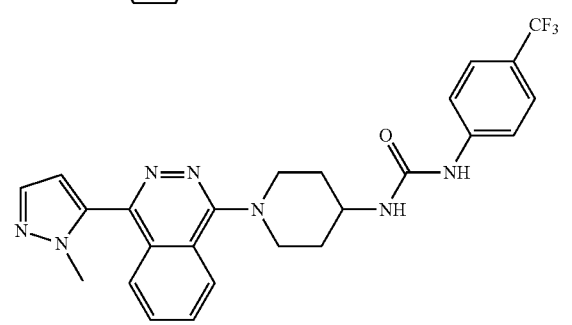

55
-continued
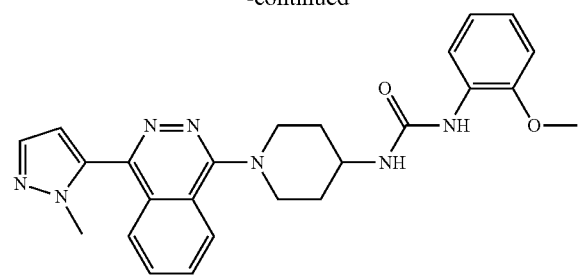
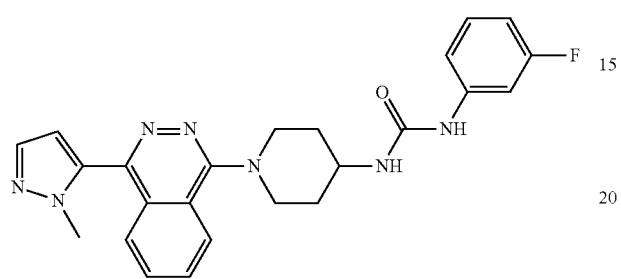
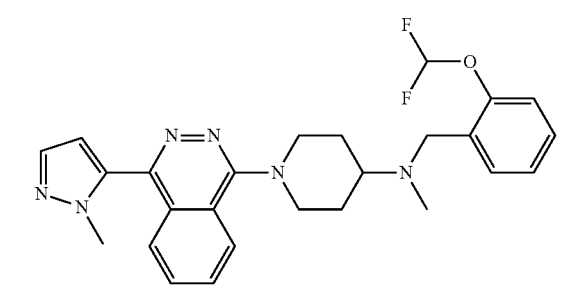
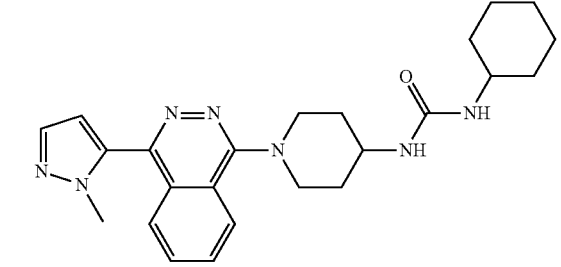
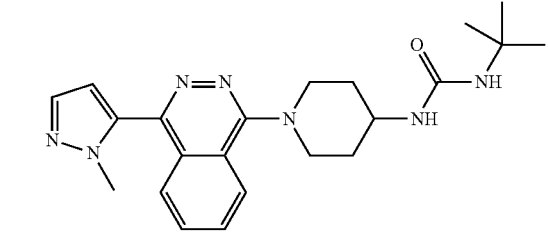
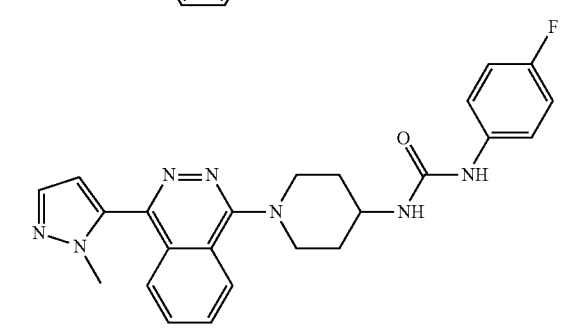
56
-continued
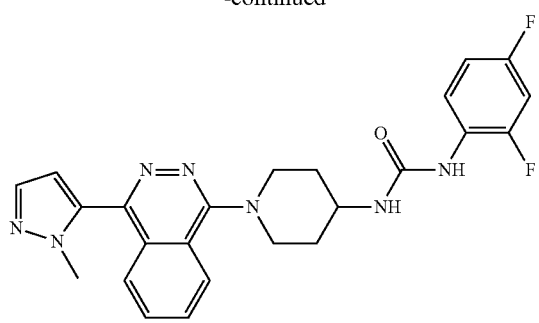
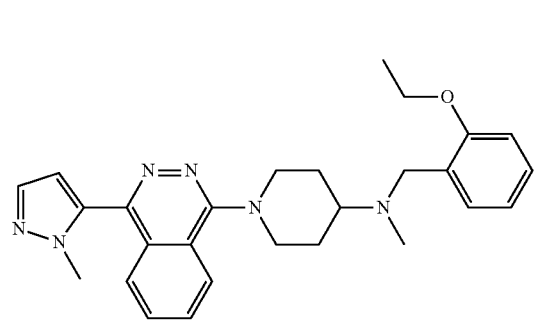
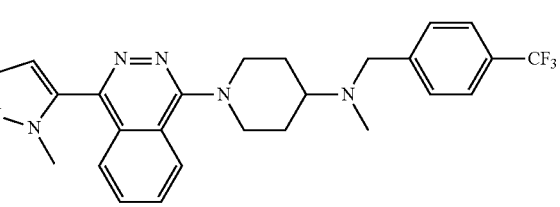
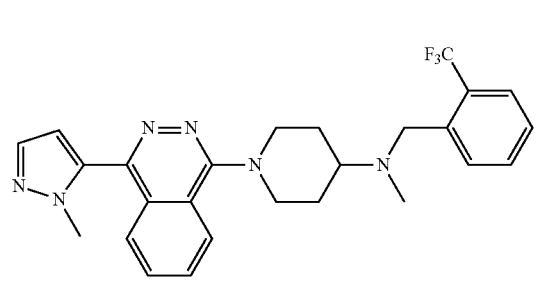
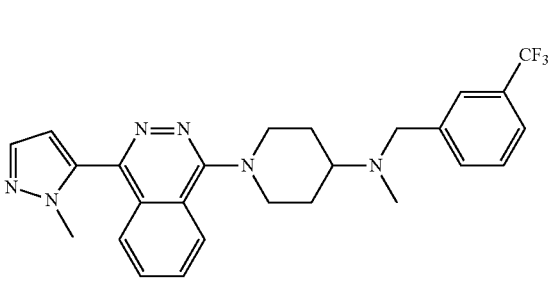
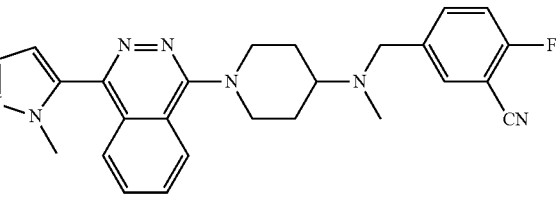

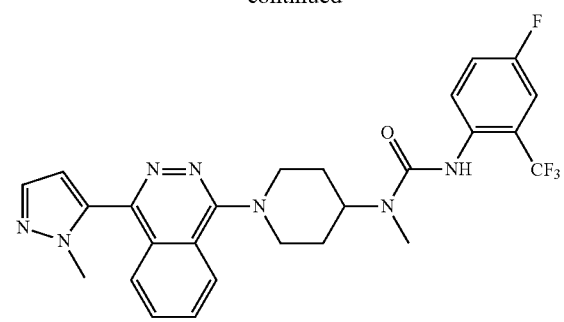
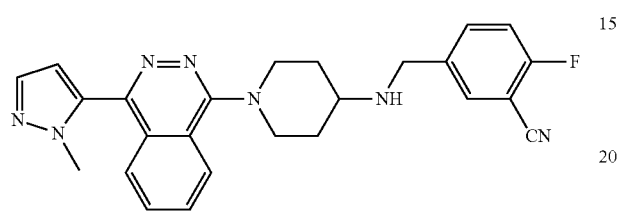
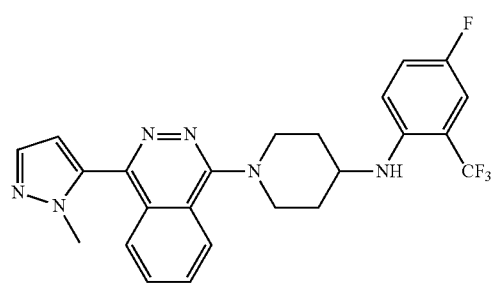
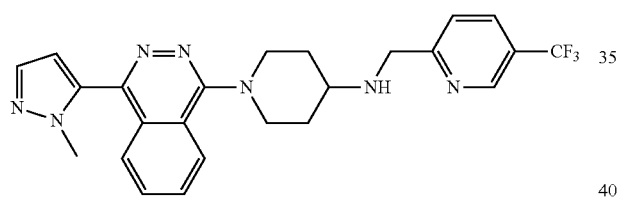
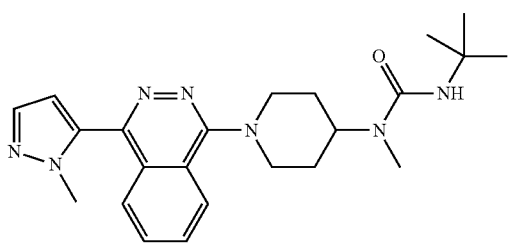
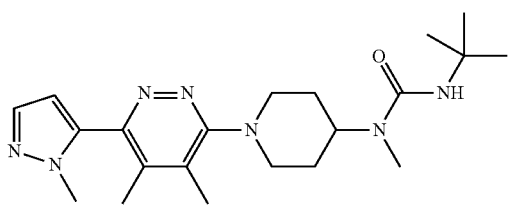
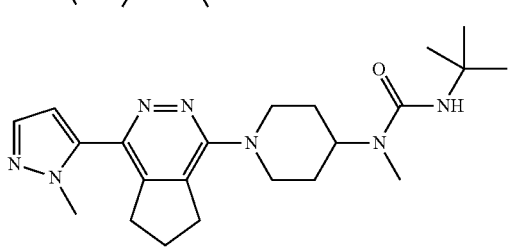
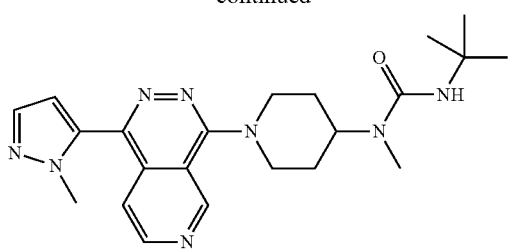
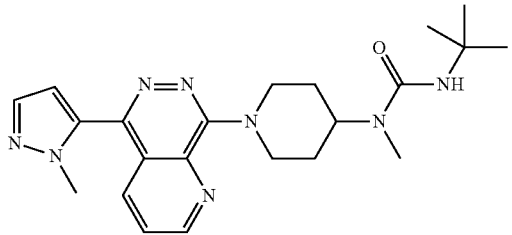
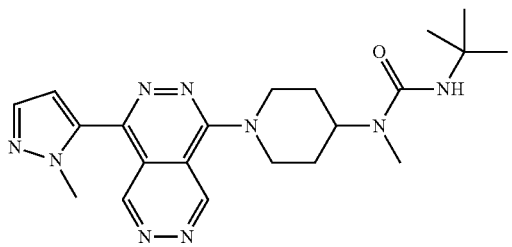
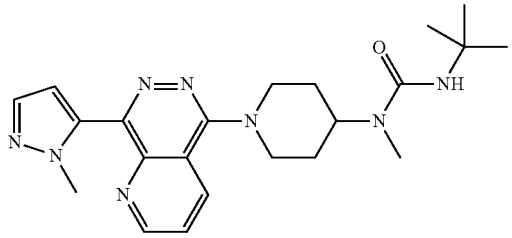
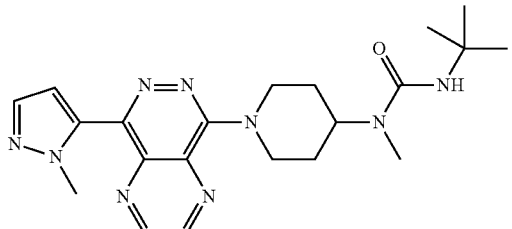
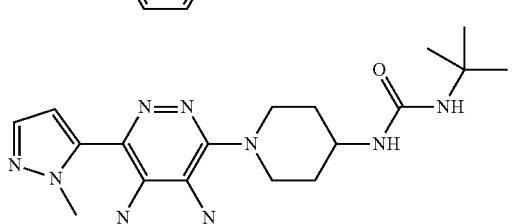
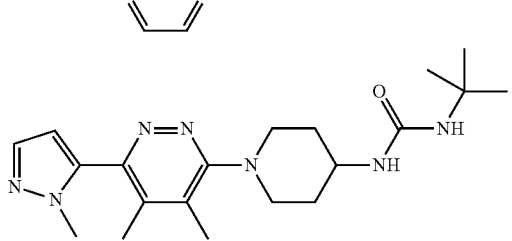

59
-continued
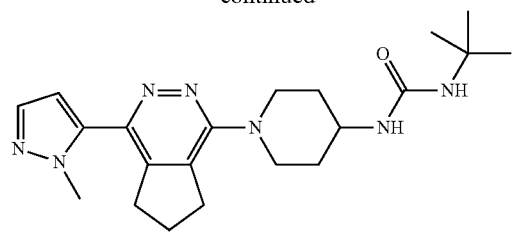
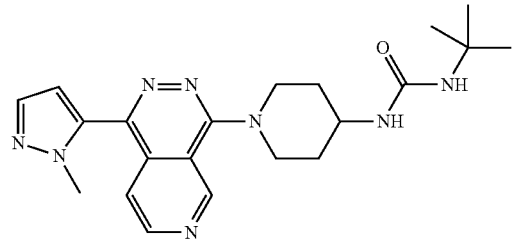
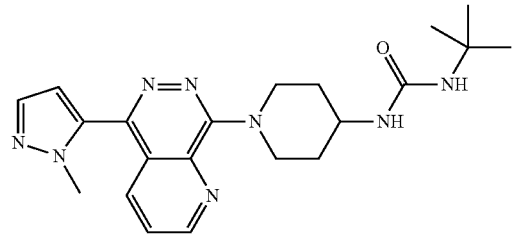
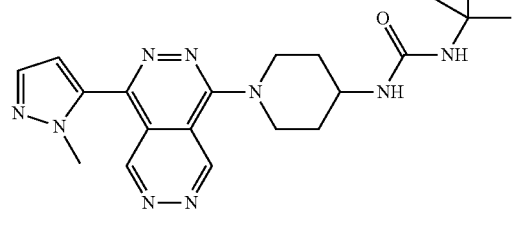
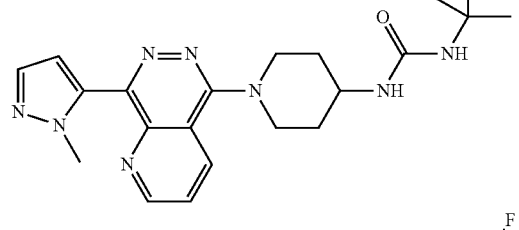
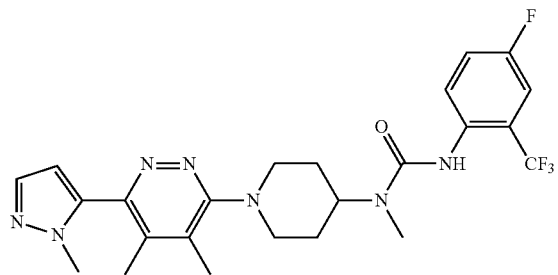
60
-continued
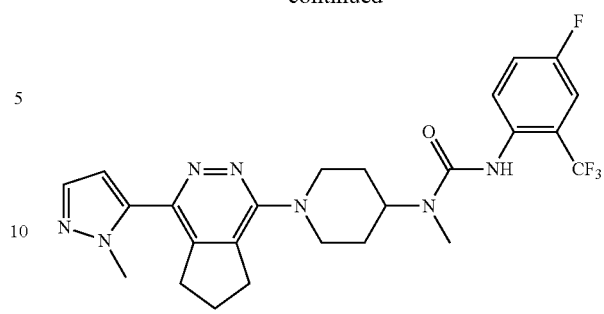
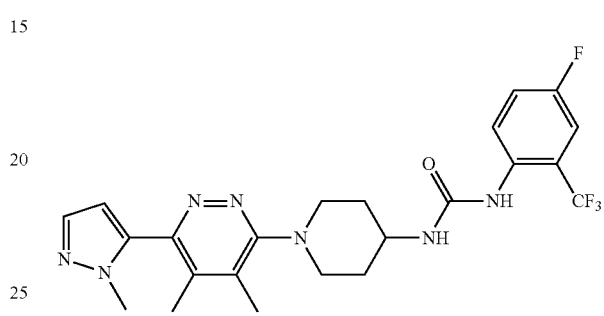
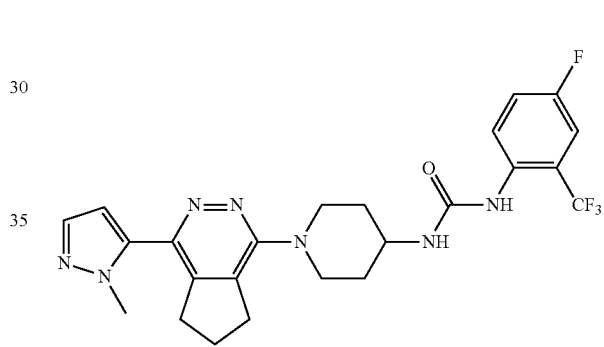
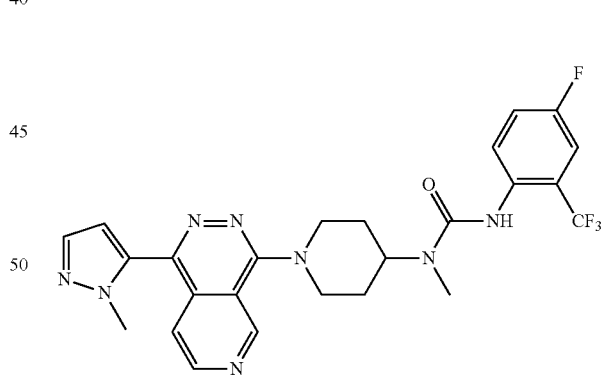
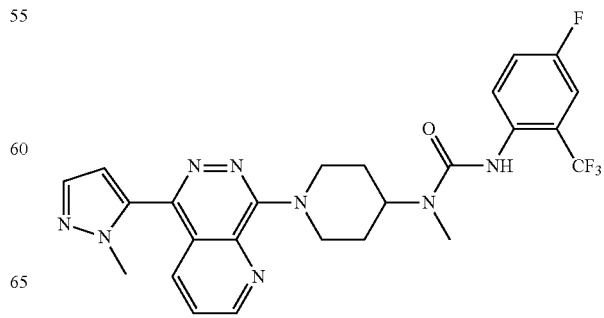

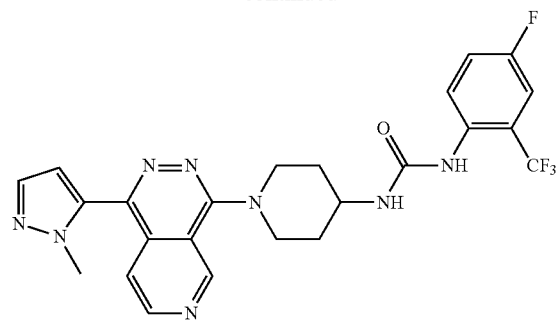
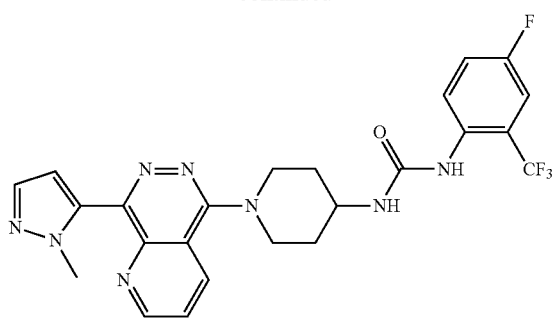
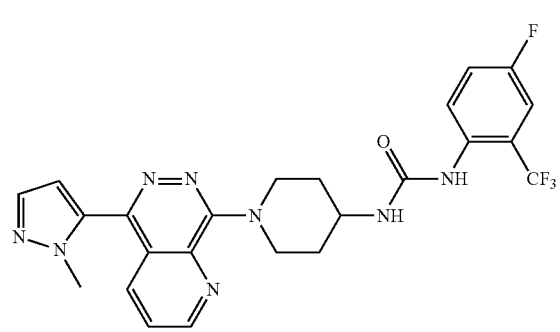
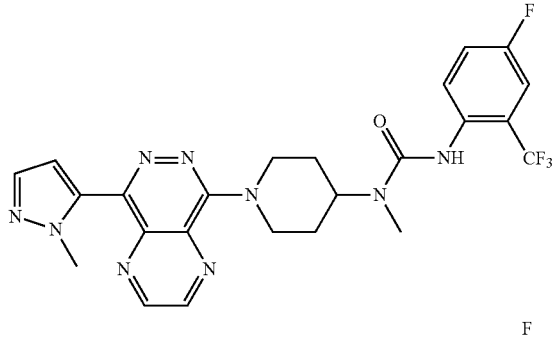
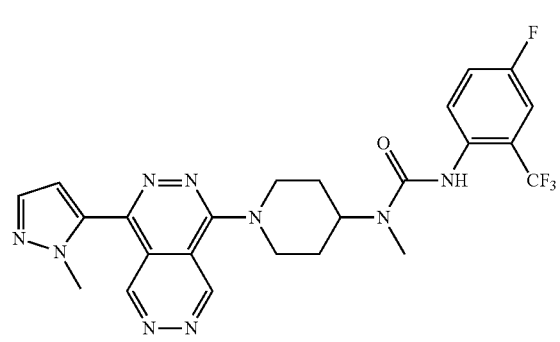
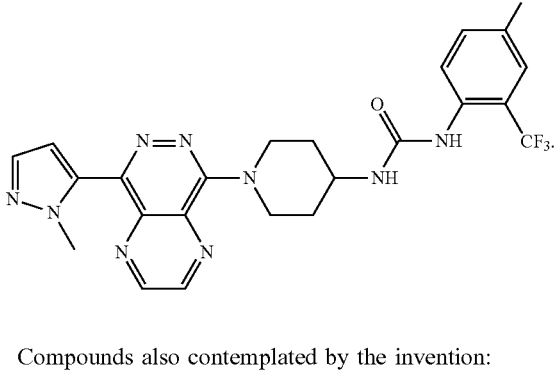
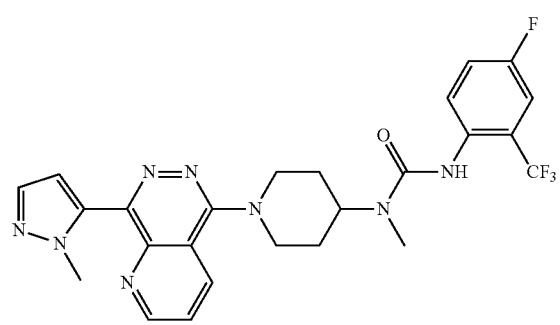
Compounds also contemplated by the invention:
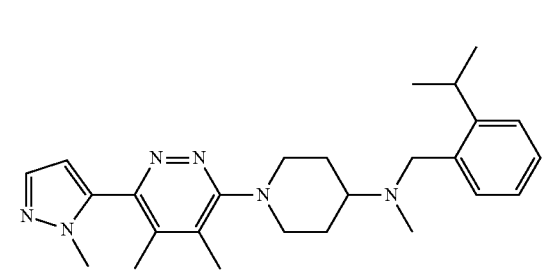
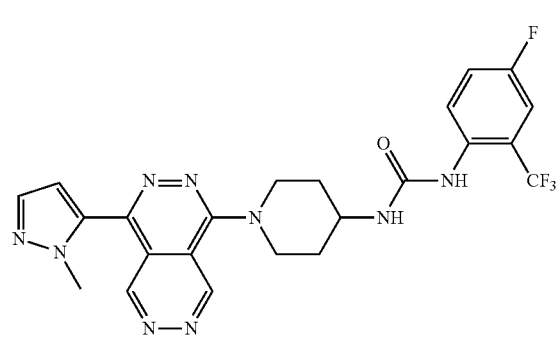
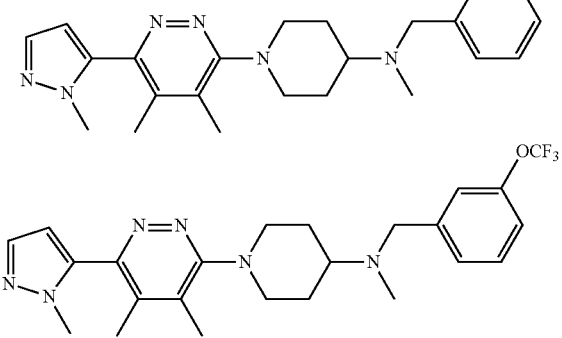

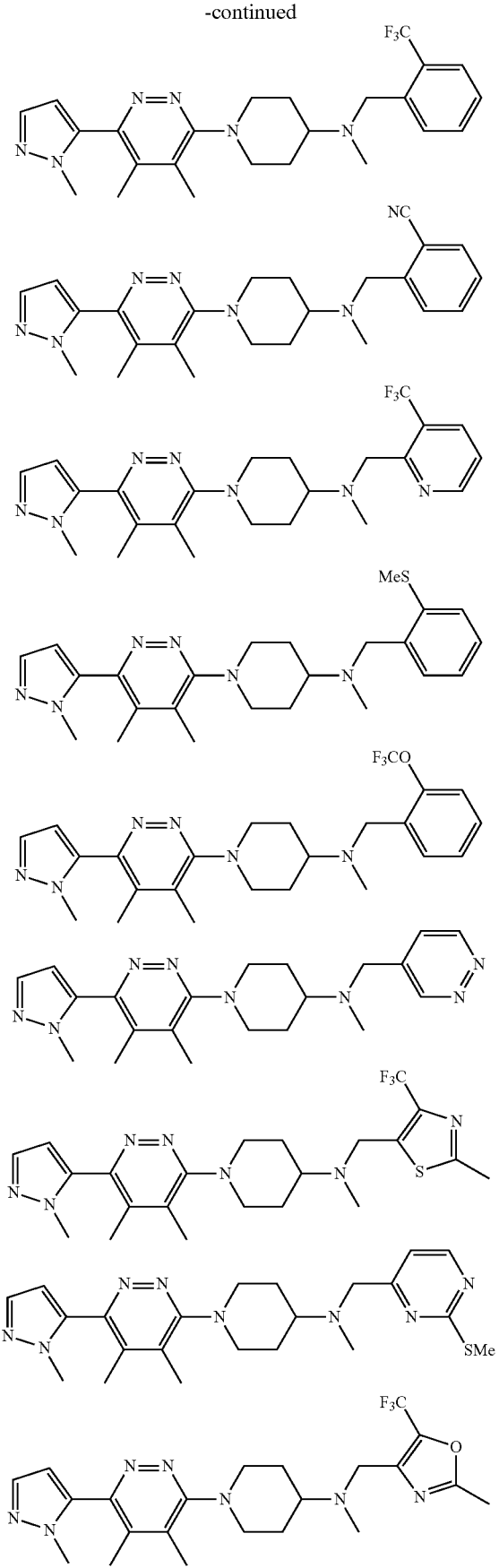
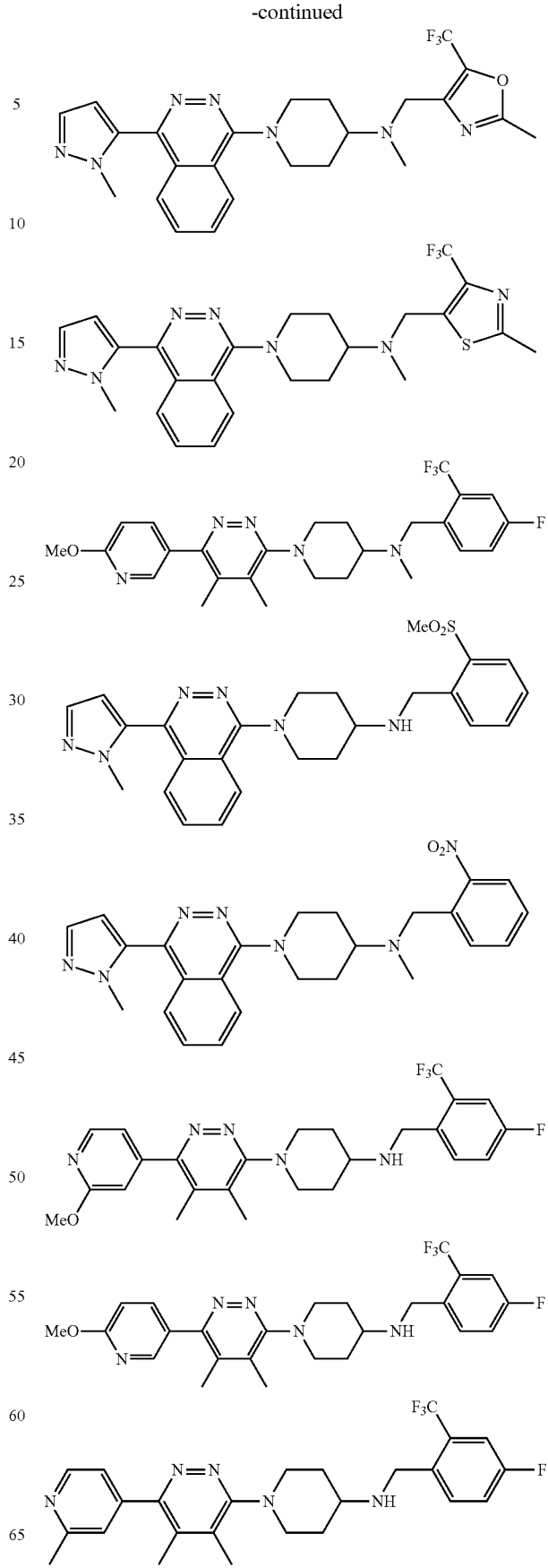

65
-continued
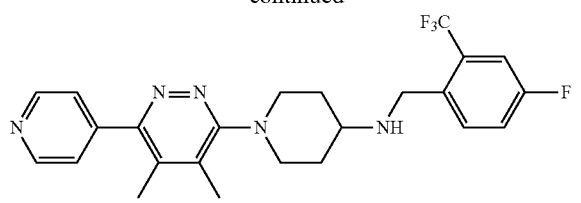
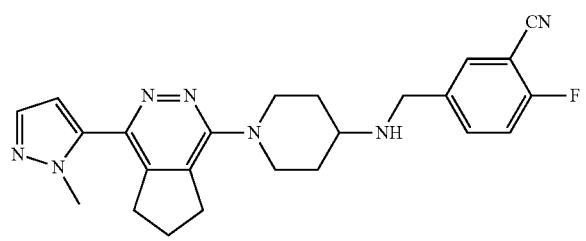
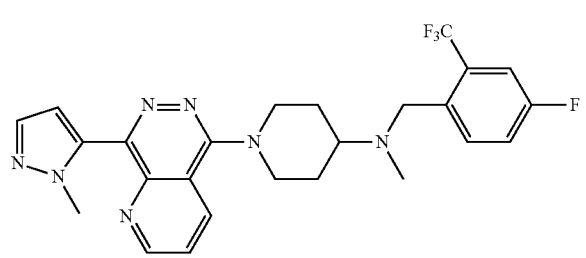
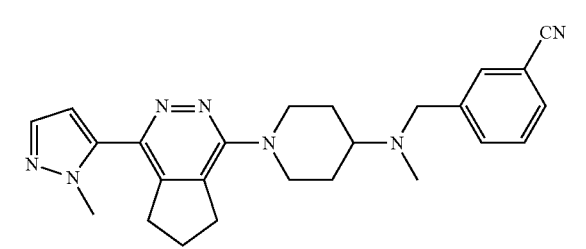
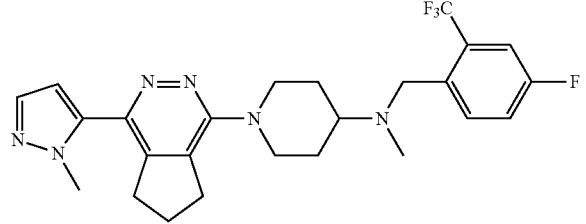
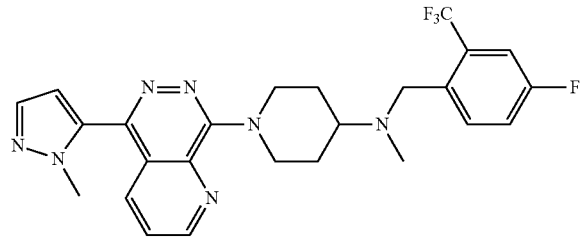
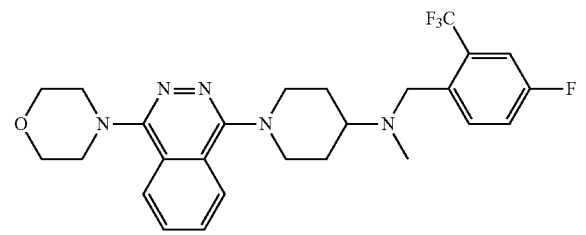
66
-continued
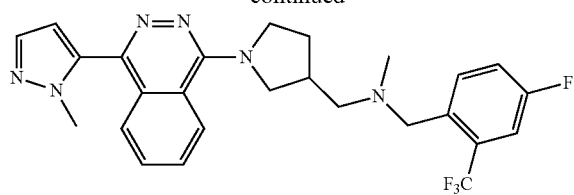
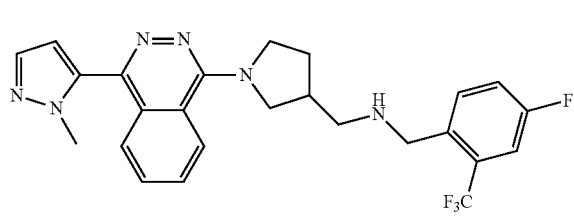
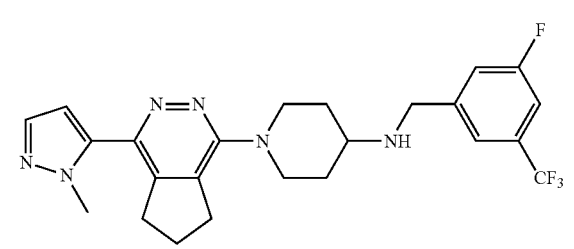
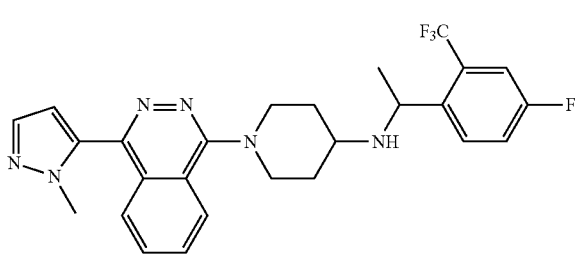
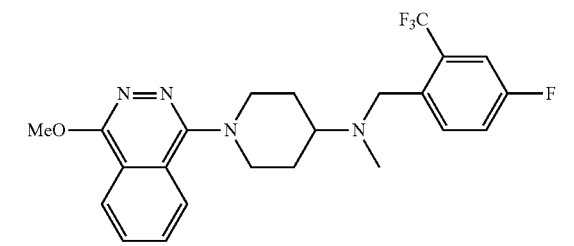
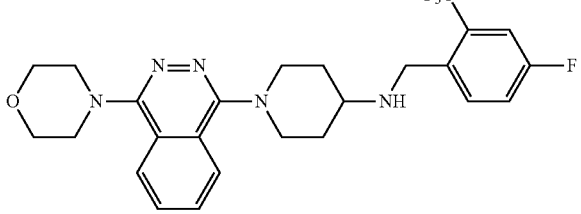
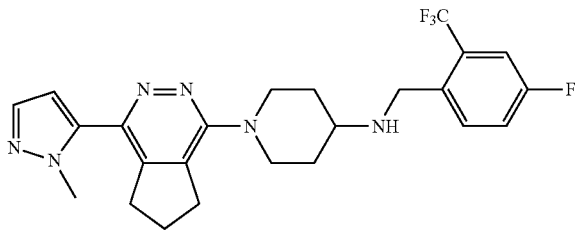

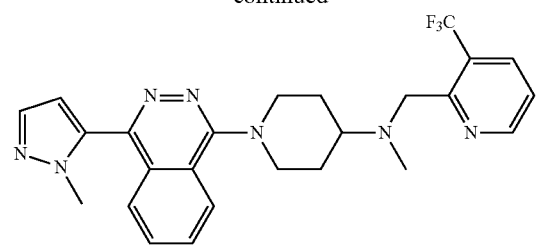
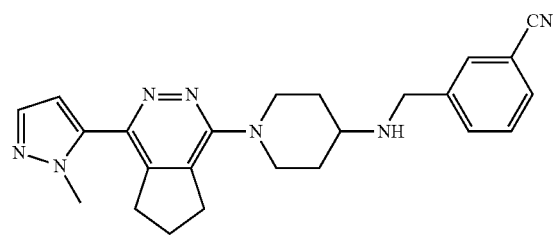
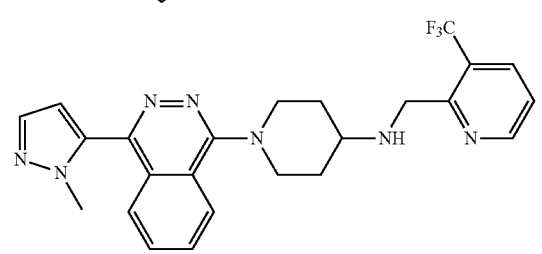
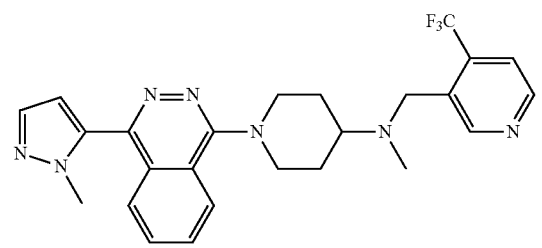
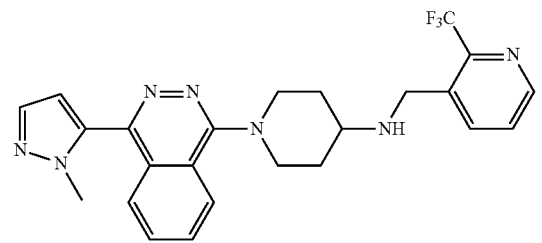
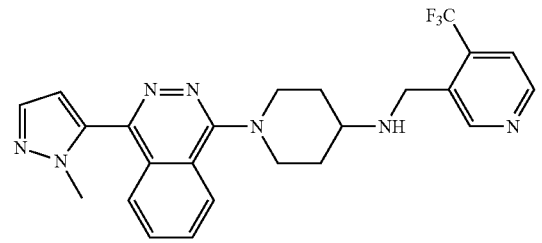
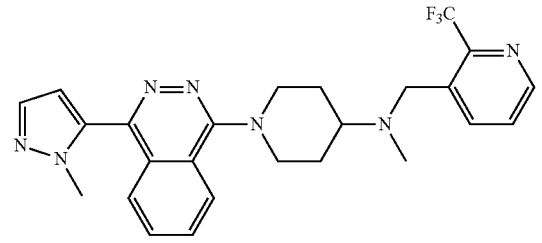
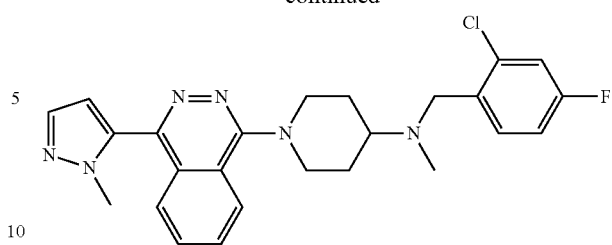
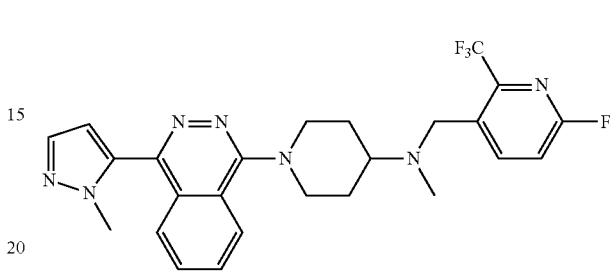
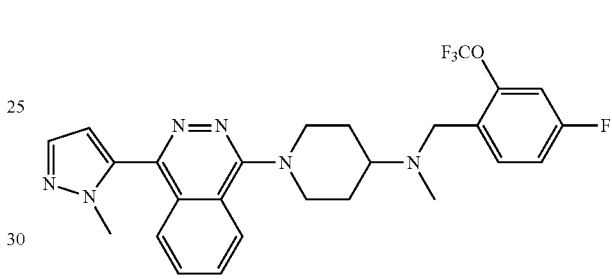
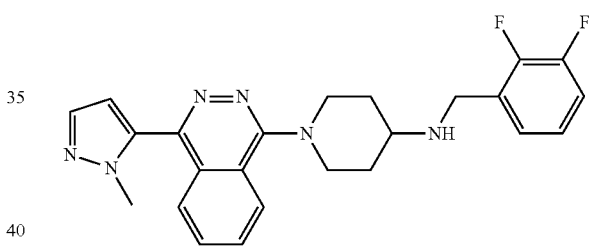
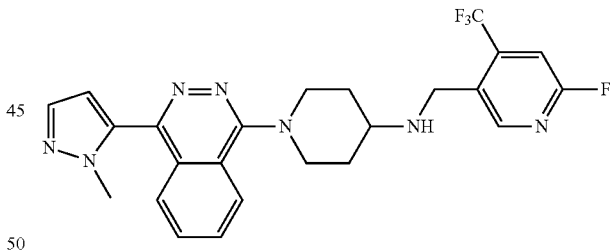
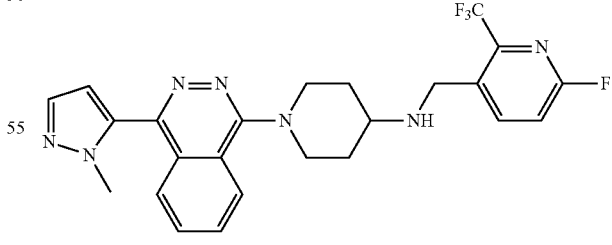
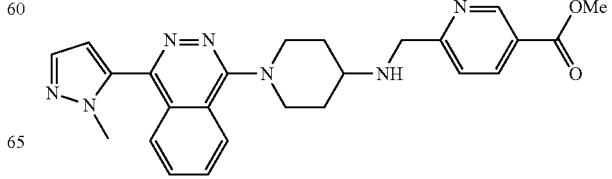

69
-continued
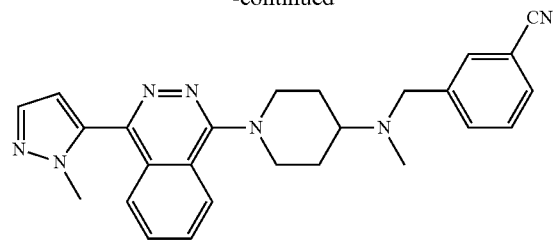
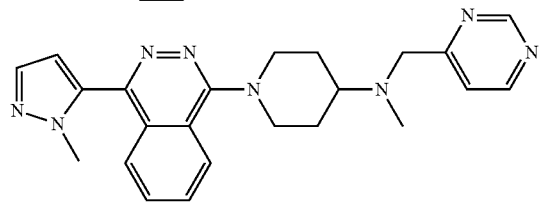
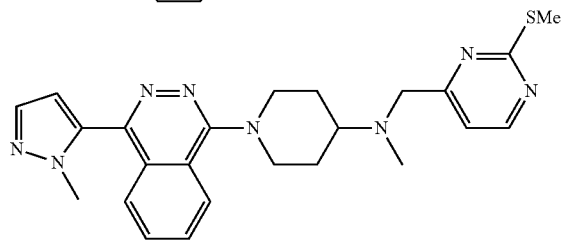
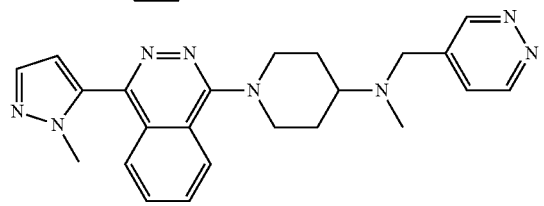
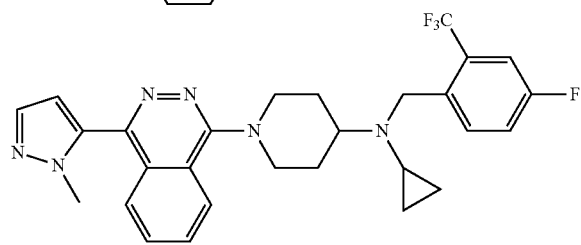
Compounds also contemplated by the invention:
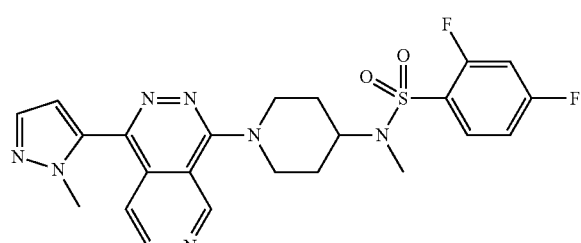
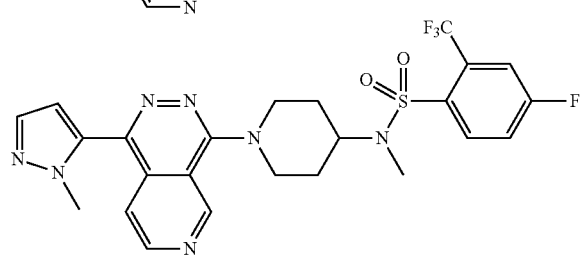
70
-continued
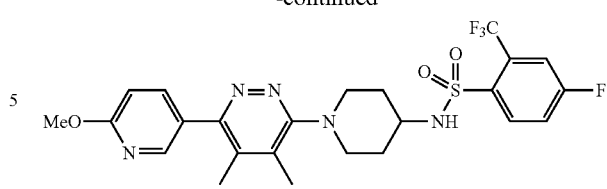
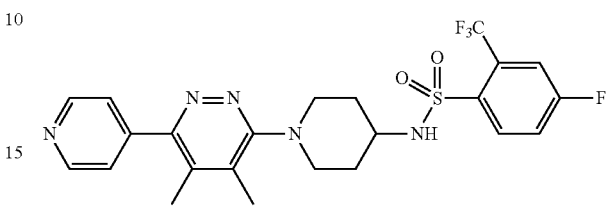
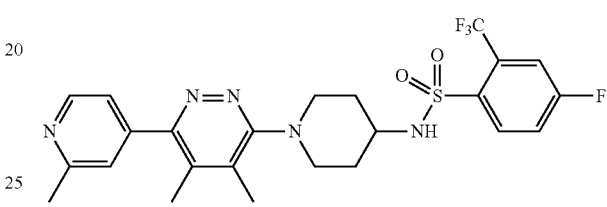
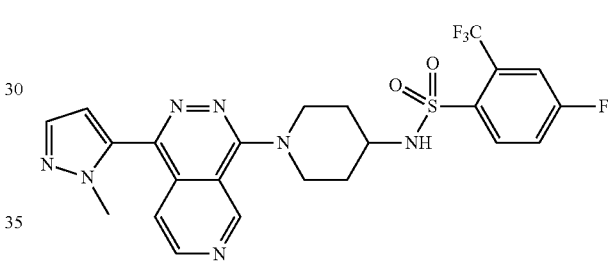
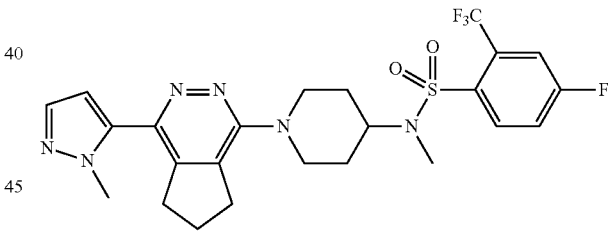
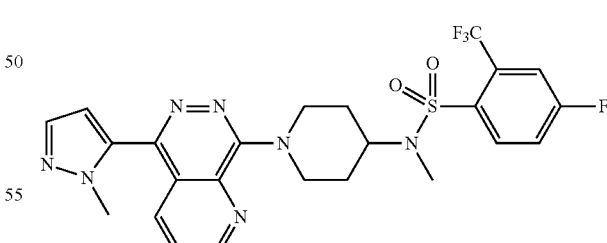
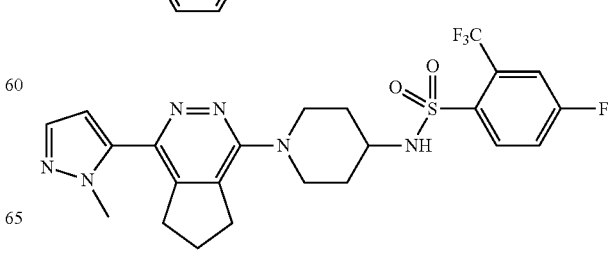

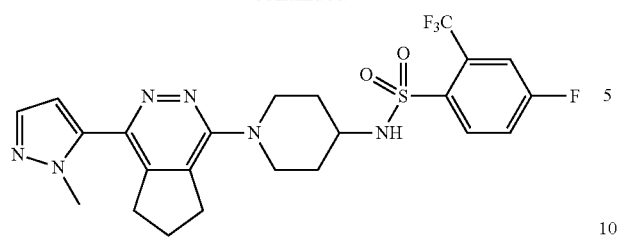
Compounds also contemplated by the invention:
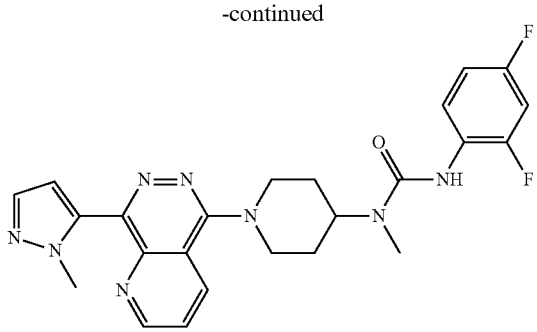
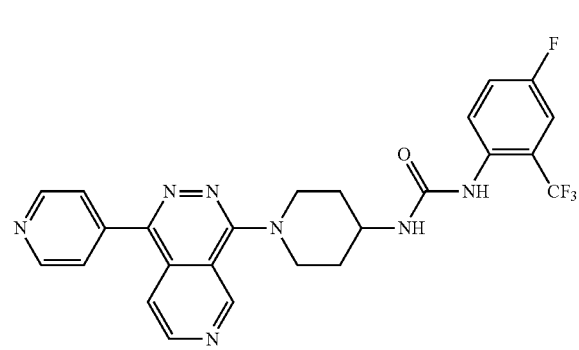
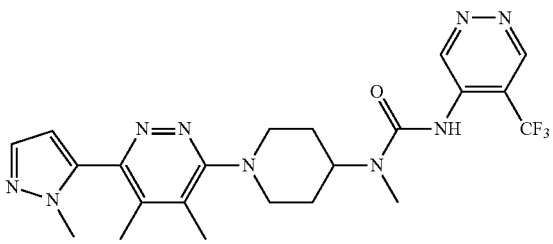
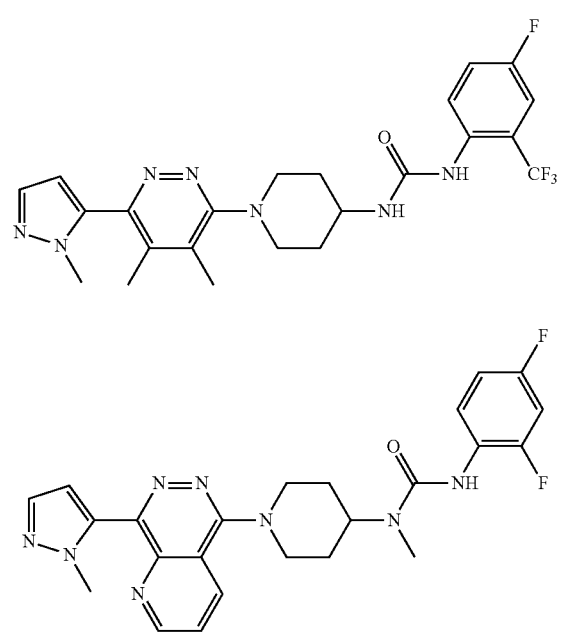
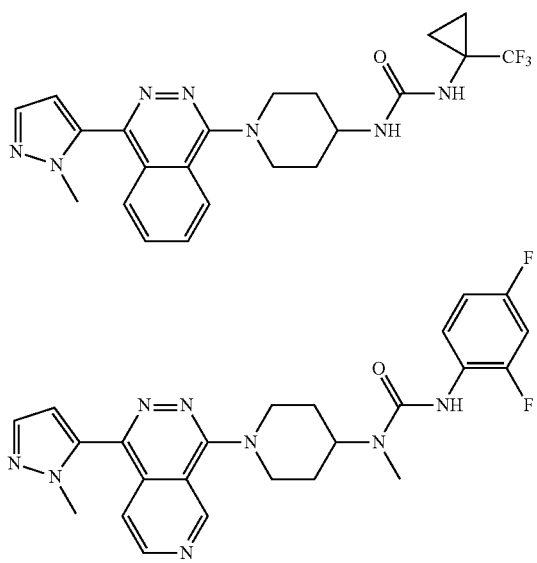
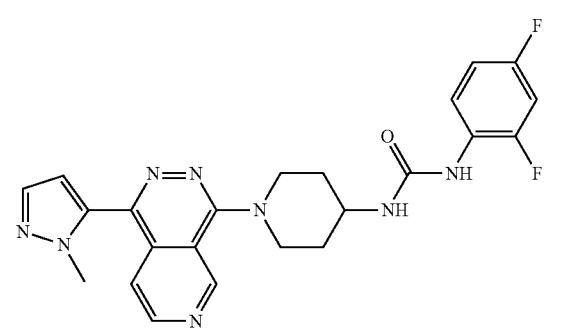
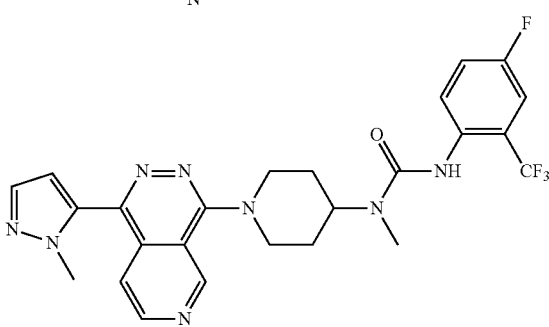

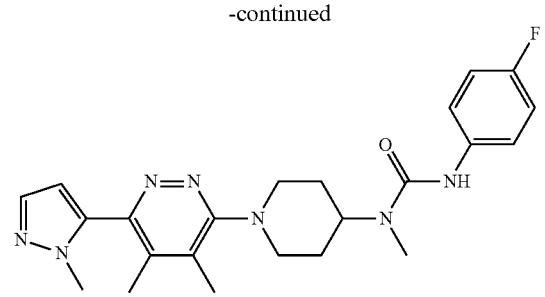
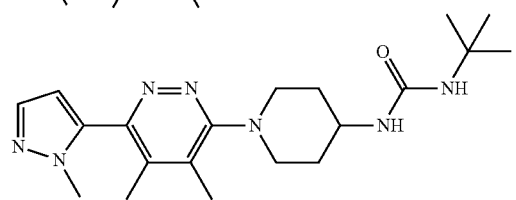
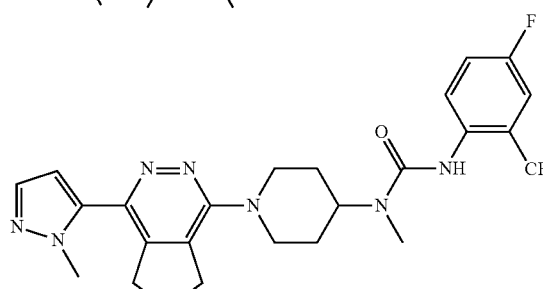
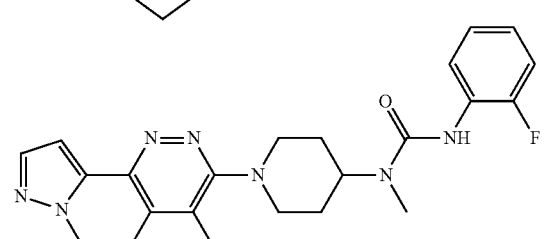
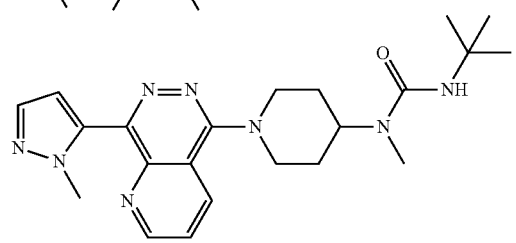
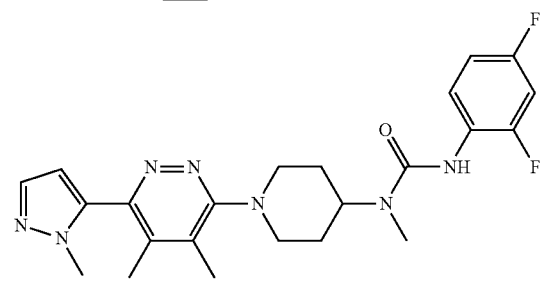
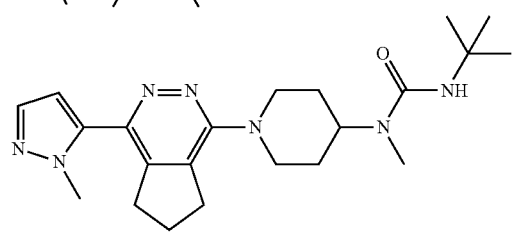
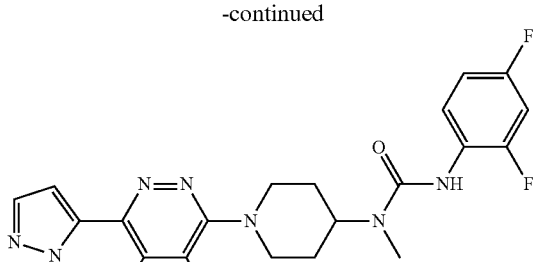
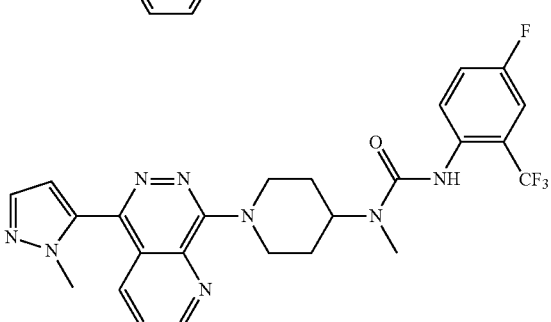
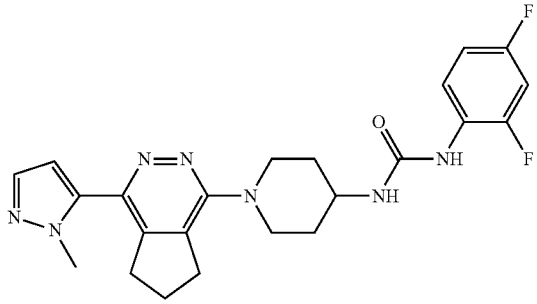
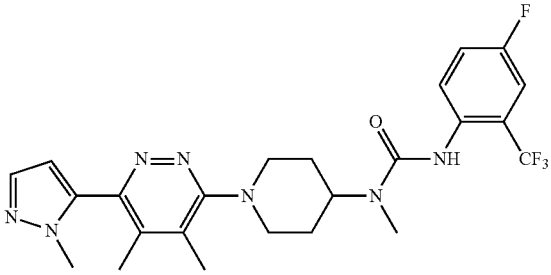
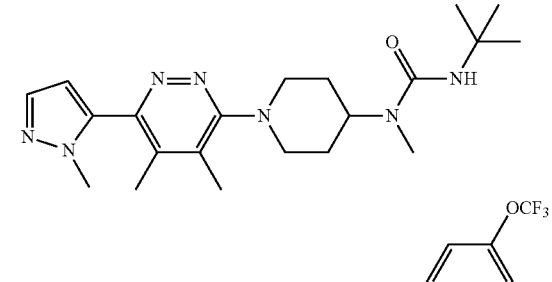
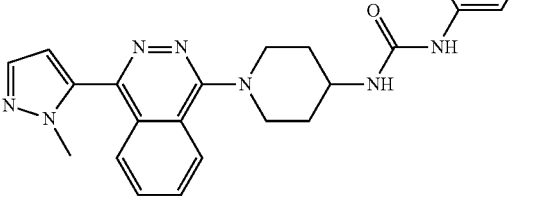

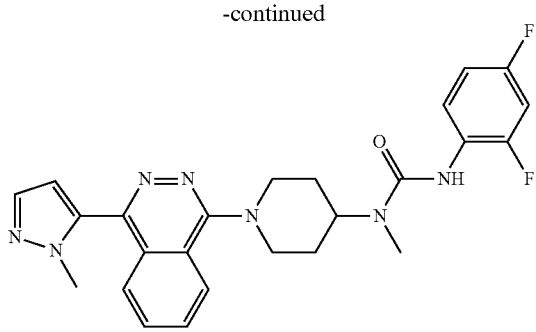

In another aspect of the invention there is provided a compound of formula (I) for use as a medicament.

In another aspect, a compound of formula (I) is for use in a method of treatment of a condition which is modulated by the Hedgehog signalling pathway. Usually conditions that are modulated by the Hedgehog signalling pathway are conditions that would be treated by the inhibition of the Hedgehog signalling pathway using a compound of the present invention. A compound of formula (I) may be for use in the treatment of a condition treatable by the inhibition of the Hedgehog signalling pathway.

In addition the compounds of the present invention are for use in a method of treatment of a condition which is modulated by Smoothened (Smo), a receptor in the Hedgehog signalling pathway. Therefore, in a related aspect a compound of formula (I) is for use in the treatment of a condition which is modulated by Smo. Usually conditions that are modulated by Smo are conditions that would be treated by the inhibition of Smo using a compound of the present invention. A compound of formula (I) may be for use in the treatment of a condition treatable by the inhibition of Smo.

In embodiments the condition treatable by the inhibition of the Hedgehog signalling pathway or Smo may be selected from: cancer, sarcoma, carcinoma, blastoma, lymphoma, leukemia and haematological malignancies.

Inhibition of the Hedgehog signalling pathway and Smo is a novel approach for treating many different human diseases associated with the inappropriate activation of the Hedgehog signalling pathway and aberrant expression of Smo, including various cancers, for example, solid tumours. In embodiments the condition treatable by the inhibition of the Hedgehog signalling pathway or Smo may be selected from: cancer, sarcoma, carcinoma, blastoma, lymphoma and leukemia. Specific conditions treatable by the inhibition of the Hedgehog signalling pathway or Smo may be selected from: basal cell carcinoma, medulloblastoma, rhabdomyosarcoma, chondrosarcoma, melanoma, small-cell lung cancer, non-small-cell lung cancer, B-cell lymphoma, multiple myeloma, brain cancer, esophagus cancer, breast cancer, ovarian cancer, stomach cancer, colorectal cancer, liver cancer, kidney cancer, head and neck cancer, mesothelioma, soft tissue sarcomas, bone sarcomas, testicular cancer, prostate cancer, pancreatic cancer, bone cancer, bone metastasis, acute leukemia, chronic leukemia, glioma, hodgkin's disease, cutaneous melanoma, bladder cancer, endocrine system cancer, parathyroid gland cancer, thyroid gland cancer, cervical cancer, endometrium cancer, ovarian cancer, skin cancer, renal cell carcinoma, pituitary adenoma, spinal axis tumours, uterine cancer, gastric cancer and biliary tract cancer.

In embodiments the preferred condition treatable by the inhibition of the hedgehog signalling pathway or Smo may be selected from: basal cell carcinoma, medulloblastoma, rhabdomyosarcoma, chondrosarcoma, melanoma, small-cell lung cancer, non-small-cell lung cancer, B-cell lymphoma, brain cancer, esophagus cancer, breast cancer, ovarian cancer, stomach cancer, colorectal cancer, liver cancer, kidney cancer, head and neck cancer, soft tissue sarcomas, bone sarcomas, testicular cancer, prostate cancer, pancreatic cancer, bone cancer, bone metastasis, acute leukemia, glioma, bladder cancer, parathyroid gland cancer, thyroid gland cancer, cervical cancer, ovarian cancer, skin cancer, renal cell carcinoma, gastric cancer and biliary tract cancer.

Conditions also treatable by the inhibition of the Hedgehog signalling pathway or Smo may be selected from inhibiting stem cell production, inhibiting stem cell renewal, inhibiting and/or modulating stem cell differentiation, benign prostatic hyperplasia, psoriasis and osteoporosis. The conditions treatable by the inhibition of the Hedgehog signalling pathway or Smo may be selected from inhibiting stem cell production, inhibiting stem cell renewal and inhibiting and/or modulating stem cell differentiation In embodiments, a compound of the invention may be for use in the treatment of: cancer, sarcoma, carcinoma, blastoma, lymphoma, leukemia and haematological malignancies.

In embodiments, a compound of the invention may be for use in the treatment of: cancer, sarcoma, carcinoma, blastoma, lymphoma and leukemia. The compound of the invention may be for use in the treatment of specific conditions selected from: basal cell carcinoma, medulloblastoma, rhabdomyosarcoma, chondrosarcoma, melanoma, small-cell lung cancer, non-small-cell lung cancer, B-cell lymphoma, multiple myeloma, brain cancer, esophagus cancer, breast cancer, ovarian cancer, stomach cancer, colorectal cancer, liver cancer, kidney cancer, head and neck cancer, mesothelioma, soft tissue sarcomas, bone sarcomas, testicular cancer, prostate cancer, pancreatic cancer, bone cancer, bone metastasis, acute leukemia, chronic leukemia, glioma, bladder cancer, endocrine system cancer, parathyroid gland cancer, thyroid gland cancer, cervical cancer, endometrium cancer, ovarian cancer, skin cancer, renal cell carcinoma, pituitary adenoma, spinal axis tumours, uterine cancer, gastric cancer and biliary tract cancer.

A compound of the invention may be for use in the treatment of: inhibiting stem cell production, inhibiting stem cell renewal, inhibiting and/or modulating stem cell differentiation, benign prostatic hyperplasia, psoriasis and osteoporosis.

The compounds of the present invention may be for use in a method of treatment wherein the treatment comprises inhibiting stem cell production, inhibiting stem cell renewal and/or inhibiting and/or modulating stem cell differentiation. In an embodiment the compounds of the present invention may be for use in a method of treatment wherein the treatment comprises inhibiting stem cell renewal and/or stem cell production and the condition being treated is selected from any of the conditions mentioned above.

In an aspect of the invention there is provided a method of treatment of a condition which is modulated by Hedgehog signalling pathway, wherein the method comprises administering a therapeutic amount of a compound of the invention, to a patient in need thereof.

In an embodiment of the invention there is provided a method of treatment of a condition which is modulated by Smo, wherein the method comprises administering a therapeutic amount of a compound of the invention, to a patient in need thereof.

The method of treatment may be a method of treating a condition treatable by the inhibition of the Hedgehog signalling pathway. Furthermore, the method of treatment may be a method of treating a condition treatable by the inhibition of Smo.

The invention provides a method of treating a condition selected from: cancer, sarcoma, carcinoma, blastoma, lymphoma, leukemia and haematological malignancies, wherein the method comprises administering a therapeutic amount of a compound of the invention, to a patient in need thereof.

The invention also provides a method of treating a condition selected from: cancer, sarcoma, carcinoma, blastoma, lymphoma and leukemia, wherein the method comprises administering a therapeutic amount of a compound of the invention, to a patient in need thereof.

The invention also provides a method of treating a specific condition selected from: basal cell carcinoma, medulloblastoma, rhabdomyosarcoma, chondrosarcoma, melanoma, small-cell lung cancer, non-small-cell lung cancer, B-cell lymphoma, multiple myeloma, brain cancer, esophagus cancer, breast cancer, ovarian cancer, stomach cancer, colorectal cancer, liver cancer, kidney cancer, head and neck cancer, mesothelioma, soft tissue sarcomas, bone sarcomas, testicular cancer, prostate cancer, pancreatic cancer, bone cancer, bone metastasis, acute leukemia, chronic leukemia, glioma, bladder cancer, endocrine system cancer, parathyroid gland cancer, thyroid gland cancer, cervical cancer, endometrium cancer, ovarian cancer, skin cancer, renal cell carcinoma, pituitary adenoma, spinal axis tumours, uterine cancer, gastric cancer and biliary tract cancer, wherein the method comprises administering a therapeutic amount of a compound of formula (I), to a patient in need thereof.

The invention also provides a method of treating a condition selected from: inhibiting stem cell production, inhibiting stem cell renewal, inhibiting and/or modulating stem cell differentiation, benign prostatic hyperplasia, psoriasis and osteoporosis wherein the method comprises administering a therapeutic amount of a compound of the invention, to a patient in need thereof.

In an aspect of the invention there is provided a method of inhibiting stem cell renewal and/or stem cell production, wherein the method comprises administering a therapeutic amount of a compound of formula (I), to a patient in need thereof.

In another aspect of the invention there is provided a pharmaceutical composition, wherein the composition comprises a compound of the invention and pharmaceutically acceptable excipients. The pharmaceutical composition may be used in the treatment of the diseases mentioned above. The method of treatment mentioned above may comprise administering a pharmaceutical composition of the invention instead of the compound of formula (I).

In an embodiment the pharmaceutical composition may be a combination product comprising an additional pharmaceutically active agent. The additional pharmaceutically active agent may be an anti-tumor agent, as described below.

In an aspect of the invention there is provided a method of treatment of a condition selected from cancer, sarcoma, carcinoma, blastoma, lymphoma and leukemia comprising administering a therapeutically effective amount of a compound of formula (I), or a pharmaceutically acceptable salt thereof simultaneously, sequentially or separately with an additional anti-tumour agent to a patient in need thereof.

In an embodiment the method of treatment may further comprise administering the compound of formula (I) to the patient topically. In an embodiment the method of treatment may further comprise administering the compound of formula (I) to the patient by any route of administration other than topically, for example by oral administration in the form of tablets, capsules, syrups, powders or granules; or by parenteral administration in the form of a sterile solution, suspension or emulsion for injection (including intravenous, subcutaneous, intramuscular, intravascular or infusion); by rectal administration in the form of suppositories or enemas; or by inhalation in the form of an aerosol.

In an embodiment the compound of formula (I) may be topically administered. In an embodiment the compound of formula (I) may be administered by any route other than topically, for example orally in the form of tablets, capsules, syrups, powders or granules; or parenterally in the form of a sterile solution, suspension or emulsion for injection (including intravenous, subcutaneous, intramuscular, intravascular or infusion); or rectally in the form of suppositories or enemas; or by inhalation in the form of an aerosol.

DETAILED DESCRIPTION

Given below are definitions of terms used in this application. Any term not defined herein takes the normal meaning as the skilled person would understand the term.

The term "halo" refers to one of the halogens, group 17 of the periodic table. In particular the term refers to fluorine, chlorine, bromine and iodine. Preferably, the term refers to fluorine or chlorine.

The term "$C_{1-6}$ alkyl" refers to a linear or branched hydrocarbon chain containing 1, 2, 3, 4, 5 or 6 carbon atoms, for example methyl, ethyl, n-propyl, iso-propyl, n-butyl, sec-butyl, tert-butyl, n-pentyl and n-hexyl. Similarly, "$C_{1-4}$ alkyl" refers to a linear or branched hydrocarbon chain containing 1, 2, 3 or 4 carbon atoms and "$C_{1-14}$ alkyl" refers to a linear or branched hydrocarbon chain containing 1, 2, 3, 4, 5, 6, 7, 8, 9, 10, 11, 12, 13 or 14 carbon atoms. Alkylene groups may likewise be linear or branched and may have two places of attachment to the remainder of the molecule. Furthermore, an alkylene group may, for example, correspond to one of those alkyl groups listed in this paragraph. The alkyl and alkylene groups may be unsubstituted or substituted by one or more substituents. Possible substituents are described below. Substituents for the alkyl group may be halogen, e.g. fluorine, chlorine, bromine and iodine, OH, $C_{1-6}$ alkoxy.

The term "$C_{1-6}$ alkoxy" refers to an alkyl group which is attached to a molecule via oxygen. This includes moieties where the alkyl part may be linear or branched and may contain 1, 2, 3, 4, 5 or 6 carbon atoms, for example methyl, ethyl, n-propyl, iso-propyl, n-butyl, sec-butyl, tert-butyl, n-pentyl and n-hexyl. Therefore, the alkoxy group may be methoxy, ethoxy, n-propoxy, iso-propoxy, n-butoxy, sec-butoxy, tert-butoxy, n-pentoxy and n-hexoxy. The alkyl part of the alkoxy group may be unsubstituted or substituted by one or more substituents. Possible substituents are described below. Substituents for the alkyl group may be halogen, e.g. fluorine, chlorine, bromine and iodine, OH, $C_{1-6}$ alkoxy.

The term "$C_{1-6}$ haloalkyl" refers to a hydrocarbon chain substituted with at least one halogen atom independently chosen at each occurrence, for example fluorine, chlorine, bromine and iodine. Similarly, "$C_{1-4}$ haloalkyl" refers to a linear or branched hydrocarbon chain containing 1, 2, 3 or 4 carbon atoms and "$C_{1-14}$ haloalkyl" refers to a linear or branched hydrocarbon chain containing 1, 2, 3, 4, 5, 6, 7, 8, 9, 10, 11, 12, 13 or 14 carbon atoms. The halogen atom may be present at any position on the hydrocarbon chain. For example, $C_{1-6}$ haloalkyl may refer to chloromethyl, flouromethyl, trifluoromethyl, chloroethyl e.g. 1-chloromethyl and 2-chloroethyl, trichloroethyl e.g. 1,2,2-trichloroethyl, 2,2,2-trichloroethyl, fluoroethyl e.g. 1-fluoromethyl and 2-fluoroethyl, trifluoroethyl e.g. 1,2,2-trifluoroethyl and 2,2,2-trifluoroethyl, chloropropyl, trichloropropyl, fluoropropyl, trifluoropropyl.

The term "$C_{2-6}$ alkenyl" refers to a branched or linear hydrocarbon chain containing at least one double bond and having 2, 3, 4, 5 or 6 carbon atoms. The double bond(s) may be present as the E or Z isomer. The double bond may be at any possible position of the hydrocarbon chain. For example, the "$C_{2-6}$ alkenyl" may be ethenyl, propenyl, butenyl, butadienyl, pentenyl, pentadienyl, hexenyl and hexadienyl.

The term "$C_{2-6}$ alkynyl" refers to a branded or linear hydrocarbon chain containing at least one triple bond and having 2, 3, 4, 5 or 6 carbon atoms. The triple bond may be at any possible position of the hydrocarbon chain. For example, the "$C_{2-6}$ alkynyl" may be ethynyl, propynyl, butynyl, pentynyl and hexynyl.

The term "$C_{1-6}$ heteroalkyl" refers to a branded or linear hydrocarbon chain containing 1, 2, 3, 4, 5, or 6 carbon atoms and at least one heteroatom selected from N, O and S positioned between any carbon in the chain or at an end of the chain. For example, the hydrocarbon chain may contain one or two heteroatoms. The $C_{1-6}$ heteroalkyl may be bonded to the rest of the molecule through a carbon or a heteroatom. For example, the "$C_{1-6}$ heteroalkyl" may be $C_{1-6}$ N-alkyl, $C_{1-6}$ N,N-alkyl, or $C_{1-6}$ O-alkyl.

The term "carbocyclic" refers to a saturated or unsaturated carbon containing ring system. A "carbocyclic" system may be monocyclic or a fused polycyclic ring system, for example, bicyclic or tricyclic. A "carbocyclic" moiety may contain from 3 to 14 carbon atoms, for example, 3 to 8 carbon atoms in a monocyclic system and 7 to 14 carbon atoms in a polycyclic system. "Carbocyclic" encompasses cycloalkyl moieties, cycloalkenyl moieties, aryl ring systems and fused ring systems including an aromatic portion. "Carbocyclic" may be $C_{3-8}$ cycloalkyl or $C_{5-6}$ aryl.

The term "heterocyclic" refers to a saturated or unsaturated ring system containing at least one heteroatom selected from N, O or S. A "heterocyclic" system may contain 1, 2, 3 or 4 heteroatoms, for example 1 or 2. A "heterocyclic" system may be monocyclic or a fused polycyclic ring system, for example, bicyclic or tricyclic. A "heterocyclic" moiety may contain from 3 to 14 carbon atoms, for example, 3 to 8 carbon atoms in a monocyclic system and 7 to 14 carbon atoms in a polycyclic system. "Heterocyclic" encompasses heterocycloalkyl moieties, heterocycloalkenyl moieties and heteroaromatic moieties. "Heterocyclic" groups may be $C_{3-8}$ heterocycloalkyl, $C_{5-6}$ heteroaryl. For example, the heterocyclic group may be: oxirane, aziridine, azetidine, oxetane, tetrahydrofuran, pyrrolidine, imidazolidine, succinimide, pyrazolidine, oxazolidine, isoxazolidine, thiazolidine, isothiazolidine, piperidine, morpholine, thiomorpholine, piperazine, and tetrahydropyran.

The term "$C_{3-8}$ cycloalkyl" refers to a saturated hydrocarbon ring system containing 3, 4, 5, 6, 7 or 8 carbon atoms. For example, the "$C_{3-8}$ cycloalkyl" may be cyclopropyl, cyclobutyl, cyclopentyl, cyclohexyl, cycloheptyl and cyclooctyl.

The term "$C_{3-8}$ cycloalkenyl" refers to an unsaturated hydrocarbon ring system containing 3, 4, 5, 6, 7 or 8 carbon atoms. The ring may contain more than one double bond.

For example, the "$C_{3-8}$ cycloalkyl" may be cyclopropenyl, cyclobutenyl, cyclopentenyl, cyclopentadienyl, cyclohexenyl, cyclohexadienyl, cycloheptenyl, cycloheptadiene, cyclooctenyl and cycloatadienyl.

The term "$C_{3-8}$ heterocycloalkyl" refers to a saturated hydrocarbon ring system containing 3, 4, 5, 6, 7 or 8 carbon atoms and at least one heteroatom within the ring selected from N, O and S. For example there may be 1, 2 or 3 heteroatoms, optionally 1 or 2. The "$C_{3-8}$ heterocycloalkyl" may be bonded to the rest of the molecule through any carbon atom or heteroatom. The "$C_{3-8}$ heterocycloalkyl" may have one or more, e.g. one or two, bonds to the rest of the molecule: these bonds may be through any of the atoms in the ring. For example, the "$C_{3-8}$ heterocycloalkyl" may be oxirane, aziridine, azetidine, oxetane, tetrahydrofuran, pyrrolidine, imidazolidine, succinimide, pyrazolidine, oxazolidine, isoxazolidine, thiazolidine, isothiazolidine, piperidine, morpholine, thiomorpholine, piperazine, and tetrahydropyran.

The term "$C_{3-8}$ heterocycloalkenyl" refers to an unsaturated hydrocarbon ring system, containing 3, 4, 5, 6, 7 or 8 carbon atoms and at least one heteroatom within the ring selected from N, O and S. For example there may be 1, 2 or 3 heteroatoms, optionally 1 or 2. The "$C_{3-8}$ heterocycloalkenyl" may be bonded to the rest of the molecule through any carbon atom or heteroatom. The "$C_{3-8}$ heterocycloalkenyl" may have one or more, e.g. one or two, bonds to the rest of the molecule: these bonds may be through any of the atoms in the ring. For example, the "$C_{3-8}$ heterocycloalkyl" may be tetrahydropyridine, dihydropyran, dihydrofuran, pyrroline.

The term "aryl" refers to an aromatic hydrocarbon ring system. The ring system has 4n+2 electrons in a conjugated π system within a ring where all atoms contributing to the conjugated π system are in the same plane. For example, the "aryl" may be phenyl and napthyl. The aryl system itself may be substituted with other groups.

The term "heteroaryl" refers to an aromatic hydrocarbon ring system with at least one heteroatom within a single ring or within a fused ring system, selected from O, N and S. The ring or ring system has 4n+2 electrons in a conjugated π system where all atoms contributing to the conjugated π system are in the same plane. For example, the "heteroaryl" may be imidazole, thiene, furane, thianthrene, pyrrol, benzimidazole, pyrazole, pyrazine, pyridine, pyrimidine and indole.

The term "alkaryl" refers to an aryl group, as defined above, bonded to a $C_{1-4}$ alkyl, where the $C_{1-4}$ alkyl group provides attachment to the remainder of the molecule.

The term "alkheteroaryl" refers to a heteroaryl group, as defined above, bonded to a $C_{1-4}$ alkyl, where the alkyl group provides attachment to the remainder of the molecule.

The term "halogen" herein includes reference to F, Cl, Br and I. Halogen may be Cl. Halogen may be F.

A bond terminating in a ⌇ represents that the bond is connected to another atom that is not shown in the structure. A bond terminating inside a cyclic structure and not terminating at an atom of the ring structure represents that the bond may be connected to any of the atoms in the ring structure where allowed by valency.

Throughout the specification $A^1$, $A^2$, $A^3$ and $A^4$ may collectively be referred to as "A groups". One of the "A groups" may generally be described as an "A group". The unsaturated ring containing $A^1$, $A^2$, $A^3$ and $A^4$ may be referred to as the "A ring".

Where a moiety is substituted, it may be substituted at any point on the moiety where chemically possible and consistent with atomic valency requirements. The moiety may be substituted by one or more substitutents, e.g. 1, 2, 3 or 4 substituents; optionally there are 1 or 2 substituents on a group. Where there are two or more substituents, the substituents may be the same or different. The substituent(s) may be selected from: OH, NHR$^9$, amidino, guanidino, hydroxyguanidino, formamidino, isothioureido, ureido, mercapto, C(O)H, acyl, acyloxy, carboxy, sulfo, sulfamoyl, carbamoyl, cyano, azo, nitro, halo, $C_{1-6}$ alkyl, $C_{1-6}$ alkoxy, $C_{1-6}$ haloalkyl, $C_{3-8}$ cycloalkyl, $C_{2-6}$ alkenyl, $C_{2-6}$ alkynyl, aryl, heteroaryl or alkaryl. Where the group to be substituted is an alkyl group the substituent may be =O. Where the moiety is substituted with two or more substituents and two of the substituents are adjacent the adjacent substituents may form a $C_{4-8}$ ring along with the atoms of the moiety on which the substituents are substituted, wherein the $C_{4-8}$ ring is a saturated or unsaturated hydrocarbon ring with 4, 5, 6, 7, or 8 carbon atoms or a saturated or unsaturated hydrocarbon ring with 4, 5, 6, 7, or 8 carbon atoms and 1, 2 or 3 heteroatoms.

Substituents are only present at positions where they are chemically possible, the person skilled in the art being able to decide (either experimentally or theoretically) without inappropriate effort which substitutions are chemically possible and which are not.

Ortho, meta and para substitution are well understood terms in the art. For the absence of doubt, "ortho" substitution is substitution at a location adjacent to the position of attachment to the rest of the molecule, for example the two groups below are ortho substituted by fluorine:

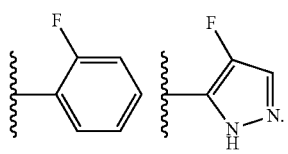

"Meta" substitution is substitution on the second atom away from the atom where the group is attached to the rest of the molecule, for example the two groups below are meta substituted by fluorine:

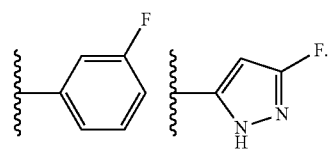

"Para" substitution is substitution on the second atom away from the atom where the group is attached to the rest of the molecule, for example the group below is para substituted by fluorine:

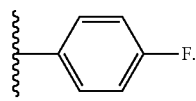 [SMILES: *c1ccc(F)cc1]

By "acyl" is meant an organic radical derived from, for example, an organic acid by the removal of the hydroxyl group, e.g. a radical having the formula R—C(O)—, where R may be selected from H, $C_{1-6}$ alkyl, $C_{3-8}$ cycloalkyl, phenyl, benzyl or phenethyl group, eg R is H or $C_{1-3}$ alkyl. In one embodiment acyl is alkyl-carbonyl. Examples of acyl groups include, but are not limited to, formyl, acetyl, propionyl and butyryl. A particular acyl group is acetyl.

The invention contemplates pharmaceutically acceptable salts of the compounds of formula (I). These may include the acid addition and base salts of the compounds.

Suitable acid addition salts are formed from acids which form non-toxic salts. Examples include the acetate, aspartate, benzoate, besylate, bicarbonate/carbonate, bisulphate/sulphate, borate, camsylate, citrate, edisylate, esylate, formate, fumarate, gluceptate, gluconate, glucuronate, hexafluorophosphate, hibenzate, hydrochloride/chloride, hydrobromide/bromide, hydroiodide/iodide, isethionate, lactate, malate, maleate, malonate, mesylate, methylsulphate, naphthylate, 1,5-naphthalenedisulfonate, 2-napsylate, nicotinate, nitrate, orotate, oxalate, palmitate, pamoate, phosphate/hydrogen phosphate/dihydrogen phosphate, saccharate, stearate, succinate, tartrate, tosylate and trifluoroacetate salts.

Suitable base salts are formed from bases which form non-toxic salts. Examples include the aluminium, arginine, benzathine, calcium, choline, diethylamine, diolamine, glycine, lysine, magnesium, meglumine, olamine, potassium, sodium, tromethamine and zinc salts. Hemisalts of acids and bases may also be formed, for example, hemisulphate and hemicalcium salts. For a review on suitable salts, see "Handbook of Pharmaceutical Salts: Properties, Selection, and Use" by Stahl and Wermuth (Wiley-VCH, Weinheim, Germany, 2002).

Preferably the salt is an acid addition salt. The salts may be formate or hydrochloride.

Pharmaceutically acceptable salts of compounds of formula (I) may be prepared by one or more of three methods:
(i) by reacting the compound of formula (I) with the desired acid or base;
(ii) by removing an acid- or base-labile protecting group from a suitable precursor of the compound of formula (I) or by ring-opening a suitable cyclic precursor, for example, a lactone or lactam, using the desired acid or base; or
(iii) by converting one salt of the compound of formula (I) to another by reaction with an appropriate acid or base or by means of a suitable ion exchange column.

All three reactions are typically carried out in solution. The resulting salt may precipitate out and be collected by filtration or may be recovered by evaporation of the solvent. The degree of ionisation in the resulting salt may vary from completely ionised to almost non-ionised.

The compounds of the invention may exist in both unsolvated and solvated forms. The term 'solvate' is used herein to describe a molecular complex comprising the compound of the invention and a stoichiometric amount of one or more pharmaceutically acceptable solvent molecules, for example, ethanol. The term 'hydrate' is employed when said solvent is water.

Included within the scope of the invention are complexes such as clathrates, drug-host inclusion complexes wherein, in contrast to the aforementioned solvates, the drug and host are present in stoichiometric or non-stoichiometric amounts. Also included are complexes of the drug containing two or more organic and/or inorganic components which may be in stoichiometric or non-stoichiometric amounts. The resulting complexes may be ionised, partially ionised, or non-ionised. For a review of such complexes, see J Pharm Sci, 64 (8), 1269-1288 by Haleblian (August 1975).

Hereinafter all references to compounds of any formula include references to salts, solvates and complexes thereof and to solvates and complexes of salts thereof.

The compounds of the invention include compounds of a number of formula as herein defined, including all polymorphs and crystal habits thereof, prodrugs and isomers thereof (including optical, geometric and tautomeric isomers) as hereinafter defined and isotopically-labeled compounds of the invention.

Before purification, the compounds of the present invention may exist as a mixture of enantiomers depending on the synthetic procedure used. The enantiomers can be separated by conventional techniques known in the art. Thus the invention covers individual enantiomers as well as mixtures thereof.

For some of the steps of the process of preparation of the compounds of formula (I), it may be necessary to protect potential reactive functions that are not wished to react, and to cleave said protecting groups in consequence. In such a case, any compatible protecting radical can be used. In particular methods of protection and deprotection such as those described by T. W. GREENE (Protective Groups in Organic Synthesis, A. Wiley—Interscience Publication, 1981) or by P. J. Kocienski (Protecting groups, Georg Thieme Verlag, 1994), can be used. All of the above reactions and the preparations of novel starting materials used in the preceding methods are conventional and appropriate reagents and reaction conditions for their performance or preparation as well as procedures for isolating the desired products will be well-known to those skilled in the art with reference to literature precedents and the examples and preparations hereto.

Also, the compounds of the present invention as well as intermediates for the preparation thereof can be purified according to various well-known methods, such as for example crystallization or chromatography.

The method of treatment or the compound for use in the treatment of cancer, sarcoma, carcinoma, blastoma, lymphoma and leukemia as defined hereinbefore may be applied as a sole therapy or be a combination therapy with an additional active agent.

The method of treatment or the compound for use in the treatment of cancer, sarcoma, carcinoma, blastoma, lymphoma and leukemia may involve, in addition to the compound of the invention, conventional surgery or radiotherapy or chemotherapy. Such chemotherapy may include one or more of the following specific anti-tumour agents listed below or anti-tumour agents from one or more of the categories of listed below:—

(i) antiproliferative/antineoplastic drugs and combinations thereof, such as alkylating agents (for example cis-platin, oxaliplatin, carboplatin, cyclophosphamide, nitrogen mustard, bendamustin, melphalan, chlorambucil, busulphan, capecitabine temozolamide, ifosamide, mitobronitol, carboquone, thiotepa, ranimustine, nimustine, AMD-473, altretamine, AP-5280, apaziquone, brostallicin, carmustine, estramustine, fotemustine, gulfosfamide, KW-2170, mafosfamide, mitolactol, etaplatin, lobaplatin, nedaplatin, strrplatin and nitrosoureas); antimetabolites (for example gemcitabine and antifolates such as fluoropyrimidines like 5-fluorouracil and tegafur, raltitrexed, methotrexate, pemetrexed, cytosine arabinoside, 6-mercaptopurine riboside, leucovarin, UFT, doxifluridine, carmoflur, cytarabine, enocitabine S-1, 5-azacitidine, cepecitabine, clofarabine, decitabine, eflornithine, ethynlcytidine, TS-1, nelarabine, nolatrexed, ocosfate, pelitrexol, triapine, trimetrexate, vidarabine, and hydroxyurea); antibiotics (for example anthracyclines like adriamycin, bleomycin, doxorubicin, daunomycin, epirubicin, idarubicin, mitomycin-C, dactinomycin, mithramycin, aclarubicin, actinomycin D, amrubicin, annamycin, elsamitrucin, galarubicin, nemorubicin, neocarzinostatin, peplomycin, piarubicin, rebeccamycin, stimalamer, streptozocin, valrubicin and zinostatin); antimitotic agents (for example vinca alkaloids like vincristine, vinblastine, vindesine and vinorelbine and taxoids like taxol, docetaxol (Taxotere), and paclitaxel and polokinase inhibitors); proteasome inhibitors, for example carfilzomib and bortezomib; interferon therapy; and topoisomerase inhibitors (for example epipodophyllotoxins like etoposide and teniposide, aclarubicin, amonafide, belotecan, 10-hydroxycamptothecin, 9-aminocamptothecin, diflomotecan, edotecarin, exatecan, gimatecan, lurtotecan, pirarubicin, pixantrone, rubitecan, sobuzoxane, SN-38, tafluposide, amsacrine, topotecan, mitoxantrone and camptothecin) and adjuvants used in combination with these therapies, for example folinic acid;

(ii) cytostatic agents such as antioestrogens (for example tamoxifen, fulvestrant, toremifene, raloxifene, droloxifene, lasofoxifeneand iodoxyfene), antiandrogens (for example bicalutamide, mifepristone, flutamide, nilutamide, casodex and cyproterone acetate), LHRH antagonists or LHRH agonists (for example goserelin, leuprorelin and buserelin), progestogens (for example megestrol acetate), aromatase inhibitors (for example as anastrozole, letrozole, vorazole and exemestane) and inhibitors of 5α-reductase such as finasteride;

(iii) anti-invasion agents, for example dasatinib and bosutinib (SKI-606), and metalloproteinase inhibitors, inhibitors of urokinase plasminogen activator receptor function or antibodies to Heparanase;

(iv) inhibitors of growth factor function: for example such inhibitors include growth factor antibodies and growth factor receptor antibodies, for example the anti-erbB2 antibody trastuzumab [Herceptin™], the anti-EGFR antibody panitumumab, the anti-erbB1 antibody cetuximab, tyrosine kinase inhibitors, for example inhibitors of the epidermal growth factor family (for example EGFR family tyrosine kinase inhibitors such as gefitinib, erlotinib and 6-acrylamido-N-(3-chloro-4-fluorophenyl)-7-(3-morpholinopropoxy)-quinazolin-4-amine (CI 1033), erbB2 tyrosine kinase inhibitors such as lapatinib); ErbB2 inhibitors (for example GW-28297, Herceptin, 2C4, pertuzumab, TAK-165, GW-572016, AR-209, and 2B-1); inhibitors of the hepatocyte growth factor family; inhibitors of the insulin growth factor family; modulators of protein regulators of cell apoptosis (for example Bcl-2 inhibitors); inhibitors of the platelet-derived growth factor family such as imatinib and/or nilotinib (AMN107); inhibitors of serine/threonine kinases (for example Ras/Raf signalling inhibitors such as farnesyl transferase inhibitors, for example sorafenib, tipifarnib and lonafarnib), inhibitors of cell signalling through MEK and/or AKT kinases, c-kit inhibitors, abl kinase inhibitors, PI3 kinase inhibitors, Plt3 kinase inhibitors, CSF-1R kinase inhibitors, IGF receptor, kinase inhibitors; aurora kinase inhibitors and cyclin dependent kinase inhibitors such as CDK2 and/or CDK4 inhibitors;

(v) antiangiogenic agents such as those which inhibit the effects of vascular endothelial growth factor, [for example the anti-vascular endothelial cell growth factor antibody bevacizumab (Avastin™); COXII inhibitors (for example Arcoxia (etoricoxib), Bextra (valdecoxib), Celebrex (celecoxib), Paracoxib Vioxx (rofecoxib)); MMP inhibitors (for example MMP-2 inhibitors, MMP-9 inhibitors, AG-3340, RO 32-3555, and RS 13-0830); thalidomide; lenalidomide;

and for example, a VEGF receptor (for example SU-11248, SU-5416, SU-6668, and angiozyme) tyrosine kinase inhibitor (such as vandetanib, vatalanib, sunitinib, axitinib and pazopanib); acitretin; fenretinide; zoledronic acid; angiostatin; aplidine; cilengtide; A-4; endostatin; halofuginome; rebimastat; removab; revlimid; squalamine; ukrain; and vitaxincombretastatin;

(vi) gene therapy approaches, including for example approaches to replace aberrant genes such as aberrant p53 or aberrant BRCA1 or BRCA2;

(vii) immunotherapy approaches, including for example antibody therapy such as alemtuzumab, rituximab, ibritumomab tiuxetan (Zevalin®) and ofatumumab; interferons such as interferon α; interleukins such as IL-2 (aldesleukin); interleukin inhibitors for example IRAK4 inhibitors; cancer vaccines including prophylactic and treatment vaccines such as HPV vaccines, for example Gardasil, Cervarix, Oncophage and Sipuleucel-T (Provenge); interferons, such as interferon alpha, interferon alpha-2a, interferon alpha-2b, interferon beta, interferon gamma-1a, and interferon gamma-n; PF3512676; Filgrastim (Neupogen); lentinan; sizofilan; TheraCys; ubenimex; WF-10; BAM-002; dacarbazine; daclizumab; denileukin; gemtuzumab; ozogamicin; imiquimod; lenograstim; melanoma vaccine (Corixa); molgramostim; OncoVAX-CL; sargramostim; tasonermin; tecleukin; thymalasin; tositumomab; Virulizin; Z-100; epratuzumab; mitumomab; oregovomab; pemtumomab; and toll-like receptor modulators for example TLR-7 or TLR-9 agonists; and (viii) cytotoxic agents for example fludaribine (fludara), cladribine, pentostatin (Nipent™) edotecarin, SU-11248, paclitaxel, Erbitux, and irinotecan;

(ix) steroids such as corticosteroids, including glucocorticoids and mineralocorticoids, for example aclometasone, aclometasone dipropionate, aldosterone, amcinonide, beclomethasone, beclomethasone dipropionate, betamethasone, betamethasone dipropionate, betamethasone sodium phosphate, betamethasone valerate, budesonide, clobetasone, clobetasone butyrate, clobetasol propionate, cloprednol, cortisone, cortisone acetate, cortivazol, deoxycortone, desonide, desoximetasone, dexamethasone, dexamethasone sodium phosphate, dexamethasone isonicotinate, difluorocortolone, fluclorolone, flumethasone, flunisolide, fluocinolone, fluocinolone acetonide, fluocinonide, fluocortin butyl, fluorocortisone, fluorocortolone, fluocortolone caproate, fluocortolone pivalate, fluorometholone, fluprednidene, fluprednidene acetate, flurandrenolone, fluticasone, fluticasone propionate, halcinonide, hydrocortisone, hydrocortisone acetate, hydrocortisone butyrate, hydrocortisone aceponate, hydrocortisone buteprate, hydrocortisone valerate, icomethasone, icomethasone enbutate, meprednisone, methylprednisolone, mometasone paramethasone, mometasone furoate monohydrate, prednicarbate, prednisolone, prednisone, tixocortol, tixocortol pivalate, triamcinolone, triamcinolone acetonide, triamcinolone alcohol and their respective pharmaceutically acceptable derivatives. A combination of steroids may be used, for example a combination of two or more steroids mentioned in this paragraph;

(x) targeted therapies, for example PI3Kd inhibitors, for example idelalisib and perifosine;

(xi) and additional active agents such as estramustine phosphate, fludarabine phosphate, farnesyl transferase inhibitors, PDGFr, streptozocin, strontium-89, suramin, hormonal therapies (for example Lupron, doxercalciferol, fadrozole, formestane and trelstar), supportive care products (for example, Filgrastim (Neupogen), ondansetron (Zofran), Fragmin, Procrit, Aloxi and Emend), biological response modifiers (e.g. Krestin, lentinan, sizofiran, picibanil and ubenimex), alitretinoin, ampligen, atrasenten, bexarotene, bosentan, calcitriol, exisulind, fotemustine, ibandronic acid, miltefosine, 1-asparaginase, procarbazine, dacarbazine, hydroxycarbamide, pegaspargase, tazarotne, TLK-286, Velcade, Tarceva, tretinoin.

The combination therapies defined above may be achieved by way of the simultaneous, sequential or separate dosing of the individual components of the treatment. Such combination products employ the compounds of this invention within a therapeutically effective dosage range described hereinbefore and the other pharmaceutically-active agent within its approved dosage range.

According to a further aspect of the invention there is provided a pharmaceutical product comprising a compound of formula (I), or a pharmaceutically acceptable salt thereof as defined hereinbefore and an additional active agent for the treatment of a condition which is modulated by the Hedgehog signalling pathway. The additional active agent may be an anti-tumour agent as defined hereinbefore.

In an embodiment there is provided a pharmaceutical product comprising a compound of formula (I), or a pharmaceutically acceptable salt thereof as defined hereinbefore and an additional active agent for the treatment of a condition which is modulated by Smo. The additional active agent may be an anti-tumour agent as defined hereinbefore.

According to a further aspect of the invention there is provided a method of treatment of a condition modulated by the Hedgehog signalling pathway comprising administering a therapeutically effective amount of a compound of formula (I), or a pharmaceutically acceptable salt thereof simultaneously, sequentially or separately with an additional anti-tumour agent, as defined hereinbefore, to a patient in need thereof.

In an embodiment the condition is a condition modulated by Smo.

According to a further aspect of the invention there is provided a compound of formula (I), or a pharmaceutically acceptable salt thereof for use simultaneously, sequentially or separately with an additional anti-tumour agent as defined hereinbefore, in the treatment of a condition modulated by the Hedgehog signalling pathway. In an embodiment the condition is a condition modulated by Smo.

According to another aspect of the invention there is provided a use of the compound of formula (I) in combination with an anti-tumour agent as hereinbefore described. The compound of formula (I) may be used simultaneously, sequentially or separately with the additional anti-tumour agent The use may be in a single combination product comprising the compound of formula (I) and the anti-tumour agent.

According to a further aspect there is provided a method of providing a combination product, wherein the method comprises providing a compound of formula (I) simultaneously, sequentially or separately with an anti-tumour agent, as defined hereinbefore. The method may comprise combining the compound of formula (I) and the anti-tumour agent in a single dosage form. Alternatively the method may comprise providing the anti-tumour agent as separate dosage forms.

The condition modulated by the Hedgehog signalling pathway or Smo described above may be cancer, sarcoma, carcinoma, blastoma, lymphoma and leukemia. More specifically the condition modulated by BTK may be selected from: cancer, sarcoma, carcinoma, blastoma, lymphoma and leukemia. Specific conditions treatable by the inhibition of the Hedgehog signalling pathway or Smo may be selected from: basal cell carcinoma, medulloblastoma, rhabdomyosarcoma, chondrosarcoma, melanoma, small-cell lung cancer, non-small-cell lung cancer, B-cell lymphoma, multiple myeloma, brain cancer, esophagus cancer, breast cancer, ovarian cancer, stomach cancer, colorectal cancer, liver cancer, kidney cancer, head and neck cancer, mesothelioma, soft tissue sarcomas, bone sarcomas, testicular cancer, prostate cancer, pancreatic cancer, bone cancer, bone metastasis, acute leukemia, chronic leukemia, glioma, hodgkin's disease, cutaneous melanoma, bladder cancer, endocrine system cancer, parathyroid gland cancer, thyroid gland cancer, cervical cancer, endometrium cancer, ovarian cancer, skin cancer, renal cell carcinoma, pituitary adenoma, spinal axis tumours, uterine cancer, gastric cancer and biliary tract cancer.

Conditions also treatable by the inhibition of the Hedgehog signalling pathway or Smo may be selected from inhibiting stem cell production, inhibiting stem cell renewal, inhibiting and/or modulating stem cell differentiation, benign prostatic hyperplasia, psoriasis and osteoporosis.

For the above-mentioned compounds of the invention the dosage administered will, of course, vary with the compound employed, the mode of administration, the treatment desired and the disorder indicated. For example, if the compound of the invention is administered orally, then the daily dosage of the compound of the invention may be in the range from 0.01 micrograms per kilogram body weight (μg/kg) to 100 milligrams per kilogram body weight (mg/kg).

A compound of the invention, or pharmaceutically acceptable salt thereof, may be used on their own but will generally be administered in the form of a pharmaceutical composition in which the compounds of the invention, or pharmaceutically acceptable salt thereof, is in association with a pharmaceutically acceptable adjuvant, diluent or carrier. Conventional procedures for the selection and preparation of suitable pharmaceutical formulations are described in, for example, "Pharmaceuticals—The Science of Dosage Form Designs", M. E. Aulton, Churchill Livingstone, 1988.

Depending on the mode of administration of the compounds of the invention, the pharmaceutical composition which is used to administer the compounds of the invention will preferably comprise from 0.05 to 99% w (percent by weight) compounds of the invention, more preferably from 0.05 to 80% w compounds of the invention, still more preferably from 0.10 to 70% w compounds of the invention, and even more preferably from 0.10 to 50% w compounds of the invention, all percentages by weight being based on total composition.

The pharmaceutical compositions may be administered topically (e.g. to the skin) in the form, e.g., of creams, gels, lotions, solutions, suspensions, or systemically, e.g. by oral administration in the form of tablets, capsules, syrups, powders or granules; or by parenteral administration in the form of a sterile solution, suspension or emulsion for injection (including intravenous, subcutaneous, intramuscular, intravascular or infusion); by rectal administration in the form of suppositories or enemas; or by inhalation in the form of an aerosol.

For oral administration the compounds of the invention may be admixed with an adjuvant or a carrier, for example, lactose, saccharose, sorbitol, mannitol; a starch, for example, potato starch, corn starch or amylopectin; a cellulose derivative; a binder, for example, gelatine or polyvinylpyrrolidone; and/or a lubricant, for example, magnesium stearate, calcium stearate, polyethylene glycol, a wax, paraffin, and the like, and then compressed into tablets. If coated tablets are required, the cores, prepared as described above, may be coated with a concentrated sugar solution which may contain, for example, gum arabic, gelatine, talcum and titanium dioxide. Alternatively, the tablet may be coated with a suitable polymer dissolved in a readily volatile organic solvent.

For the preparation of soft gelatine capsules, the compounds of the invention may be admixed with, for example, a vegetable oil or polyethylene glycol. Hard gelatine capsules may contain granules of the compound using either the above-mentioned excipients for tablets. Also liquid or semi-solid formulations of the compound of the invention may be filled into hard gelatine capsules. Liquid preparations for oral application may be in the form of syrups or suspensions, for example, solutions containing the compound of the invention, the balance being sugar and a mixture of ethanol, water, glycerol and propylene glycol. Optionally such liquid preparations may contain colouring agents, flavouring agents, sweetening agents (such as saccharine), preservative agents and/or carboxymethylcellulose as a thickening agent or other excipients known to those skilled in art.

For intravenous (parenteral) administration the compounds of the invention may be administered as a sterile aqueous or oily solution.

The size of the dose for therapeutic purposes of compounds of the invention will naturally vary according to the nature and severity of the conditions, the age and sex of the animal or patient and the route of administration, according to well-known principles of medicine.

Dosage levels, dose frequency, and treatment durations of compounds of the invention are expected to differ depending on the formulation and clinical indication, age, and co-morbid medical conditions of the patient. The standard duration of treatment with compounds of the invention is expected to vary between one and seven days for most clinical indications. It may be necessary to extend the duration of treatment beyond seven days in instances of recurrent infections or infections associated with tissues or implanted materials to which there is poor blood supply including bones/joints, respiratory tract, endocardium, and dental tissues.

EXAMPLES AND SYNTHESIS

As used herein the following terms have the meanings given: "Boc" refers to tert-butoxycarbonyl; "CV" refers to column volumes, "DCM" refers to dichloromethane; "DIPEA" refers to N,N-Diisopropylethylamine; "LCMS" refers to liquid chromatography/mass spectrometry; "MIM" refers to monoisotopic mass; "min" refers to minutes; "NMP" refers to N-methylpyrrolidinone; "TLC" refers to thin layer chromatography; "Rf" refers to Retention factor; "RT" refers to retention time; "SCX" refers to strong cation exchange; "TFA" refers to trifluoroacetic acid; "THF" refers to tetrahydrofuran; and "TBME" refers to tert-Butyl methyl ether.

The compounds of the invention may be synthesised by analogy with the following reaction route.

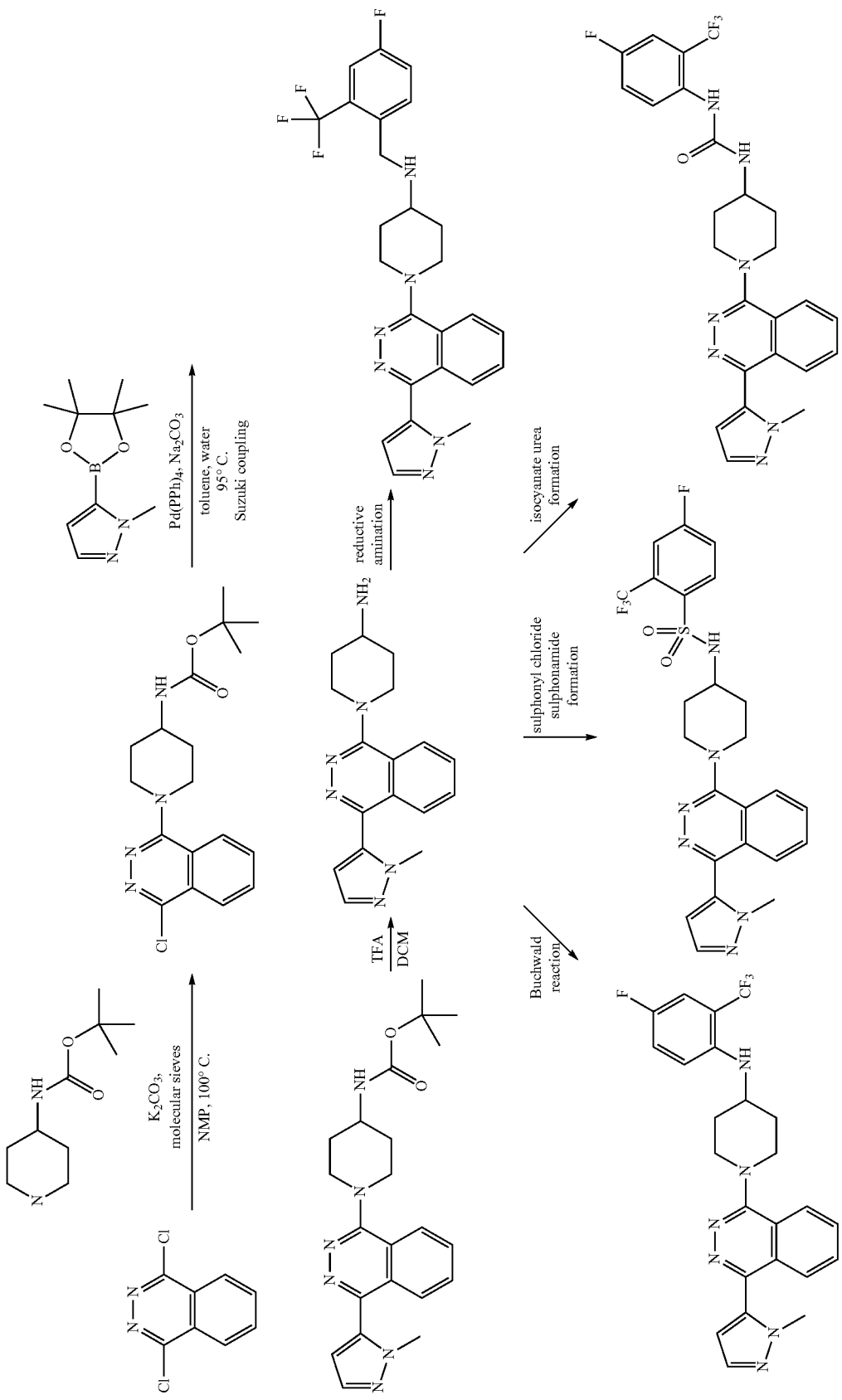

The steps within the route shown above may be performed in the order shown above or in a different order. For example, as the skilled person would appreciate, the Suzuki coupling could be carried out after the reductive amination or after the urea formation etc. Protecting groups may be present or absent as necessary. For example a nitrogen atom may be protected or unprotected.

Solvents, reagents and starting materials were purchased from commercial vendors and used as received unless otherwise described. All reactions were performed at room temperature unless otherwise stated. Compound identity and purity confirmations were performed by LCMS UV using a Waters Acquity SQ Detector 2 (ACQ-SQD2#LCA081). The diode array detector wavelength was 254 nM and the MS was in positive and negative electrospray mode (m/z: 150-800). A 2 µL aliquot was injected onto a guard column (0.2 µm×2 mm filters) and UPLC column (C18, 50×2.1 mm, <2 µm) in sequence maintained at 40° C. The samples were eluted at a flow rate of 0.6 mL/min with a mobile phase system composed of A (0.1% (v/v) Formic Acid in Water) and B (0.1% (v/v) Formic Acid in Acetonitrile) according to the gradients outlined in Table 1 below. Retention times RT are reported in minutes.

TABLE 1

| Time (min) | % A | % B |
|---|---|---|
| Method 1 | | |
| 0 | 95 | 5 |
| 1.1 | 95 | 5 |
| 6.1 | 5 | 95 |
| 7 | 5 | 95 |
| 7.5 | 95 | 5 |
| 8 | 95 | 5 |
| Method 2 | | |
| 0 | 95 | 5 |
| 0.3 | 95 | 5 |
| 2 | 5 | 95 |
| 2.6 | 95 | 5 |
| 3 | 95 | 5 |

NMR was also used to characterise final compounds. NMR spectra were obtained on a Bruker AVIII 400 Nanobay with 5 mm BBFO probe. Optionally, compound Rf values on silica thin layer chromatography (TLC) plates were measured.

Compound purification was performed by flash column chromatography on silica or by preparative LCMS. LCMS purification was performed using a Waters 3100 Mass detector in positive and negative electrospray mode (m/z: 150-800) with a Waters 2489 UV/Vis detector. Samples were eluted at a flow rate of 20 mL/min on a XBridge™ prep C18 5 µM OBD 19×100 mm column with a mobile phase system composed of A (0.1% (v/v) Formic Acid in Water) and B (0.1% (v/v) Formic Acid in Acetonitrile) according to the gradient outlined in Table 2 below.

TABLE 2

| Time (min) | % A | % B |
|---|---|---|
| 0 | 90 | 10 |
| 1.5 | 90 | 10 |
| 11.7 | 5 | 95 |
| 13.7 | 5 | 95 |
| 14 | 90 | 90 |
| 15 | 90 | 90 |

Chemical names in this document were generated using mol2nam—Structure to Name Conversion by OpenEye Scientific Software. Starting materials were purchased from commercial sources or synthesised according to literature procedures.

Certain starting materials in the synthesis of compounds of formula (I) can be produced by the following procedures:

Procedure A

Pyrido[3,4-d]pyridazine-1,4-diol

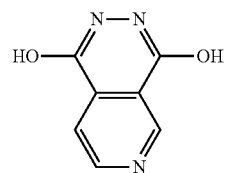 [SMILES: Oc1nnc(O)c2cnccc12]

Pyridine-3,4-dicarboxylic acid (3.10 g, 18.6 mmol) and acetic anhydride (7.0 mL, 74.2 mmol) were added to a 50 mL round bottomed flask and heated to reflux at 140° C. The white suspension turned into a black solution. The reaction was heated at this temperature for 3 hours. The reaction was cooled and the acetic anhydride was taken off by rotary evaporation to afford crude 3,4-pyridinedicarboxylic anhydride (2.68 g, 18.0 mmol, 97%) as brown crystals which was taken onto the next step without further purification.

To a round bottomed flask were added 3,4-pyridinedicarboxylic anhydride (690 mg, 4.6 mmol) and acetic acid (8.9 mL). To this was added hydrazine hydrate (1.6 mL, 18.5 mmol) dropwise with ice bath cooling. The yellow suspension was refluxed at 100° C. overnight. Analytical LCMS indicated formation of product and the reaction was cooled. The resultant cream solid was filtered and washed with water. The product was then dried by rotary evaporation to afford pyrido[3,4-d]pyridazine-1,4-diol (600 mg, 3.7 mmol, 79.5%).

$^1$H NMR (400 MHz, d6 DMSO) δ/ppm: 11.9 (s (br), 2H), 9.34 (s (br), 1H), 9.03 (d, J 5.3 Hz, 1H), 7.90 (s (br), 1H).

MS Method 2: RT: 0.54 min, ES$^+$ m/z 164.0 [M+H]$^+$.

1,4-Dichloropyrido[3,4-d]pyridazine

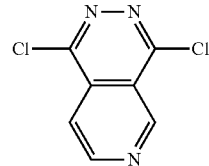 [SMILES: Clc1nnc(Cl)c2cnccc12]

Pyrido[3,4-c]pyridazine-1,4-diol (1.83 g, 11.2 mmol) and phosphorus oxychloride (8.4 mL, 89.7 mmol) were added to a round bottomed flask. To this was added DIPEA (2.0 mL, 11.2 mmol) slowly. The suspension was then heated for 1 hour at 100° C. The reaction turned into a brown solution. The phosphorus oxychloride was then removed by rotary evaporator. The resulting brown residue was dissolved in DCM and added dropwise to a mixture of ice and saturated NaHCO$_3$ solution (aq). Saturated NaHCO$_3$ solution (aq) was added until the aqueous layer was neutral. The organic and aqueous layers were separated and the aqueous layer was further extracted with DCM (500 mL). The organic layers were combined and dried (MgSO₄) and then concentrated in vacuo to afford 1,4-dichloropyrido[3,4-c]pyridazine (1.74 g, 8.7 mmol, 77.6%).

¹H NMR (400 MHz, CDCl₃) δ/ppm: 9.78 (d, J 0.9 Hz, 1H), 9.27 (d, J 5.7 Hz, 1H), 8.09 (dd, J 5.7 Hz, 0.9 Hz, 1H).

MS Method 2: RT: 1.16 min, ES⁺ m/z 200.0/202.0 [M+H]⁺.

Similarly prepared were:

1,4-Dichloro-6,7-dihydro-5H-cyclopenta[c]pyridazine

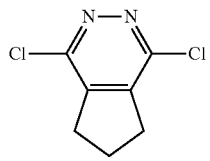 [SMILES: Clc1nnc(Cl)c2c1CCC2]

¹H NMR (400 MHz, CDCl₃) δ/ppm: 3.13 (t, J 7.8 Hz, 2H), 2.27 (m, J 7.8 Hz, 4H).

3,6-Dichloro-4,5-dimethyl-pyridazine

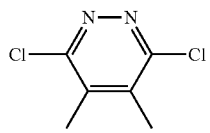

¹H NMR (400 MHz, CDCl₃) δ/ppm: 2.46 (s, 6H).

Procedure B

Preparation of 1-[4-(2-methylpyrazol-3-yl)phthalazin-1-yl]piperidin-4-amine and related compounds, intermediates in the synthesis of compounds of formula (I)

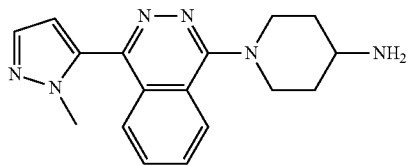 [SMILES: Cn1nccc1-c1nnc(N2CCC(N)CC2)c2ccccc12]

tert-Butyl N-[1-(4-chlorophthalazin-1-yl)-4-piperidyl]carbamate

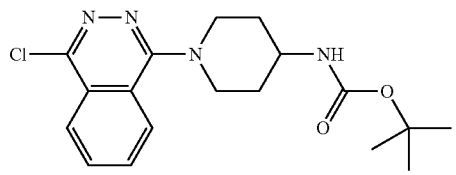 [SMILES: CC(C)(C)OC(=O)NC1CCN(c2nnc(Cl)c3ccccc23)CC1]

1,4 Dichlorophthalazine (4.80 g, 24.1 mmol) and 4-Boc-aminopiperidine (5.00 g, 25.0 mmol) were combined in NMP at room temperature and potassium carbonate (3.67 g, 26.5 mmol) was added followed by activated molecular sieves. Then the reaction was heated to 100° C. overnight. The reaction was cooled to room temperature and poured over ice water, creating an off white semisolid precipitate. The products were extracted into ethyl acetate (×3) and then back washed with more water. The combined organics were washed with brine, dried (MgSO₄) and then concentrated in vacuo to afford tert-butyl N-[1-(4-chlorophthalazin-1-yl)-4-piperidyl]carbamate (7.08 g 19.5 mmol, 80%) as an off white/fawn coloured amorphous solid.

¹H NMR (400 MHz, CDCl₃) δ/ppm: 8.27-8.22 (m, 1H), 8.06-8.01 (m, 1H), 7.94-7.88 (m, 2H), 4.59 (s (br), 1H), 3.87 (m (br), 2H), 3.79 (s (br), 1H), 3.25 (m (br), 2H), 2.2-2.13 (m, 2H), 1.80-1.68 (m, 2H), 1.49 (s, 9H).

MS Method 1: RT: 3.94 min, ES⁺ m/z 363.3 [M+H]⁺ tert-Butyl N-[1-[4-(2-methylpyrazol-3-yl)phthalazin-1-yl]-4-piperidyl]carbamate

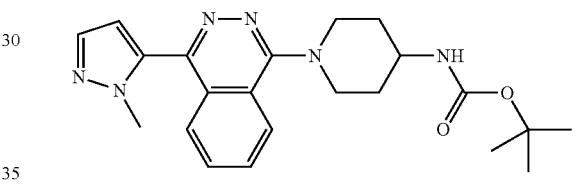

tert-Butyl N-[1-(4-chlorophthalazin-1-yl)-4-piperidyl]carbamate (2.0 g, 5.5 mmol) was dissolved in toluene (45 mL) (required heating) and a solution of catalyst generated from triphenylphosphine (0.52 g, 2.0 mmol) and palladium acetate (112 mg, 0.5 mmol) in toluene (5 mL) and ethanol (15 mL) was added. 1-Methyl-1H-pyrazole-5-boronic acid, pinacolester (1.67 g, 8.0 mmol) was then added followed by water (15 mL) and the sodium carbonate (1.75 g 16.5 mmol). The solution was de-gassed under vacuum and purged with nitrogen three times before heating to 95° C. overnight. LCMS confirmed the presence of the desired product hence the reaction was cooled to room temperature and diluted with ethyl acetate and water. The organic and aqueous layers were separated and the organic layer washed with brine, dried (MgSO₄) and then concentrated in vacuo to afford a dark brown oil/gum. Purification by silica flash chromatography using 10% 3M NH₃/MeOH: 30% ethyl acetate: 60% heptane afforded tert-butyl N-[1-[4-(2-methylpyrazol-3-yl)phthalazin-1-yl]-4-piperidyl]carbamate (1.99 g 4.87 mmol, 88%) as an off-white solid.

¹H NMR (400 MHz, CDCl₃) δ/ppm: 8.11-8.06 (m, 2H), 7.90-7.81 (m, 2H), 7.67 (d, J 1.9 Hz, 1H), 6.60 (d, J 1.9 Hz, 1H), 4.61 (s (br), 1H), 4.07 (s, 3H), 4.00 (m (br), 2H), 3.82 (s (br), 1H), 3.32 (m (br), 2H), 2.24-2.17 (m, 2H), 1.84-1.73 (m, 2H), 1.50 (s, 9H).

MS Method 1: RT: 3.65 min, ES⁺ m/z 409.4 [M+H]⁺

1-[4-(2-Methylpyrazol-3-yl)phthalazin-1-yl]piperidin-4-amine

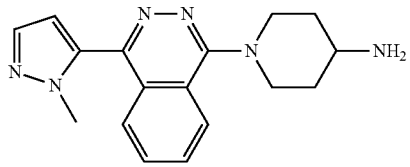 [SMILES: Cn1nccc1-c1nnc(N2CCC(N)CC2)c2ccccc12]

A solution containing tert-butyl N-[1-[4-(2-methylpyrazol-3-yl)phthalazin-1-yl]-4-piperidyl]carbamate (6.0 g, 14.7 mmol) and trifluoroacetic acid (12.6 mL, 176 mmol) in DCM (40 mL) was prepared and stirred overnight. The reaction mixture was concentrated in vacuo. The crude material was purified by SCX with MeOH washings followed by 2M $NH_3$ in MeOH to elute the product. The resulting solution was concentrated under reduced pressure to afford 1-[4-(2-methylpyrazol-3-yl)phthalazin-1-yl]piperidin-4-amine (2.82 g, 9.1 mmol, 62% yield) as an oil.

$^1$H NMR (400 MHz, CDCl$_3$) δ/ppm: 8.11-8.02 (m, 2H), 7.88-7.78 (m, 2H), 7.65 (d, J 1.9 Hz, 1H), 6.58 (d, J 1.9 Hz, 1H), 4.04 (s, 3H), 4.00 (m (br), 2H), 3.22 (m (br), 2H), 3.02 (tt, J 10.5 hz, 4.2 Hz 1H), 2.10-2.01 (m, 2H), 1.77-1.67 (m, 2H).

MS Method 2: RT: 0.91 min. m/z 309.2 [M+H]$^+$

Similarly prepared was:

N-Methyl-1-[1-(2-methylpyrazol-3-yl)pyrido[3,4-d]pyridazin-4-yl]piperidin-4-amine

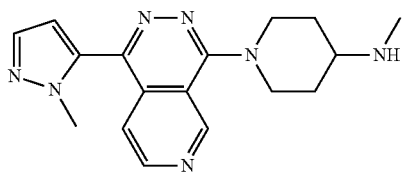 [SMILES: CNC1CCN(c2nnc(-c3ccnn3C)c3ccncc23)CC1]

To a round bottomed flask were added tert-butyl piperidin-4-ylmethylcarbamate (0.29 mL, 55 mmol), 1,4-dichloropyrido[3,4-c]pyridazine (13.48 mL, 50 mmol), N,N-diisopropylethylamine (26 mL, 150 mmol), NMP (50 mL) and heated to 100° C. for 1 hour. The reaction was diluted with EtOAc and washed with water (5×100 mL). The organic layer was dried over sodium sulphate, filtered and concentrated in vacuo. The resulting residue was purified by silica flash chromatography using 30% EtOAc in heptane using a slow isocratic elution and concentrated in vacuo to afford the major regioisomer tert-butyl N-[1-(1-chloropyrido[3,4-d]pyridazin-4-yl)-4-piperidyl]-N-methyl-carbamate (1.1 g, 2.9 mmol, 5.8%, 98% purity). Further mixed fractions of lower purity were also obtained.

$^1$H NMR (400 MHz, CDCl$_3$) δ/ppm: 9.46 (s, 1H), 9.03 (d, J 5.6 Hz, 1H), 7.94 (d, J 5.6 Hz, 1H), 4.33 (m (br), 1H), 4.22-4.12 (m (br), 2H), 3.29 (t, J 12.5 Hz, 2H), 2.83 (s, 3H), 2.11-1.97 (m, 2H), 1.90-1.81 (m, 2H), 1.50 (s, 9H).

MS Method 2: RT: 1.73 min. m/z 378.9[M+H]$^+$

Split between 2×10-20 mL microwave vials was added tert-butyl N-[1-(1-chloropyrido[3,4-d]pyridazin-4-yl)-4-piperidyl]-N-methyl-carbamate (2.03 g, 5.38 mmol), toluene (12 mL), ethanol (8 mL), water (4 mL), 1-methyl-1H-pyrazole-5-boronic acid, pinacolester (1.57 g, 7.53 mmol) and sodium carbonate (1.09 g, 10.8 mmol. The mixture was purged with nitrogen for 10 minutes. To the reaction vials was then added Palladium (0) tetrakis(triphenylphosphine) (935 mg, 0.81 mmol) and the vials were immediately capped and heated in the microwave for 1 hour at 150° C. The contents of the vials were combined and diluted with EtOAc and partitioned with water. The organic layer was washed with 3×50 mL of water. The organic layer was dried over sodium sulphate, filtered and then concentrated to give a brown oil. The resulting residue was then purified by silica flash chromatography using 0% EtOAc in heptane to 90% ethyl acetate in heptane followed by a slow isocratic elution at 90% ethyl acetate in heptane to afford tert-butyl N-methyl-N-[1-[1-(2-methylpyrazol-3-yl)pyrido[3,4-d]pyridazin-4-yl]-4-piperidyl]carbamate (1.50 g, 3.54 mmol, 65.9%) $^1$H NMR (400 MHz, CDCl$_3$) δ/ppm: 9.54 (s, 1H), 8.96 (d, J5.7 Hz, 1H), 7.87 (d, J5.7 Hz, 1H), 7.69 (d, J2.0 Hz, 1H), 6.63 (d, J2.0 Hz, 1H), 4.49-4.27 (m (br), 3H), 4.12 (s, 3H), 3.38 (t, J12.5 Hz, 2H), 2.85 (s, 3H), 2.15-2.01 (m, 2H), 1.95-1.87 (m, 2H).

MS Method 2: RT: min. m/z 378.9[M+H]$^+$

To a round bottomed flask was added tert-butyl N-methyl-N-[1-[1-(2-methylpyrazol-3-yl)pyrido[3,4-d]pyridazin-4-yl]-4-piperidyl]carbamate (1.50 g, 3.54 mmol) and trifluoroacetic acid (4. mL, 52 mmol) and stirred at room temperature for 2 hours. The reaction was concentrated in vacuo and the resulting red oil was purified by SCX with MeOH washings followed by 2M $NH_3$ in MeOH to elute the product. The resulting solution was concentrated under reduced pressure to afford N-methyl-1-[1-(2-methylpyrazol-3-yl)pyrido[3,4-d]pyridazin-4-yl]piperidin-4-amine (947 mg, 2.93 mmol, 82.7%).

$^1$H NMR (400 MHz, CDCl$_3$) δ/ppm: 9.53 (d, J0.9 Hz, 1H), 8.95 (d, J5.7 Hz, 1H), 7.85 (dd, J5.7 Hz, 0.9 Hz, 1H), 7.69 (d, J2.0 Hz, 1H), 6.62 (d, J2.0 Hz, 1H), 4.26-4.18 (m, 2H), 4.11 (s, 3H), 3.42-3.34 (m, 2H), 2.77 (tt, J 10.1 hz, 4.0 Hz, 1H), 2.55 (s, 3H), 2.23-2.14 (m, 2H), 1.79-1.67 (m, 2H).

MS Method 2: RT: 0.87 min. m/z 324.2[M+H]$^+$

And similarly prepared was:

1-[4,5-dimethyl-6-(2-methylpyrazol-3-yl)pyridazin-3-yl]-N-methyl-piperidin-4-amine

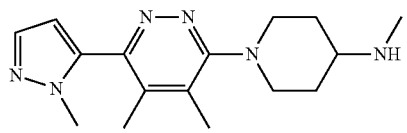

tert-Butyl piperidin-4-ylmethylcarbamate (3.81 g, 17.8 mmol), 3,6-dichloro-4,5-dimethyl-pyridazine (3.0 g, 17.0 mmol), NMP (14 mL) and N,N-Diisopropylethylamine (4.43 mL, 25.4 mmol) were added to a round bottom flask and heated to 150° C. for 5 h. The mixture was partitioned between EtOAc (100 mL) and 1M Na$_2$CO$_3$ aq. (50 mL). The organic layer was washed with 1M Na$_2$CO$_3$ aq. (50 mL), water (2×70 mL), brine (70 mL), before passage through a hydrophobic frit and concentrated in vacuo to give an orange/brown solid. The crude material was purified by silica flash chromatography using 0% EtOAc in heptane with tri ethylamine 1% with a gradient increasing to 30% ethyl acetate. Fractions containing product were combined and concentrated in vacuo to afford tert-butyl N-[1-(6- chloro-4,5-dimethyl-pyridazin-3-yl)-4-piperidyl]-N-methyl-carbamate (1.8 g, 5.1 mmol, 30% yield).

¹H NMR (400 MHz, CDCl₃) δ/ppm: 4.34-3.84 (m, 2H), 3.56-3.47 (m (br), 2H), 3.00 (t (br), J12.0 Hz, 2H), 2.78 (s, 3H), 2.31 (s, 3H), 2.25 (s, 3H), 1.93-1.80 (m, 2H), 1.78-1.71 (m (br), 2H), 1.47 (s, 9H).

MS Method 2: RT: 1.88 min, m/z 355.9 [M+H]⁺

The reaction was carried out in 3×20 mL microwave tubes: 1-methyl-1H-pyrazole-5-boronic acid, pinacolester (5.28 g, 25.4 mmol), tert-butyl N-[1-(6-chloro-4,5-dimethyl-pyridazin-3-yl)-4-piperidyl]-N-methyl-carbamate (6.0 g, 16.9 mmol), palladium(0) tetrakis(triphenylphosphine) (0.98 g, 0.85 mmol) were combined in 1,2-dimethoxyethane (30. mL, 16.91 mmol) and a solution of potassium hydrophosphate (5.9 g, 33.8 mmol in 15 mL water) was added, The vessels were sealed, the reaction mixture degassed with nitrogen and heated to 120° C. in the microwave for 2 hrs. Further 1-methyl-1H-pyrazole-5-boronic acid, pinacolester (2.14 g, 12.7 mmol), palladium(0) tetrakis(triphenylphosphine) (0.49 g, 0.425 mmol) and potassium hydrophosphate (2.85 g, 16.9 mmol in 7.5 mL water) were added and the vessels were resealed, the reaction mixture was again degassed with nitrogen and heated to 120° C. in the microwave for 2 hrs. The reaction was cooled to room temperature, the organic and aqueous layers were separated and the aqueous layer was extracted with ethyl acetate (×3). The organic layers were combined, dried over brine and sodium sulphate. Filtered and evaporated in vacuo to a dark brown gum. The crude material was purified by silica flash chromatography using 100% heptane with a gradient to 40% ethyl acetate in heptane then an isocratic flow of 40% ethyl acetate in heptane for 4 column volumes before increasing the gradient to 100% ethyl acetate. Fractions containing the product were combined and evaporated in vacuo to afford tert-butyl N-[1-[4,5-dimethyl-6-(2-methylpyrazol-3-yl)pyridazin-3-yl]-4-piperidyl]-N-methyl-carbamate (5.2 g, 13 mmol, 76.8%)

¹H NMR (400 MHz, CDCl₃) δ/ppm: 7.56 (d, J1.9 Hz, 1H), 6.35 (d, J1.9 Hz, 1H), 4.36-3.93 (m (br), 1H), 3.92 (s, 3H), 3.68-3.61 (m (br), 2H), 3.09 (t, J12.1 Hz, 2H), 2.81 (s, 3H), 2.28 (s, 3H), 2.22 (s, 3H), 1.97-1.85 (m, 2H), 1.83-1.76 (m (br), 2H), 1.49 (s, 9H).

MS Method 2: RT: 1.66 min, m/z 401.3 [M+H]⁺

Trifluoroacetic acid (3.0 mL, 39.2 mmol) was added dropwise to a stirring solution of tert-butyl N-[1-[4,5-dimethyl-6-(2-methylpyrazol-3-yl)pyridazin-3-yl]-4-piperidyl]-N-methyl-carbamate (2.0 g, 4.99 mmol) in DCM (30 mL) at room temperature and the reaction was stirred for 2 h. Further TFA (0.8 mL) was added and the reaction was stirred overnight. The mixture was concentrated in vacuo and then the resulting residue was loaded onto a primed SCX-2 cartridge, which was eluted with methanol (5 CV) to remove impurities and then 1M NH₃/MeOH (2CV) to isolate the product. The latter fraction was concentrated in vacuo to afford an orange oil that solidified on standing, 1-[4,5-dimethyl-6-(2-methylpyrazol-3-yl)pyridazin-3-yl]-N-methyl-piperidin-4-amine (1.12 g, 3.73 mmol, 74.7% yield).

¹H NMR (400 MHz, CDCl₃) δ/ppm: 7.56 (d, J1.9 Hz, 1H), 6.35 (d, J1.9 Hz, 1H), 3.91 (s, 3H), 3.61-3.54 (m (br), 3H), 3.03 (t, J12.2 Hz, 2H), 2.61 (tt, J10.5 Hz, 4.3 Hz, 1H), 2.50 (s, 3H), 2.27 (s, 3H), 2.21 (s, 3H), 2.09-2.02 (m (br), 2H), 1.61-1.49 (m, 2H).

MS Method 2: RT: 0.92 min, m/z 301.2 [M+H]⁺

And similarly prepared were:

N-methyl-1-[4-(2-methylpyrazol-3-yl)phthalazin-1-yl]piperidin-4-amine

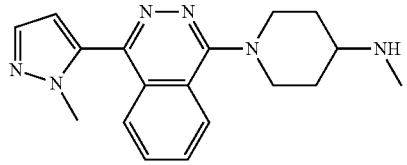 [SMILES: CNC1CCN(c2nnc(-c3ccnn3C)c3ccccc23)CC1]

¹H NMR (400 MHz, CDCl₃) δ/ppm: 8.10 (d, J 8.1 Hz, 1H), 8.08 (d, J 8.1 Hz, 1H), 7.90-7.80 (m, 2H), 7.67 (d, J 1.9 Hz, 1H), 6.60 (d, J 1.9 Hz, 1H), 4.07 (s, 3H), 4.07-4.01 (m (br), 2H), 3.28-3.20 (m (br), 2H), 2.73 (tt, J 10.5 Hz, 3.9 Hz, 1H), 2.55 (s, 3H), 2.20-2.13 (m, 2H), 1.78-1.67 (m, 2H).

1-[1-(2-Methylpyrazol-3-yl)-6,7-dihydro-5H-cyclopenta[d]pyridazin-4-yl]piperidin-4-amine

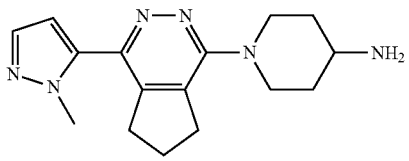 [SMILES: Cn1nccc1-c1nnc(N2CCC(N)CC2)c2c1CCC2]

¹H NMR (400 MHz, MeOD) δ/ppm: 7.56 (d, J 2.0 Hz, 1H), 6.55 (d, 1H), 4.14-4.08 (m (br), 2H), 4.02 (s, 3H), 3.11-3.02 (m, 4H), 3.00-2.92 (m, 3H), 2.17-2.10 (m, 2H), 2.03-1.96 (m, 2H), 1.59-1.48 (m, 2H).

MS Method 2: RT: 0.89 min m/z 299.3 [M+H]⁺ racemic [1-[4-(2-methylpyrazol-3-yl)phthalazin-1-yl]pyrrolidin-3-yl]methanamine

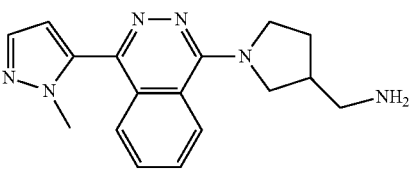 [SMILES: Cn1nccc1-c1nnc(N2CCC(CN)C2)c2ccccc12]

¹H NMR (400 MHz, MeOD) δ/ppm: 8.53-8.49 (m, 1H), 7.95-7.81 (m, 3H), 7.69 (d, J2.0 Hz, 1H), 6.63 (d, J2.0 Hz, 1H), 4.17-4.00 (m, 3H), 3.88 (s, 3H), 3.80 (dd, J10.8 Hz, 8.0 Hz, 1H), 2.87 (d, J7.0 Hz, 2H), 2.58-2.46 (m, 1H), 2.33-2.25 (m, 1H), 1.91-1.80 (m, 1H).

MS Method 2: RT: 0.60 min m/z 309.2 [M+H]⁺

Also prepared was:

1-(4-morpholinophthalazin-1-yl)piperidin-4-amine

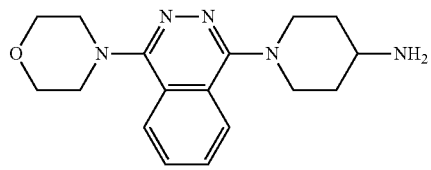

tert-Butyl N-[1-(4-chlorophthalazin-1-yl)-4-piperidyl]carbamate (150. mg, 0.4100 mmol), morpholine (0.05 mL, 0.62 mmol) and triethylamine (0.07 mL, 0.50 mmol) were dissolved in NMP (0.50 mL) and heated in microwave at 150° C. for 1 hour. LCMS. Water (5 mL) was added resulting in the precipitation of a white solid, the suspension was stirred rapidly for 10 minutes before filtering, the collected solid was washed with more water and dried under suction to yield tert-butyl N-[1-(4-morpholinophthalazin-1-yl)-4-piperidyl]carbamate (140 mg, 0.3386 mmol, 81.898% yield). as an off white solid.

$^1$H NMR (400 MHz, CDCl$_3$) δ/ppm: 8.07-7.98 (m, 2H), 7.80-7.75 (m, 2H), 4.56 (s (br), 1H), 3.99-3.95 (m, 4H), 3.78-3.70 (m, 3H), 3.46-3.41 (m, 4H), 3.16 (t, J12.0 Hz, 2H), 2.17-2.08 (m, 2H), 1.78-1.67 (m, 2H), 1.47 (s, 9H)

MS Method 2: RT: 1.29 min, m/z 414.4 [M+H]$^+$ tert-Butyl N-[1-(4-morpholinophthalazin-1-yl)-4-piperidyl]carbamate (140 mg, 0.34 mmol) was dissolved in DCM (3 mL) and trifluoroacetic acid (0.26 mL, 3.39 mmol) was added. The solution was stirred for 1 hour. The reaction mixture was concentrated in vacuo to a brown oil which was desalted on a 5 g SCX cartridge washing with methanol then eluting with 10% (7M NH$_3$ in MeOH) in MeOH to afford 1-(4-morpholinophthalazin-1-yl)piperidin-4-amine (106 mg, 0.34 mmol, 99.9% yield) as a white solid.

$^1$H NMR (400 MHz, CDCl$_3$) δ/ppm: 8.08-8.04 (m, 2H), 7.82-7.77 (m, 2H), 4.01-3.98 (m, 4H), 3.83-3.76 (m (br), 2H), 3.48-3.44 (m, 4H), 3.11 (t, J12.5 Hz, 2H), 2.98 (tt, J10.5 Hz, 4.4 Hz, 1H), 2.07-2.00 (m (br), 2H), 1.76-1.65 (m, 2H).

MS Method 2: RT: 0.78 min, m/z 314.3 [M+H]$^+$

Procedure C

Preparation of N-[[4-Fluoro-2-(trifluoromethyl)phenyl]methyl]-N-methyl-piperidin-4-amine an intermediate in the synthesis of compounds of formula (I)

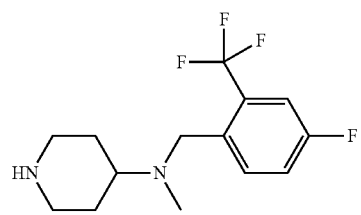 [SMILES: CN(Cc1ccc(F)cc1C(F)(F)F)C1CCNCC1]

1-Boc-4-(methylamino)piperidine (800 mg, 3.7 mmol), and 4-fluoro-2-(trifluoromethyl)benzaldehyde (0.56 mL, 4.1 mmol) were dissolved in DCM (12 mL) (plus molecular sieves) and stirred for 2 hours at room temperature. To the clear solution was added sodium triacetoxyborohydride (1.18 g, 5.6 mmol) and the reaction was stirred over the weekend at room temperature. The reaction was diluted with DCM and then quenched with saturated NaHCO$_3$ solution (aq). The organic and aqueous layers were separated and the aqueous layer further extracted with DCM. The organic layers were combined and concentrated in vacuo to give 1.6 g of crude product as a yellow oil. Purification by silica flash chromatography using 0% EtOAc in heptane with a gradient increasing to 50% ethyl acetate afforded tert-butyl 4-[[4-fluoro-2-(trifluoromethyl)phenyl]methyl-methyl-amino]piperidine-1-carboxylate (1.15 g, 2.9 mmol, 79%) as a pale yellow/clear oil.

tert-Butyl 4-[[4-fluoro-2-(trifluoromethyl)phenyl]methyl-methyl-amino]piperidine-1-carboxylate (1.15 g, 2.95 mmol) and trifluoroacetic acid (4.5 mL, 58.9 mmol) were combined and stirred at room temperature for 4 hours. The solution turned from to clear to light pink. The reaction was concentrated in vacuo and the resulting pink oil was dissolved in methanol and loaded onto a methanol primed SCX cartridge and washed with methanol (×3 column volumes) and triethylamine in methanol (×3 column volumes). The triethylamine wash was then concentrated in vacuo to afford N-[[4-fluoro-2-(trifluoromethyl)phenyl]methyl]-N-methyl-piperidin-4-amine (750 mg, 2.6 mmol, 88%).

$^1$H NMR (400 MHz, CDCl$_3$) δ/ppm: 7.84 (dd, J 8.5 Hz, 5.8 Hz 1H), (dd, J 5.8 Hz, 2.7 Hz 1H), 7.22 (td, J 8.5 Hz, 2.7 Hz, 1H), 3.73 (s (br), 2H), 3.24-3.18 (m (br), 2H), 2.85 (s (br), 1H), 2.63 (td, J12.2 Hz, 2.4 Hz, 2H), 2.56 (tt, J 11.5 Hz, 3.6 Hz, 1H), 2.22 (s, 3H), 1.89-1.82 (m (br), 2H), 1.56 (qd, J 12.1 Hz, 3.9 Hz, 2H)

MS Method 2: RT: 0.73 min, m/z 291.3 [M+H]$^+$

Similarly prepared was:

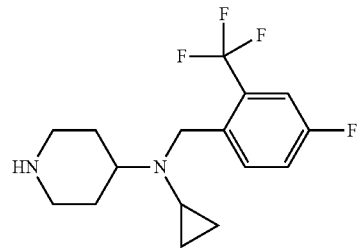 [SMILES: Fc1ccc(CN(C2CCNCC2)C2CC2)c(C(F)(F)F)c1]

MS Method 2: RT: 1.34 min, m/z 317.3 [M+H]$^+$

Procedure D

Preparation of 2,2,2-trifluoro-N-[[4-fluoro-2-(trifluoromethyl)phenyl]methyl]-N-(4-piperidyl)acetamide hydrochloride an intermediate in the synthesis of compounds of formula (I)

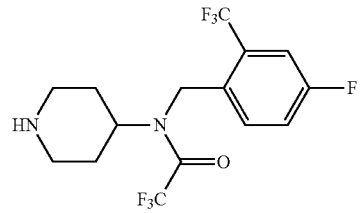 [SMILES: O=C(N(Cc1ccc(F)cc1C(F)(F)F)C1CCNCC1)C(F)(F)F]

tert-butyl 4-[[4-fluoro-2-(trifluoromethyl)benzoyl]amino]piperidine-1-carboxylate

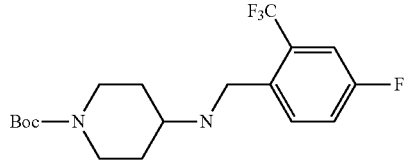 [SMILES: CC(C)(C)OC(=O)N1CCC(NCc2ccc(F)cc2C(F)(F)F)CC1]

4-Fluoro-2-(trifluoromethyl)phenyl]methanamine (28.0 g, 145 mmol) and 1-Boc-4-piperidone (28.9 g, 145 mmol) were mixed in dry toluene (250 mL). The reaction was flushed with nitrogen and stirred at room temperature under an atmosphere of nitrogen for 30 min before heating overnight under dean stark conditions to distil off the water formed. The reaction was cooled and concentrated in vacuo to give a dark orange oil. The crude oil was taken up in methanol (250 mL) and sodium borohydride (25 g, 290 mmol) was added portionwise over ten minutes with ice bath cooling. The reaction was then allowed to warm to room temperature and stirred for 3 days and left to stand for 1 day. The methanol was concentrated in vacuo and the residue partitioned between ethyl acetate and water and stirred. Solid ammonium chloride was added to aid separation. The aqueous layer was extracted with ethyl acetate and the combined organics were further washed with water then brine, then dried (MgSO$_4$), filtered then concentrated in vacuo to afford an orange oil (55 g). The crude material was purified by silica flash chromatography using 10% ethyl acetate in heptane with a gradient increasing to 100% ethyl acetate to afford tert-butyl 4-[[4-fluoro-2-(trifluoromethyl)benzyl]amino]piperidine-1-carboxylate (24.58 g, 65 mmol, 55%) as a yellow oil.

$^1$H NMR (400 MHz, CDCl$_3$) δ/ppm: 7.68 (dd, J 8.4 Hz, 5.6 Hz, 1H), 7.35 (dd, J 5.0, 2.5, 1H), 7.24 (td, J 8.4 Hz, 2.5 Hz, 1H), 4.03 (s (br), 2H), 3.95 (s, 2H), 2.84 (t (br), J 12.1 Hz, 2H), 2.69 (tt, J 10.9 Hz, 3.1 Hz, 1H), 1.92-1.84 (m, 1H), 1.48 (s, 9H), 1.37-1.25 (m, 4H).

tert-butyl 4-[[4-fluoro-2-(trifluoromethyl)phenyl]methyl-(2,2,2-trifluoroacetyl)amino]piperidine-1-carboxylate

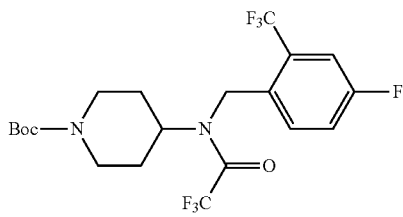

tert-Butyl 4-[[4-fluoro-2-(trifluoromethyl)phenyl]methylamino]piperidine-1-carboxylate (1.87 g, 4.97 mmol) and triethylamine (1.38 mL, 9.94 mmol) were dissolved in DCM (40 mL) and the reaction mixture cooled to 0° C. Trifluoroacetic anhydride (0.69 mL, 4.97 mmol) was added dropwise and the mixture was gradually allowed to warm to room temperature over 2 hours. The reaction mixture was washed with water (3×20 mL) then with brine (30 mL). The organics were dried (MgSO$_4$), filtered then concentrated in vacuo to give a yellow oil (2.3 g). This was purified using silica flash column chromatography eluting using 0% ethyl acetate in heptane with a gradient increasing to 50% ethyl acetate to afford tert-butyl 4-[[4-fluoro-2-(trifluoromethyl)phenyl]methyl-(2,2,2-trifluoroacetyl)amino]piperidine-1-carboxylate (1.47 g, 3.11 mmol, 63% yield) as a pale straw coloured oil.

$^1$H NMR (400 MHz, CDCl$_3$) δ/ppm: 7.45-7.40 (m, 1H), 7.39-7.34 (m, 0.3H, rotamer), 7.32-7.26 (m, 0.3H, rotamer), 7.22 (td, J 8.1 Hz, 2.4 Hz, 0.7H, rotamer), 7.11 (dd, J 8.5 Hz, 5.2 Hz, 0.7H, rotamer), 4.77 (s, 2H), 4.36-4.04 (m, 3H), 2.74 (s (br), 2H), 1.73-1.54 (m, 4H), 1.46 (s, 6.3H), 1.45 (s, 2.7H, rotamer).

2,2,2-trifluoro-N-[[4-fluoro-2-(trifluoromethyl)phenyl]methyl]-N-(4-piperidyl)acetamide hydrochloride

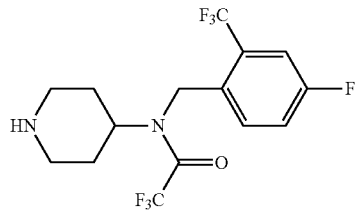

tert-Butyl 4-[[4-fluoro-2-(trifluoromethyl)phenyl]methyl-(2,2,2-trifluoroacetyl)amino]piperidine-1-carboxylate (1.47 g, 3.11 mmol) was taken up in a solution of 4M hydrogen chloride in dioxane (10 mL, 40 mmol) and stirred at room temperature for 90 min. The excess hydrogen chloride and solvent were removed in vacuo and the resulting solid was washed twice with DCM to remove any traces of HCl to afford 2,2,2-trifluoro-N-[[4-fluoro-2-(trifluoromethyl)phenyl]methyl]-N-(4-piperidyl)acetamide hydrochloride (1.5 g, 3.67 mmol, quantitative) as an off-white solid. This was used without further purification.

$^1$H NMR (400 MHz, CDCl$_3$) δ/ppm: 9.96-9.60 (m, 2H), 7.48-7.40 (m, 1H), 7.34-7.26 (m, 1H, rotamers), 7.25-7.17 (m, 0.5H, rotamer), 7.06-7.01 (m, 0.5H, rotamer), 4.82 (s, 2H), 4.36-4.14 (m, 1H), 3.61-3.49 (m, 2H), 3.03-2.83 (m, 2H), 2.39-2.25 (m, 2H), 1.90 (dd, J 23.2 Hz, 13.8 Hz, 2H).

MS Method 2: RT: 1.25 min, m/z 373.2 [M+H]$^+$

Compounds produced in the Procedures described above may take part in reactions to produce compounds of the invention, such as those exemplified below.

Example 1

Compounds produced in Procedure B described above can be used in the preparation of N-[[4-fluoro-2-(trifluoromethyl)phenyl]methyl]-1-[4-(2-methylpyrazol-3-yl)phthalazin-1-yl]piperidin-4-amine a compound of formula (I).

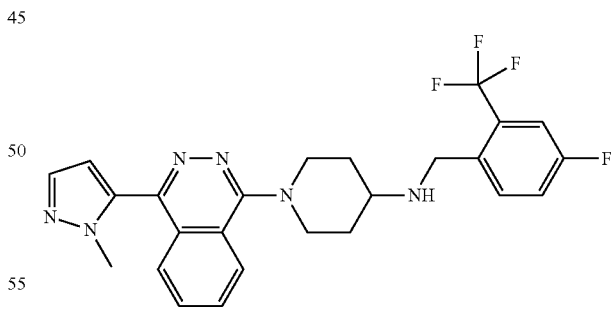

1-[4-(2-Methylpyrazol-3-yl)phthalazin-1-yl]piperidin-4-amine (228 mg, 0.74 mmol) and 4-fluoro-2-(trifluoromethyl)benzaldehyde (142 mg, 0.74 mmol) were added to Methanol (15 mL). Molecular sieves were added and the reaction mixture stirred at room temperature under an atmosphere of nitrogen overnight. The reaction mixture was filtered and the resulting reaction mixture passed through the H-Cube using a 10% Pd/C CatCart cartridge at 1.0 mL/min at 40° C. The crude material was purified in the silica flash chromatography eluting with 0% DCM-heptane with a gradient increasing to 25% DCM followed by 0% MeOH-DCM with a gradient increasing to 10% MeOH. Fractions containing the product were combined and concentrated in vacuo to give an off white solid. This material was further purified by flash column chromatography eluting with 0% MeOH-DCM with a gradient to 5% MeOH to afford N-[[4-fluoro-2-(trifluoromethyl)phenyl]methyl]-1-[4-(2-methylpyrazol-3-yl)phthalazin-1-yl]piperidin-4-amine (100 mg, 0.21 mmol, 28%) as an off white solid.

$^1$H NMR (400 MHz, CDCl$_3$) δ/ppm: 8.12 (d, J 8.1 Hz, 1H), 8.06 (d, J 8.1 Hz, 1H), 7.90-7.80 (m, 2H), 7.77 (d, J 8.4 Hz, 5.6 Hz, 1H), 7.67 (d, J 1.9 Hz, 1H), 7.39 (dd, J 9.1 Hz, 2.6 Hz, 1H), 7.3-7.25 (m, 1H), 6.60 (d, J 1.9 Hz, 1H), 4.07 (s, 3H), 4.05 (s, 2H), 4.07-4.01 (m, 2H), 3.30-3.22 (m, 2H), 2.97-2.88 (m, 1H), 2.22-2.15 (m, 2H), 1.85-1.75 (m, 2H).

MS Method 2: RT: 1.24 min, m/z 485.3 [M+H]$^+$

Example 2

The compound of Example 1 may be used as a starting material in the preparation of another compound of formula (I), N-[[4-fluoro-2-(trifluoromethyl)phenyl]methyl]-N-methyl-1-[4-(2-methylpyrazol-3-yl)phthalazin-1-yl]piperidin-4-amine.

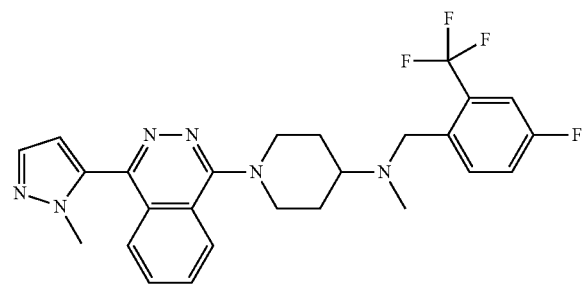 [SMILES: CN(Cc1ccc(F)cc1C(F)(F)F)C1CCN(c2nnc(-c3ccnn3C)c3ccccc23)CC1]

N-[[4-Fluoro-2-(trifluoromethyl)phenyl]methyl]-1-[4-(2-methylpyrazol-3-yl)phthalazin-1-yl]piperidin-4-amine (23 mg, 0.05 mmol) and formaldehyde solution (36.5-38%) in water (0.01 mL, 0.24 mmol) were dissolved in methanol (5 mL) and stirred at room temperature for 1 hour. Sodium triacetoxyborohydride (30.3 mg, 0.14 mmol) was added and the reaction left to stir at room temperature overnight. LCMS analysis confirmed formation of product. The reaction mixture was concentrated under reduced pressure to give a crude oil. The crude material was dissolved in ethyl acetate (20 mL), washed with saturated NaHCO3 solution (aq) (10 mL), dried (MgSO4), filtered and concentrated under reduced pressure. Purification by SCX with MeOH washings followed by 2M NH3 in MeOH to elute the product afforded a colourless oil. The resulting colourless oil was dissolved in 1:1 MeCN:H2O and the solvent removed under vacuum to give N-[[4-fluoro-2-(trifluoromethyl)phenyl]methyl]-N-methyl-1-[4-(2-methylpyrazol-3-yl)phthalazin-1-yl]piperidin-4-amine (18.4 mg, 0.04 mmol, 77%) as a white crystalline solid.

1H NMR (400 MHz, CDCl$_3$) □/ppm: 8.14 (d, J 8.3 Hz, 1H), 8.07 (d, J 8.3 Hz, 1H), 7.90-7.81 (m, 3H), 7.68 (d, J 2.0 Hz, 1H), 7.37 (dd, J 9.1 Hz, 2.6 Hz, 1H), 7.29-7.23 (m, 1H), 6.61 (d, J 2.0 Hz, 1H), 4.17-4.11 (m (br), 2H), 4.08 (s, 3H), 3.83 (s, 2H), 3.24-3.16 (m (br), 2H), 2.85-2.77 (m, 1H), 2.32 (s, 3H), 2.11-1.93 (m, 4H).

MS Method 2: RT: 1.23 min, m/z 499.4 [M+H]$^+$

Example 3

The compound of Example 1 may be used as a starting material in the preparation of another compound of formula (I), N-[[4-Fluoro-2-(trifluoromethyl)phenyl]methyl]-N-[1-[4-(2-methylpyrazol-3-yl)phthalazin-1-yl]-4-piperidyl]acetamide

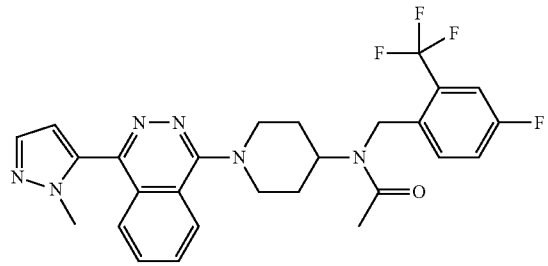 [SMILES: CC(=O)N(Cc1ccc(F)cc1C(F)(F)F)C1CCN(c2nnc(-c3ccnn3C)c3ccccc23)CC1]

N-[[4-Fluoro-2-(trifluoromethyl)phenyl]methyl]-N-[1-[4-(2-methylpyrazol-3-yl)phthalazin-1-yl]-4-piperidyl]acetamide was prepared from N-[[4-Fluoro-2-(trifluoromethyl)phenyl]methyl]-1-[4-(2-methylpyrazol-3-yl)phthalazin-1-yl]piperidin-4-amine (45 mg, 0.090 mmol) using acetylation methods known to those skilled in the art. The crude product was purified using silica flash chromatography eluting with 0% methanol in DCM with a gradient to 10% methanol to afford N-[[4-fluoro-2-(trifluoromethyl)phenyl]methyl]-N-[1-[4-(2-methylpyrazol-3-yl)phthalazin-1-yl]-4-piperidyl]acetamide (18.8 mg, 0.034 mmol, 38%) as an off white solid $^1$H NMR (400 MHz, CDCl$_3$) δ/ppm: 8.10-8.02 (m, 2H), 7.92-7.80 (m, 2H), 7.69-7.66 (m, 1H), 7.52-7.21 (m, 3H), 6.61-6.59 (m, 1H), 4.99-4.89 (m, 0.6H, rotamer), 4.85 (s, 0.8H, rotamer), 4.75 (s, 1.2H, rotamer), 4.12-4.02 (m, 2.4H, including rotamer), 4.06 (s, 3H), 3.35-3.16 (m, 2H), 2.42 (s, 1.2H, rotamer), 2.07 (s, 1.8H, rotamer), 2.14-1.84 (m, 4H).

MS Method 2: RT: 1.65 min, m/z 527.3 [M+H]$^+$

Example 4

Compounds produced in Procedure A and Procedure E described above can be used in the preparation of N-[[4-fluoro-2-(trifluoromethyl)phenyl]methyl]-1-[1-(2-methylpyrazol-3-yl)pyrido[3,4-d]pyridazin-4-yl]piperidin-4-amine a compound of formula (I).

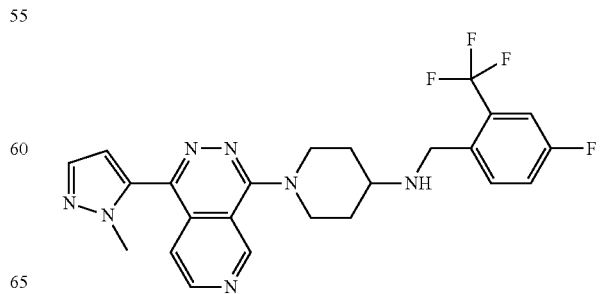

N-[1-(1-chloropyrido[3,4-c]pyridazin-4-yl)-4-piperidyl]-2,2,2-trifluoro-N-[[4-fluoro-2-(trifluoromethyl)phenyl]methyl]acetamide

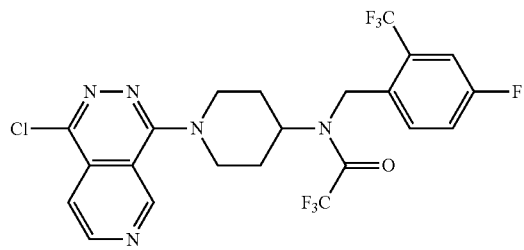 [SMILES: O=C(N(Cc1ccc(F)cc1C(F)(F)F)C1CCN(c2nnc(Cl)c3ccncc23)CC1)C(F)(F)F]

To a 50 mL round bottomed flask were added 1,4-dichloropyrido[3,4-d]pyridazine (200 mg, 1 mmol), potassium carbonate (0.37 mL, 2 mmol), 2,2,2-trifluoro-N-[[4-fluoro-2-(trifluoromethyl)phenyl]methyl]-N-(4-piperidyl)acetamide (409 mg, 1.1 mmol), NMP (3.0 mL) and the reaction was refluxed at 100° C. overnight. The reaction was cooled and diluted with ethyl acetate. The organic layer was washed with water (5×20 mL). The organic layer was dried (MgSO$_4$) and concentrated in vacuo to afford N-[1-(1-chloropyrido[3,4-d]pyridazin-4-yl)-4-piperidyl]-2,2,2-trifluoro-N-[[4-fluoro-2-(trifluoromethyl)phenyl]methyl]acetamide (480 mg, 0.90 mmol, 90%) which was used without further purification.

MS Method 2: RT: 1.94 min, m/z 536.2/538.2 [M+H]$^+$ 2,2,2-trifluoro-N-[[4-fluoro-2-(trifluoromethyl)phenyl]methyl]-N-[1-[1-(2-methylpyrazol-3-yl)pyrido[3,4-d]pyridazin-4-yl]-4-piperidyl]acetamide

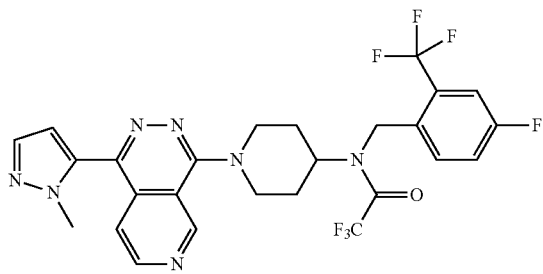 [SMILES: Cn1nccc1-c1nnc(N2CCC(N(Cc3ccc(F)cc3C(F)(F)F)C(=O)C(F)(F)F)CC2)c2cnccc12]

To a 10-20 mL microwave vial were added Palladium (0) tetrakis(triphenylphosphine) (0.14 mL, 0.09 mmol), 1-methyl-1H-pyrazole-5-boronic acid, pinacolester (280 mg, 1.34 mmol), sodium carbonate (193 mg, 1.8 mmol), water (3.3 mL), ethanol (3.3 mL) and toluene (3.3 mL) and the reaction was degassed with a flow of nitrogen for 10 min. N-[1-(1-chloropyrido[3,4-d]pyridazin-4-yl)-4-piperidyl]-2,2,2-trifluoro-N-[[4-fluoro-2-(trifluoromethyl)phenyl]methyl]acetamide (480 mg, 0.90 mmol) was then added and heated in the microwave for 40 min at 100° C. The reaction was concentrated in vacuo and then taken up in DCM. The organic layer was washed with water. The aqueous layer was extracted with DCM (3×10 mL). The organic layers were combined and concentrated. The resulting brown oil was purified by silica flash chromatography using 0% ethyl acetate in heptane with a gradient increasing to 100% ethyl acetate to afford 2,2,2-trifluoro-N-[[4-fluoro-2-(trifluoromethyl)phenyl]methyl]-N-[1-[1-(2-methylpyrazol-3-yl)pyrido[3,4-c]pyridazin-4-yl]-4-piperidyl]acetamide (150 mg, 0.26 mmol, 29%).

MS Method 2: RT: 1.81 min, m/z 582.4 [M+H]$^+$

N-[[4-fluoro-2-(trifluoromethyl)phenyl]methyl]-1-[1-(2-methylpyrazol-3-yl)pyrido[3,4-c]pyridazin-4-yl]piperidin-4-amine

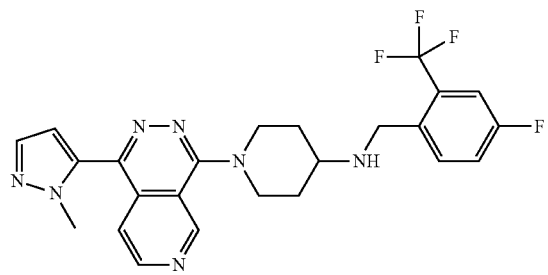 [SMILES: Cn1nccc1-c1nnc(N2CCC(NCc3ccc(F)cc3C(F)(F)F)CC2)c2cnccc12]

To a round bottomed flask were added phenyl]methyl]-N-[1-[1-(2-methylpyrazol-3-yl)pyrido[3,4-c]pyridazin-4-yl]-4-piperidyl]acetamide (150 mg, 0.26 mmol), sodium hydroxide (1.0 mL, 1.0 mmol), Methanol (1 mL) and the reaction was stirred at room temperature over the weekend. The reaction mixture was concentrated in vacuo and purified by silica flash chromatography using 0% methanol in ethyl acetate with a gradient to 20% methanol to afford N-[[4-fluoro-2-(trifluoromethyl)phenyl]methyl]-1-[1-(2-methylpyrazol-3-yl)pyrido[3,4-d]pyridazin-4-yl]piperidin-4-amine (23.6 mg, 0.05 mmol, 19%).

MS Method 2: RT: 1.17 min, m/z 486.3[M+H]$^+$ $^1$H NMR (400 MHz, CDCl$_3$) δ/ppm: 9.44 (d, J 0.9 Hz, 1H), 8.86 (d, J 5.7 Hz, 1H), 7.77 (dd, J 5.7 Hz, 0.9 Hz, 1H), 7.66 (dd, J8.5 Hz, 5.7 Hz, 1H), 7.60 (d, J 1.9 Hz, 1H), 7.30 (dd, J 9.2 Hz, 2.8 Hz, 1H), 7.22-7.16 (m, 1H), 6.52-6.53 (d, J1.9 Hz, 1H) 4.17-4.10 (m (br), 2H), 4.02 (s, 3H), 3.96 (s (br), 2H), 3.35-3.27 (m, 2H), 2.92-2.83 (m, 1H), 2.15-2.07 (m (br), 2H), 1.77-1.65 (m, 2H).

Example 5

In a similar way to Example 1, but using different conditions, compounds of formula (I) can be prepared by the General Method A1, shown below. General Method A1 may be carried out using the compound prepared by Procedure B or another appropriate method for producing the compound.

General Method A1

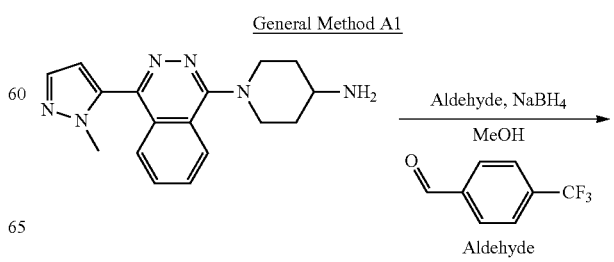

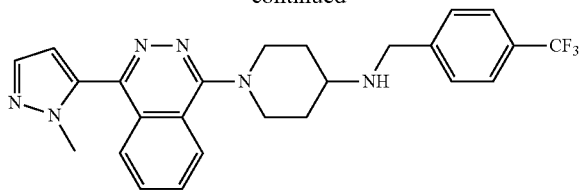

1-[4-(2-Methylpyrazol-3-yl)phthalazin-1-yl]-N-[[4-(trifluoromethyl)phenyl]methyl]piperidin-4-amine

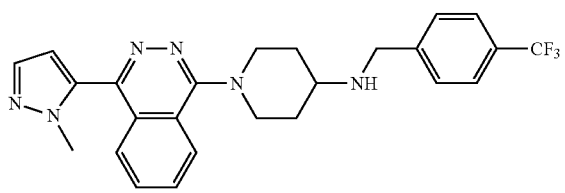 [SMILES: Cn1nccc1-c1nnc(N2CCC(NCc3ccc(C(F)(F)F)cc3)CC2)c2ccccc12]

1-[4-(2-Methylpyrazol-3-yl)phthalazin-1-yl]piperidin-4-amine (100 mg, 0.32 mmol) and 4-(trifluoromethyl)benzaldehyde (44 uL, 0.32 mmol) were dissolved in dry methanol (5 mL) and stirred at room temperature under an atmosphere of nitrogen overnight. Sodium borohydride (14.7 mg, 0.39 mmol) was added and the reaction was stirred at room temperature for 1 h. The reaction mixture was loaded onto an SCX cartridge, washed with 2 column volumes of methanol and then eluted with 2 column volumes of 2N ammonia in methanol. The ammonia in methanol was then removed in vacuo to afford a crude oil which was purified by preparative LCMS to afford the formate salt. This was then dissolved in methanol and loaded onto a carbonate column which was eluted with 2 column volumes of MeOH to produce the free base of 1-[4-(2-methylpyrazol-3-yl)phthalazin-1-yl]-N-[[4-(trifluoromethyl)phenyl]methyl]piperidin-4-amine (16.4 mg, 0.032 mmol, 10%).

$^1$H NMR (400 MHz, MeOD) δ/ppm: 8.26 (d, J 8.2 Hz, 1H), 8.05-8.00 (m, 1H), 7.98-7.95 (m, 2H), 7.71 (d, J 2.0 Hz, 1H), 7.68 (d, J 8.3 Hz, 2H), 7.63 (d, J 8.3 Hz, 2H), 6.70 (d, J 2.1 Hz, 1H), 4.10-4.04 (m (br), 2H), 3.99 (s, 2H), 3.91 (s, 3H), 3.23-3.15 (m, 2H), 2.86 (m, 1H), 2.24-2.17 (m, 2H), 1.88-1.77 (m, 2H).

MS Method 1: RT: 2.83 min, m/z 467.3 [M+H]$^+$

The compounds shown below in Table 3 were similarly prepared by varying the aldehyde shown in the reaction scheme for General Method A1:

TABLE 3

| COMPOUND | COMPOUND NAME | LCMS RT | m/z MIM |
|---|---|---|---|
|  | 1-[4-(2-methylpyrazol-3-yl)phthalazin-1-yl]-N-[(2-methylsulfanylphenyl)methyl]piperidin-4-amine | 2.74 min (Method 1) | 445.3 [M + H]$^+$ |
|  | N-[(2-chloro-4-fluorophenyl)methyl]-1-[4-(2-methylpyrazol-3-yl)phthalazin-1-yl]piperidin-4-amine | 2.68 min (Method 1) | 451.3 [M + H]$^+$ |
|  | 1-[4-(2-methylpyrazol-3-yl)phthalazin-1-yl]-N-[[4-(trifluoromethoxy)phenyl]methyl]piperidin-4-amine | 2.92 min (Method 1) | 483.3 [M + H]$^+$ |

TABLE 3-continued

| COMPOUND | COMPOUND NAME | LCMS RT | m/z MIM |
|---|---|---|---|
| | N-[[2-(difluoromethoxy)phenyl]methyl]-1-[4-(2-methylpyrazol-3-yl)phthalazin-1-yl]piperidin-4-amine | 2.72 min (Method 1) | 465.3 [M + H]+ |
| | 1-[4-(2-methylpyrazol-3-yl)phthalazin-1-yl]-N-[[3-(trifluoromethoxy)phenyl]methyl]piperidin-4-amine | 4.19 min (Method 1) | 483.3 [M + H]+ |
| | N-[(4-chlorophenyl)methyl]-1-[4-(2-methylpyrazol-3-yl)phthalazin-1-yl]piperidin-4-amine | 3.95 min (Method 1) | 433.3 [M + H]+ |
| | 1-[4-(2-methylpyrazol-3-yl)phthalazin-1-yl]-N-[[2-(trifluoromethoxy)phenyl]methyl]piperidin-4-amine | 4.18 min (Method 1) | 483.3 [M + H]+ |
| | N-[(2-chlorophenyl)methyl]-1-[4-(2-methylpyrazol-3-yl)phthalazin-1-yl]piperidin-4-amine | 3.94 min (Method 1) | 433.3 [M + H]+ |
| | 1-[4-(2-methylpyrazol-3-yl)phthalazin-1-yl]-N-[[3-(trifluoromethyl)phenyl]methyl]piperidin-4-amine | 2.99 min (Method 1) | 467.3 [M + H]+ |

TABLE 3-continued

| COMPOUND | COMPOUND NAME | LCMS RT | m/z MIM |
|---|---|---|---|
| | 1-[4-(2-methylpyrazol-3-yl)phthalazin-1-yl]-N-[[2-(trifluoromethyl)phenyl]methyl]piperidin-4-amine | 2.94 min (Method 1) | 467.3 [M + H]+ |
| | N-[(2-isopropylphenyl)methyl]-1-[4-(2-methylpyrazol-3-yl)phthalazin-1-yl]piperidin-4-amine | 3.02 min (Method 1) | 441.1 [M + H]+ |
| | 1-[4-(2-methylpyrazol-3-yl)phthalazin-1-yl]-N-(o-tolylmethyl)piperidin-4-amine | 2.66 min (Method 1) | 413.4 [M + H]+ |
| | N-[(2-ethoxyphenyl)methyl]-1-[4-(2-methylpyrazol-3-yl)phthalazin-1-yl]piperidin-4-amine | 2.85 min (Method 1) | 443.4 [M + H]+ |
| | N-benzyl-1-[4-(2-methylpyrazol-3-yl)phthalazin-1-yl]piperidin-4-amine | 2.69 min (Method 1) | 399.4 [M + H]+ |
| | 4-[[[1-[4-(2-methylpyrazol-3-yl)phthalazin-1-yl]-4-piperidyl]amino]methyl]benzonitrile | 3.49 min (Method 1) | 424.3 [M + H]+ |

TABLE 3-continued

| COMPOUND | COMPOUND NAME | LCMS RT | m/z MIM |
|---|---|---|---|
| | 3-[[[1-[4-(2-methylpyrazol-3-yl)phthalazin-1-yl]-4-piperidyl]amino]methyl]benzonitrile | 2.89 min (Method 1) | 424.3 [M + H]+ |
| | N-[(2-methoxyphenyl)methyl]-1-[4-(2-methylpyrazol-3-yl)phthalazin-1-yl]piperidin-4-amine | 3.03 min (Method 1) | 429.4 [M + H]+ |
| | N-[(3-methoxyphenyl)methyl]-1-[4-(2-methylpyrazol-3-yl)phthalazin-1-yl]piperidin-4-amine | 3.63 min (Method 1) | 429.4 [M + H]+ |
| | N-[(4-methoxyphenyl)methyl]-1-[4-(2-methylpyrazol-3-yl)phthalazin-1-yl]piperidin-4-amine | 2.95 min (Method 1) | 429.4 [M + H]+ |
| | N-[(2-fluorophenyl)methyl]-1-[4-(2-methylpyrazol-3-yl)phthalazin-1-yl]piperidin-4-amine | 3.69 min (Method 1) | 417.3 [M + H]+ |
| | N-[(3-fluorophenyl)methyl]-1-[4-(2-methylpyrazol-3-yl)phthalazin-1-yl]piperidin-4-amine | 2.97 min (Method 1) | 417.3 [M + H]+ |

TABLE 3-continued

| COMPOUND | COMPOUND NAME | LCMS RT | m/z MIM |
|---|---|---|---|
| | N-[(2,4-difluorophenyl)methyl]-1-[4-(2-methylpyrazol-3-yl)phthalazin-1-yl]piperidin-4-amine | 3.79 min (Method 1) | 435.3 [M + H]$^+$ |
| | N-[(4-fluorophenyl)methyl]-1-[4-(2-methylpyrazol-3-yl)phthalazin-1-yl]piperidin-4-amine | 2.95 min (Method 1) | 417.3 [M + H]$^+$ |
| | 1-[4-(2-methylpyrazol-3-yl)phthalazin-1-yl]-N-[(2-methylsulfonylphenyl)methyl]piperidin-4-amine | 2.41 min (Method 1) | 477.3 [M + H]$^+$ |
| | N-[(2,3-difluorophenyl)methyl]-1-[4-(2-methylpyrazol-3-yl)phthalazin-1-yl]piperidin-4-amine | 2.57 min (Method 1) | 435.3 [M + H]$^+$ |

In cases where ketones rather than aldehydes are used it may be necessary to perform the reaction with a Lewis acid as further activation for example:

racemic N-[1-[4-Fluoro-2-(trifluoromethyl)phenyl]ethyl]-1-[4-(2-methylpyrazol-3-yl)phthalazin-1-yl]piperidin-4-amine

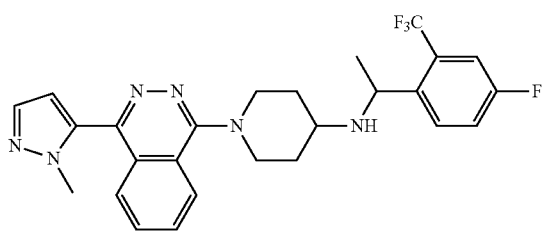 [SMILES: CC(NC1CCN(c2nnc(-c3ccnn3C)c3ccccc23)CC1)c1ccc(F)cc1C(F)(F)F]

1-[4-(2-Methylpyrazol-3-yl)phthalazin-1-yl]piperidin-4-amine (50 mg, 0.16 mmol) and 4-fluoro-2-trifluoromethyl-acetophenone (0.05 mL, 0.32 mmol) were combined in DCM (1.6 mL) with 4 Å molecular sieves. Titanium(IV) isopropoxide (0.1 mL, 0.32 mmol) was added and the reaction stirred at room temperature overnight. Reaction heated in the microwave at 80° C. for 20 min. Addition of further 4-Fluoro-2-trifluoromethylacetophenone (0.05 mL, 0.32 mmol) and titanium(IV) isopropoxide (0.1 mL, 0.32 mmol) and the reaction was heated in the microwave at 100° C. for 1 h. A solution of sodium borohydride (24.5 mg, 0.65 mmol) in methanol (1.6 mL) was made up under nitrogen and the reaction solution from the microwave was added to it. The reaction was stirred at room temperature for a further hour. Addition of further sodium borohydride (24.5 mg, 0.65 mmol). Reaction stirred for 1 h then quenched by addition of water. The reaction mixture was extracted into DCM, the organic and aqueous layers were separated by hydrophobic frit and then concentrated in vacuo. The crude oil was purified by preparative LCMS to afford N-[1-[4-fluoro-2-(trifluoromethyl)phenyl]ethyl]-1-[4-(2-methylpyrazol-3-yl)phthalazin-1-yl]piperidin-4-amine (5.2 mg, 0.0104 mmol, 6.4% yield)

$^1$H NMR (400 MHz, CDCl$_3$) δ/ppm: 8.09-8.02 (m, 2H), 7.93-7.79 (m, 3H), 7.66 (d, J1.9 Hz, 1H), 7.37-7.29 (m, 2H), 6.59 (d, J1.9 Hz, 1H), 4.48 (q, J6.4 Hz, 1H), 4.05 (s, 3H), 4.04-3.90 (m, 2H), 3.18-3.08 (2H), 2.66-2.58 (m, 1H), 2.24-2.16 (m (br), 1H), 1.92-1.85 (m (br), 1H), 1.73-1.57 (m, 2H), 1.44 (d, J6.4 Hz, 3H).

MS Method 1: RT: 3.02 min m/z 499.4 [M+H]$^+$

Example 6

In a similar way to Example 2, but using different conditions, compounds of formula (I) can be prepared by the General Method A2, shown below. General Method A2 may be carried out using the compound prepared by Procedure B as starting material or another appropriate method for producing the starting material may be used.

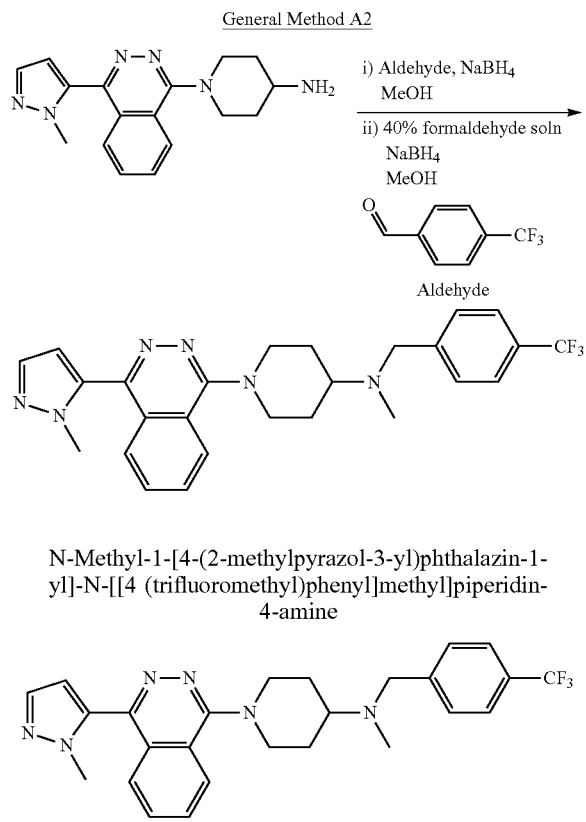

N-Methyl-1-[4-(2-methylpyrazol-3-yl)phthalazin-1-yl]-N-[[4 (trifluoromethyl)phenyl]methyl]piperidin-4-amine 1-[4-(2-Methylpyrazol-3-yl)phthalazin-1-yl]piperidin-4-amine (100 mg, 0.32 mmol) and 4-(trifluoromethyl)benzaldehyde (44.3 uL, 0.32 mmol) were dissolved in dry methanol (5 mL) and stirred at room temperature under an atmosphere of nitrogen overnight. Sodium borohydride (14.7 mg, 0.39 mmol) was added and the reaction stirred until completion (LCMS). Formaldehyde solution (36.5-38%) in water (0.09 mL, 3.24 mmol) was added to the reaction mixture and the reaction was stirred overnight. Sodium borohydride (14.72 mg, 0.39 mmol) was added and the reaction was monitored by LCMS. On completion, the reaction mixture was loaded onto an SCX cartridge before being washed with 2 column volumes of methanol followed by elution with 2 column volumes of 2N ammonia in methanol. The ammonia in methanol was then removed in vacuo and the crude product purified by preparative LCMS to afford N-methyl-1-[4-(2-methylpyrazol-3-yl)phthalazin-1-yl]-N-[[4 (trifluoromethyl)phenyl]methyl]piperidin-4-amine (31.3 mg, 0.065 mmol, 20%).

$^1$H NMR (400 MHz, CDCl$_3$) δ/ppm: 8.14 (d, J 8.1 Hz, 1H), 8.07 (d, J 8.1 Hz, 1H), 7.91-7.81 (m, 2H), 7.68 (d, J 2.0 Hz, 1H), 7.61 (AA'BB', d, J 8.1 Hz, 2H), 7.52 (AA'BB', d, J 8.1 Hz, 2H), 6.61 (d, J 2.0 Hz, 1H), 4.19-4.12 (m (br), 2H), 4.08 (s, 3H), 3.76 (s, 2H), 3.25-3.17 (dt, J12.0 Hz, 2.1 Hz, 2H), 2.81 (tt, J 11.0, 4.0 Hz, 1H), 2.32 (s, 3H), 2.13-1.95 (m, 4H).

MS Method 2: RT: 1.28 min, m/z 481.3 [M+H]$^+$

The compounds shown below in Table 4 were similarly prepared by varying the aldehyde shown in the reaction scheme for General Method A2:

TABLE 4

| Compound | Compound name | LCMS RT | m/z MIM |
|---|---|---|---|
| ![structure] | N-methyl-1-[4-(2-methylpyrazol-3-yl)phthalazin-1-yl]-N-[[3-(trifluoromethyl)phenyl]methyl]piperidin-4-amine | 1.28 min (Method 2) | 481.3 [M + H]$^+$ |
| ![structure] | N-methyl-1-[4-(2-methylpyrazol-3-yl)phthalazin-1-yl]-N-[[2-(trifluoromethyl)phenyl]methyl]piperidin-4-amine | 1.26 min (Method 2) | 481.3 [M + H]$^+$ |

TABLE 4-continued

| Compound | Compound name | LCMS RT | m/z MIM |
|---|---|---|---|
| | N-[[2-(difluoromethoxy)phenyl]methyl]-N-methyl-1-[4-(2-methylpyrazol-3-yl)phthalazin-1-yl]piperidin-4-amine | 2.80 (Method 1) | 479.3 [M + H]+ |
| | N-methyl-1-[4-(2-methylpyrazol-3-yl)phthalazin-1-yl]-N-[(2-methylsulfanylphenyl)methyl]piperidin-4-amine | 2.80 min (Method 2) | 459.3 [M + H]+ |
| | N-[(2-isopropylphenyl)methyl]-N-methyl-1-[4-(2-methylpyrazol-3-yl)phthalazin-1-yl]piperidin-4-amine | 1.30 min (Method 2) | 455.3 [M + H]+ |
| | N-methyl-1-[4-(2-methylpyrazol-3-yl)phthalazin-1-yl]-N-(o-tolylmethyl)piperidin-4-amine | 3.07 min (Method 1) | 427.4 [M + H]+ |
| | N-[(4-fluorophenyl)methyl]-N-methyl-1-[4-(2-methylpyrazol-3-yl)phthalazin-1-yl]piperidin-4-amine | 2.90 min (Method 1) | 431.4 [M + H]+ |
| | N-benzyl-N-methyl-1-[4-(2-methylpyrazol-3-yl)phthalazin-1-yl]piperidin-4-amine | 2.95 min (Method 1) | 413.4 [M + H]+ |

TABLE 4-continued

| Compound | Compound name | LCMS RT | m/z MIM |
|---|---|---|---|
| | 4-[[methyl-[1-[4-(2-methylpyrazol-3-yl)phthalazin-1-yl]-4-piperidyl]amino]methyl]benzonitrile | 2.84 min (Method 1) | 438.4 [M + H]+ |
| | N-[(2-methoxyphenyl)methyl]-N-methyl-1-[4-(2-methylpyrazol-3-yl)phthalazin-1-yl]piperidin-4-amine | 3.24 min (Method 1) | 443.4 [M + H]+ |
| | N-[(3-methoxyphenyl)methyl]-N-methyl-1-[4-(2-methylpyrazol-3-yl)phthalazin-1-yl]piperidin-4-amine | 2.93 min (Method 1) | 443.4 [M + H]+ |
| | (4-methoxyphenyl)methyl-methyl-[1-[4-(2-methylpyrazol-3-yl)phthalazin-1-yl]-4-piperidyl]ammonium | 3.04 min (Method 1) | 443.4 [M + H]+ |
| | (2-fluorophenyl)methyl-methyl-[1-[4-(2-methylpyrazol-3-yl)phthalazin-1-yl]-4-piperidyl]ammonium | 2.93 min (Method 1) | 431.4 [M + H]+ |
| | (3-fluorophenyl)methyl-methyl-[1-[4-(2-methylpyrazol-3-yl)phthalazin-1-yl]-4-piperidyl]ammonium | 3.02 min (Method 1) | 431.4 [M + H]+ |

TABLE 4-continued

| Compound | Compound name | LCMS RT | m/z MIM |
|---|---|---|---|
| 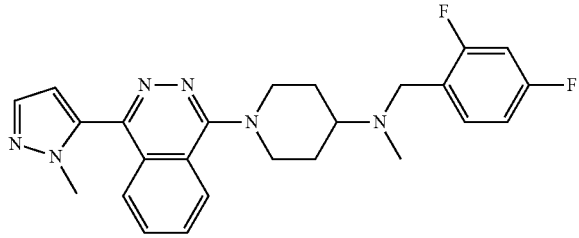 [SMILES: CN(Cc1ccc(F)cc1F)C1CCN(c2nnc(-c3ccnn3C)c3ccccc23)CC1] | N-[(2,4-difluorophenyl)methyl]-N-methyl-1-[4-(2-methylpyrazol-3-yl)phthalazin-1-yl]piperidin-4-amine | 1.90 min (Method 2) | 449.3 [M + H]$^+$ |
| 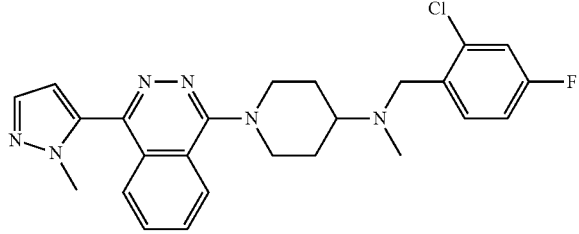 | N-[(2-chloro-4-fluoro-phenyl)methyl]-N-methyl-1-[4-(2-methylpyrazol-3-yl)phthalazin-1-yl]piperidin-4-amine | 2.74 min (Method 1) | 465.3 [M + H]$^+$ |
| 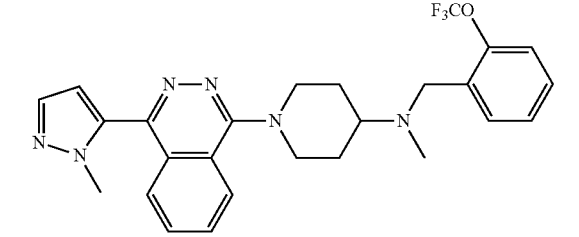 | N-methyl-1-[4-(2-methylpyrazol-3-yl)phthalazin-1-yl]-N-[[2-(trifluoromethoxy)phenyl]methyl]piperidin-4-amine | 2.90 min (Method 1) | 497.4 [M + H]$^+$ |

Example 7

In a similar way to Example 2, but using different conditions, compounds of formula (I) can be prepared by the General Method A3, shown below. General Method A3 may be carried out using the compound prepared by Procedure B as starting material or another appropriate method for producing the starting material may be used. Those skilled in the art will appreciate that in cases where step i) alone is performed with one equivalent of aldehyde the procedure can be used to afford the resulting secondary amine products.

General Method A3

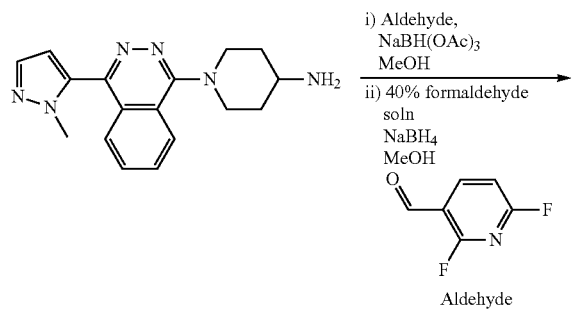

i) Aldehyde, NaBH(OAc)$_3$ MeOH ii) 40% formaldehyde soln NaBH$_4$ MeOH

Aldehyde

-continued

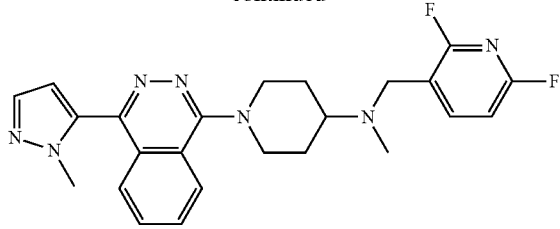

N-[(2,6-difluoro-3-pyridyl)methyl]-N-methyl-1-[4-(2-methylpyrazol-3-yl)phthalazin-1-yl]-4-piperidyl]amine

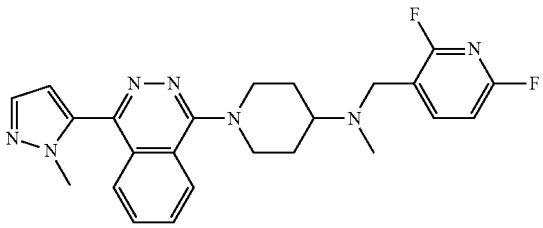

To a solution of 1-[4-(2-methylpyrazol-3-yl)phthalazin-1-yl]piperidin-4-amine (135 mg, 0.44 mmol) and 2,6-difluoropyridine-3-carbaldehyde (63 mg, 0.44 mmol) in DCM (2 mL) at room temperature was added sodium triacetoxyborohydride (131 mg, 0.62 mmol). The reaction mixture was stirred at room temperature under nitrogen for 72 h. The reaction was quenched with a saturated NaHCO₃ solution (aq) and extracted with ethyl acetate. The organic layer was concentrated in vacuo. Purification by silica flash column chromatography with 10% ethyl acetate in heptane with a gradient increasing to 80% ethyl acetate followed by 2% DCM in methanol with a gradient increasing to 10% MeOH afforded the crude product as a brown oil. Further purification by preparative LCMS afforded N-[(2,6-difluoro-3-pyridyl)methyl]-1-[4-(2-methylpyrazol-3-yl)phthalazin-1-yl]piperidin-4-amine (50 mg, 0.11 mmol, 26%) as a colourless oil.

$^1$H NMR (400 MHz, MeOD) δ/ppm: 8.25 (d, J 8.2 Hz, 1H), 8.2-8.14 (dd, J 8.0 Hz, $^3$J$_{HF}$ 17.0 Hz, 1H), 8.04-7.99 (m, 1H), 7.97-7.94 (m, 2H), 7.70 (d, J 2.0 Hz, 1H), 7.01 (dd, J 8.2 Hz, 2.5 Hz, 1H), 6.69 (d, J 2.0 Hz, 1H) 4.10-4.03 (m (br), 2H), 3.94 (s, 2H), 3.91 (s, 3H), 3.25-3.27 (m, 2H), 2.87 (tt, J 10.7 Hz, 4.1 Hz, 1H), 2.24-2.17 (m (br), 2H), 1.87-1.76 (m, 2H).

MS Method 1: RT: 2.89 min, m/z 436.4 [M+H]⁺

N-[(2,6-Difluoro-3-pyridyl)methyl]-1-[4-(2-methylpyrazol-3-yl)phthalazin-1-yl]piperidin-4-amine (153. mg, 0.35 mmol) was taken up in THF (5 mL) and formaldehyde solution (36.5-38%) in water (0.05 mL, 1.76 mmol) and acetic acid (0.2 mL, 3.5 mmol) were added. This mixture was stirred at room temperature for 1 hour then sodium borohydride (18.6 mg, 0.49 mmol) was added and the mixture stirred for a further 2 hours then analysed by LCMS which showed the reaction had gone to completion. The mixture was quenched with a saturated solution of sodium carbonate (10 mL) then extracted with DCM (3×20 mL). The organics were combined, washed with brine (25 mL), dried (NaSO₄), filtered then concentrated in vacuo to give a yellow oil. The crude product was purified by preparative LCMS to afford the formate salt: (2,6-difluoro-3-pyridyl)methyl-methyl-[1-[4-(2-methylpyrazol-3-yl)phthalazin-1-yl]-4-piperidyl]ammonium formate (10 mg, 0.02 mmol, 6%) as a white solid.

$^1$H NMR (400 MHz, CDCl₃) δ/ppm: 8.23 (s, 1H), 8.20-8.06 (m, 3H), 7.93-7.83 (m, 2H), 7.69 (d, J 1.9 Hz, 1H), 6.90 (dd, J 8.0 Hz, 2.7 Hz, 1H), 6.61 (d, J 1.9 Hz, 1H), 4.22-4.15 (m (br), 2H), 4.07 (s, 3H), 3.89 (s, 2H), 3.28-3.19 (m (br), 2H), 3.06-2.96 (m (br), 1H), 2.45 (3H), 2.19-2.00 (m (br), 4H).

MS Method 1: RT: 2.48 min, m/z 450.3 [M+H]⁺

The compounds shown below in Table 5 were similarly prepared by varying the aldehyde shown in the reaction scheme for General Method A3. Where a compound in Table 4 does not possess the N-methyl as in the final compound in the scheme depicted for General Method A3 then the compound has been obtained by carrying out step i) of the General Method A3 and not the second step, step ii). In cases where a secondary amine starting material such as N-methyl-1-[4-(2-methylpyrazol-3-yl)phthalazin-1-yl]piperidin-4-amine is used then step i) alone can be used to obtain the final products.

TABLE 4

| Compound | Compound Name | LCMS RT | m/z MIM |
|---|---|---|---|
| (structure) | 1-[4,5-dimethyl-6-(2-methylpyrazol-3-yl)pyridazin-3-yl]-N-[[4-fluoro-2-(trifluoromethyl)phenyl]methyl]piperidin-4-amine | 1.23 min (Method 2) | 463.3 [M + H]⁺ |
| (structure) | 4-fluoro-3-[[[1-[4-(2-methylpyrazol-3-yl)phthalazin-1-yl]-4-piperidyl]amino]methyl]benzonitrile | 2.45 min (Method 1) | 442.3 [M + H]⁺ |
| (structure) | 2-fluoro-5-[[[1-[4-(2-methylpyrazol-3-yl)phthalazin-1-yl]-4-piperidyl]amino]methyl]benzonitrile | 2.53 (Method 1) | 442.3 [M + H]⁺ |

TABLE 4-continued

| Compound | Compound Name | LCMS RT | m/z MIM |
|---|---|---|---|
| | N-[(2,6-difluoro-3-pyridyl)methyl]-1-[4-(2-methylpyrazol-3-yl)phthalazin-1-yl]piperidin-4-amine | 2.89 (Method 1) | 436.4 [M + H]⁺ |
| | methyl 6-[[[1-[4-(2-methylpyrazol-3-yl)phthalazin-1-yl]-4-piperidyl]amino]methyl]pyridine-3-carboxylate | 2.44 (Method 1) | 458.3 [M + H]⁺ |
| | N-[(5-fluoro-2-pyridyl)methyl]-1-[4-(2-methylpyrazol-3-yl)phthalazin-1-yl]piperidin-4-amine | 1.06 min (Method 2) | 418.4 [M + H]⁺ |
| | 1-[4-(2-methylpyrazol-3-yl)phthalazin-1-yl]-N-[[3-(trifluoromethyl)-4-pyridyl]methyl]piperidin-4-amine | 2.55 min (Method 1) | 468.4 [M + H]⁺ |
| | N-ethyl-N-[[4-fluoro-2-(trifluoromethyl)phenyl]methyl]-1-[4-(2-methylpyrazol-3-yl)phthalazin-1-yl]piperidin-4-amine | 3.18 min (Method 1) | 513.3 [M + H]⁺ |
| | N-[[4-fluoro-2-(trifluoromethyl)phenyl]methyl]-1-(4-morpholinophthalazin-1-yl)piperidin-4-amine | 1.10 min (Method 2) | 490.3 [M + H]⁺ |

TABLE 4-continued

| Compound | Compound Name | LCMS RT | m/z MIM |
|---|---|---|---|
| | 1-[4-(2-methylpyrazol-3-yl)phthalazin-1-yl]-N-[[4-(trifluoromethyl)-3-pyridyl]methyl]piperidin-4-amine | 2.50 min (Method 1) | 468.3 [M + H]+ |
| | N-[[4-fluoro-2-(trifluoromethyl)phenyl]methyl]-N-methyl-1-[1-(2-methylpyrazol-3-yl)-6,7-dihydro-5H-cyclopenta[d]pyridazin-4-yl]piperidin-4-amine | 2.92 min (Method 1) | 489.4 [M + H]+ |
| | 3-[[methyl-[1-[1-(2-methylpyrazol-3-yl)-6,7-dihydro-5H-cyclopenta[d]pyridazin-4-yl]-4-piperidyl]amino]methyl]benzonitrile | 2.49 min (Method 1) | 428.5 [M + H]+ |
| | 1-[4,5-dimethyl-6-(2-methylpyrazol-3-yl)pyridazin-3-yl]-N-methyl-N-[[2-methyl-4-(trifluoromethyl)thiazol-5-yl]methyl]piperidin-4-amine | 2.68 min (Method 1) | 480.4 [M + H]+ |
| | N-methyl-1-[4-(2-methylpyrazol-3-yl)phthalazin-1-yl]-N-(pyridazin-4-ylmethyl)piperidin-4-amine | 2.15 min (Method 1) | 415.4 [M + H]+ |
| | N-methyl-1-[4-(2-methylpyrazol-3-yl)phthalazin-1-yl]-N-[(2-methylsulfanylpyrimidin-4-yl)methyl]piperidin-4-amine | 2.51 min (Method 1) | 461.3 [M + H]+ |
| | 1-[4,5-dimethyl-6-(2-methylpyrazol-3-yl)pyridazin-3-yl]-N-methyl-N-[(2-methylsulfanylpyrimidin-4-yl)methyl]piperidin-4-amine | 2.47 min (Method 1) | 439.4 [M + H]+ |

TABLE 4-continued

| Compound | Compound Name | LCMS RT | m/z MIM |
|---|---|---|---|
| | 1-[4,5-dimethyl-6-(2-methylpyrazol-3-yl)pyridazin-3-yl]-N-methyl-N-(pyridazin-4-ylmethyl)piperidin-4-amine | 2.05 min (Method 1) | 393.4 [M + H]⁺ |
| | 1-[4,5-dimethyl-6-(2-methylpyrazol-3-yl)pyridazin-3-yl]-N-methyl-N-[(2-methylsulfanylphenyl)methyl]piperidin-4-amine | 2.73 min (Method 1) | 437.4 [M + H]⁺ |
| | 1-[4,5-dimethyl-6-(2-methylpyrazol-3-yl)pyridazin-3-yl]-N-methyl-N-[2-(trifluoromethoxy)phenyl]methyl]piperidin-4-amine | 2.90 min (Method 1) | 475.4 [M + H]⁺ |
| | 2-[[[1-[4,5-dimethyl-6-(2-methylpyrazol-3-yl)pyridazin-3-yl]-4-piperidyl]-methyl-amino]methyl]benzonitrile | 2.47 min (Method 1) | 416.4 [M + H]⁺ |
| | 1-[4,5-dimethyl-6-(2-methylpyrazol-3-yl)pyridazin-3-yl]-N-methyl-N-[[3-(trifluoromethyl)-2-pyridyl]methyl]piperidin-4-amine | 2.49 min (Method 1) | 460.4 [M + H]⁺ |
| | 1-[4,5-dimethyl-6-(2-methylpyrazol-3-yl)pyridazin-3-yl]-N-methyl-N-[[3-(trifluoromethoxy)phenyl]methyl]piperidin-4-amine | 2.89 min (Method 1) | 475.4 [M + H]⁺ |
| | 1-[4,5-dimethyl-6-(2-methylpyrazol-3-yl)pyridazin-3-yl]-N-[(2-isopropylphenyl)methyl]-N-methyl-piperidin-4-amine | 2.91 min (Method 1) | 433.4 [M + H]⁺ |

TABLE 4-continued

| Compound | Compound Name | LCMS RT | m/z MIM |
|---|---|---|---|
| | 1-[4,5-dimethyl-6-(2-methylpyrazol-3-yl)pyridazin-3-yl]-N-methyl-N-[[2-(trifluoromethyl)phenyl]methyl]piperidin-4-amine | 2.81 min (Method 1) | 459.4 [M + H]+ |
| | N-methyl-1-[4-(2-methylpyrazol-3-yl)phthalazin-1-yl]-N-(pyrimidin-4-ylmethyl)piperidin-4-amine | 2.17 min (Method 1) | 415.4 [M + H]+ |
| | 1-[4,5-dimethyl-6-(2-methylpyrazol-3-yl)pyridazin-3-yl]-N-methyl-N-[(2-nitrophenyl)methyl]piperidin-4-amine | 2.49 min (Method 1) | 436.4 [M + H]+ |
| | 1-[4-fluoro-2-(trifluoromethyl)phenyl]-N-[[1-[4-(2-methylpyrazol-3-yl)phthalazin-1-yl]pyrrolidin-3-yl]methyl]methanamine | 1.04 min (Method 2) | 485.3 [M + H]+ |
| | N-[[4-fluoro-2-(trifluoromethyl)phenyl]methyl]-N-methyl-1-[5-(2-methylpyrazol-3-yl)pyrido[2,3-d]pyridazin-8-yl]piperidin-4-amine | 1.20 min (Method 2) | 500.3 [M + H]+ |
| | N-[[4-fluoro-2-(trifluoromethyl)phenyl]methyl]-N-methyl-1-[8-(2-methylpyrazol-3-yl)pyrido[2,3-d]pyridazin-5-yl]piperidin-4-amine | 1.19 min (Method 2) | 500.3 [M + H]+ |
| | 2-fluoro-5-[[[1-(2-methylpyrazol-3-yl)-6,7-dihydro-5H-cyclopenta[d]pyridazin-4-yl]-4-piperidyl]amino]methyl]benzonitrile | 2.48 min (Method 2) | 476.4 [M + H]+ |

TABLE 4-continued

| Compound | Compound Name | LCMS RT | m/z MIM |
|---|---|---|---|
| | N-[[4-fluoro-2-(trifluoromethyl)phenyl]methyl]-1-[6-(6-methoxy-3-pyridyl)-4,5-dimethyl-pyridazin-3-yl]piperidin-4-amine | 1.29 min (Method 2) | 490.4 [M + H]+ |
| | N-[[4-fluoro-2-(trifluoromethyl)phenyl]methyl]-1-[6-(2-methoxy-4-pyridyl)-4,5-dimethyl-pyridazin-3-yl]piperidin-4-amine | 1.28 min (Method 2) | 490.4 [M + H]+ |
| | 1-[4,5-dimethyl-6-(2-methyl-4-pyridyl)pyridazin-3-yl]-N-[[4-fluoro-2-(trifluoromethyl)phenyl]methyl]piperidin-4-amine | 1.03 min (Method 2) | 474.4 [M + H]+ |
| | 1-[4,5-dimethyl-6-(4-pyridyl)pyridazin-3-yl]-N-[[4-fluoro-2-(trifluoromethyl)phenyl]methyl]piperidin-4-amine | 1.07 min (Method 2) | 460.3 [M + H]+ |
| | 1-[4-(2-methylpyrazol-3-yl)phthalazin-1-yl]-N-[[3-(trifluoromethyl)-2-pyridyl]methyl]piperidin-4-amine | 2.61 min (Method 1) | 468.3 [M + H]+ |
| | 3-[[[1-[1-(2-methylpyrazol-3-yl)-6,7-dihydro-5H-cyclopenta[d]pyridazin-4-yl]-4-piperidyl]amino]methyl]benzonitrile | 2.40 min (Method 1) | 414.3 [M + H]+ |
| | N-[[4-fluoro-2-(trifluoromethyl)phenyl]methyl]-1-[1-(2-methylpyrazol-3-yl)-6,7-dihydro-5H-cyclopenta[d]pyridazin-4-yl]piperidin-4-amine | 2.74 min (Method 1) | 475.4 [M + H]+ |

TABLE 4-continued

| Compound | Compound Name | LCMS RT | m/z MIM |
|---|---|---|---|
| | N-methyl-1-[4-(2-methylpyrazol-3-yl)phthalazin-1-yl]-N-[[3-(trifluoromethyl)-2-pyridyl]methyl]piperidin-4-amine | 2.66 min (Method 1) | 482.3 [M + H]+ |
| | N-[[4-fluoro-2-(trifluoromethyl)phenyl]methyl]-1-[5-(2-methylpyrazol-3-yl)pyrido[2,3-d]pyridazin-8-yl]piperidin-4-amine | 1.18 min (Method 2) | 486.3 [M + H]+ |
| | N-methyl-1-[4-(2-methylpyrazol-3-yl)phthalazin-1-yl]-N-[[2-methyl-4-(trifluoromethyl)thiazol-5-yl]methyl]piperidin-4-amine | 2.78 min (Method 1) | 502.3 [M + H]+ |
| | 1-[4,5-dimethyl-6-(2-methylpyrazol-3-yl)pyridazin-3-yl]-N-methyl-N-[[2-methyl-5-(trifluoromethyl)oxazol-4-yl]methyl]piperidin-4-amine | 2.63 min (Method 1) | 464.4 [M + H]+ |
| | N-methyl-1-[4-(2-methylpyrazol-3-yl)phthalazin-1-yl]-N-[[2-methyl-5-(trifluoromethyl)oxazol-4-yl]methyl]piperidin-4-amine | 2.65 min (Method 1) | 486.4 [M + H]+ |

Example 8

Compounds of formula (I) can be prepared by the General Method A4, shown below.

General Method A4

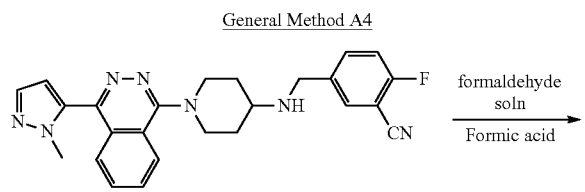

formaldehyde soln
Formic acid

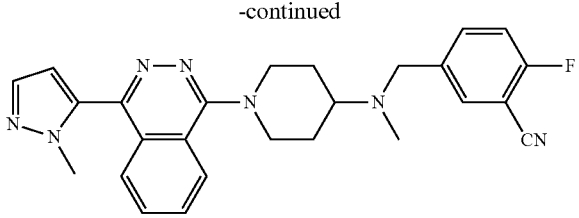

2-Fluoro-5-[[[1-[4-(2-methylpyrazol-3-yl)phthalazin-1-yl]-4-piperidyl]amino]methyl]benzonitrile (175 mg, 0.40 mmol) was dissolved in a mixture of formaldehyde solution (36.5-38%) in water (5.0 mL, 0.40 mmol) and formic acid (5.0 mL, 109 mmol). The reaction was then heated at 80° C. for 1.5 hours. The reaction was cooled, saturated NaHCO$_3$ solution (aq) was added and the mixture was extracted with ethyl acetate. The combined organic layers were washed a further three times with saturated NaHCO$_3$ solution (aq). The organic layer was separated and dried (NaSO$_4$) and concentrated in vacuo to afford 0.108 g of crude product. Purification by preparative LCMS afforded the formate salt of 2-fluoro-5-[[methyl-[1-[4-(2-methylpyrazol-3-yl)phthalazin-1-yl]-4-piperidyl]amino]methyl]benzonitrile (36 mg, 0.079 mmol, 20%) as a white solid.

$^1$H NMR (400 MHz, CDCl$_3$) δ/ppm: 8.16 (s, 1H), 8.13 (d, J 8.0 Hz, 1H), 8.07 (d, J 8.0 Hz, 1H), 7.93-7.83 (m, 2H), 7.72-7.65 (m, 2H), 7.69 (d, J 1.9 Hz, 1H), 7.23 (t, J 8.6 Hz, 1H), 6.61 (d, J 1.9 Hz, 1H), 4.20-4.14 (m (br), 2H), 4.07 (s, 3H), 3.78 (s, 2H), 3.26-3.18 (m, 2H), 2.92 (tt, J 11.3 Hz, 4.0 Hz, 1H), 2.35 (s, 3H), 2.14-1.97 (m, 4H).

MS Method 1: RT: 2.60 min, m/z 456.3 [M+H]$^+$

The compounds shown below in Table 5 were similarly prepared by General Method A4.

TABLE 5

| Structure | Name | LCMS RT | m/z MIM |
|---|---|---|---|
| 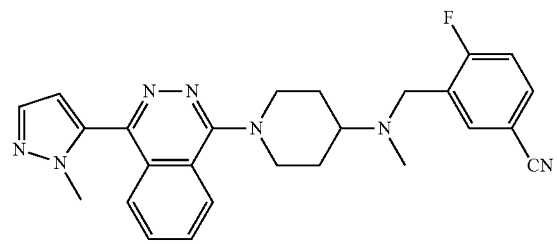 [SMILES: CN(Cc1cc(C#N)ccc1F)C1CCN(c2nnc(-c3ccnn3C)c3ccccc23)CC1] | 4-fluoro-3-[[methyl-[1-[4-(2-methylpyrazol-3-yl)phthalazin-1-yl]-4-piperidyl]amino]methyl]benzonitrile | 1.10 min (Method 2) | 456.3 [M + H]$^+$ |
| 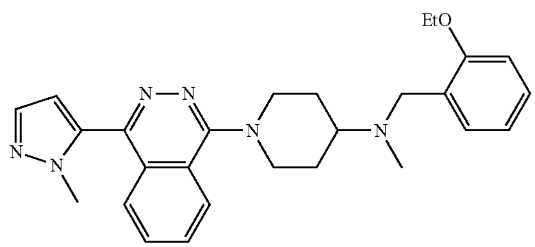 | N-[(2-ethoxyphenyl)methyl]-N-methyl-1-[4-(2-methylpyrazol-4-yl)phthalazin-1-yl]piperidin-4-amine | 2.89 min (Method 1) | 457.4 [M + H]$^+$ |
| 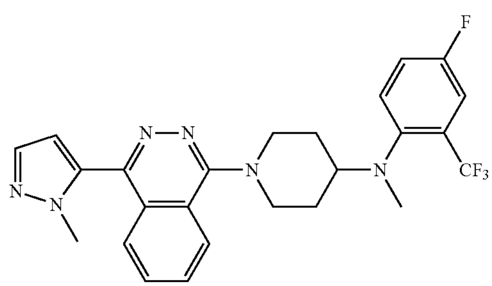 [SMILES: CN(c1ccc(F)cc1C(F)(F)F)C1CCN(c2nnc(-c3ccnn3C)c3ccccc23)CC1] | [4-fluoro-2-(trifluoromethyl)phenyl]-methyl-[1-[4-(2-methylpyrazol-3-yl)phthalazin-1-yl]-4-piperidyl]ammonium | 4.38 min (Method 1) | 485.3 [M + H]$^+$ |
| 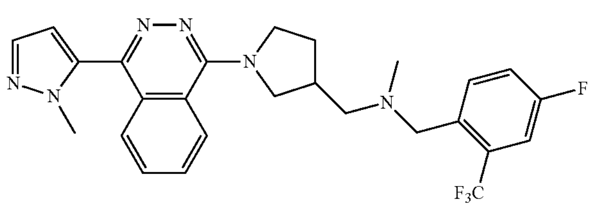 [SMILES: CN(Cc1ccc(F)cc1C(F)(F)F)CC1CCN(c2nnc(-c3ccnn3C)c3ccccc23)C1] | 1-[4-fluoro-2-(trifluoromethyl)phenyl]-N-methyl-N-[[1-[4-(2-methylpyrazol-3-yl)phthalazin-1-yl]pyrrolidin-3-yl]methyl]methanamine | 1.09 min (Method 2) | 499.3 [M + H]$^+$ |
| 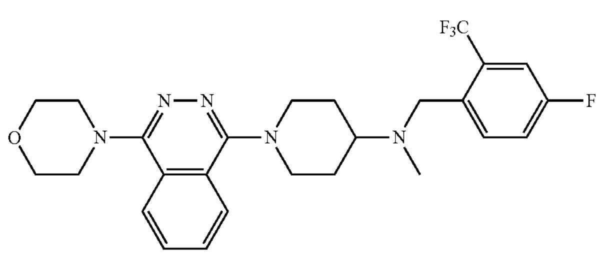 [SMILES: CN(Cc1ccc(F)cc1C(F)(F)F)C1CCN(c2nnc(N3CCOCC3)c3ccccc23)CC1] | N-[[4-fluoro-2-(trifluoromethyl)phenyl]methyl]-N-methyl-1-(4-morpholinophthalazin-1-yl)piperidin-4-amine | 1.14 min (Method 2) | 504.3 [M + H]$^+$ |

TABLE 5-continued

| Structure | Name | LCMS RT | m/z MIM |
|---|---|---|---|
| 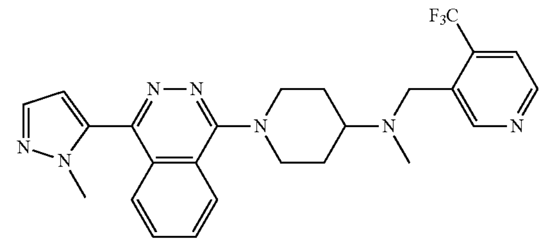 [SMILES: CN(Cc1cnccc1C(F)(F)F)C1CCN(c2nnc(-c3ccnn3C)c3ccccc23)CC1] | N-methyl-1-[4-(2-methylpyrazol-3-yl)phthalazin-1-yl]-N-[[4-(trifluoromethyl)-3-pyridyl]methyl]piperidin-4-amine | 2.59 min (Method 1) | 482.4 [M + H]⁺ |
| 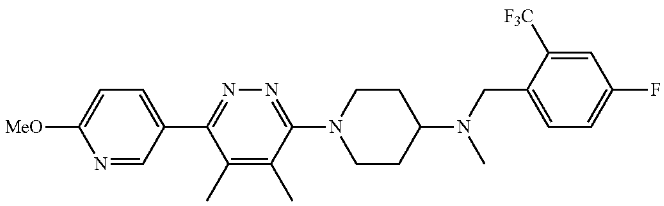 [SMILES: COc1ccc(-c2nnc(N3CCC(N(C)Cc4ccc(F)cc4C(F)(F)F)CC3)c(C)c2C)cn1] | N-[[4-fluoro-2-(trifluoromethyl)phenyl]methyl]-1-[6-(6-methoxy-3-pyridyl)-4,5-dimethyl-pyridazin-3-yl]-N-methyl-piperidin-4-amine | 1.31 min (Method 2) | 504.4 [M + H]⁺ |

Example 9

Compounds of formula (I) can be prepared by the General Method B, shown below. General Method B may be carried out using compounds prepared by Procedure A and Procedure D as starting materials or another appropriate method for producing the starting materials may be used.

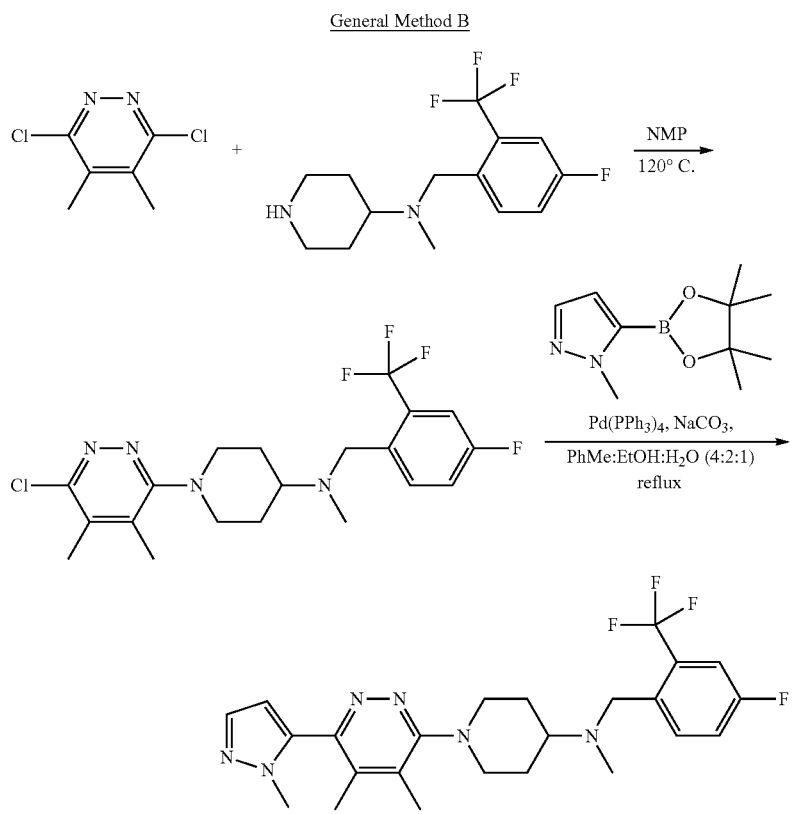

General Method B

1-(6-chloro-4,5-dimethyl-pyridazin-3-yl)-N-[[4-fluoro-2-(trifluoromethyl)phenyl]methyl]-N-methyl-piperidin-4-amine

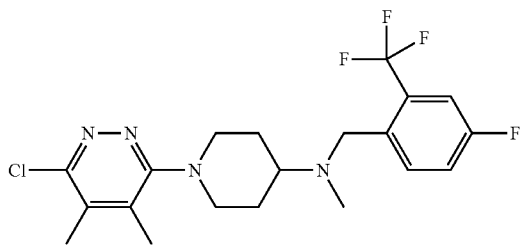 [SMILES: Cc1c(Cl)nnc(N2CCC(N(C)Cc3ccc(F)cc3C(F)(F)F)CC2)c1C]

3,6-Dichloro-4,5-dimethyl-pyridazine (153 mg, 0.86 mmol), N-[[4-fluoro-2-(trifluoromethyl)phenyl]methyl]-N-methyl-piperidin-4-amine (250 mg, 0.86 mmol) and sodium carbonate (100 mg, 0.95 mmol) were added to NMP (4 mL) and stirred at 120° C. for 2 days. LCMS analysis showed consumption of starting material and formation of product with desired mass. The reaction mixture was allowed to cool to room temperature, diluted with EtOAc (50 mL), washed with saturated NaHCO$_3$ (20 mL), washed with water (2×20 mL) and brine (10 mL). The EtOAc layer was dried (MgSO$_4$), filtered and concentrated under reduced pressure to give a crude brown oil. The crude material was purified by silica flash chromatography eluting with 0% EtOAc in heptane with a gradient to 30% EtOAc. Fractions containing the product were combined and concentrated under reduced pressure to give 1-(6-chloro-4,5-dimethyl-pyridazin-3-yl)-N-[[4-fluoro-2-(trifluoromethyl)phenyl]methyl]-N-methyl-piperidin-4-amine (113 mg, 0.26 mmol, 30%) as a white solid.

MS Method 2: RT: 1.37 min, m/z 431.3 [M+H]$^+$

1-[4,5-dimethyl-6-(2-methylpyrazol-3-yl)pyridazin-3-yl]-N-[[4-fluoro-2-(trifluoromethyl)phenyl]methyl]-N-methyl-piperidin-4-amine

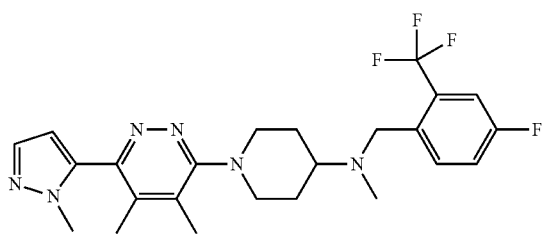 [SMILES: Cc1c(-c2ccnn2C)nnc(N2CCC(N(C)Cc3ccc(F)cc3C(F)(F)F)CC2)c1C]

1-(6-Chloro-4,5-dimethyl-pyridazin-3-yl)-N-[[4-fluoro-2-(trifluoromethyl)phenyl]methyl]-N-methyl-piperidin-4-amine (251 mg, 0.58 mmol), 1-methyl-1H-pyrazole-5-boronic acid, pinacolester (182 mg, 0.87 mmol), Tetrakis(triphenylphosphine)palladium(0) (67 mg, 0.060 mmol) and sodium carbonate (185 mg, 1.75 mmol) were added to PhMe:EtOH:H$_2$O (4:2:1) (3.5 mL). The reaction mixture was degassed and stirred at reflux overnight. The reaction mixture was cooled and filtered through a plug of Celite eluting with MeOH:DCM (10%). The eluent was concentrated under reduced pressure to give the crude dark brown oil. The crude material was purified by silica flash chromatography eluting with 0% EtOAc in heptane with a gradient to 30% EtOAc to afford a gum. The product was further purified by SCX washing with MeOH followed by elution with 2M NH$_3$ MeOH to afford 1-[4,5-dimethyl-6-(2-methylpyrazol-3-yl)pyridazin-3-yl]-N-[[4-fluoro-2-(trifluoromethyl)phenyl]methyl]-N-methyl-piperidin-4-amine (54 mg, 0.11 mmol, 20%) as a gum.

$^1$H NMR (400 MHz, DMSO-d6) δ/ppm: 7.9-7.85 (m, 1H), 7.59-7.51 (m, 3H), 6.45 (d, J 1.7 Hz, 1H), 3.75 (s, 2H), 3.73 (s, 3H), 3.63-3.55 (d (br), 2H), 2.93-2.83 (m (br), 2H), 2.73-2.64 (m, 1H), 2.26 (s, 3H), 2.18 (s, 3H), 2.14 (s, 3H), 1.94-1.87 (m (br), 2H), 1.80-1.68 (m, 2H).

MS Method 2: RT: 1.26 min, m/z 477.3 [M+H]$^+$

Those skilled in the art will appreciate that there are several alternative metal mediated cross coupling reactions which can be used as an alternative to the Suzuki-Miyura cross coupling of a boronic acid described above, for example the Stille or Kumada, or Negishi or Hiyama or Heck-Matsuda coupling.

The compounds shown below in Table 6 were similarly prepared by varying General Method B.

TABLE 6

| Structure | Name | LCMS RT | m/z MIM |
|---|---|---|---|
| 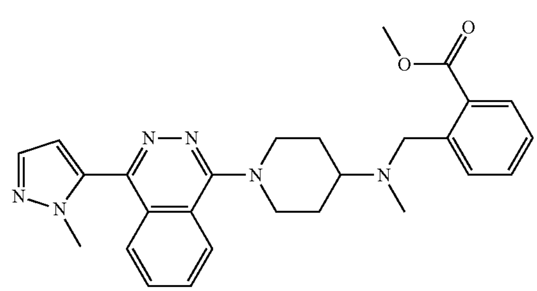 [SMILES: COC(=O)c1ccccc1CN(C)C1CCN(c2nnc(-c3ccnn3C)c3ccccc23)CC1] | methyl 2-[[methyl-[1-[4-(2-methylpyrazol-3-yl)phthalazin-1-yl]-4-piperidyl]amino]methyl]benzoate | 1.20 min (Method 2) | 471.3 [M + H]$^+$ |

TABLE 6-continued

| Structure | Name | LCMS RT | m/z MIM |
|---|---|---|---|
| 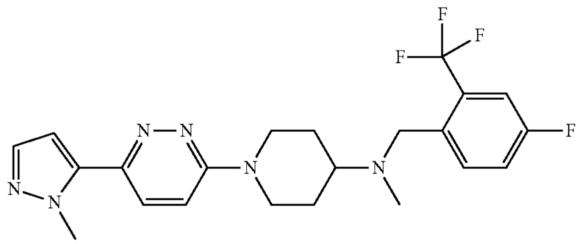 [SMILES: CN(Cc1ccc(F)cc1C(F)(F)F)C1CCN(c2ccc(-c3ccnn3C)nn2)CC1] | N-[[4-fluoro-2-(trifluoromethyl)phenyl]methyl]-N-methyl-1-[6-(2-methylpyrazol-3-yl)pyridazin-3-yl]piperidin-4-amine | 1.16 min (Method 2) | 449.3 [M + H]+ |
| 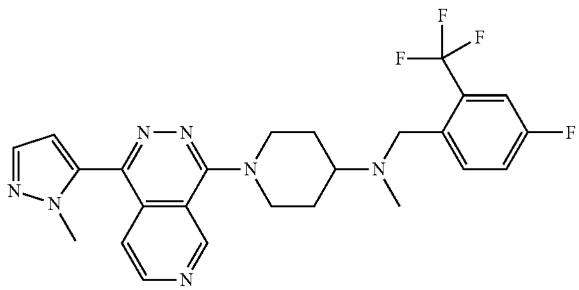 [SMILES: CN(Cc1ccc(F)cc1C(F)(F)F)C1CCN(c2nnc(-c3ccnn3C)c3ccncc23)CC1] | N-[[4-fluoro-2-(trifluoromethyl)phenyl]methyl]-N-methyl-1-[1-(2-methylpyrazol-3-yl)pyrido[3,4-d]pyridazin-4-yl]piperidin-4-amine | 1.19 min (Method 2) | 500.3 [M + H]+ |
| 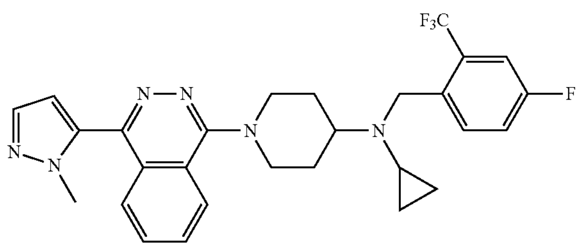 [SMILES: Cn1nccc1-c1nnc(N2CCC(N(Cc3ccc(F)cc3C(F)(F)F)C3CC3)CC2)c2ccccc12] | N-cyclopropyl-N-[[4-fluoro-2-(trifluoromethyl)phenyl]methyl]-1-[4-(2-methylpyrazol-3-yl)phthalazin-1-yl]piperidin-4-amine | 3.97 min (Method 1) | 525.4 [M + H]+ |

Example 10

Compounds of formula (I) can be prepared by the General Method C, shown below. General Method C may be carried out using compounds prepared by Procedure B as starting materials or another appropriate method for producing the starting materials may be used.

General Method C

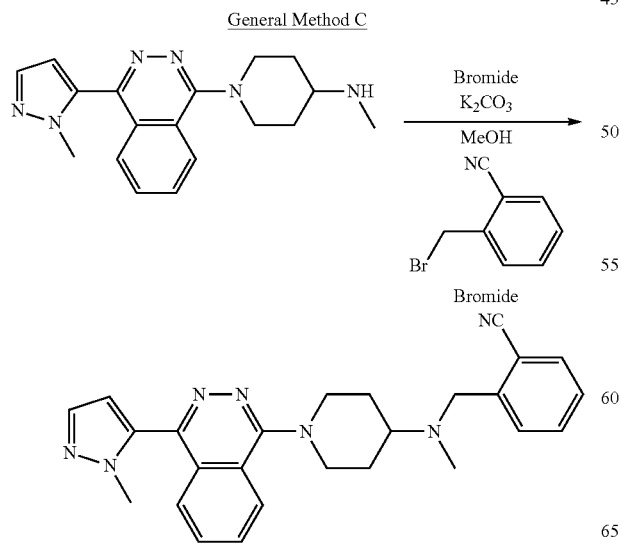

2-[[methyl-[1-[4-(2-methylpyrazol-3-yl)phthalazin-1-yl]-4-piperidyl]amino]methyl]benzonitrile

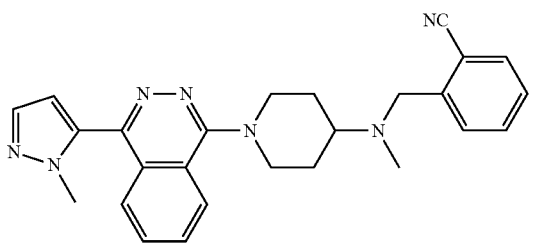

N-Methyl-1-[4-(2-methylpyrazol-3-yl)phthalazin-1-yl]piperidin-4-amine (120 mg, 0.37 mmol), 2-(bromomethyl)benzonitrile (88 mg, 0.45 mmol) and potassium carbonate (77 mg, 0.56 mmol) were combined in acetonitrile and stirred for four days at room temperature. The reaction solvent was evaporated, the material partitioned between water and ethyl acetate and the product extracted with ethyl acetate (×3). The organic layer was washed with brine then dried (NaSO₄) and concentrated in vacuo to afford the crude product as a brown-orange gum. The crude material was purified by silica column chromatography using 100% DCM with a gradient to 5% methanol in DCM to elute the product. Concentration in vacuo afforded 2-[[methyl-[1-[4-(2-methylpyrazol-3-yl)phthalazin-1-yl]-4-piperidyl]amino]methyl]benzonitrile (109 mg, 0.25 mmol, 67%) as a yellow gum.

¹H NMR (400 MHz, CDCl₃) δ/ppm: 8.14 (d, J 8.1 Hz, 1H), 8.06 (d, J 8.1 Hz, 1H), 7.91-7.81 (t, J 7.1 Hz, 1H), 7.84-7.81 (t, J7.1 Hz, 1H), 7.70-7.57 (m, 4H), 7.41-7.36 (m, 1H), 6.60 (d, J 2.0 Hz, 1H), 4.19-4.13 (m (br), 2H), 4.07 (s, 3H), 3.90 (s, 2H), 3.24-3.16 (m, 2H), 2.91-2.83 (m, 1H), 2.33 (s, 3H), 2.16-1.98 (m, 4H).

MS Method 1: RT: 2.52 min, m/z 438.3 [M+H]⁺

The compounds shown below in Table 7 were similarly prepared by varying the bromide used in General Method C.

TABLE 7

| Compound | Compound Name | LCMS RT | m/z |
|---|---|---|---|
|  | 1-[4-(2-methylpyrazol-3-yl)phthalazin-1-yl]-N-[(2-nitrophenyl)methyl]piperidin-4-amine | 1.14 min (Method 2) | 444.3 [M + H]⁺ |
|  | N-[[6-chloro-2-(trifluoromethyl)-3-pyridyl]methyl]-N-methyl-1-[4-(2-methylpyrazol-3-yl)phthalazin-1-yl]piperidin-4-amine | 3.04 min (Method 1) | 516.2 [M + H]⁺ |
|  | N-[[6-chloro-2-(trifluoromethyl)-3-pyridyl]methyl]-1-[4-(2-methylpyrazol-3-yl)phthalazin-1-yl]piperidin-4-amine | 2.88 (Method 1) | 502.3 [M + H]⁺ |
|  | N-methyl-1-[4-(2-methylpyrazol-3-yl)phthalazin-1-yl]-N-[(2-nitrophenyl)methyl]piperidin-4-amine | 2.57 min (Method 1) | 458.3 [M + H]⁺ |
|  | N-methyl-1-[4-(2-methylpyrazol-3-yl)phthalazin-1-yl]-N-[[2-(trifluoromethyl)-3-pyridyl]methyl]piperidin-4-amine | 2.61 min (Method 1) | 482.3 [M + H]⁺ |

TABLE 7-continued

| Compound | Compound Name | LCMS RT | m/z |
|---|---|---|---|
| 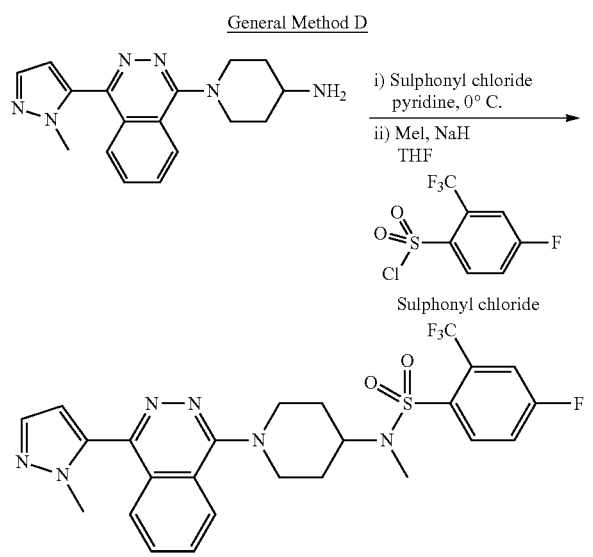 | 1-[4-(2-methylpyrazol-3-yl)phthalazin-1-yl]-N-[[2-(trifluoromethyl)-3-pyridyl]methyl]piperidin-4-amine | 2.52 min (Method 1) | 468.4 [M + H]⁺ |

Example 11

Compounds of formula (I) can be prepared by the General Method D, shown below. General Method D may be carried out using compounds prepared by Procedure B as starting materials or another appropriate method for producing the starting materials may be used.

General Method D

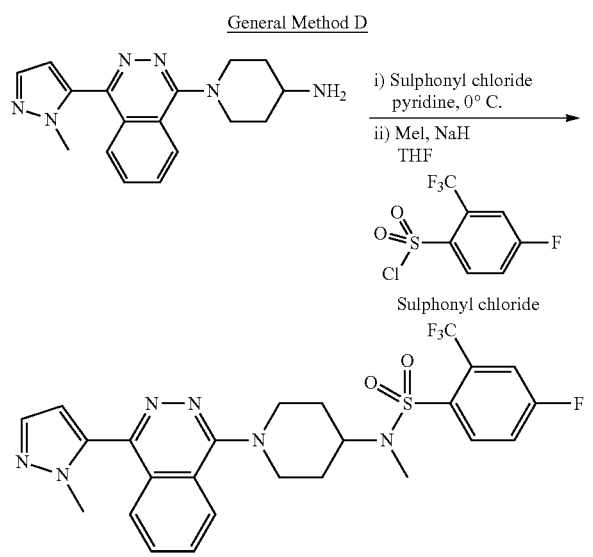

4-Fluoro-N-[1-[4-(2-methylpyrazol-3-yl)phthalazin-1-yl]-4-piperidyl]-2-(trifluoromethyl)benzenesulfonamide

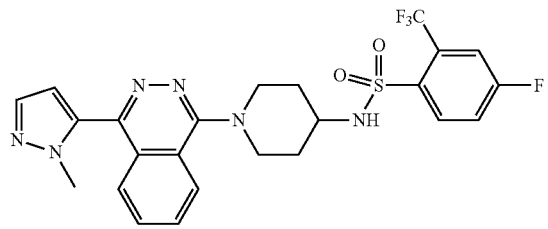 [SMILES: Cn1nccc1-c1nnc(N2CCC(NS(=O)(=O)c3ccc(F)cc3C(F)(F)F)CC2)c2ccccc12]

1-[4-(2-Methylpyrazol-3-yl)phthalazin-1-yl]piperidin-4-amine (297 mg, 0.96 mmol) was taken up in pyridine (0.5 mL, 6.2 mmol) and cooled to 0° C. 4-Fluoro-2-(trifluoromethyl)benzenesulfonyl chloride (230 mg, 0.88 mmol) was added in portions and the mixture stirred for 1 hour slowly warming to room temperature. The mixture was left to stir for another hour at room temperature. The reaction mixture was diluted in DCM (20 mL) and washed with brine (20 mL). The organics were collected, dried (MgSO₄), and concentrated in vacuo to afford 250 mg of crude product as a yellow oil. Purification by silica column chromatography using 30% ethyl acetate in heptane with a gradient to 100% ethyl acetate afforded 250 mg of crude yellow oil. 40 mg of the crude oil was purified by preparative LCMS. Fractions containing product were evaporated to dryness then further dried in the vacuum oven for 2 hours to give 4-fluoro-N-[1-[4-(2-methylpyrazol-3-yl)phthalazin-1-yl]-4-piperidyl]-2-(trifluoromethyl)benzenesulfonamide (18 mg) as a white solid.

$^1$H NMR (400 MHz, CDCl₃) δ/ppm: 8.38 (dd, J 8.9 Hz, 5.4 Hz, 1H), 8.09-8.03 (m, 2H), 7.90-7.81 (m, 2H), 7.67 (d, J 2.0 Hz, 1H), 7.64 (dd, J 8.9 Hz, 2.6 Hz, 1H), 7.49-7.42 (m, 1H), 6.59 (d, 1.9 Hz, 1H), 4.78 (d (br), J 7.6 Hz, 1H), 4.05 (s, 3H), 3.97-3.91 (m (br), 2H), 3.63-3.52 (m, 1H), 3.27-3.19 (m, 2H), 2.07-1.99 (m, 2H), 1.89-1.78 (m, 2H).

MS Method 1: RT: 3.75 min, m/z 535.3 [M+H]⁺

4-Fluoro-N-methyl-N-[1-[4-(2-methylpyrazol-3-yl)phthalazin-1-yl]-4-piperidyl]-2-(trifluoromethyl)benzenesulfonamide

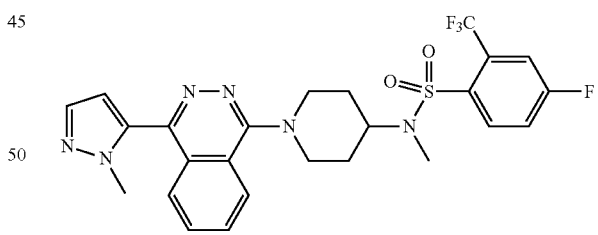

4-Fluoro-N-[1-[4-(2-methylpyrazol-3-yl)phthalazin-1-yl]-4-piperidyl]-2-(trifluoromethyl)benzenesulfonamide (286 mg, 0.54 mmol) was taken up in THF (2 mL) and cooled to 0° C. Sodium Hydride 60% In Oil (15.4 mg, 0.64 mmol) was added and the mixture stirred at this temperature for 40 minutes at which point Iodomethane (70 uL, 1.07 mmol) was added. The mixture was allowed to reach room temperature and then left to stir overnight at room temperature. The reaction was quenched by the addition of water followed by extraction with ethyl acetate (3×20 mL). The organics were combined, washed with brine (20 mL), dried over sodium sulfate, filtered then evaporated to dryness to give the crude product as an orange solid. Purification with silica column chromatography using ethyl acetate in heptane with a gradient to 100% ethyl acetate afforded 60 mg of a yellow oil. Further purification was performed on the preparative LCMS to give 4-Fluoro-N-methyl-N-[1-[4-(2-methylpyrazol-3-yl)phthalazin-1-yl]-4-piperidyl]-2-(trifluoromethyl)benzenesulfonamide (26.4 mg, 0.05 mmol, 9.0%) as a white solid.

$^1$H NMR (400 MHz, CDCl$_3$) δ/ppm: 8.29 (dd, 8.8 Hz, 5.5 Hz, 1H), 8.10-8.06 (m, 2H), 7.91-7.82 (m, 2H), 7.67 (d, J 1.9 Hz, 1H), 7.63 (dd, J 9.0 Hz, 2.6 Hz, 1H), 7.45-7.40 (m, 1H), 6.60 (d, J 1.9 Hz, 1H), 4.18-4.11 (m (br), 3H), 4.07 (s, 3H), 3.32-3.23 (m, 2H), 2.88 (s, 3H), 2.16 (qd, J 12.3 Hz, 3.9 Hz, 2H), 1.90-1.83 (m, 2H).

MS Method 1: RT: 3.97 min, m/z 549.3 [M+H]$^+$

The compounds shown below in Table 8 were similarly prepared by varying the sulphonyl chloride used in General Method D.

TABLE 8

| Structure | Name | LCMS RT | m/z MIM |
|---|---|---|---|
| 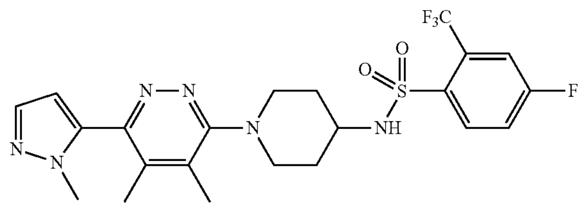 [SMILES: Cc1c(-c2ccnn2C)nnc(N2CCC(NS(=O)(=O)c3ccc(F)cc3C(F)(F)F)CC2)c1C] | N-[1-[4,5-dimethyl-6-(2-methylpyrazol-3-yl)pyridazin-3-yl]-4-piperidyl]-4-fluoro-2-(trifluoromethyl)benzenesulfonamide | 1.60 min (Method 2) | 513.3 [M + H]$^+$ |
| 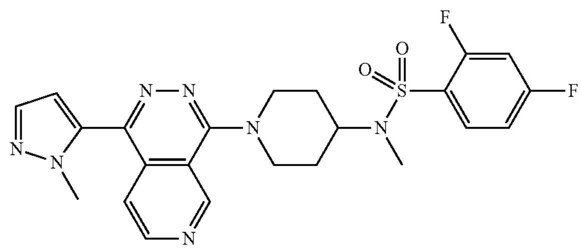 [SMILES: CN(C1CCN(c2nnc(-c3ccnn3C)c3ccncc23)CC1)S(=O)(=O)c1ccc(F)cc1F] | 2,4-difluoro-N-methyl-N-[1-[1-(2-methylpyrazol-3-yl)pyrido[3,4-d]pyridazin-4-yl]-4-piperidyl]benzenesulfonamide | 1.57 min (Method 2) | 500.4 [M + H]$^+$ |
| 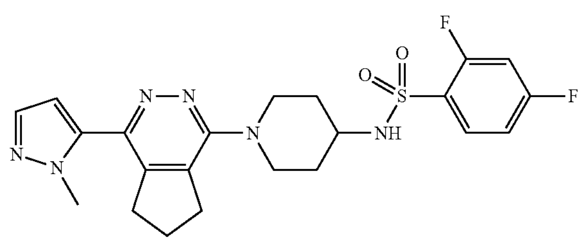 [SMILES: Cn1nccc1-c1nnc(N2CCC(NS(=O)(=O)c3ccc(F)cc3F)CC2)c2c1CCC2] | 2,4-difluoro-N-[1-[1-(2-methylpyrazol-3-yl)-6,7-dihydro-5H-cyclopenta[d]pyridazin-4-yl]-4-piperidyl]benzenesulfonamide | 1.43 min (Method 2) | 475.3 [M + H]$^+$ |
| 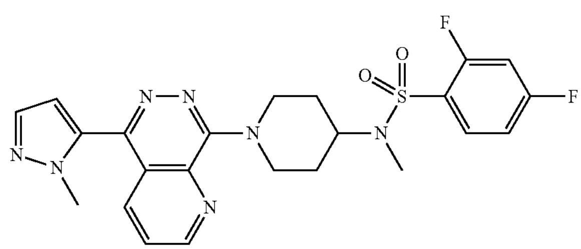 | 4-fluoro-N-methyl-N-[1-[5-(2-methylpyrazol-3-yl)pyrido[2,3-d]pyridazin-8-yl]-4-piperidyl]-2-(trifluoromethyl)benzenesulfonamide | 1.63 min (Method 2) | 550.3 [M + H]$^+$ |
| 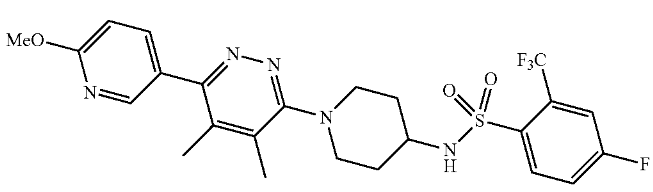 [SMILES: COc1ccc(-c2nnc(N3CCC(NS(=O)(=O)c4ccc(F)cc4C(F)(F)F)CC3)c(C)c2C)cn1] | 4-fluoro-N-[1-[6-(6-methoxy-3-pyridyl)-4,5-dimethyl-pyridazin-3-yl]-4-piperidyl]-2-(trifluoromethyl)benzenesulfonamide | 1.64 min (Method 2) | 540.3 [M + H]$^+$ |
| 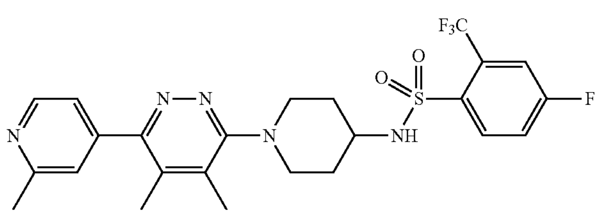 [SMILES: Cc1cc(-c2nnc(N3CCC(NS(=O)(=O)c4ccc(F)cc4C(F)(F)F)CC3)c(C)c2C)ccn1] | N-[1-[4,5-dimethyl-6-(2-methyl-4-pyridyl)pyridazin-3-yl]-4-piperidyl]-4-fluoro-2-(trifluoromethyl)benzenesulfonamide | 1.37 min (Method 2) | 524.3 [M + H]$^+$ |

TABLE 8-continued

| Structure | Name | LCMS RT | m/z MIM |
|---|---|---|---|
| 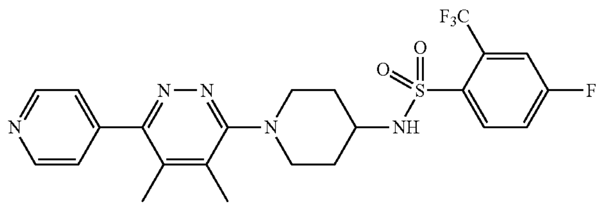 [SMILES: Cc1c(-c2ccncc2)nnc(N2CCC(NS(=O)(=O)c3ccc(F)cc3C(F)(F)F)CC2)c1C] | N-[1-[4,5-dimethyl-6-(4-pyridyl)pyridazin-3-yl]-4-piperidyl]-4-fluoro-2-(trifluoromethyl)benzenesulfonamide | 1.41 min (Method 2) | 510.3 [M + H]+ |
| 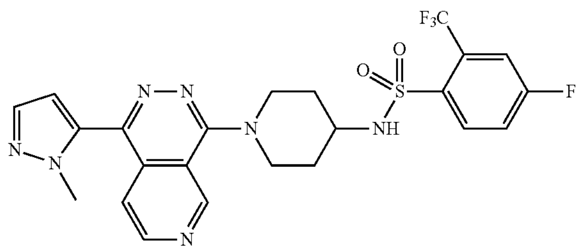 [SMILES: Cn1nccc1-c1nnc(N2CCC(NS(=O)(=O)c3ccc(F)cc3C(F)(F)F)CC2)c2cnccc12] | 4-fluoro-N-[1-[1-(2-methylpyrazol-3-yl)pyrido[3,4-b]pyridazin-4-yl]-4-piperidyl]-2-(trifluoromethyl)benzenesulfonamide | 1.57 min (Method 2) | 536.4 [M + H]+ |
| 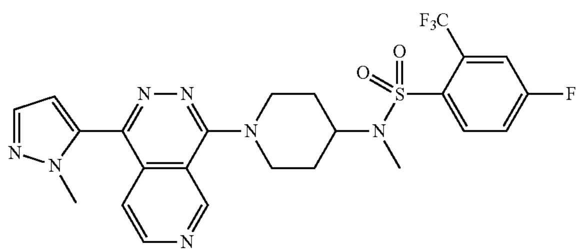 [SMILES: CN(C1CCN(c2nnc(-c3ccnn3C)c3ccncc23)CC1)S(=O)(=O)c1ccc(F)cc1C(F)(F)F] | 4-fluoro-N-methyl-N-[1-[1-(2-methylpyrazol-3-yl)pyrido[3,4-d]pyridazin-4-yl]-4-piperidyl]-2-(trifluoromethyl)benzenesulfonamide | 1.68 min (Method 2) | 550.4 [M + H]+ |
| 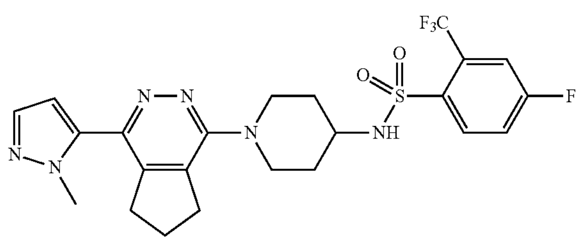 [SMILES: Cn1nccc1-c1nnc(N2CCC(NS(=O)(=O)c3ccc(F)cc3C(F)(F)F)CC2)c2c1CCC2] | 4-fluoro-N-[1-[1-(2-methylpyrazol-3-yl)-6,7-dihydro-5H-cyclopenta[d]pyridazin-4-yl]-4-piperidyl]-2-(trifluoromethyl)benzenesulfonamide | 3.59 min (Method 1) | 525.3 [M + H]+ |
| 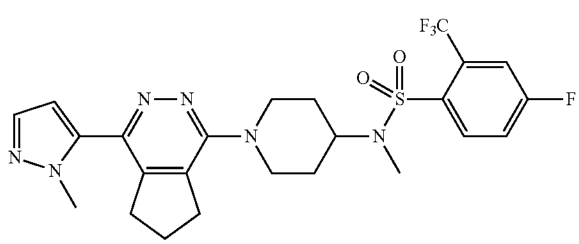 [SMILES: CN(C1CCN(c2nnc(-c3ccnn3C)c3c2CCC3)CC1)S(=O)(=O)c1ccc(F)cc1C(F)(F)F] | 4-fluoro-N-methyl-N-[1-[1-(2-methylpyrazol-3-yl)-6,7-dihydro-5H-cyclopenta[d]pyridazin-4-yl]-4-piperidyl]-2-(trifluoromethyl)benzenesulfonamide | 1.67 min (Method 2) | 539.3 [M + H]+ |

Example 12

Compounds of formula (I) can be prepared by the General Method E, shown below. General Method E may be carried out using compounds prepared by Procedure B as starting materials or another appropriate method for producing the starting materials may be used.

General Method E

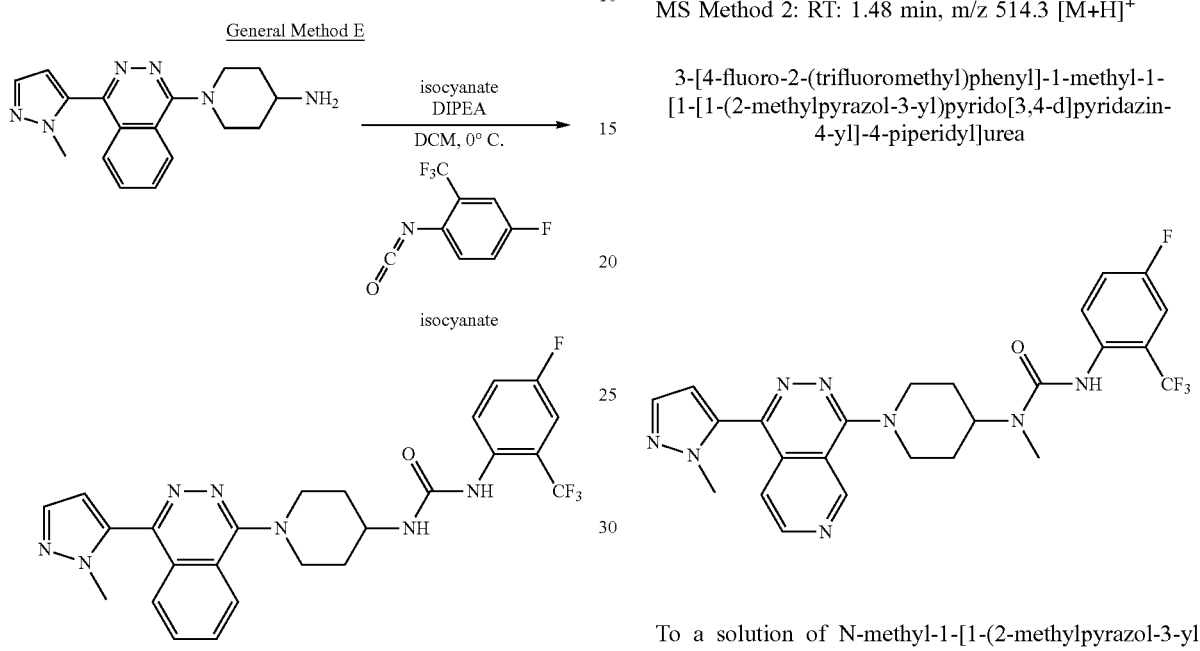

1-[4-Fluoro-2-(trifluoromethyl)phenyl]-3-[1-[4-(2-methylpyrazol-3-yl)phthalazin-1-yl]-4-piperidyl]urea

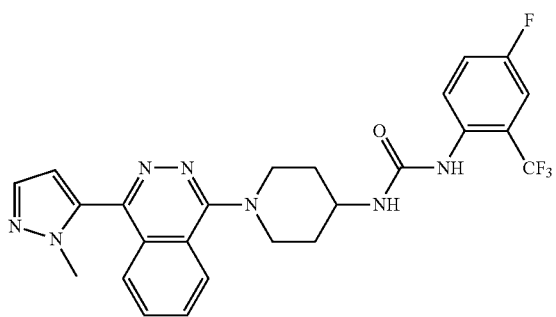 [SMILES: Cn1nccc1-c1nnc(N2CCC(NC(=O)Nc3ccc(F)cc3C(F)(F)F)CC2)c2ccccc12]

In dried glassware DIPEA (0.06 mL, 0.34 mmol), DCM (1 mL) and 1-[4-(2-methylpyrazol-3-yl)phthalazin-1-yl]piperidin-4-amine (0.05 mL, 0.23 mmol) were combined. The suspension was cooled to 0° C. and to this was added 4-fluoro-2-(trifluoromethyl)phenyl isocyanate (0.04 mL, 0.2500 mmol) dropwise. The reaction was stirred at 0° C. and then stirred overnight at room temperature. An off-white precipitate formed. The reaction was filtered and the solid was washed with DCM. The white solid was then dried in the vacuum oven overnight to afford 1-[4-fluoro-2-(trifluoromethyl)phenyl]-3-[1-[4-(2-methylpyrazol-3-yl)phthalazin-1-yl]-4-piperidyl]urea (57.7 mg, 0.11 mmol, 50%).

$^1$H NMR (400 MHz, DMSO-d6) δ/ppm: 8.19 (d, J 8.2 Hz, 1H), 8.05-7.92 (m, 4H), 7.80 (s, 1H), 7.66 (d, J 1.9 Hz, 1H), 7.55-7.47 (m, 2H), 7.15 (d, J 7.5 Hz, 1H), 6.69 (d, J 1.9 Hz, 1H), 3.89-3.82 (m (br), 3H), 3.87 (s, 3H), 3.34-3.26 (m, 2H), 2.14-2.06 (m, 2H), 1.82-1.71 (m, 2H).

MS Method 2: RT: 1.48 min, m/z 514.3 [M+H]$^+$

3-[4-fluoro-2-(trifluoromethyl)phenyl]-1-methyl-1-[1-[1-(2-methylpyrazol-3-yl)pyrido[3,4-d]pyridazin-4-yl]-4-piperidyl]urea

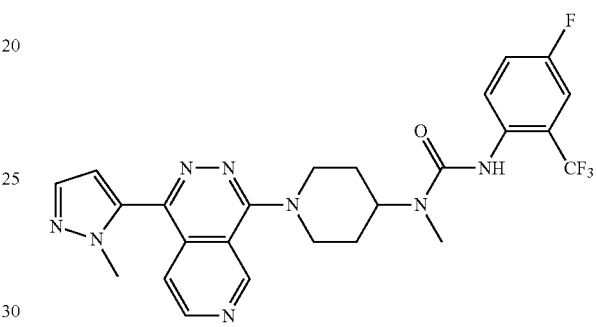

To a solution of N-methyl-1-[1-(2-methylpyrazol-3-yl)pyrido[3,4-d]pyridazin-4-yl]piperidin-4-amine (947 mg, 2.93 mmol) and N,N-diisopropylethylamine (0.76 mL, 4.39 mmol) in DCM (30 mL) (dried over 4 Å MS) was added 4-fluoro-2-(trifluoromethyl)phenyl isocyanate (0.42 mL, 2.93 mmol) dropwise at 0° C. The reaction was stirred at this temperature for 30 minutes and then stirred at room temperature for 4 hours. The reaction was quenched with saturated aqueous. sodium bicarbonate and diluted with DCM, The mixture was passed through a phase separator and the aqueous layer was re-extracted several times with DCM, the organic layers were combined and concentrated. The resulting residue was purified by silica flash chromatography using 0% methanol in ethyl acetate with a gradient increasing to 20% methanol in ethyl acetate to afford 3-[4-fluoro-2-(trifluoromethyl)phenyl]-1-methyl-1-[1-[1-(2-methylpyrazol-3-yl)pyrido[3,4-d]pyridazin-4-yl]-4-piperidyl]urea (920 mg, 1.74 mmol, 59.5% yield) as a yellow solid. The product was then dried in the vacuum oven for 4 days.

$^1$H NMR (400 MHz, CDCl$_3$) δ/ppm: 9.53 (s, 1H), 8.95 (d, J5.7 Hz, 1H), 8.11 (dd, J9.0 Hz, 5.0 Hz, 1H), 7.86 (d, J5.7 Hz, 1H), 7.68 (d, J1.9 Hz, 1H), 7.33-7.23 (m, 2H), 6.73 (s, 1H), 6.61 (d, J1.9 Hz, 1H), 4.66-4.55 (m, 1H), 4.39-4.31 (m (br), 2H), 4.11 (s, 3H), 3.47-3.37 (m, 2H), 2.99 (s, 3H), 2.16-2.04 (m, 2H), 1.99-1.92 (m, 2H).

MS Method 1: RT: 3.41 min, m/z 529.4 [M+H]$^+$

And similarly prepared was:

3-[4-fluoro-2-(trifluoromethyl)phenyl]-1-methyl-1-[1-[4-(2-methylpyrazol-3-yl)phthalazin-1-yl]-4-piperidyl]urea

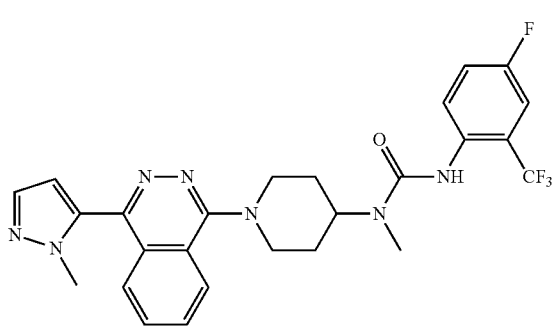 [SMILES: CN(C(=O)Nc1ccc(F)cc1C(F)(F)F)C1CCN(c2nnc(-c3ccnn3C)c3ccccc23)CC1]

¹H NMR (400 MHz, CDCl₃) δ/ppm: 8.17-8.07 (m, 3H), 7.92-7.82, (m, 2H), 7.68 (d, J1.9 Hz, 1H), 7.34-7.25 (m, 2H), 6.76 (s, 1H), 6.61 (d, J1.9 Hz, 1H), 4.61-4.51 (m, 1H), 4.24-4.16 (m (br), 2H), 4.08 (s, 3H), 3.40-3.30 (t, J 12.5 Hz, 2H), 3.02 (s, 3H), 2.20-2.08 (m, 2H), 1.98-1.91 (m, 2H).

MS Method 1: RT: 3.47 min, m/z 528.3 [M+H]⁺

And similarly prepared was:

1-[1-[4,5-dimethyl-6-(2-methylpyrazol-3-yl)pyridazin-3-yl]-4-piperidyl]-3-[4-fluoro-2-(trifluoromethyl)phenyl]-1-methyl-urea

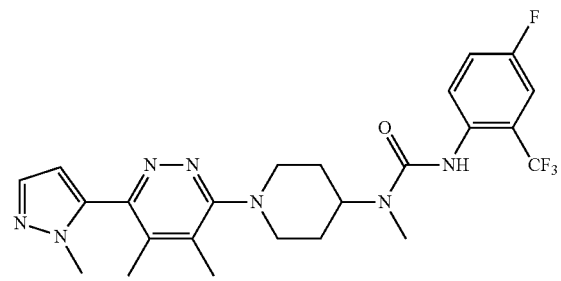 [SMILES: Cc1c(-c2ccnn2C)nnc(N2CCC(N(C)C(=O)Nc3ccc(F)cc3C(F)(F)F)CC2)c1C]

¹H NMR (400 MHz, CDCl₃) δ/ppm: 8.15-8.09 (m, 1H), 7.57 (d, J2.0 Hz, 1H), 7.31-7.21 (m, 2H), 6.72 (s, 1H), 6.36 (d, J2.0 Hz, 1H), 4.48-4.37 (m, 1H), 3.93 (s, 3H), 3.74-3.67 (m (br), 2H), 3.16 (t, J12.8 Hz, 2H), 2.96 (s, 3H), 2.30 (s, 3H), 2.23 (s, 3H), 2.03-1.91 (m, 2H), 1.90-1.83 (m, 2H).

MS Method 1: RT: 3.63 min, m/z 506.3 [M+H]⁺

The compounds shown below in Table 9 were also similarly prepared by varying the isocyanate used in General Method E.

TABLE 9

| Structure | Name | LCMS RT | m/z MIM |
|---|---|---|---|
| 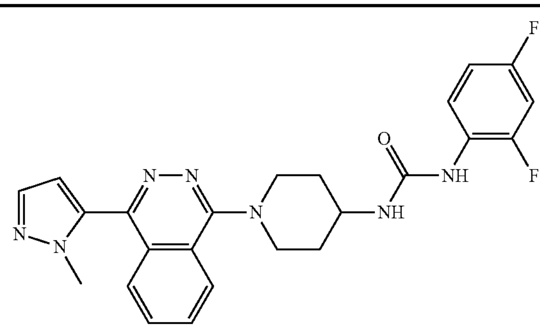 | 1-(2,4-difluorophenyl)-3-[1-[4-(2-methylpyrazol-3-yl)phthalazin-1-yl]-4-piperidyl]urea | 1.37 min (Method 2) | 464.3 [M + H]⁺ |
| 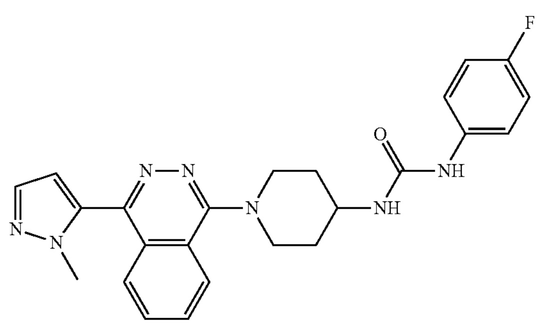 [SMILES: Cn1nccc1-c1nnc(N2CCC(NC(=O)Nc3ccc(F)cc3)CC2)c2ccccc12] | 1-(4-fluorophenyl)-3-[1-[4-(2-methylpyrazol-3-yl)phthalazin-1-yl]-4-piperidyl]urea | 1.33 min (Method 2) | 446.3 [M + H]⁺ |
| 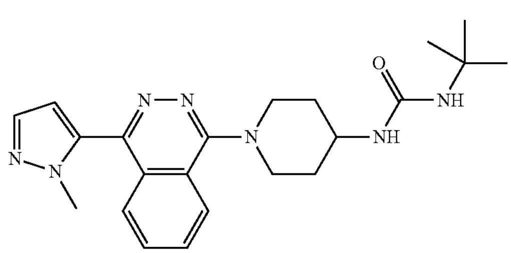 [SMILES: Cn1nccc1-c1nnc(N2CCC(NC(=O)NC(C)(C)C)CC2)c2ccccc12] | 1-tert-butyl-3-[1-[4-(2-methylpyrazol-3-yl)phthalazin-1-yl]-4-piperidyl]urea | 1.24 min (Method 2) | 408.3 [M + H]⁺ |

TABLE 9-continued

| Structure | Name | LCMS RT | m/z MIM |
|---|---|---|---|
| 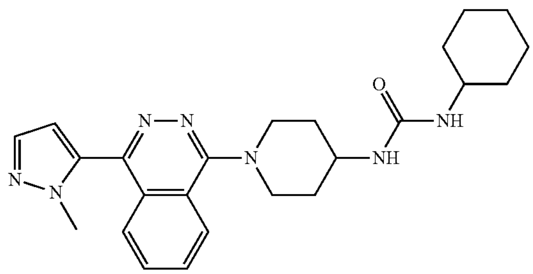 [SMILES: Cn1nccc1-c1nnc(N2CCC(NC(=O)NC3CCCCC3)CC2)c2ccccc12] | 1-cyclohexyl-3-[1-[4-(2-methylpyrazol-3-yl)phthalazin-1-yl]-4-piperidyl]urea | 1.32 min (Method 2) | 434.3 [M + H]+ |
| 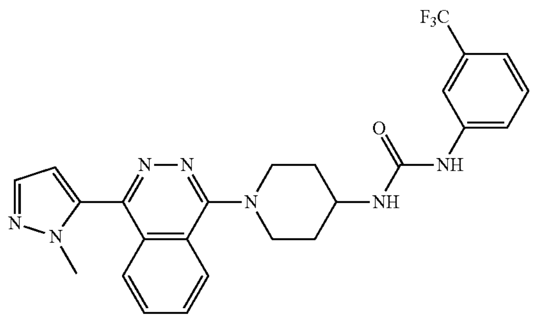 [SMILES: Cn1nccc1-c1nnc(N2CCC(NC(=O)Nc3cccc(C(F)(F)F)c3)CC2)c2ccccc12] | 1-[1-[4-(2-methylpyrazol-3-yl)phthalazin-1-yl]-4-piperidyl]-3-[3-(trifluoromethyl)phenyl]urea | 1.53 min (Method 2) | 496.3 [M + H]+ |
| 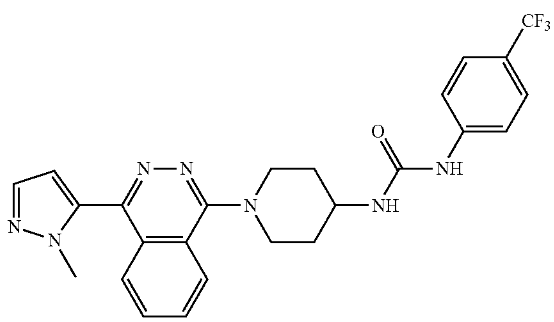 [SMILES: Cn1nccc1-c1nnc(N2CCC(NC(=O)Nc3ccc(C(F)(F)F)cc3)CC2)c2ccccc12] | 1-[1-[4-(2-methylpyrazol-3-yl)phthalazin-1-yl]-4-piperidyl]-3-[4-(trifluoromethyl)phenyl]urea | 1.54 min (Method 2) | 497.1 [M + H]+ |
| 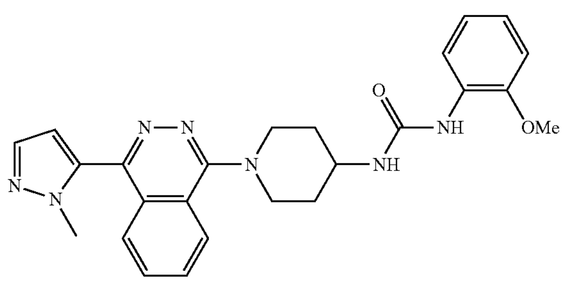 [SMILES: COc1ccccc1NC(=O)NC1CCN(c2nnc(-c3ccnn3C)c3ccccc23)CC1] | 1-(2-methoxyphenyl)-3-[1-[4-(2-methylpyrazol-3-yl)phthalazin-1-yl]-4-piperidyl]urea | 1.37 min (Method 2) | 458.3 [M + H]+ |
| 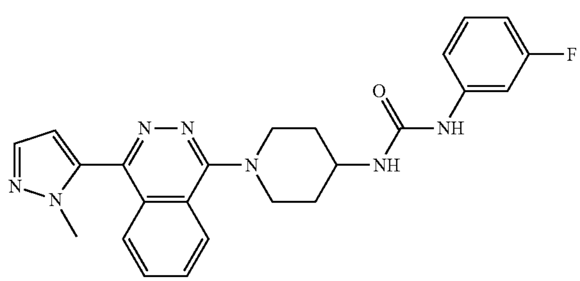 [SMILES: Cn1nccc1-c1nnc(N2CCC(NC(=O)Nc3cccc(F)c3)CC2)c2ccccc12] | 1-(3-fluorophenyl)-3-[1-[4-(2-methylpyrazol-3-yl)phthalazin-1-yl]-4-piperidyl]urea | 1.37 min (Method 2) | 446.3 [M + H]+ |

TABLE 9-continued

| Structure | Name | LCMS RT | m/z MIM |
|---|---|---|---|
| | 1-[1-[4-(2-methylpyrazol-3-yl)phthalazin-1-yl]-4-piperidyl]-3-[2-(trifluoromethyl)phenyl]urea | 1.46 min (Method 2) | 496.3 [M + H]$^+$ |
| 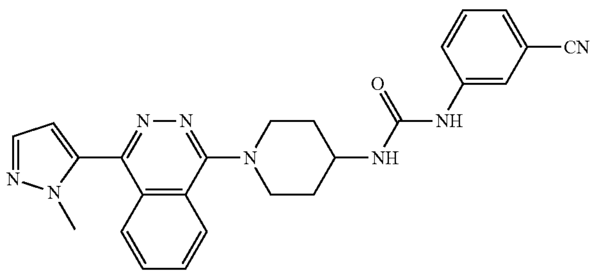 [SMILES: Cn1nccc1-c1nnc(N2CCC(NC(=O)Nc3cccc(C#N)c3)CC2)c2ccccc12] | 1-(3-cyanophenyl)-3-[1-[4-(2-methylpyrazol-3-yl)phthalazin-1-yl]-4-piperidyl]urea | 1.33 min (Method 2) | 453.3 [M + H]$^+$ |
| 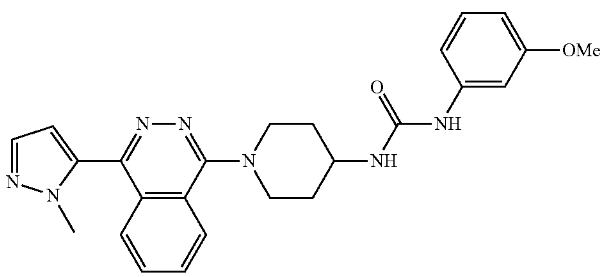 [SMILES: COc1cccc(NC(=O)NC2CCN(c3nnc(-c4ccnn4C)c4ccccc34)CC2)c1] | 1-(3-methoxyphenyl)-3-[1-[4-(2-methylpyrazol-3-yl)phthalazin-1-yl]-4-piperidyl]urea | 1.33 min (Method 2) | 458.2 [M + H]$^+$ |
| | 1-[1-[4-(2-methylpyrazol-3-yl)phthalazin-1-yl]-4-piperidyl]-3-[2-(trifluoromethyl)phenyl]urea | 1.54 min (Method 2) | 512.4 [M + H]$^+$ |
| 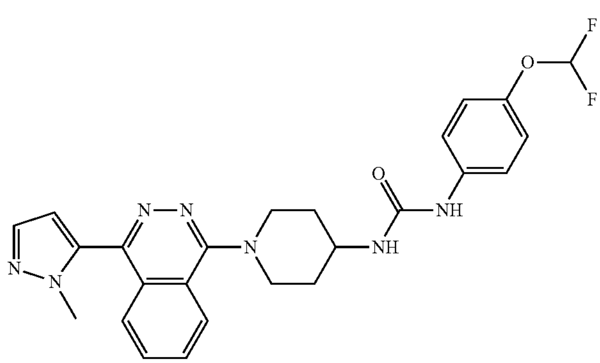 [SMILES: Cn1nccc1-c1nnc(N2CCC(NC(=O)Nc3ccc(OC(F)F)cc3)CC2)c2ccccc12] | 1-[4-(difluoromethoxy)phenyl]-3-[1-[4-(2-methylpyrazol-3-yl)phthalazin-1-yl]-4-piperidyl]urea | 1.41 min (Method 2) | 494.3 [M + H]$^+$ |

TABLE 9-continued

| Structure | Name | LCMS RT | m/z MIM |
|---|---|---|---|
| 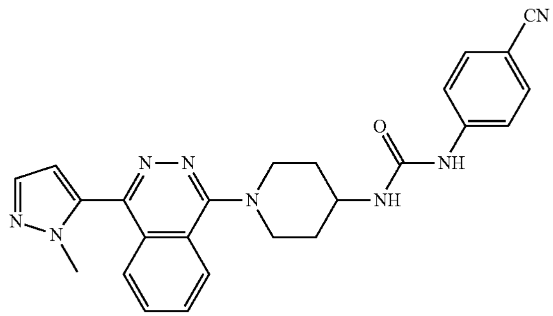 [SMILES: Cn1nccc1-c1nnc(N2CCC(NC(=O)Nc3ccc(C#N)cc3)CC2)c2ccccc12] | 1-(4-cyanophenyl)-3-[1-[4-(2-methylpyrazol-3-yl)phthalazin-1-yl]-4-piperidyl]urea | 1.32 min (Method 2) | 453.2 [M + H]+ |
| 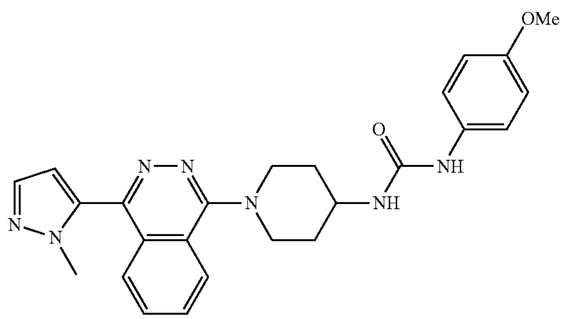 [SMILES: COc1ccc(NC(=O)NC2CCN(c3nnc(-c4ccnn4C)c4ccccc34)CC2)cc1] | 1-(4-methoxyphenyl)-3-[1-[4-(2-methylpyrazol-3-yl)phthalazin-yl]-4-piperidyl]urea | 1.29 min (Method 2) | 458.3 [M + H]+ |
| 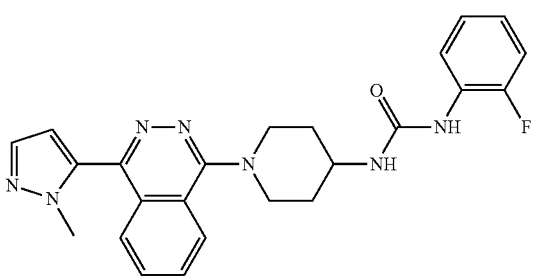 [SMILES: Cn1nccc1-c1nnc(N2CCC(NC(=O)Nc3ccccc3F)CC2)c2ccccc12] | 1-(2-fluorophenyl)-3-[1-[4-(2-methylpyrazol-3-yl)phthalazin-1-yl]-4-piperidyl]urea | 1.35 min (Method 2) | 446.3 [M + H]+ |
| 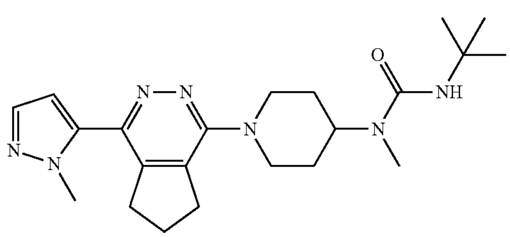 [SMILES: CN(C(=O)NC(C)(C)C)C1CCN(c2nnc(-c3ccnn3C)c3c2CCC3)CC1] | 3-tert-butyl-1-methyl-1-[1-[1-(2-methylpyrazol-3-yl)-6,7-dihydro-5H-cyclopenta[d]pyridazin-4-yl]-4-piperidyl]urea | 1.32 min (Method 2) | 412.4 [M + H]+ |
| 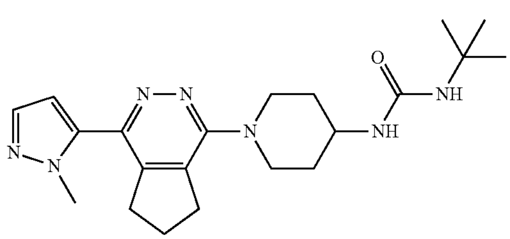 [SMILES: Cn1nccc1-c1nnc(N2CCC(NC(=O)NC(C)(C)C)CC2)c2c1CCC2] | 1-tert-butyl-3-[1-[1-(2-methylpyrazol-3-yl)-6,7-dihydro-5H-cyclopenta[d]pyridazin-4-yl]-4-piperidyl]urea | 2.74 min (Method 1) | 398.4 [M + H]+ |

TABLE 9-continued

| Structure | Name | LCMS RT | m/z MIM |
|---|---|---|---|
| 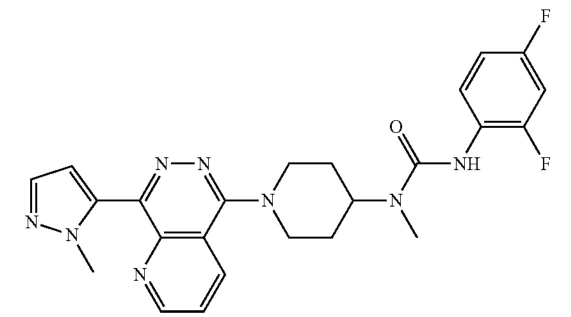 [SMILES: CN(C(=O)Nc1ccc(F)cc1F)C1CCN(c2nnc(-c3ccnn3C)c3ncccc23)CC1] | 3-(2,4-difluorophenyl)-1-methyl-1-[1-[8-(2-methylpyrazol-3-yl)pyrido[2,3-d]pyridazin-5-yl]-4-piperidyl]urea | 3.09 min (Method 1) | 479.4 [M + H]+ |
| 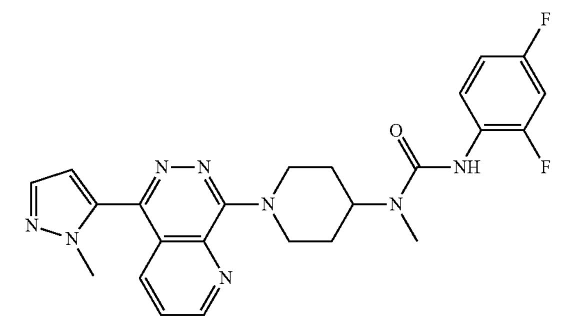 [SMILES: CN(C(=O)Nc1ccc(F)cc1F)C1CCN(c2nnc(-c3ccnn3C)c3cccnc23)CC1] | 3-(2,4-difluorophenyl)-1-methyl-1-[1-[5-(2-methylpyrazol-4-yl)pyrido[2,3-d]pyridazin-8-yl]-4-piperidyl]urea | 3.02 min (Method 1) | 479.4 [M + H]+ |
| 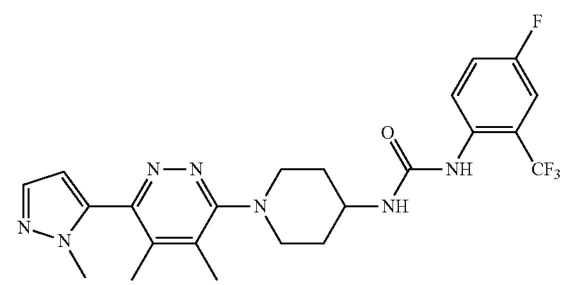 [SMILES: Cc1c(-c2ccnn2C)nnc(N2CCC(NC(=O)Nc3ccc(F)cc3C(F)(F)F)CC2)c1C] | 1-[1-[4,5-dimethyl-6-(2-methylpyrazol-3-yl)pyridazin-3-yl]-4-piperidyl]-3-[4-fluoro-2-(trifluoromethyl)phenyl]urea | 3.56 min (Method 1) | 492.4 [M + H]+ |
| 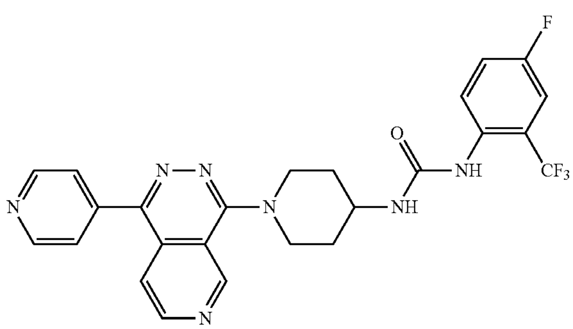 [SMILES: O=C(Nc1ccc(F)cc1C(F)(F)F)NC1CCN(c2nnc(-c3ccncc3)c3ccncc23)CC1] | 1-[4-fluoro-2-(trifluoromethyl)phenyl]-3-[1-[1-(4-pyridyl)pyrido[3,4-d]pyridazin-4-yl]-4-piperidyl]urea | 2.98 min (Method 1) | 512.4 [M + H]+ |
| 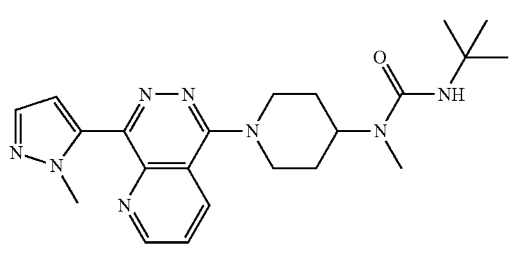 [SMILES: CN(C(=O)NC(C)(C)C)C1CCN(c2nnc(-c3ccnn3C)c3ncccc23)CC1] | 3-tert-butyl-1-methyl-1-[1-[8-(2-methylpyrazol-3-yl)pyrido[2,3-d]pyridazin-5-yl]-4-piperidyl]urea | 1.32 min (Method 2) | 423.3 [M + H]+ |

TABLE 9-continued

| Structure | Name | LCMS RT | m/z MIM |
|---|---|---|---|
| 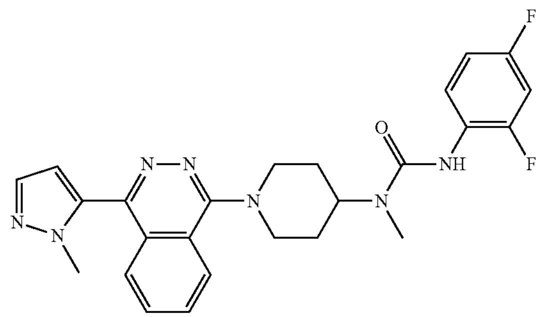 [SMILES: CN(C(=O)Nc1ccc(F)cc1F)C1CCN(c2nnc(-c3ccnn3C)c3ccccc23)CC1] | 3-(2,4-difluorophenyl)-1-methyl-1-[1-[4-(2-methylpyrazol-3-yl)phthalazin-1-yl]-4-piperidyl]urea | 3.16 min (Method 1) | 478.4 [M + H]+ |
| 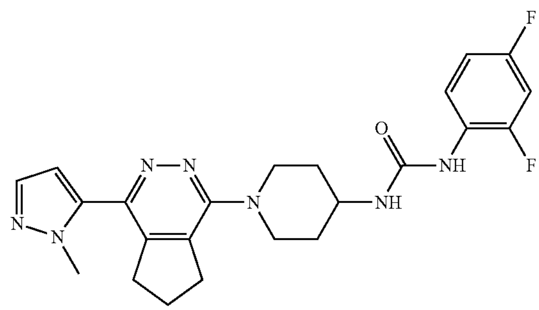 [SMILES: Cn1nccc1-c1nnc(N2CCC(NC(=O)Nc3ccc(F)cc3F)CC2)c2c1CCC2] | 1-(2,4-difluorophenyl)-3-[1-[1-(2-methylpyrazol-3-yl)-6,7-dihydro-5H-cyclopenta[d]pyridazin-4-yl]-4-piperidyl]urea | 3.04 min (Method 1) | 454.3 [M + H]+ |
| 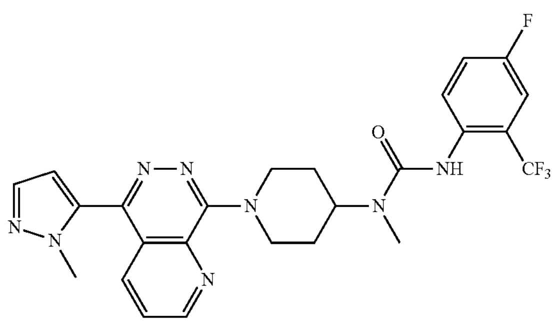 [SMILES: CN(C(=O)Nc1ccc(F)cc1C(F)(F)F)C1CCN(c2nnc(-c3ccnn3C)c3cccnc23)CC1] | 3-[4-fluoro-2-(trifluoromethyl)phenyl]-1-methyl-1-[1-[5-(2-methylpyrazol-3-yl)pyrido[2,3-d]pyridazin-8-yl]-4-piperidyl]urea | 1.44 min (Method 2) | 529.3 [M + H]+ |
| 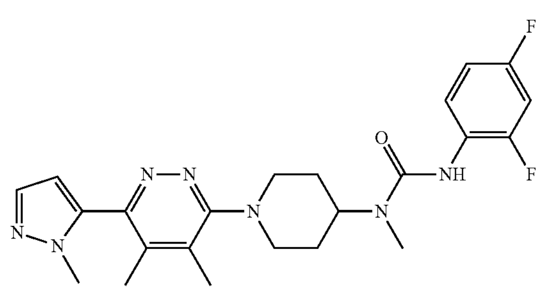 [SMILES: Cc1c(-c2ccnn2C)nnc(N2CCC(N(C)C(=O)Nc3ccc(F)cc3F)CC2)c1C] | 3-(2,4-difluorophenyl)-1-[1-[4,5-dimethyl-6-(2-methylpyrazol-3-yl)pyridazin-3-yl]-4-piperidyl]-1-methyl-urea | 3.31 min (Method 1) | 456.4 [M + H]+ |
| 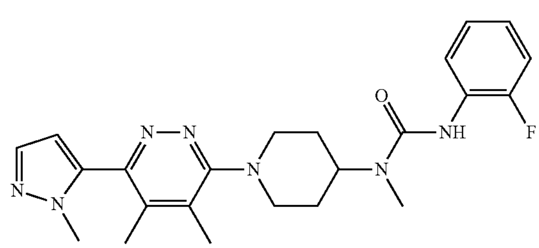 [SMILES: Cc1c(-c2ccnn2C)nnc(N2CCC(N(C)C(=O)Nc3ccccc3F)CC2)c1C] | 1-[1-[4,5-dimethyl-6-(2-methylpyrazol-3-yl)pyridazin-3-yl]-4-piperidyl]-3-(2-fluorophenyl)-1-methyl-urea | 3.28 min (Method 1) | 438.4 [M + H]+ |

TABLE 9-continued

| Structure | Name | LCMS RT | m/z MIM |
|---|---|---|---|
| 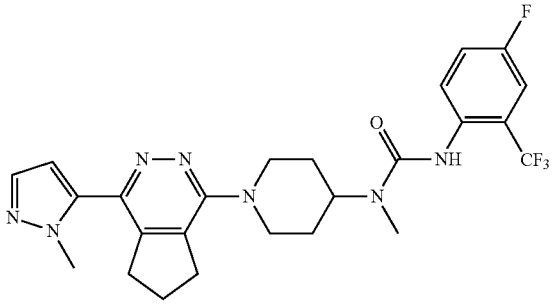 [SMILES: CN(C(=O)Nc1ccc(F)cc1C(F)(F)F)C1CCN(c2nnc(-c3ccnn3C)c3c2CCC3)CC1] | 3-[4-fluoro-2-(trifluoromethyl)phenyl]-1-methyl-1-[1-[1-(2-methylpyrazol-3-yl)-6,7-dihydro-5H-cyclopenta[d]pyridazin-4-yl]-4-piperidyl]urea | 1.47 min (Method 2) | 518.4 [M + H]$^+$ |
| 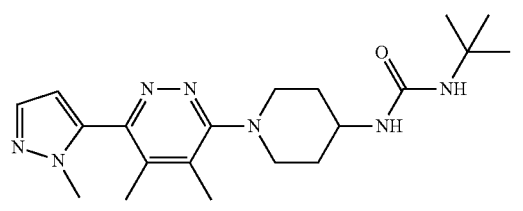 [SMILES: Cc1c(-c2ccnn2C)nnc(N2CCC(NC(=O)NC(C)(C)C)CC2)c1C] | 1-tert-butyl-3-[1-[4,5-dimethyl-6-(2-methylpyrazol-3-yl)pyridazin-3-yl]-4-piperidyl]urea | 1.32 min (Method 2) | 386.4 [M + H]$^+$ |
| 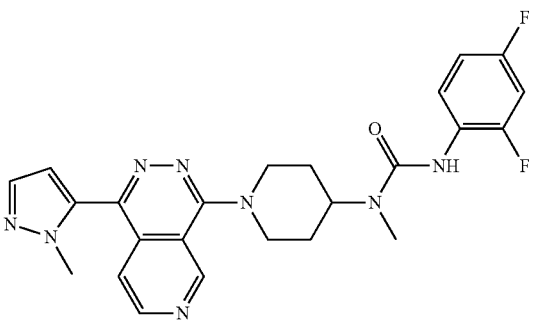 [SMILES: CN(C(=O)Nc1ccc(F)cc1F)C1CCN(c2nnc(-c3ccnn3C)c3ccncc23)CC1] | 3-(2,4-difluorophenyl)-1-methyl-1-[1-[1-(2-methylpyrazol-3-yl)pyrido[3,4-d]pyridazin-4-yl]-4-piperidyl]urea | 3.07 min (Method 1) | 479.4 [M + H]$^+$ |
| 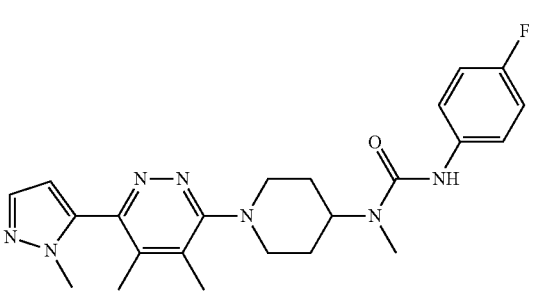 [SMILES: Cc1c(-c2ccnn2C)nnc(N2CCC(N(C)C(=O)Nc3ccc(F)cc3)CC2)c1C] | 1-[1-[4,5-dimethyl-6-(2-methylpyrazol-3-yl)pyridazin-3-yl]-4-piperidyl]-3-(4-fluorophenyl)-1-methyl-urea | 3.29 min (Method 1) | 438.4 [M + H]$^+$ |
| 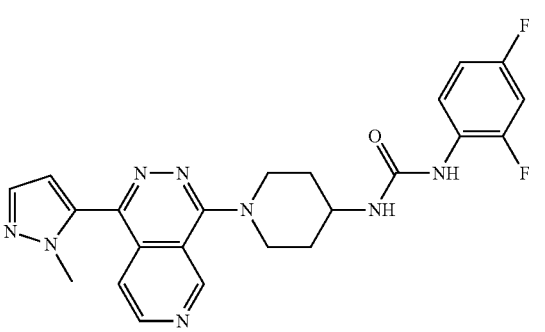 [SMILES: Cn1nccc1-c1nnc(N2CCC(NC(=O)Nc3ccc(F)cc3F)CC2)c2cnccc12] | 1-(2,4-difluorophenyl)-3-[1-[1-(2-methylpyrazol-3-yl)pyrido[3,4-d]pyridazin-4-yl]-4-piperidyl]urea | 3.11 min (Method 1) | 465.4 [M + H]$^+$ |

TABLE 9-continued

| Structure | Name | LCMS RT | m/z MIM |
|---|---|---|---|
| 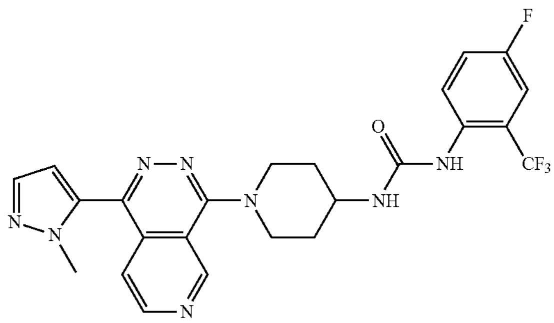 [SMILES: Cn1nccc1-c1nnc(N2CCC(NC(=O)Nc3ccc(F)cc3C(F)(F)F)CC2)c2cnccc12] | 1-[4-fluoro-2-(trifluoromethyl)phenyl]-3-[1-[1-(2-methylpyrazol-3-yl)pyrido[3,4-d]pyridazin-4-yl]-4-piperidyl]urea | 3.37 min (Method 1) | 515.4 [M + H]⁺ |
| 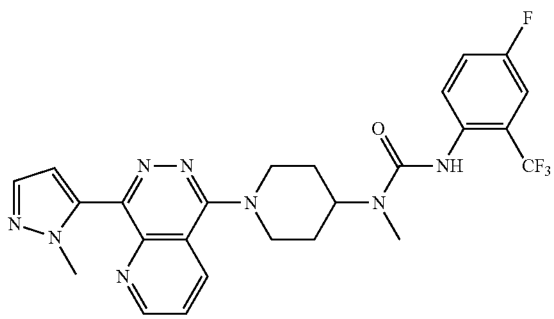 [SMILES: CN(C(=O)Nc1ccc(F)cc1C(F)(F)F)C1CCN(c2nnc(-c3ccnn3C)c3ncccc23)CC1] | 3-[4-fluoro-2-(trifluoromethyl)phenyl]-1-methyl-1-[1-[8-(2-methylpyrazol-3-yl)pyrido[2,3-d]pyridazin-5-yl]-4-piperidyl]urea | 3.41 min (Method 1) | 529.4 [M + H]⁺ |
| 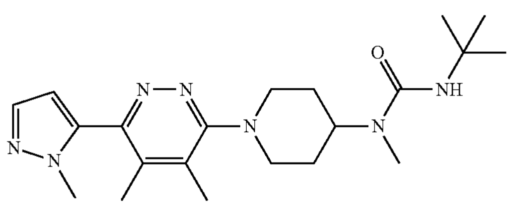 [SMILES: Cc1c(-c2ccnn2C)nnc(N2CCC(N(C)C(=O)NC(C)(C)C)CC2)c1C] | 3-tert-butyl-1-[1-[4,5-dimethyl-6-(2-methylpyrazol-3-yl)pyridazin-3-yl]-4-piperidyl]-1-methyl-urea | 1.44 min (Method 2) | 400.4 [M + H]⁺ |
| 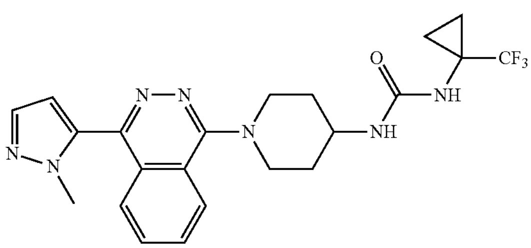 [SMILES: Cn1nccc1-c1nnc(N2CCC(NC(=O)NC3(C(F)(F)F)CC3)CC2)c2ccccc12] | 1-[1-[4-(2-methylpyrazol-2-yl)phthalazin-1-yl]-4-piperidyl]-3-[1-(trifluoromethyl)cyclopropyl]urea | 1.25 min (Method 2) | 460.4 [M + H]⁺ |

In cases where the isocyanate is not readily commercially available it can be prepared in situ via various methods known to those skilled In the art for example, similarly prepared was:

1-[1-[4,5-dimethyl-6-(2-methylpyrazol-3-yl)pyridazin-3-yl]-4-piperidyl]-1-methyl-3-[5-(trifluoromethyl)pyridazin-4-yl]urea

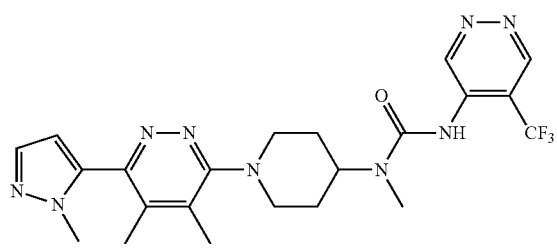 [SMILES: Cc1c(-c2ccnn2C)nnc(N2CCC(N(C)C(=O)Nc3cnncc3C(F)(F)F)CC2)c1C]

To a solution of 5-(trifluoromethyl)pyridazine-4-carboxylic acid (96 mg, 0.50 mmol) and triethylamine (0.1 mL, 0.75 mmol) in toluene (4 mL) was added diphenyl phosphoryl azide (137.6 mg, 0.50 mmol). The reaction was stirred for 1 h, then heated to 100° C. and maintained at this temperature for 2 h. A solution of 1-[4,5-dimethyl-6-(2-methylpyrazol-3-yl)pyridazin-3-yl]-N-methyl-piperidin-4-amine (150 mg, 0.50 mmol) in toluene (4 mL) was added, and stirring at 100° C. continued for 30 min. The reaction was concentrated in vacuo and then purified by silica flash chromatography using 0% methanol in ethyl acetate with a gradient to 80% methanol and the fractions containing the desired product were concentrated in vacuo. Further purification by prep LC/MS, repeated twice, afforded a the formate salt of 1-[1-[4,5-dimethyl-6-(2-methylpyrazol-3-yl)pyridazin-3-yl]-4-piperidyl]-1-methyl-3-[5-(trifluoromethyl)pyridazin-4-yl]urea (4.0 mg, 0.0073 mmol, 10.5%) as a colourless oil.

MS Method 2: RT: 1.39 min, m/z 490.4 [M+H]⁺

Similarly prepared was:

1-[1-[4,5-dimethyl-6-(2-methylpyrazol-3-yl)pyridazin-3-yl]-4-piperidyl]-3-[1-(trifluoromethyl)cyclopropyl]urea

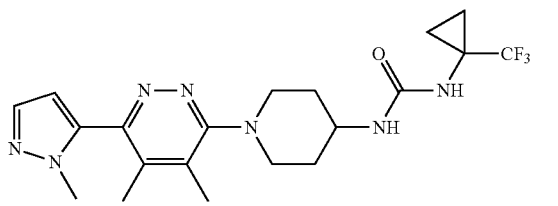 [SMILES: Cc1c(-c2ccnn2C)nnc(N2CCC(NC(=O)NC3(C(F)(F)F)CC3)CC2)c1C]

To a solution of 1,1'-Carbonyldiimidazole (55.5 mg, 0.34 mmol) in DCM (1 mL) was added 1-trifluoromethyl-1-cyclopropylamine (0.03 mL, 0.30 mmol), the reaction vessel was sealed and the reaction was left to stir at room temperature for three days. After this 4A MS were added, followed by 1-[4,5-dimethyl-6-(2-methylpyrazol-3-yl)pyridazin-3-yl]piperidin-4-amine (28. mg, 0.10 mmol) and triethylamine (0.07 mL, 0.49 mmol) in DCM (1 mL). The reaction was stirred at room temperature for 1 hour then quenched by the addition of saturated aqueous NaHCO$_3$. The organic and aqueous layers were separated, the reaction mixture was extracted with DCM×3 and the combined organic extracts were concentrated in vacuo to afford the crude material which was then purified by silica flash chromatography using 0% methanol in ethyl acetate with a gradient to 10% methanol and the fractions containing the desired product were concentrated in vacuo. Further purification by preparative LCMS was performed to afford 1-[1-[4,5-dimethyl-6-(2-methylpyrazol-3-yl)pyridazin-3-yl]-4-piperidyl]-3-[1-(trifluoromethyl)cyclopropyl]urea (12 mg, 0.0274 mmol, 28.1% yield) as a white solid.

$^1$H NMR (400 MHz, DMSO-d6) δ/ppm: 7.58 (d, J1.9 Hz, 1H), 6.37 (d, J1.9 Hz, 1H), 5.26 (s, 1H), 5.00 (d, J7.9 Hz, 1H), 4.01-3.90 (m, 1H), 3.92 (s, 3H), 3.60-3.52 (m, 2H), 3.21-3.12 (m, 2H), 2.30 (s, 3H), 2.28 (s, 3H), 2.16-2.08 (m, 2H), 1.71-1.60 (m, 2H). 1.39-1.34 (m, 2H), 1.19-1.14 (m, 2H).

MS Method 2: RT: 1.35 min, m/z 438.4 [M+H]$^+$

Example 13

Compounds of formula (I) can be prepared by the General Method F, shown below. General Method F may be carried out using compounds prepared by Procedure B as starting materials or another appropriate method for producing the starting materials may be used.

General Method F

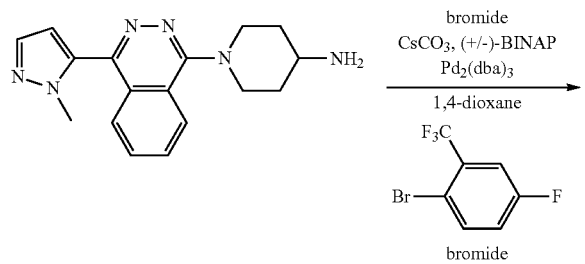

[4-fluoro-2-(trifluoromethyl)phenyl]-[1-[4-(2-methylpyrazol-3-yl)phthalazin-1-yl]-4-piperidyl]ammonium formate

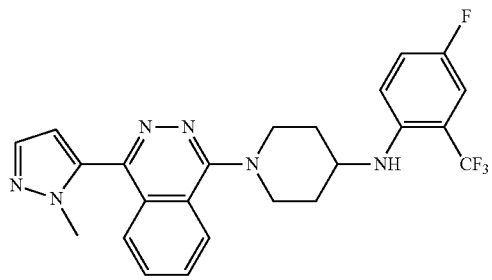

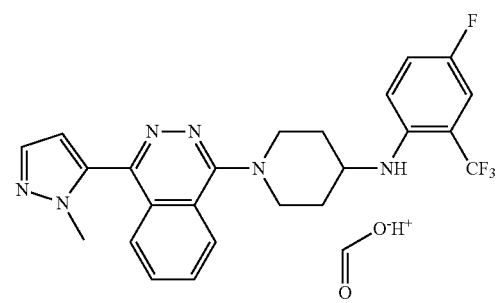

A solution of 1-[4-(2-methylpyrazol-3-yl)phthalazin-1-yl]piperidin-4-amine (0.05 g, 0.17 mmol), 1-bromo-4-fluoro-2-(trifluoromethyl)benzene (24 uL, 0.17 mmol), caesium carbonate (110 mg, 0.34 mmol), (+/−) BINAP (10 mg, 0.02 mmol) and Pd$_2$(dba)$_3$ (7.71 mg, 0.0100 mmol) in 1,4-dioxane (1.5 mL) was prepared, degassed with nitrogen and heated at 110° C. overnight. The reaction mixture was cooled and then concentrated in vacuo. The crude material was purified by preparative LCMS to afford the formate salt: [4-fluoro-2-(trifluoromethyl)phenyl]-[1-[4-(2-methylpyrazol-3-yl)phthalazin-1-yl]-4-piperidyl]ammonium formate (11.6 mg, 0.02 mmol, 13%) as an oil.

$^1$H NMR (400 MHz, MeOD) δ/ppm: 8.57 (s, 1H), 8.28 (d, J 8.2 Hz, 1H) 8.05-7.95 (m, 3H), 7.71 (d, J 1.87 Hz, 1H), 7.24 (d, J 8.2 Hz, 1H), 7.24 (m, 1H), 7.02-7.02 (m, 1H), 6.71 (d, J 1.8 Hz, 1H), 4.08-4.01 (m (br), 2H), 3.92 (s, 3H), 3.85-3.76 (m, 1H), 3.39-3.345 (m, 2H), 2.17-2.11 (m (br), 2H), 1.97-1.86 (m, 2H)

MS Method 2: RT: 4.42 min, m/z 471.3 [M+H]$^+$

The compounds shown below in Table 10 were similarly prepared by varying the aryl halide used in General Method F.

TABLE 10

| Structure | Name | LCMS RT | m/z MIM |
|---|---|---|---|
| 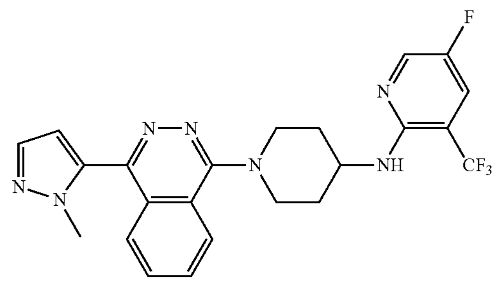 | 5-fluoro-N-[1-[4-(2-methylpyrazol-3-yl)phthalazin-1-yl]-4-piperidyl]-3-(trifluoromethyl)pyridin-2-amine | 2.54 min (Method 1) | 458.3 [M + H]+ |
| 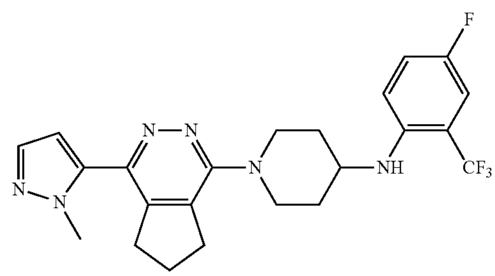 [SMILES: Cn1nccc1-c1nnc(N2CCC(Nc3ccc(F)cc3C(F)(F)F)CC2)c2c1CCC2] | N-[4-fluoro-2-(trifluoromethyl)phenyl]-1-[1-(2-methylpyrazol-3-yl)-6,7-dihydro-5H-cyclopenta[d]pyridazin-4-yl]piperidin-4-amine | 1.85 min (Method 2) | 461.3 [M + H]+ |

Example 14

Compounds of formula (I) can be prepared by the General Method G, shown below. Shown is a procedure to prepare N-[[4-fluoro-2-(trifluoromethyl)phenyl]methyl]-N-methyl-1-[4-(2-methylpyrazol-3-yl)phthalazin-1-yl]pyrrolidin-3-amine.

General Method G

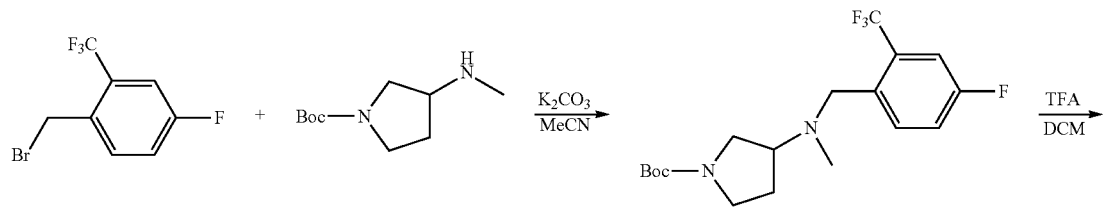

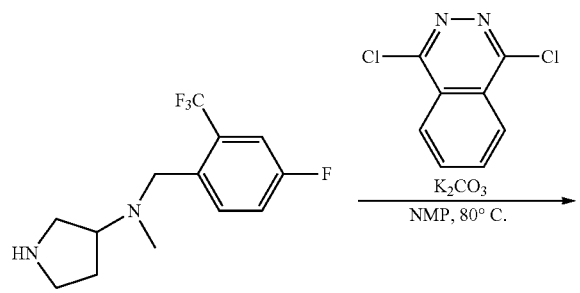

-continued

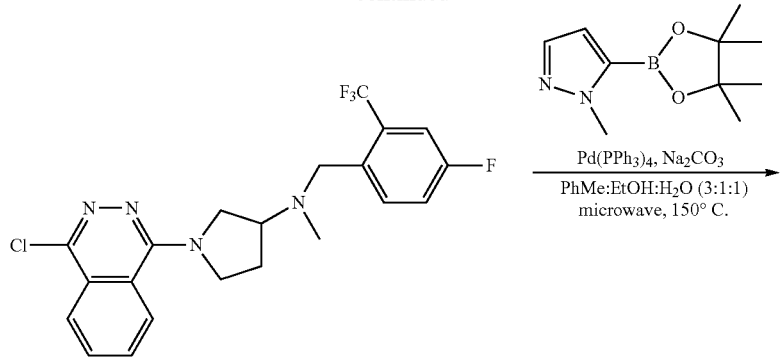

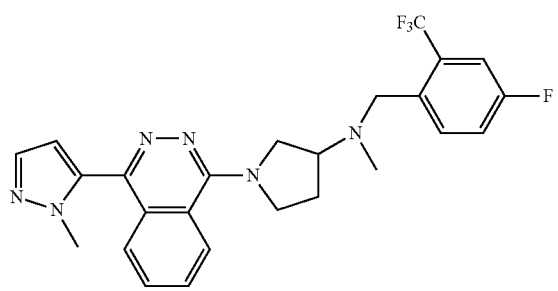

tert-butyl 3-[[4-fluoro-2-(trifluoromethyl)phenyl]methyl-methyl-amino]pyrrolidine-1-carboxylate N-[[4-fluoro-2-(trifluoromethyl)phenyl]methyl]-N-methyl-pyrrolidin-3-amine

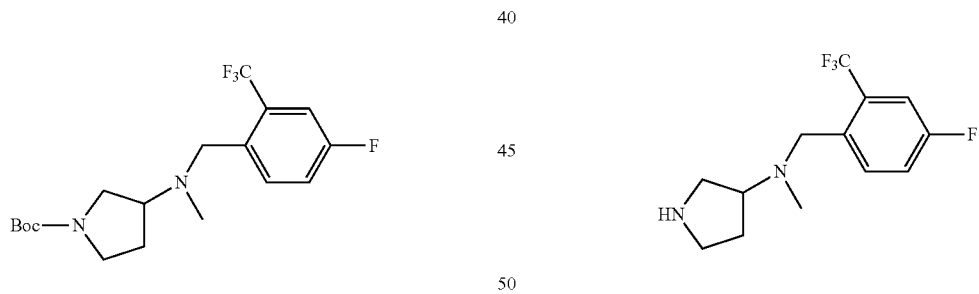

Potassium carbonate (1.0 g, 7.49 mmol) was added to a solution of tert-butyl 3-(methylamino)pyrrolidine-1-carboxylate (500 mg, 2.5 mmol) and 1-(bromomethyl)-4-fluoro-2-(trifluoromethyl)benzene (642 mg, 2.5 mmol) in MeCN (30 mL) and stirred overnight at room temperature. The potassium carbonate was filtered off and the filtrate was concentrated and purified by silica flash column chromatography eluting with 0% ethyl acetate in heptane with a gradient to 50% ethyl acetate to afford tert-butyl 3-[[4-fluoro-2-(trifluoromethyl)phenyl]methyl-methyl-amino]pyrrolidine-1-carboxylate (751 mg, 2.0 mmol, 80% yield) as an oil.

MS Method 2: RT: 1.51 min, m/z 399.2 [M+Na]$^+$

Trifluoroacetic acid (1.7 mL, 23.94 mmol) was added to a solution of tert-butyl 3-[[4-fluoro-2-(trifluoromethyl)phenyl]methyl-methyl-amino]pyrrolidine-1-carboxylate (751 mg, 2.0 mmol) in DCM (15 mL) and stirred overnight. The reaction mixture was concentrated under reduced pressure. The resulting oil was loaded onto an SCX cartridge using MeOH then washed using 2 column volumes of methanol followed by elution with 2 column volumes of 1M ammonia in methanol solution. The fractions were then concentrated to afford N-[[4-fluoro-2-(trifluoromethyl)phenyl]methyl]-N-methyl-pyrrolidin-3-amine (421 mg, 1.52 mmol, 76%) as an oil which was used directly in the next reaction.

MS Method 2: RT: 1.09 min, m/z 277.2 [M+H]$^+$

179

1-(4-chlorophthalazin-1-yl)-N-[[4-fluoro-2-(trifluoromethyl)phenyl]methyl]-N-methyl-pyrrolidin-3-amine

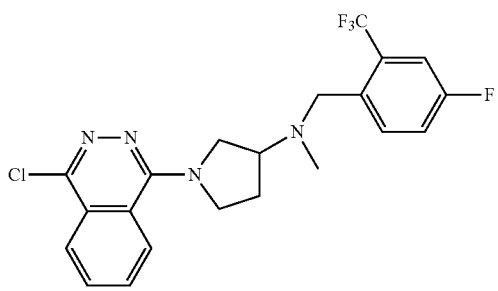 [SMILES: CN(Cc1ccc(F)cc1C(F)(F)F)C1CCN(c2nnc(Cl)c3ccccc23)C1]

A solution containing 1,4-dichlorophthalazine (334 mg, 1.68 mmol), N-[[4-fluoro-2-(trifluoromethyl)phenyl]methyl]-N-methyl-pyrrolidin-3-amine (421 mg, 1.52 mmol) and potassium carbonate (241 mg, 1.74 mmol) in NMP (5 mL) was prepared and stirred at 80° C. overnight. The reaction was cooled to room temperature and water was added to the reaction mixture at which point a cloudying of the mixture was observed. The NMP and water mixture was extracted with ethyl acetate several times and the organic layer was then concentrated in vacuo to afford the crude product. The crude material was purified by silica flash chromatography eluting with 10% ethyl acetate in heptane with a gradient to 60% ethyl acetate to afford 1-(4-chlorophthalazin-1-yl)-N-[[4-fluoro-2-(trifluoromethyl)phenyl]methyl]-N-methyl-pyrrolidin-3-amine (226 mg, 0.52 mmol, 33.8% yield) as an oil which was used directly in the next reaction MS Method 2: RT: 1.47 min, m/z 439.2 [M+H]$^+$

180

N-[[4-fluoro-2-(trifluoromethyl)phenyl]methyl]-N-methyl-1-[4-(2-methylpyrazol-3-yl)phthalazin-1-yl]pyrrolidin-3-amine

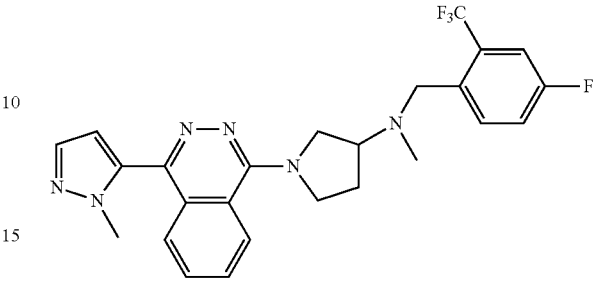

1-Methyl-5-(4,4,5,5-tetramethyl-1,3,2-dioxaborolan-2-yl)pyrazole (536 mg, 2.57 mmol), 1-(4-chlorophthalazin-1-yl)-N-[[4-fluoro-2-(trifluoromethyl)phenyl]methyl]-N-methyl-pyrrolidin-3-amine (226 mg, 0.51 mmol), sodium carbonate (109 mg, 1.03 mmol) and tetrakis(triphenylphosphine)palladium(0) (60 mg, 0.05 mmol) were combined in a microwave vial which was sealed and flushed with nitrogen. A solution of toluene (1.8 mL), ethanol (0.60 mL) and water (0.60 mL) was also prepared and degassed, then transferred into the microwave vial. The reaction was then heated in the microwave at 150° C. for 10 min. The reaction mixture was extracted with DCM and washed with brine. The organic layer was concentrated in vacuo to afford the crude product. This material was purified by silica flash column chromatography eluting with 0% 2M NH$_3$ in methanol, in DCM with a gradient to 5% 2M NH$_3$ in methanol to afford an oil which was further purified by preparative LCMS. Fractions containing the desired product were combined and concentrated. The product was desalted by SCX cartridge. The product was loaded and washed with methanol then eluted with 2M ammonia methanol solution to afford N-[[4-fluoro-2-(trifluoromethyl)phenyl]methyl]-N-methyl-1-[4-(2-methylpyrazol-3-yl)phthalazin-1-yl]pyrrolidin-3-amine (108 mg, 0.22 mmol, 43% yield).

$^1$H NMR (400 MHz, MeOD) δ/ppm: 8.41-8.37 (m, 1H), 7.95-7.80 (m, 4H), 7.67 (d, J 1.9 Hz, 1H), 7.36 (dd, J 9.2 Hz, 2.6 Hz, 1H), 7.30 (td, J 8.3 Hz, 2.6 Hz, 1H), 6.62 (d, J 1.9 Hz, 1H), 4.13-4.06 (m, 3H), 3.97 (dd, J 10.4 Hz, 8.0 Hz, 1H), 3.86 (s, 3H), 3.84 (d, J 14.6 Hz, 1H), 3.77 (d, J 14.6 Hz, 1H), 3.32-3.25 (m, 1H), 2.38-2.30 (m, 1H), 2.29 (s, 3H), 2.17-2.06 (m, 1H)

MS Method 1: RT: 3.66 min, m/z 485.3 [M+H]$^+$

The compounds shown below in Table 11 were similarly prepared by varying the isocyanate used in General Method G.

TABLE 11

| Structure | Name | LCMS RT | m/z MIM |
|---|---|---|---|
| 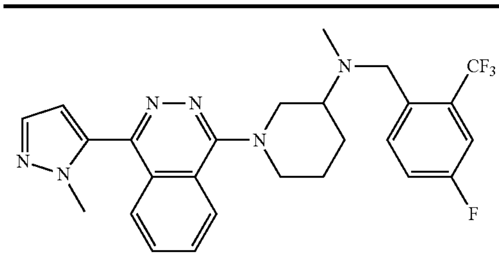 | N-[[4-fluoro-2-(trifluoromethyl)phenyl]methyl]-N-methyl-1-[4-(2-methylpyrazol-3-yl)phthalazin-1-yl]piperidin-3-amine | 3.51 min (Method 1) | 499.4 [M + H]$^+$ |

Example 15

Compounds of formula (I) can be prepared by the General Method H, shown below.

General Method H

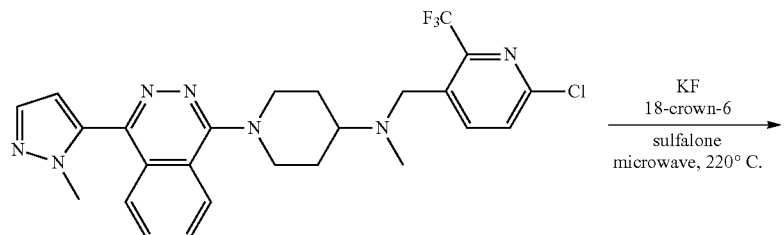

N-[[6-Fluoro-2-(trifluoromethyl)-3-pyridyl]methyl]-N-methyl-1-[4-(2-methylpyrazol-3-yl)phthalazin-1-yl]piperidin-4-amine

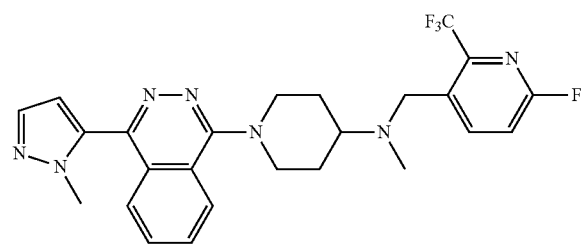 [SMILES: CN(Cc1ccc(F)nc1C(F)(F)F)C1CCN(c2nnc(-c3ccnn3C)c3ccccc23)CC1]

N-[[6-chloro-2-(trifluoromethyl)-3-pyridyl]methyl]-N-methyl-1-[4-(2-methylpyrazol-3-yl)phthalazin-1-yl]piperidin-4-amine (36 mg, 0.0700 mmol), potassium fluoride (Spray dried) (64 mg, 0.42 mmol) (ground in a pestle and mortar) and 18-crown-6 (2 mg, 0.01 mmol) were added to sulfolane (1 mL) and heated in a microwave vial at 220° C. for 7 h. The mixture was cooled, and taken up in water (20 mL) and filtered. The filtrate was extracted with TBME (×2) and the combined extracts washed with water (×2), dried (Na$_2$SO$_4$) and concentrated in vacuo, then purified by preparative HPLC, and passed through a carbonate cartridge to afford N-[[6-fluoro-2-(trifluoromethyl)-3-pyridyl]methyl]-N-methyl-1-[4-(2-methylpyrazol-3-yl)phthalazin-1-yl]piperidin-4-amine as the partial formate salt (4 mg, 0.008 mmol; 11%).

$^1$H NMR (400 MHz, MeOH) δ/ppm: 8.48 (t, J 8.0 Hz, 1H), 8.28 (d, J 8.2 Hz, 1H), 8.15 (s, 0.78H), 8.05-8.00 (m, 1H), 7.98-7.95 (m, 2H), 7.71 (d, J 2.0 Hz, 1H), 7.37 (dd, J 8.5 Hz, 3.1 Hz, 1H), 6.70 (d, J 2.0 Hz, 1H), 4.20-4.17 (m, 2H), 3.96 (s, 2H), 3.91 (s, 3H), 3.24-3.14 (m, 2H), 2.96-2.87 (m, 1H), 2.36 (s, 3H), 2.16-2.00 (m, 4H).

MS Method 2: RT: 1.24 min. m/z 500.3 [M+H]$^+$

Similarly prepared were:

N-[[6-Fluoro-4-(trifluoromethyl)-3-pyridyl]methyl]-1-[4-(2-methylpyrazol-3-yl)phthalazin-1-yl]piperidin-4-amine

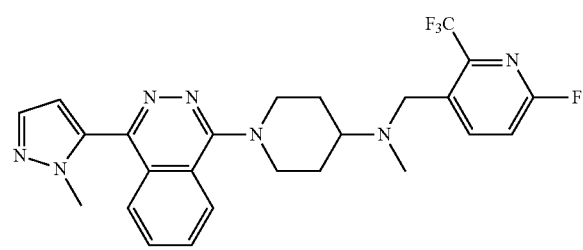

Partial formate salt (43% by nmr) of N-[[6-fluoro-4-(trifluoromethyl)-3-pyridyl]methyl]-1-[4-(2-methylpyrazol-3-yl)phthalazin-1-yl]piperidin-4-amine (9 mg, 0.017 mmol, 25%).

$^1$H NMR (400 MHz, MeOH) δ/ppm: 8.66 (s, 1H), 8.57 (s, 0.43H), 8.26 (d, J 8.2 Hz, 1H), 8.05-7.99 (m, 1H), 7.97-7.94 (m, 2H), 7.71 (d, J 2.0 Hz, 1H), 7.44 (d, J 2.2 Hz, 1H), 6.70 (d, J 2.0 Hz, 1H), 4.09 (s, 2H), 4.06 (m, 2H), 3.91 (s, 3H), 3.28-3.20 (m, 2H), 2.96-2.89 (m, 1H), 2.22-2.20 (m, 2H), 1.89-1.76 (m, 2H).

MS Method 1: RT: 2.58 min. m/z 486.3 [M+H]$^+$

N-[[6-fluoro-2-(trifluoromethyl)-3-pyridyl]methyl]-1-[4-(2-methylpyrazol-3-yl)phthalazin-1-yl]piperidin-4-amine

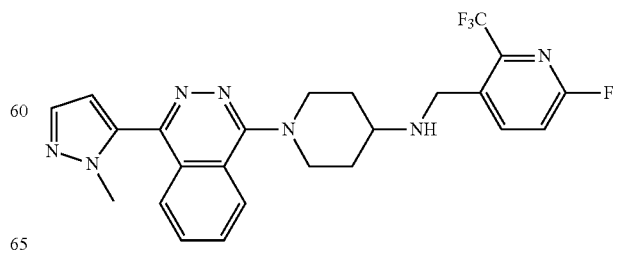

4 mg, 0.008 mmol; 12%.

$^1$H NMR (400 MHz, MeOH) δ/ppm: 8.31 (t, J 8.0 Hz, 1H), 8.14 (d, J 8.2 Hz, 1H), 7.93-7.88 (m, 1H), 7.87-7.83 (m, 2H), 7.59 (d, J 2.0 Hz, 1H), 7.29 (dd, J 8.5 Hz, 3.1 Hz, 1H), 6.58 (d, J 2.0 Hz, 1H), 4.03 (s, 2H), 4.00-3.92 (m, 2H), 3.79 (s, 3H), 3.16-3.08 (m, 2H), 2.93-2.82 (m, 1H), 2.14-2.06 (m, 2H), 1.80-1.67 (m, 2H).

MS Method 1: RT: 2.71 min. m/z 486.3 [M+H]$^+$

Example 16

In vitro biological evaluation of compounds of the invention was carried out using the procedure detailed below. The procedure provides activity data for the compounds of the invention against the Hedgehog signalling pathway. The activity is represented as IC50 values in Table 12 below.

The Gli-reporter NIH3T3 cell line (BPS Biosciences) was grown according to the suppliers recommendations. Briefly, cells were maintained in growth medium (DMEM supplemented with 10% calf serum, 1% Penicillin/Streptomycin, and 500 g/mL of Geneticin) and grown at 37° C., 5% $CO_2$. In order to passage cells they were first rinsed with phosphate buffered saline before the addition of 0.05% Trypsin/EDTA. Fresh growth media was added and the cells were transferred to a centrifuge tube, spun and resuspended at an appropriate cell density.

Gli-reporter NIH-3T3 cells were seeded at 20,000 cells/well into 96 well, poly-D-lysine coated white clear bottomed full area TC plates in growth media (without geneticin). Three wells were left with just media as cell free controls. Cells were then incubated for 24 hours at 37° C. in a 5% $CO_2$.

Serial dilutions of the test compounds were prepared in 100% DMSO. 10 μl of compound or DMSO from each well was pipetted into a sterile, 0.5 ml deep well conical bottomed 96 well plate (intermediate plate). 190 μl of warmed assay media (Opti-MEM supplemented with 0.5% calf serum, 1% non-essential amino acids, 1 mM sodium pyruvate, 10 mM HEPES, 1% penicillin/Streptomycin) was then added to each well and mixed five times at 180 μl by electronic pipette to ensure homogeneity of the compound solution. This 1:20 dilution gives a top concentration of 50 μM in 5% DMSO, 95% assay media. 10 μl was pipetted from each well of the intermediate plate into a second deep well sterile plate. 490 μl of warm assay media was then added to each well and mixed five times at 300 μl. This gives a final top concentration of 1 μM in 0.1% DMSO.

After the 24 hour incubation, media was carefully removed by pipette and replaced with 45 μl of compound dilutions in triplicate. This was incubated for one hour at 37° C. in a 5% $CO_2$. After an hour, 5 μl 10 μg/mL recombinant mouse sonic hedgehog (R&D Systems) was added to each well and the plates were incubated for a further 24 hours at 37° C., 5% $CO_2$.

After 24 hours, plates were removed from the incubator and left to acclimatise to room temperature for 20 minutes. 50 μl of OneGLO assay reagent (Promega) was then added to each well and the plates gently shaken for a further 30 minutes. Plates were then read for luminescence on the EnVision plate reader (PerkinElmer).

The results of the in vitro biological data for certain compounds of the invention are given in Table 12 below. The table shows the Hedgehog pathway inhibition activity of each compound characterised based on the IC50 value of the compound as "+", "++" and "+++". The category "+" refers to compounds with an IC50 of 200 nM to 2 μM. The category "++" refers to compounds with an IC50 of 10 nM to 200 nM. The category "+++" refers to compounds with an IC50 of <10 nM.

TABLE 12

| ID No. | Compound | Category |
|---|---|---|
| 1 | N-methyl-1-[4-(2-methylpyrazol-3-yl)phthalazin-1-yl]-N-[[4-(trifluoromethyl)phenyl]methyl]piperidin-4-amine | ++ |
| 2 | N-methyl-1-[4-(2-methylpyrazol-3-yl)phthalazin-1-yl]-N-[[3-(trifluoromethyl)phenyl]methyl]piperidin-4-amine | ++ |
| 3 | N-methyl-1-[4-(2-methylpyrazol-3-yl)phthalazin-1-yl]-N-[[2-(trifluoromethyl)phenyl]methyl]piperidin-4-amine | +++ |
| 4 | 2-fluoro-5-[[methyl-[1-[4-(2-methylpyrazol-3-yl)phthalazin-1-yl]-4-piperidyl]amino]methyl]benzonitrile | ++ |
| 5 | 3-[4-fluoro-2-(trifluoromethyl)phenyl]-1-methyl-1-[1-[4-(2-methylpyrazol-3-yl)phthalazin-1-yl]-4-piperidyl]urea | +++ |
| 6 | 2-fluoro-5-[[[1-[4-(2-methylpyrazol-3-yl)phthalazin-1-yl]-4-piperidyl]amino]methyl]benzonitrile | + |
| 7 | N-[(2-ethoxyphenyl)methyl]-N-methyl-1-[4-(2-methylpyrazol-3-yl)phthalazin-1-yl]piperidin-4-amine | ++ |
| 8 | 1-(2,4-difluorophenyl)-3-[1-[4-(2-methylpyrazol-3-yl)phthalazin-1-yl]-4-piperidyl]urea | +++ |
| 9 | 1-(4-fluorophenyl)-3-[1-[4-(2-methylpyrazol-3-yl)phthalazin-1-yl]-4-piperidyl]urea | +++ |
| 10 | 1-tert-butyl-3-[1-[4-(2-methylpyrazol-3-yl)phthalazin-1-yl]-4-piperidyl]urea | +++ |
| 11 | 1-cyclohexyl-3-[1-[4-(2-methylpyrazol-3-yl)phthalazin-1-yl]-4-piperidyl]urea | +++ |
| 12 | N-[[2-(difluoromethoxy)phenyl]methyl]-N-methyl-1-[4-(2-methylpyrazol-3-yl)phthalazin-1-yl]piperidin-4-amine | ++ |
| 13 | 1-[1-[4-(2-methylpyrazol-3-yl)phthalazin-1-yl]-4-piperidyl]-3-[3-(trifluoromethyl)phenyl]urea | +++ |
| 14 | 1-[1-[4-(2-methylpyrazol-3-yl)phthalazin-1-yl]-4-piperidyl]-3-[4-(trifluoromethyl)phenyl]urea | +++ |
| 15 | 1-(2-methoxyphenyl)-3-[1-[4-(2-methylpyrazol-3-yl)phthalazin-1-yl]-4-piperidyl]urea | +++ |
| 16 | 1-(3-fluorophenyl)-3-[1-[4-(2-methylpyrazol-3-yl)phthalazin-1-yl]-4-piperidyl]urea | +++ |
| 17 | 1-[4-(2-methylpyrazol-3-yl)phthalazin-1-yl]-N-[(2-methylsulfanylphenyl)methyl]piperidin-4-amine | ++ |

TABLE 12-continued

| ID No. | Compound | Category |
|---|---|---|
| 18 | N-[[6-fluoro-2-(trifluoromethyl)-3-pyridyl]methyl]-1-[4-(2-methylpyrazol-3-yl)phthalazin-1-yl]piperidin-4-amine | ++ |
| 19 | N-[(2-chloro-4-fluoro-phenyl)methyl]-1-[4-(2-methylpyrazol-3-yl)phthalazin-1-yl]piperidin-4-amine | ++ |
| 20 | 1-[4-(2-methylpyrazol-3-yl)phthalazin-1-yl]-N-[[4-(trifluoromethoxy)phenyl]methyl]piperidin-4-amine | ++ |
| 21 | 1-[1-[4-(2-methylpyrazol-3-yl)phthalazin-1-yl]-4-piperidyl]-3-[2-(trifluoromethyl)phenyl]urea | +++ |
| 22 | 1-(3-cyanophenyl)-3-[1-[4-(2-methylpyrazol-3-yl)phthalazin-1-yl]-4-piperidyl]urea | +++ |
| 23 | 1-[4-fluoro-2-(trifluoromethyl)phenyl]-3-[1-[4-(2-methylpyrazol-3-yl)phthalazin-1-yl]-4-piperidyl]urea | +++ |
| 24 | 1-(3-methoxyphenyl)-3-[1-[4-(2-methylpyrazol-3-yl)phthalazin-1-yl]-4-piperidyl]urea | +++ |
| 25 | 1-[1-[4-(2-methylpyrazol-3-yl)phthalazin-1-yl]-4-piperidyl]-3-[2-(trifluoromethoxy)phenyl]urea | +++ |
| 26 | 1-[4-(difluoromethoxy)phenyl]-3-[1-[4-(2-methylpyrazol-3-yl)phthalazin-1-yl]-4-piperidyl]urea | +++ |
| 27 | N-[(2,6-difluoro-3-pyridyl)methyl]-N-methyl-1-[4-(2-methylpyrazol-3-yl)phthalazin-1-yl]piperidin-4-amine | ++ |
| 28 | N-methyl-1-[4-(2-methylpyrazol-3-yl)phthalazin-1-yl]-N-[(2-methylsulfanylphenyl)methyl]piperidin-4-amine | +++ |
| 29 | N-[(2-isopropylphenyl)methyl]-N-methyl-1-[4-(2-methylpyrazol-3-yl)phthalazin-1-yl]piperidin-4-amine | ++ |
| 30 | N-methyl-1-[4-(2-methylpyrazol-3-yl)phthalazin-1-yl]-N-(o-tolylmethyl)piperidin-4-amine | +++ |
| 31 | 1-[4-(2-methylpyrazol-3-yl)phthalazin-1-yl]-N-[(2-nitrophenyl)methyl]piperidin-4-amine | ++ |
| 32 | 1-(4-cyanophenyl)-3-[1-[4-(2-methylpyrazol-3-yl)phthalazin-1-yl]-4-piperidyl]urea | +++ |
| 33 | 2-[[methyl-[1-[4-(2-methylpyrazol-3-yl)phthalazin-1-yl]-4-piperidyl]amino]methyl]benzonitrile | ++ |
| 34 | 1-[4-(2-methylpyrazol-3-yl)phthalazin-1-yl]-N-[[3-(trifluoromethoxy)phenyl]methyl]piperidin-4-amine | ++ |
| 35 | N-[(4-chlorophenyl)methyl]-1-[4-(2-methylpyrazol-3-yl)phthalazin-1-yl]piperidin-4-amine | ++ |
| 36 | 1-[4-(2-methylpyrazol-3-yl)phthalazin-1-yl]-N-[[2-(trifluoromethoxy)phenyl]methyl]piperidin-4-amine | ++ |
| 37 | 1-[4-(2-methylpyrazol-3-yl)phthalazin-1-yl]-N-[[4-(trifluoromethyl)phenyl]methyl]piperidin-4-amine | ++ |
| 38 | N-[(2-chlorophenyl)methyl]-1-[4-(2-methylpyrazol-3-yl)phthalazin-1-yl]piperidin-4-amine | ++ |
| 39 | 1-[4-(2-methylpyrazol-3-yl)phthalazin-1-yl]-N-[[3-(trifluoromethyl)phenyl]methyl]piperidin-4-amine | ++ |
| 40 | 1-[4-(2-methylpyrazol-3-yl)phthalazin-1-yl]-N-[[2-(trifluoromethyl)phenyl]methyl]piperidin-4-amine | +++ |
| 41 | 1-[4,5-dimethyl-6-(2-methylpyrazol-3-yl)pyridazin-3-yl]-N-[[4-fluoro-2-(trifluoromethyl)phenyl]methyl]-N-methyl-piperidin-4-amine | ++ |
| 42 | N-[[4-fluoro-2-(trifluoromethyl)phenyl]methyl]-N-methyl-1-[6-(2-methylpyrazol-3-yl)pyridazin-3-yl]piperidin-4-amine | +++ |
| 43 | N-[(2-isopropylphenyl)methyl]-1-[4-(2-methylpyrazol-3-yl)phthalazin-1-yl]piperidin-4-amine | ++ |
| 44 | N-[[6-chloro-2-(trifluoromethyl)-3-pyridyl]methyl]-1-[4-(2-methylpyrazol-3-yl)phthalazin-1-yl]piperidin-4-amine | +++ |
| 45 | 1-(4-methoxyphenyl)-3-[1-[4-(2-methylpyrazol-3-yl)phthalazin-1-yl]-4-piperidyl]urea | ++ |
| 46 | 1-(2-fluorophenyl)-3-[1-[4-(2-methylpyrazol-3-yl)phthalazin-1-yl]-4-piperidyl]urea | +++ |
| 47 | N-[[4-fluoro-2-(trifluoromethyl)phenyl]methyl]-N-methyl-1-[1-(2-methylpyrazol-3-yl)pyrido[3,4-d]pyridazin-4-yl]piperidin-4-amine | +++ |
| 48 | 4-fluoro-N-methyl-N-[1-[4-(2-methylpyrazol-3-yl)phthalazin-1-yl]-4-piperidyl]-2-(trifluoromethyl)benzenesulfonamide | +++ |
| 49 | N-[[4-fluoro-2-(trifluoromethyl)phenyl]methyl]-1-[1-(2-methylpyrazol-3-yl)pyrido[3,4-d]pyridazin-4-yl]piperidin-4-amine | ++ |
| 50 | 4-fluoro-N-[1-[4-(2-methylpyrazol-3-yl)phthalazin-1-yl]-4-piperidyl]-2-(trifluoromethyl)benzenesulfonamide | +++ |
| 51 | 1-[4-(2-methylpyrazol-3-yl)phthalazin-1-yl]-N-[[3-(trifluoromethyl)-4-pyridyl]methyl]piperidin-4-amine | ++ |
| 52 | N-[(2-ethoxyphenyl)methyl]-1-[4-(2-methylpyrazol-3-yl)phthalazin-1-yl]piperidin-4-amine | ++ |
| 53 | N-[4-fluoro-2-(trifluoromethyl)phenyl]-1-[4-(2-methylpyrazol-3-yl)phthalazin-1-yl]piperidin-4-amine | +++ |
| 54 | N-[[4-fluoro-2-(trifluoromethyl)phenyl]methyl]-N-methyl-1-[4-(2-methylpyrazol-3-yl)phthalazin-1-yl]piperidin-3-amine | + |
| 55 | N-[[4-fluoro-2-(trifluoromethyl)phenyl]methyl]-N-methyl-1-[4-(2-methylpyrazol-3-yl)phthalazin-1-yl]pyrrolidin-3-amine | ++ |

TABLE 12-continued

| ID No. | Compound | Category |
|---|---|---|
| 56 | 2,2,2-trifluoro-N-[[4-fluoro-2-(trifluoromethyl)phenyl]methyl]-N-[1-[4-(2-methylpyrazol-3-yl)phthalazin-1-yl]-4-piperidyl]acetamide | ++ |
| 57 | N-benzyl-1-[4-(2-methylpyrazol-3-yl)phthalazin-1-yl]piperidin-4-amine | + |
| 58 | N-[[4-fluoro-2-(trifluoromethyl)phenyl]methyl]-1-(4-methoxyphthalazin-1-yl)piperidin-4-amine | + |
| 59 | N-benzyl-N-methyl-1-[4-(2-methylpyrazol-3-yl)phthalazin-1-yl]piperidin-4-amine | ++ |
| 60 | 4-[[methyl-[1-[4-(2-methylpyrazol-3-yl)phthalazin-1-yl]-4-piperidyl]amino]methyl]benzonitrile | ++ |
| 61 | N-[(2-methoxyphenyl)methyl]-N-methyl-1-[4-(2-methylpyrazol-3-yl)phthalazin-1-yl]piperidin-4-amine | + |
| 62 | N-[(3-methoxyphenyl)methyl]-N-methyl-1-[4-(2-methylpyrazol-3-yl)phthalazin-1-yl]piperidin-4-amine | ++ |
| 63 | (4-methoxyphenyl)methyl-methyl-[1-[4-(2-methylpyrazol-3-yl)phthalazin-1-yl]-4-piperidyl]ammonium | + |
| 64 | (2-fluorophenyl)methyl-methyl-[1-[4-(2-methylpyrazol-3-yl)phthalazin-1-yl]-4-piperidyl]ammonium | ++ |
| 65 | (3-fluorophenyl)methyl-methyl-[1-[4-(2-methylpyrazol-3-yl)phthalazin-1-yl]-4-piperidyl]ammonium | ++ |
| 66 | tert-butyl N-[1-[4-(2-methylpyrazol-3-yl)phthalazin-1-yl]-4-piperidyl]carbamate | ++ |
| 67 | N-[(2,4-difluorophenyl)methyl]-N-methyl-1-[4-(2-methylpyrazol-3-yl)phthalazin-1-yl]piperidin-4-amine | ++ |
| 68 | 4-[[[1-[4-(2-methylpyrazol-3-yl)phthalazin-1-yl]-4-piperidyl]amino]methyl]benzonitrile | + |
| 69 | N-[(2-methoxyphenyl)methyl]-1-[4-(2-methylpyrazol-3-yl)phthalazin-1-yl]piperidin-4-amine | + |
| 70 | N-[(3-methoxyphenyl)methyl]-1-[4-(2-methylpyrazol-3-yl)phthalazin-1-yl]piperidin-4-amine | ++ |
| 71 | N-[(4-methoxyphenyl)methyl]-1-[4-(2-methylpyrazol-3-yl)phthalazin-1-yl]piperidin-4-amine | + |
| 72 | N-[(2-fluorophenyl)methyl]-1-[4-(2-methylpyrazol-3-yl)phthalazin-1-yl]piperidin-4-amine | ++ |
| 73 | N-[(3-fluorophenyl)methyl]-1-[4-(2-methylpyrazol-3-yl)phthalazin-1-yl]piperidin-4-amine | ++ |
| 74 | N-[(2,4-difluorophenyl)methyl]-1-[4-(2-methylpyrazol-3-yl)phthalazin-1-yl]piperidin-4-amine | + |
| 75 | N-[(4-fluorophenyl)methyl]-1-[4-(2-methylpyrazol-3-yl)phthalazin-1-yl]piperidin-4-amine | + |
| 76 | N-[(2,6-difluoro-3-pyridyl)methyl]-1-[4-(2-methylpyrazol-3-yl)phthalazin-1-yl]piperidin-4-amine | ++ |
| 77 | N-[[4-fluoro-2-(trifluoromethyl)phenyl]methyl]-N-[1-[4-(2-methylpyrazol-3-yl)phthalazin-1-yl]-4-piperidyl]acetamide | ++ |
| 78 | N-[[4-fluoro-2-(trifluoromethyl)phenyl]methyl]-N-methyl-1-[4-(2-methylpyrazol-3-yl)phthalazin-1-yl]piperidin-4-amine | +++ |
| 79 | N-[[4-fluoro-2-(trifluoromethyl)phenyl]methyl]-1-[4-(2-methylpyrazol-3-yl)phthalazin-1-yl]piperidin-4-amine | +++ |

Further results of the in vitro biological evaluation for certain compounds of the invention are given in Table 13 below. The table shows the Hedgehog pathway inhibition activity of each compound characterised based on the IC50 value of the compound as "+", "++" and "+++". The category "+" refers to compounds with an IC50 of >200 nM. The category "++" refers to compounds with an IC50 of 10 nM to 200 nM. The category "+++" refers to compounds with an IC50 of <10 nM. Compounds that did not exhibit an IC50 value within the upper concentration limit of the assay have been indicated with a "−".

TABLE 13

| ID No. s | STRUCTURE_NAME | Gli luc IC50 nM |
|---|---|---|
| 80 | 3-[4-fluoro-2-(trifluoromethyl)phenyl]-1-methyl-1-[1-[8-(2-methylpyrazol-3-yl)pyrido[2,3-d]pyridazin-5-yl]-4-piperidyl]urea | +++ |
| 81 | 1-[4,5-dimethyl-6-(2-methylpyrazol-3-yl)pyridazin-3-yl]-N-methyl-N-[(2-nitrophenyl)methyl]piperidin-4-amine | +++ |
| 82 | 1-[4,5-dimethyl-6-(2-methylpyrazol-3-yl)pyridazin-3-yl]-N-[(2-isopropylphenyl)methyl]-N-methyl-piperidin-4-amine | ++ |
| 83 | 1-[4,5-dimethyl-6-(2-methylpyrazol-3-yl)pyridazin-3-yl]-N-methyl-N-[[3-(trifluoromethoxy)phenyl]methyl]piperidin-4-amine | ++ |
| 84 | 1-[4,5-dimethyl-6-(2-methylpyrazol-3-yl)pyridazin-3-yl]-N-methyl-N-[[2-(trifluoromethyl)phenyl]methyl]piperidin-4-amine | ++ |
| 85 | 1-[4,5-dimethyl-6-(2-methylpyrazol-3-yl)pyridazin-3-yl]-N-methyl-N-[[3-(trifluoromethyl)-2-pyridyl]methyl]piperidin-4-amine | ++ |

TABLE 13-continued

| ID No. s | STRUCTURE_NAME | Gli luc IC50 nM |
|---|---|---|
| 86 | N-methyl-1-[4-(2-methylpyrazol-3-yl)phthalazin-1-yl]-N-(pyrimidin-4-ylmethyl)piperidin-4-amine | + |
| 87 | 2-[[[1-[4,5-dimethyl-6-(2-methylpyrazol-3-yl)pyridazin-3-yl]-4-piperidyl]-methyl-amino]methyl]benzonitrile | ++ |
| 88 | 1-[4,5-dimethyl-6-(2-methylpyrazol-3-yl)pyridazin-3-yl]-N-methyl-N-[(2-methylsulfanylphenyl)methyl]piperidin-4-amine | + |
| 89 | 1-[4,5-dimethyl-6-(2-methylpyrazol-3-yl)pyridazin-3-yl]-N-methyl-N-[[2-(trifluoromethoxy)phenyl]methyl]piperidin-4-amine | + |
| 90 | 1-[4,5-dimethyl-6-(2-methylpyrazol-3-yl)pyridazin-3-yl]-N-methyl-N-(pyridazin-4-ylmethyl)piperidin-4-amine | + |
| 91 | N-methyl-1-[4-(2-methylpyrazol-3-yl)phthalazin-1-yl]-N-(pyridazin-4-ylmethyl)piperidin-4-amine | + |
| 92 | N-methyl-1-[4-(2-methylpyrazol-3-yl)phthalazin-1-yl]-N-[(2-methylsulfanylpyrimidin-4-yl)methyl]piperidin-4-amine | ++ |
| 93 | 1-[4,5-dimethyl-6-(2-methylpyrazol-3-yl)pyridazin-3-yl]-N-methyl-N-[(2-methylsulfanylpyrimidin-4-yl)methyl]piperidin-4-amine | + |
| 94 | N-cyclopropyl-N-[[4-fluoro-2-(trifluoromethyl)phenyl]methyl]-1-[4-(2-methylpyrazol-3-yl)phthalazin-1-yl]piperidin-4-amine | + |
| 95 | 1-[4,5-dimethyl-6-(2-methylpyrazol-3-yl)pyridazin-3-yl]-N-methyl-N-[[2-methyl-4-(trifluoromethyl)thiazol-5-yl]methyl]piperidin-4-amine | ++ |
| 96 | N-methyl-1-[4-(2-methylpyrazol-3-yl)phthalazin-1-yl]-N-[[2-methyl-4-(trifluoromethyl)thiazol-5-yl]methyl]piperidin-4-amine | +++ |
| 97 | 1-[4,5-dimethyl-6-(2-methylpyrazol-3-yl)pyridazin-3-yl]-N-methyl-N-[[2-methyl-5-(trifluoromethyl)oxazol-4-yl]methyl]piperidin-4-amine | ++ |
| 98 | N-methyl-1-[4-(2-methylpyrazol-3-yl)phthalazin-1-yl]-N-[[2-methyl-5-(trifluoromethyl)oxazol-4-yl]methyl]piperidin-4-amine | ++ |
| 99 | 1-[4-fluoro-2-(trifluoromethyl)phenyl]-3-[1-[1-(4-pyridyl)pyrido[3,4-d]pyridazin-4-yl]-4-piperidyl]urea | +++ |
| 100 | 1-[1-[4,5-dimethyl-6-(2-methylpyrazol-3-yl)pyridazin-3-yl]-4-piperidyl]-3-[4-fluoro-2-(trifluoromethyl)phenyl]urea | ++ |
| 101 | 3-(2,4-difluorophenyl)-1-methyl-1-[1-[8-(2-methylpyrazol-3-yl)pyrido[2,3-d]pyridazin-5-yl]-4-piperidyl]urea | + |
| 102 | 2,4-difluoro-N-methyl-N-[1-[1-(2-methylpyrazol-3-yl)pyrido[3,4-d]pyridazin-4-yl]-4-piperidyl]benzenesulfonamide | ++ |
| 103 | 4-fluoro-N-methyl-N-[1-[1-(2-methylpyrazol-3-yl)pyrido[3,4-d]pyridazin-4-yl]-4-piperidyl]-2-(trifluoromethyl)benzenesulfonamide | ++ |
| 104 | 1-(2,4-difluorophenyl)-3-[1-[1-(2-methylpyrazol-3-yl)pyrido[3,4-d]pyridazin-4-yl]-4-piperidyl]urea | ++ |
| 105 | 1-[4-fluoro-2-(trifluoromethyl)phenyl]-3-[1-[1-(2-methylpyrazol-3-yl)pyrido[3,4-d]pyridazin-4-yl]-4-piperidyl]urea | +++ |
| 106 | 4-fluoro-N-[1-[1-(2-methylpyrazol-3-yl)pyrido[3,4-d]pyridazin-4-yl]-4-piperidyl]-2-(trifluoromethyl)benzenesulfonamide | ++ |
| 107 | 1-[1-[4,5-dimethyl-6-(2-methylpyrazol-3-yl)pyridazin-3-yl]-4-piperidyl]-1-methyl-3-[5-(trifluoromethyl)pyridazin-4-yl]urea | + |
| 108 | 1-[1-[4,5-dimethyl-6-(2-methylpyrazol-3-yl)pyridazin-3-yl]-4-piperidyl]-3-[1-(trifluoromethyl)cyclopropyl]urea | ++ |
| 109 | 1-[1-[4-(2-methylpyrazol-3-yl)phthalazin-1-yl]-4-piperidyl]-3-[1-(trifluoromethyl)cyclopropyl]urea | ++ |
| 110 | N-[[4-fluoro-2-(trifluoromethyl)phenyl]methyl]-1-[6-(6-methoxy-3-pyridyl)-4,5-dimethyl-pyridazin-3-yl]-N-methyl-piperidin-4-amine | ++ |
| 111 | 3-(2,4-difluorophenyl)-1-methyl-1-[1-[1-(2-methylpyrazol-3-yl)pyrido[3,4-d]pyridazin-4-yl]-4-piperidyl]urea | ++ |
| 112 | 3-[4-fluoro-2-(trifluoromethyl)phenyl]-1-methyl-1-[1-[1-(2-methylpyrazol-3-yl)pyrido[3,4-d]pyridazin-4-yl]-4-piperidyl]urea | +++ |
| 113 | 1-[1-[4,5-dimethyl-6-(2-methylpyrazol-3-yl)pyridazin-3-yl]-4-piperidyl]-3-(4-fluorophenyl)-1-methyl-urea | + |
| 114 | N-methyl-1-[4-(2-methylpyrazol-3-yl)phthalazin-1-yl]-N-[(2-nitrophenyl)methyl]piperidin-4-amine | ++ |
| 115 | 1-[4-(2-methylpyrazol-3-yl)phthalazin-1-yl]-N-[(2-methylsulfonylphenyl)methyl]piperidin-4-amine | ++ |
| 116 | 1-tert-butyl-3-[1-[4,5-dimethyl-6-(2-methylpyrazol-3-yl)pyridazin-3-yl]-4-piperidyl]urea | ++ |
| 117 | 4-fluoro-N-[1-[6-(6-methoxy-3-pyridyl)-4,5-dimethyl-pyridazin-3-yl]-4-piperidyl]-2-(trifluoromethyl)benzenesulfonamide | ++ |
| 118 | N-[1-[4,5-dimethyl-6-(2-methyl-4-pyridyl)pyridazin-3-yl]-4-piperidyl]-4-fluoro-2-(trifluoromethyl)benzenesulfonamide | + |
| 119 | N-[1-[4,5-dimethyl-6-(4-pyridyl)pyridazin-3-yl]-4-piperidyl]-4-fluoro-2-(trifluoromethyl)benzenesulfonamide | ++ |
| 120 | N-[[4-fluoro-2-(trifluoromethyl)phenyl]methyl]-1-[6-(6-methoxy-3-pyridyl)-4,5-dimethyl-pyridazin-3-yl]piperidin-4-amine | ++ |
| 121 | N-[[4-fluoro-2-(trifluoromethyl)phenyl]methyl]-1-[6-(2-methoxy-4-pyridyl)-4,5-dimethyl-pyridazin-3-yl]piperidin-4-amine | + |
| 122 | 1-[4,5-dimethyl-6-(2-methyl-4-pyridyl)pyridazin-3-yl]-N-[[4-fluoro-2-(trifluoromethyl)phenyl]methyl]piperidin-4-amine | + |
| 123 | 1-[4,5-dimethyl-6-(4-pyridyl)pyridazin-3-yl]-N-[[4-fluoro-2-(trifluoromethyl)phenyl]methyl]piperidin-4-amine | ++ |

TABLE 13-continued

| ID No. s | STRUCTURE_NAME | Gli luc IC50 nM |
|---|---|---|
| 124 | 4-fluoro-N-methyl-N-[1-[1-(2-methylpyrazol-3-yl)-6,7-dihydro-5H-cyclopenta[d]pyridazin-4-yl]-4-piperidyl]-2-(trifluoromethyl)benzenesulfonamide | ++ |
| 125 | 3-[4-fluoro-2-(trifluoromethyl)phenyl]-1-methyl-1-[1-[1-(2-methylpyrazol-3-yl)-6,7-dihydro-5H-cyclopenta[d]pyridazin-4-yl]-4-piperidyl]urea | +++ |
| 126 | 1-[1-[4,5-dimethyl-6-(2-methylpyrazol-3-yl)pyridazin-3-yl]-4-piperidyl]-3-(2-fluorophenyl)-1-methyl-urea | ++ |
| 127 | 3-(2,4-difluorophenyl)-1-[1-[4,5-dimethyl-6-(2-methylpyrazol-3-yl)pyridazin-3-yl]-4-piperidyl]-1-methyl-urea | + |
| 128 | 2-fluoro-5-[[[1-[1-(2-methylpyrazol-3-yl)-6,7-dihydro-5H-cyclopenta[d]pyridazin-4-yl]-4-piperidyl]amino]methyl]benzonitrile | + |
| 129 | 3-tert-butyl-1-methyl-1-[1-[8-(2-methylpyrazol-3-yl)pyrido[2,3-d]pyridazin-5-yl]-4-piperidyl]urea | + |
| 130 | N-[[4-fluoro-2-(trifluoromethyl)phenyl]methyl]-N-methyl-1-[8-(2-methylpyrazol-3-yl)pyrido[2,3-d]pyridazin-5-yl]piperidin-4-amine | + |
| 131 | 3-[[methyl-[1-[1-(2-methylpyrazol-3-yl)-6,7-dihydro-5H-cyclopenta[d]pyridazin-4-yl]-4-piperidyl]amino]methyl]benzonitrile | ++ |
| 132 | N-[[4-fluoro-2-(trifluoromethyl)phenyl]methyl]-N-methyl-1-[1-(2-methylpyrazol-3-yl)-6,7-dihydro-5H-cyclopenta[d]pyridazin-4-yl]piperidin-4-amine | ++ |
| 133 | 3-tert-butyl-1-methyl-1-[1-[1-(2-methylpyrazol-3-yl)-6,7-dihydro-5H-cyclopenta[d]pyridazin-4-yl]-4-piperidyl]urea | ++ |
| 134 | 4-fluoro-N-methyl-N-[1-[5-(2-methylpyrazol-3-yl)pyrido[2,3-d]pyridazin-8-yl]-4-piperidyl]-2-(trifluoromethyl)benzenesulfonamide | ++ |
| 135 | N-[[4-fluoro-2-(trifluoromethyl)phenyl]methyl]-N-methyl-1-[5-(2-methylpyrazol-3-yl)pyrido[2,3-d]pyridazin-8-yl]piperidin-4-amine | ++ |
| 136 | 3-(2,4-difluorophenyl)-1-methyl-1-[1-[5-(2-methylpyrazol-3-yl)pyrido[2,3-d]pyridazin-8-yl]-4-piperidyl]urea | ++ |
| 137 | 3-[4-fluoro-2-(trifluoromethyl)phenyl]-1-methyl-1-[1-[5-(2-methylpyrazol-3-yl)pyrido[2,3-d]pyridazin-8-yl]-4-piperidyl]urea | +++ |
| 138 | 1-(2,4-difluorophenyl)-3-[1-[1-(2-methylpyrazol-3-yl)-6,7-dihydro-5H-cyclopenta[d]pyridazin-4-yl]-4-piperidyl]urea | ++ |
| 139 | 1-[4-fluoro-2-(trifluoromethyl)phenyl]-N-methyl-N-[[1-[4-(2-methylpyrazol-3-yl)phthalazin-1-yl]pyrrolidin-3-yl]methyl]methanamine | ++ |
| 140 | 1-[4-fluoro-2-(trifluoromethyl)phenyl]-N-[[1-[4-(2-methylpyrazol-3-yl)phthalazin-1-yl]pyrrolidin-3-yl]methyl]methanamine | ++ |
| 141 | 2,4-difluoro-N-[1-[1-(2-methylpyrazol-3-yl)-6,7-dihydro-5H-cyclopenta[d]pyridazin-4-yl]-4-piperidyl]benzenesulfonamide | ++ |
| 142 | N-[4-fluoro-2-(trifluoromethyl)phenyl]-1-[1-(2-methylpyrazol-3-yl)-6,7-dihydro-5H-cyclopenta[d]pyridazin-4-yl]piperidin-4-amine | ++ |
| 143 | N-[1-[4-fluoro-2-(trifluoromethyl)phenyl]ethyl]-1-[4-(2-methylpyrazol-3-yl)phthalazin-1-yl]piperidin-4-amine | ++ |
| 144 | N-[[4-fluoro-2-(trifluoromethyl)phenyl]methyl]-N-methyl-1-(4-morpholinophthalazin-1-yl)piperidin-4-amine | + |
| 145 | N-[[4-fluoro-2-(trifluoromethyl)phenyl]methyl]-1-(4-morpholinophthalazin-1-yl)piperidin-4-amine | + |
| 146 | N-[[4-fluoro-2-(trifluoromethyl)phenyl]methyl]-1-[5-(2-methylpyrazol-3-yl)pyrido[2,3-d]pyridazin-8-yl]piperidin-4-amine | + |
| 147 | N-methyl-1-[4-(2-methylpyrazol-3-yl)phthalazin-1-yl]-N-[[3-(trifluoromethyl)-2-pyridyl]methyl]piperidin-4-amine | ++ |
| 148 | N-[[4-fluoro-2-(trifluoromethyl)phenyl]methyl]-1-[1-(2-methylpyrazol-3-yl)-6,7-dihydro-5H-cyclopenta[d]pyridazin-4-yl]piperidin-4-amine | ++ |
| 149 | 3-[[[1-[1-(2-methylpyrazol-3-yl)-6,7-dihydro-5H-cyclopenta[d]pyridazin-4-yl]-4-piperidyl]amino]methyl]benzonitrile | + |
| 150 | 1-[4-(2-methylpyrazol-3-yl)phthalazin-1-yl]-N-[[3-(trifluoromethyl)-2-pyridyl]methyl]piperidin-4-amine | ++ |
| 151 | 1-[1-[4,5-dimethyl-6-(2-methylpyrazol-3-yl)pyridazin-3-yl]-4-piperidyl]-3-[4-fluoro-2-(trifluoromethyl)phenyl]-1-methyl-urea | +++ |
| 152 | 3-tert-butyl-1-[1-[4,5-dimethyl-6-(2-methylpyrazol-3-yl)pyridazin-3-yl]-4-piperidyl]-1-methyl-urea | + |
| 153 | N-[[4-fluoro-2-(trifluoromethyl)phenyl]methyl]-N-methyl-1-(4-pyrazin-2-ylphthalazin-1-yl)piperidin-4-amine | + |
| 154 | N-methyl-1-[4-(2-methylpyrazol-3-yl)phthalazin-1-yl]-N-[[4-(trifluoromethyl)-3-pyridyl]methyl]piperidin-4-amine | +++ |
| 155 | 1-[4-(2-methylpyrazol-3-yl)phthalazin-1-yl]-N-[[2-(trifluoromethyl)-3-pyridyl]methyl]piperidin-4-amine | +++ |
| 156 | 1-[4-(2-methylpyrazol-3-yl)phthalazin-1-yl]-N-[[4-(trifluoromethyl)-3-pyridyl]methyl]piperidin-4-amine | +++ |
| 157 | N-methyl-1-[4-(2-methylpyrazol-3-yl)phthalazin-1-yl]-N-[[2-(trifluoromethyl)-3-pyridyl]methyl]piperidin-4-amine | +++ |
| 158 | N-[(2-chloro-4-fluoro-phenyl)methyl]-N-methyl-1-[4-(2-methylpyrazol-3-yl)phthalazin-1-yl]piperidin-4-amine | ++ |
| 159 | 4-fluoro-N-[1-[1-(2-methylpyrazol-3-yl)-6,7-dihydro-5H-cyclopenta[d]pyridazin-4-yl]-4-piperidyl]-2-(trifluoromethyl)benzenesulfonamide | +++ |
| 160 | N-[[6-fluoro-2-(trifluoromethyl)-3-pyridyl]methyl]-N-methyl-1-[4-(2-methylpyrazol-3-yl)phthalazin-1-yl]piperidin-4-amine | +++ |

TABLE 13-continued

| ID No. s | STRUCTURE_NAME | Gli luc IC50 nM |
|---|---|---|
| 161 | 1-tert-butyl-3-[1-[1-(2-methylpyrazol-3-yl)-6,7-dihydro-5H-cyclopenta[d]pyridazin-4-yl]-4-piperidyl]urea | ++ |
| 162 | N-methyl-1-[4-(2-methylpyrazol-3-yl)phthalazin-1-yl]-N-[[2-(trifluoromethoxy)phenyl]methyl]piperidin-4-amine | +++ |
| 163 | N-[(2,3-difluorophenyl)methyl]-1-[4-(2-methylpyrazol-3-yl)phthalazin-1-yl]piperidin-4-amine | ++ |
| 164 | N-[[6-fluoro-4-(trifluoromethyl)-3-pyridyl]methyl]-1-[4-(2-methylpyrazol-3-yl)phthalazin-1-yl]piperidin-4-amine | ++ |
| 165 | N-[[6-fluoro-2-(trifluoromethyl)-3-pyridyl]methyl]-1-[4-(2-methylpyrazol-3-yl)phthalazin-1-yl]piperidin-4-amine | ++ |
| 166 | methyl 6-[[[1-[4-(2-methylpyrazol-3-yl)phthalazin-1-yl]-4-piperidyl]amino]methyl]pyridine-3-carboxylate | + |
| 167 | 1-[1-[4-(2-methylpyrazol-3-yl)phthalazin-1-yl]-4-piperidyl]-3-[4-(trifluoromethoxy)phenyl]urea | +++ |
| 168 | 3-[[methyl-[1-[4-(2-methylpyrazol-3-yl)phthalazin-1-yl]-4-piperidyl]amino]methyl]benzonitrile | ++ |
| 169 | 3-(2,4-difluorophenyl)-1-methyl-1-[1-[4-(2-methylpyrazol-3-yl)phthalazin-1-yl]-4-piperidyl]urea | +++ |
| 170 | 1-[4-(2-methylpyrazol-3-yl)phthalazin-1-yl]-N-(o-tolylmethyl)piperidin-4-amine | ++ |
| 171 | 1-[4,5-dimethyl-6-(2-methylpyrazol-3-yl)pyridazin-3-yl]-N-methyl-N-(pyrimidin-4-ylmethyl)piperidin-4-amine | − |
| 172 | 4-fluoro-N-[1-[6-(2-methoxy-4-pyridyl)-4,5-dimethyl-pyridazin-3-yl]-4-piperidyl]-2-(trifluoromethyl)benzenesulfonamide | − |

Examples of compounds of the invention with values for their IC50 are given in Table 14, below.

TABLE 14

| ID No. | Compound | Gli Luc nM |
|---|---|---|
| 3 | N-methyl-1-[4-(2-methylpyrazol-3-yl)phthalazin-1-yl]-N-[[2-(trifluoromethyl)phenyl]methyl]piperidin-4-amine | 3.94 |
| 5 | 3-[4-fluoro-2-(trifluoromethyl)phenyl]-1-methyl-1-[1-[4-(2-methylpyrazol-3-yl)phthalazin-1-yl]-4-piperidyl]urea | 0.05 |
| 8 | 1-(2,4-difluorophenyl)-3-[1-[4-(2-methylpyrazol-3-yl)phthalazin-1-yl]-4-piperidyl]urea | 0.99 |
| 9 | 1-(4-fluorophenyl)-3-[1-[4-(2-methylpyrazol-3-yl)phthalazin-1-yl]-4-piperidyl]urea | 1.33 |
| 14 | 1-[1-[4-(2-methylpyrazol-3-yl)phthalazin-1-yl]-4-piperidyl]-3-[4-(trifluoromethyl)phenyl]urea | 0.71 |
| 23 | 1-[4-fluoro-2-(trifluoromethyl)phenyl]-3-[1-[4-(2-methylpyrazol-3-yl)phthalazin-1-yl]-4-piperidyl]urea | 0.66 |
| 42 | N-[[4-fluoro-2-(trifluoromethyl)phenyl]methyl]-N-methyl-1-[6-(2-methylpyrazol-3-yl)pyridazin-3-yl]piperidin-4-amine | 0.04 |
| 50 | 4-fluoro-N-[1-[4-(2-methylpyrazol-3-yl)phthalazin-1-yl]-4-piperidyl]-2-(trifluoromethyl)benzenesulfonamide | 1.79 |
| 79 | N-[[4-fluoro-2-(trifluoromethyl)phenyl]methyl]-1-[4-(2-methylpyrazol-3-yl)phthalazin-1-yl]piperidin-4-amine | 7.85 |
| 112 | 3-[4-fluoro-2-(trifluoromethyl)phenyl]-1-methyl-1-[1-[1-(2-methylpyrazol-3-yl)pyrido[3,4-d]pyridazin-4-yl]-4-piperidyl]urea | 1.26 |
| 151 | 1-[1-[4,5-dimethyl-6-(2-methylpyrazol-3-yl)pyridazin-3-yl]-4-piperidyl]-3-[4-fluoro-2-(trifluoromethyl)phenyl]-1-methyl-urea | 5.12 |

Thermodynamic Solubility with Filtration 0.5 mg is weighed into a Mini Uniprep filter vial (Whatman, PVDF, 0.2 μm). 0.5 mL of pH 7.4 phosphate buffer (0.1 M) is dispensed and the vial is shaken at 600 rpm for 24 h at room temperature. At the end of this period, the solution is then filtered and an aliquot of the filtrate is used to create a tenfold dilution. Standards are prepared by serially diluting a 1250 μg/mL DMSO stock solution of the compound to 125 and 2.5 μg/mL, in Acetonitrile/Water (50:50, v/v). The concentration of the filtrate and tenfold dilution is measured by detection against the two calibration standards. Representative data for examples of the invention are given in Table 15.

TABLE 15

| ID | STRUCTURE_NAME | Solubility mg/L |
|---|---|---|
| 97 | 1-[4,5-dimethyl-6-(2-methylpyrazol-3-yl)pyridazin-3-yl]-N-methyl-N-[[2-methyl-5-(trifluoromethyl)oxazol-4-yl]methyl]piperidin-4-amine | 1009 |
| 98 | N-methyl-1-[4-(2-methylpyrazol-3-yl)phthalazin-1-yl]-N-[[2-methyl-5-(trifluoromethyl)oxazol-4-yl]methyl]piperidin-4-amine | 106 |
| 112 | 3-[4-fluoro-2-(trifluoromethyl)phenyl]-1-methyl-1-[1-[1-(2-methylpyrazol-3-yl)pyrido[3,4-d]pyridazin-4-yl]-4-piperidyl]urea | 399 |
| 116 | 1-tert-butyl-3-[1-[4,5-dimethyl-6-(2-methylpyrazol-3-yl)pyridazin-3-yl]-4-piperidyl]urea | 1262 |

TABLE 15-continued

| ID | STRUCTURE_NAME | Solubility mg/L |
|---|---|---|
| 156 | 1-[4-(2-methylpyrazol-3-yl)phthalazin-1-yl]-N-[[4-(trifluoromethyl)-3-pyridyl]methyl]piperidin-4-amine | 321 |
| 170 | 1-[4-(2-methylpyrazol-3-yl)phthalazin-1-yl]-N-(o-tolylmethyl)piperidin-4-amine | 1193 |

It can be seen from the above data that in addition to good IC50 values the compounds of the invention also possess good thermodynamic solubility. This provides a further potential benefit when the compounds are used in therapy.

Throughout the description and claims of this specification, the words "comprise" and "contain" and variations of them mean "including but not limited to", and they are not intended to (and do not) exclude other moieties, additives, components, integers or steps. Throughout the description and claims of this specification, the singular encompasses the plural unless the context otherwise requires. In particular, where the indefinite article is used, the specification is to be understood as contemplating plurality as well as singularity, unless the context requires otherwise.

Features, integers, characteristics, compounds, chemical moieties or groups described in conjunction with a particular aspect, embodiment or example of the invention are to be understood to be applicable to any other aspect, embodiment or example described herein unless incompatible therewith. All of the features disclosed in this specification (including any accompanying claims, abstract and drawings), and/or all of the steps of any method or process so disclosed, may be combined in any combination, except combinations where at least some of such features and/or steps are mutually exclusive. The invention is not restricted to the details of any foregoing embodiments. The invention extends to any novel one, or any novel combination, of the features disclosed in this specification (including any accompanying claims, abstract and drawings), or to any novel one, or any novel combination, of the steps of any method or process so disclosed.

The reader's attention is directed to all papers and documents which are filed concurrently with or previous to this specification in connection with this application and which are open to public inspection with this specification, and the contents of all such papers and documents are incorporated herein by reference.

The invention claimed is:

1. A compound of formula (Ia) or a pharmaceutically acceptable salt or solvate thereof:

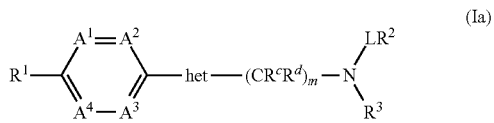

(Ia)

wherein

"het" is selected from the group consisting of substituted or unsubstituted: aziridinylene, azetidinylene, pyrolidinylene, piperidinylene and azepanylene;

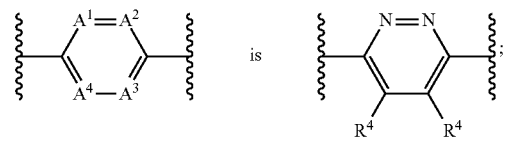

wherein two adjacent $R^4$ groups are both $C_{1-6}$ alkyl or both form a ring with the atom to which the $R^4$ groups are attached forming a fused bicyclic ring system of 8 to 12 atoms, wherein the ring formed by the two $R^4$ groups is a saturated or unsaturated carbocyclic ring with 4, 5, 6, 7 or 8 carbon atoms or a saturated or unsaturated heterocyclic ring with 4, 5, 6, 7 or 8 atoms or a saturated or unsaturated heterocyclic ring with 4, 5, 6, 7 or 8 atoms containing 1, 2 or 3 heteroatoms;

L is selected from the group consisting of a bond, —$CR^cR^d$—, —$CR^cR^dCR^cR^d$—, —$C(NR^a)$—, —$C(O)NR^3$— and —$SO_2$—;

$R^1$ is selected from the group consisting of —$OR^5$, —$NR^5R^a$, —$NR^aC(O)R^a$, —CN, —$C_{1-4}$ acyl, —$C(O)R^a$, —$C(O)NR^a$, —$C(O)OR^a$, —$SO_2R^a$, —$SO_3R^a$, $C_{1-6}$ haloalkyl, substituted or unsubstituted $C_{2-6}$ alkenyl, substituted or unsubstituted $C_{2-6}$ alkynyl, substituted or unsubstituted $C_{3-8}$ cycloalkyl, substituted or unsubstituted $C_{3-8}$ cycloalkenyl, substituted or unsubstituted aryl, and substituted or unsubstituted heterocyclic, wherein $R^5$ is H, —$SO_2R^a$, —$SO_2NR^aR^b$, substituted or unsubstituted $C_{1-4}$ alkyl, $C_{1-4}$ haloalkyl, substituted or unsubstituted $C_{3-8}$ cycloalkyl, substituted or unsubstituted $C_{3-8}$ cycloalkenyl, substituted or unsubstituted aryl, or substituted or unsubstituted heterocyclic;

$R^2$ is represented by —$CR^6R^7R^8$, wherein $R^6$, $R^7$ and $R^8$ are independently selected at each occurrence from the group consisting of substituted or unsubstituted: $C_{1-14}$ alkyl, $C_{1-14}$ haloalkyl, carbocyclic, and heterocyclic, or $R^2$ is selected from the group consisting of substituted or unsubstituted: $C_{1-14}$ haloalkyl, carbocyclic, and heterocyclic;

$R^3$ is selected from the group consisting of H, —$SO_2R^a$, —$SO_2NR^aR^b$, substituted or unsubstituted $C_{1-4}$ alkyl, $C_{1-4}$ haloalkyl, substituted or unsubstituted $C_{3-8}$ cycloalkyl, substituted or unsubstituted $C_{3-8}$ cycloalkenyl, substituted or unsubstituted aryl, and substituted or unsubstituted heterocyclic;

$R^a$ and $R^b$ are independently selected at each occurrence from the group consisting of: H, $C_{1-4}$ alkyl, $C_{1-4}$ haloalkyl, $C_{1-4}$ acyl, $C_{3-7}$ cycloalkyl, and $C_{3-7}$ halocycloalkyl;

$R^c$ and $R^d$ are independently selected from the group consisting of H, halo, —$OR^a$, $C_{1-4}$ alkyl, $C_{1-4}$ haloalkyl, $C_{1-4}$ acyl, $C_{3-7}$ cycloalkyl, and $C_{3-7}$ halocycloalkyl;

m is 0, 1 or 2; and when a group is substituted, the group contains 1 to 5 substituents independently selected at each occurrence from the group consisting of: halo, —$OR^a$, —$SR^a$, —$NR^aR^b$, $NO_2$, =O, —CN, acyl, $C_{1-6}$ alkyl, $C_{1-6}$ haloalkyl, $C_{3-8}$ cycloalkyl, —$SO_2R^a$, and $SO_3R^a$, —$C(OR^a)R^aR^b$, —$C(O)R^a$ and $C(O)OR^a$;

provided that:

(1) $LR^2$ is not —$CO(O)tBu$; and (2) $R^1$ is not a substituted or unsubstituted thiadiazolinyl group when

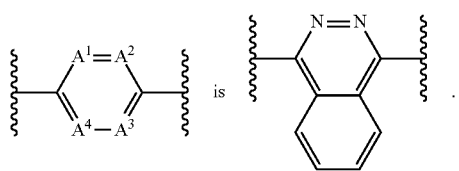 is 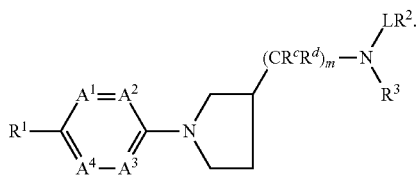.

2. The compound of any preceding claim, wherein "het" is selected from the group consisting of substituted or unsubstituted:

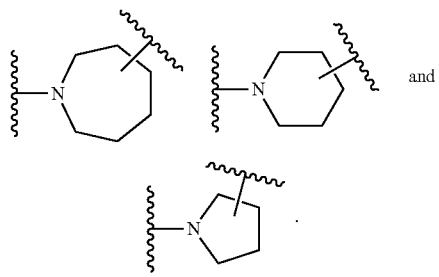

3. The compound of claim 1, wherein "het" is selected from the group consisting of substituted or unsubstituted:

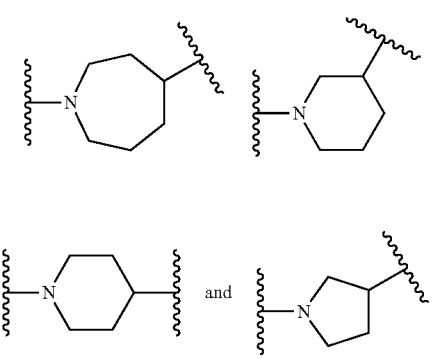

4. The compound of claim 1, wherein the compound of formula (Ia) is a compound according to formula (II), (IIa) or (IIb) and pharmaceutically acceptable salts and solvates thereof:

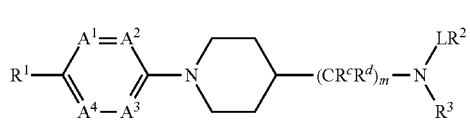
(II)

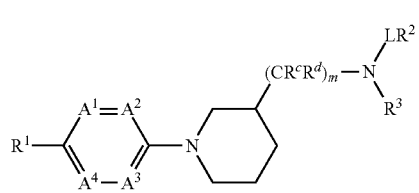
(IIa)

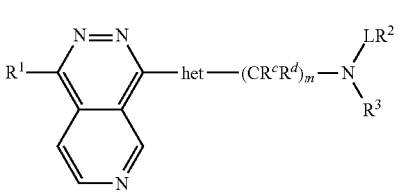
(IIb)

5. The compound of claim 1, wherein

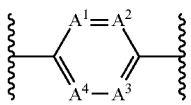

is selected from the group consisting of:

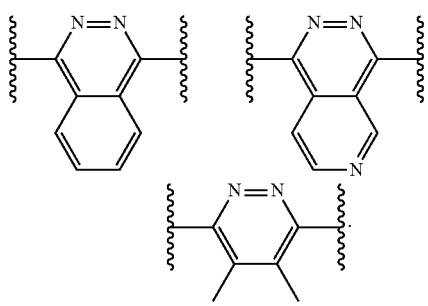 and

6. The compound of claim 1, wherein

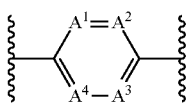

is

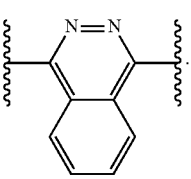 [SMILES: *c1nnc(*)c2ccccc12].

7. The compound of claim 1, wherein the compound of formula (Ia) is a compound according to formula (Va) or (Vb), or a pharmaceutically acceptable salt or solvate thereof:

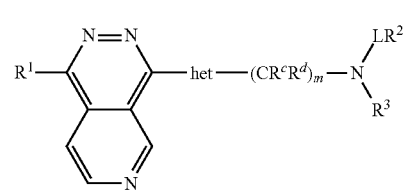
(Va)

-continued

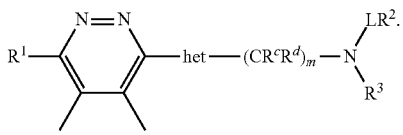

(Vb)

8. The compound of claim 1, wherein L is selected from the group consisting of a bond, —CH₂—, —CH₂CH₂—, —CH(CH₃)—, —C(NH)—, —C(O)NH—, —C(O)N(CH₃)— and —SO₂—.

9. The compound of claim 1, wherein R¹ is selected from the group consisting of —OR⁵, —NR⁵Rᵃ, —NRᵃC(O)Rᵃ, —CN, substituted or unsubstituted aryl and substituted or unsubstituted heterocyclic.

10. The compound of claim 9, wherein R¹ is selected from the group consisting of hydroxyl, methoxy, N-methylamino, Me₂N(CH₂)NH—, nitrile, phenyloxy and substituted or unsubstituted: pyrazolyl, pyridyl, morpholinyl, pyrazinyl, pyrimidinyl, piperazinyl, pyridazinyl, pyrolidin-yl-one, imidazolin-yl-one, or pyridazinyl.

11. The compound of claim 10, wherein R¹ is selected from the group consisting of substituted or unsubstituted: pyrrolyl, imidazolyl, pyrazolyl, oxazolyl, oxadiazolyl, isoxazolyl, triazolyl, tetrazolyl, thiazolyl, isothiazolyl, furanyl, pyridinyl, pyridazinyl, pyrazinyl and pyrimidinyl.

12. The compound of claim 11, wherein R¹ is substituted or unsubstituted pyrazolyl.

13. The compound of claim 9, wherein R¹ is selected from the group consisting of:

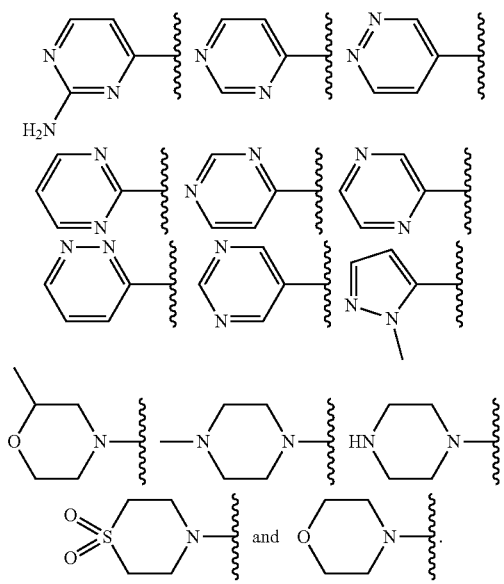

14. The compound of claim 9, wherein R¹ is:

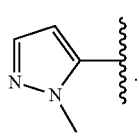

15. The compound of 9, wherein R¹ is selected from the group consisting of —OMe, —OPh, —OC₁₋₄ alkyl, —N(CH₃)CH₃, —NHCH₂CH₂N(CH₃)₂, —NHSO₂CH₃, —N(CH₃)SO₂CH₃, —NHSO₂NCH₃, —N(CH₃)SO₂CH₃, —NC(O)Rᵃ, and —CN.

16. The compound of claim 1, wherein R² is represented by —CR⁶R⁷R⁸, wherein R⁶, R⁷ and R⁸ are independently selected at each occurrence from the group consisting of substituted or unsubstituted: C₁₋₁₄ alkyl, C₁₋₁₄ haloalkyl, C₃₋₈ cycloalkyl, C₃₋₈ heterocycloalkyl, phenyl, toluenyl, pyridinyl, pyridazinyl, pyrimidinyl, pyrazinyl, pyrrolyl, pyrazolyl, triazolyl, tetrazolyl, oxazolyl, isoxazolyl, oxadiazolyl, thiazolyl, and isothiazolyl.

17. The compound of claim 16, wherein R⁶, R⁷ and R⁸ are all one of the groups selected from the group consisting of: methyl, trifluoromethyl, cyclohexanyl and phenyl.

18. The compound of claim 1, wherein R² is selected from the group consisting of substituted or unsubstituted: C₁₋₁₄ alkyl, C₁₋₁₄ haloalkyl, carbocyclic, and heterocyclic.

19. The compound of claim 18, wherein R² is selected from the group consisting of substituted or unsubstituted: C₁₋₁₄ alkyl, C₁₋₁₄ haloalkyl, C₃₋₈ cycloalkyl, C₃₋₈ heterocycloalkyl, phenyl, toluenyl, pyridinyl, pyridazinyl, pyrimidinyl, pyrazinyl, pyrrolyl, pyrazolyl, triazolyl, tetrazolyl, oxazolyl, isoxazolyl, oxadiazolyl, thiazolyl, and isothiazolyl.

20. The compound of claim 18, wherein R² is selected from the group consisting of tert-butyl or substituted or unsubstituted: cyclopropyl, phenyl, toluenyl, pyridinyl, pyridazinyl, pyrimidinyl, pyrazinyl, pyrrolyl, pyrazolyl, triazolyl, tetrazolyl, oxazolyl, isoxazolyl, oxadiazolyl, thiazolyl, and isothiazolyl.

21. The compound of claim 18, wherein R² is selected from the group consisting of substituted or unsubstituted phenyl, toluenyl and pyridinyl.

22. The compound of claim 1, wherein R² is substituted by 1 to 5 substituents, optionally 1, 2 or 3 substituents, independently selected at each occurrence from the group consisting of halo, —ORᵃ, —NO₂, C₁₋₆ alkyl, C₁₋₆ haloalkyl, —C(ORᵃ)RᵃRᵇ, —SC₁₋₄ alkyl, —C(O)RₐRᵦ, —N(CO)Rₐ, and —CN.

23. The compound of claim 22, wherein R² is substituted by: trifluoromethyl; —OCF₃; —C(OH)(CH₃)CH₃; methyl; fluoro; chloro; —CN; fluoro and trifluoromethyl; fluoro and —OCF₃; or fluoro and methyl.

24. The compound of claim 18, wherein R² is:

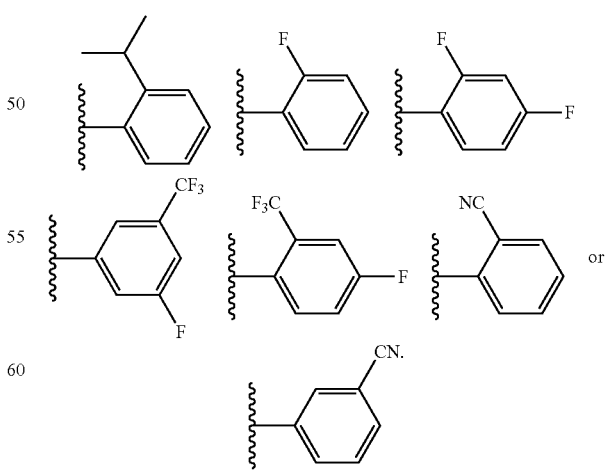

25. The compound of claim 1, wherein all occurrences of Rᵃ and Rᵇ are hydrogen.

26. The compound of claim 1, wherein all occurrences of $R^c$ and $R^d$ are hydrogen.
27. The compound of claim 1, wherein m is 0 or 1.
28. The compound of claim 1, wherein the compound of formula (Ia) is selected from the group consisting of:
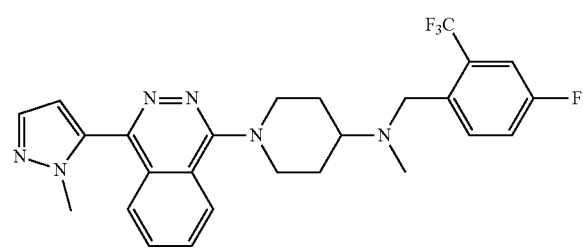
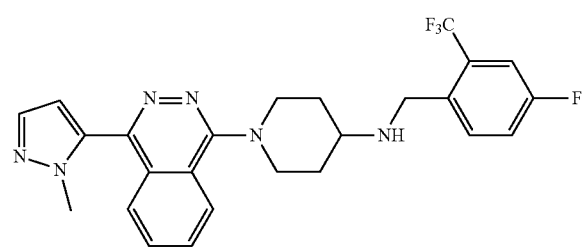
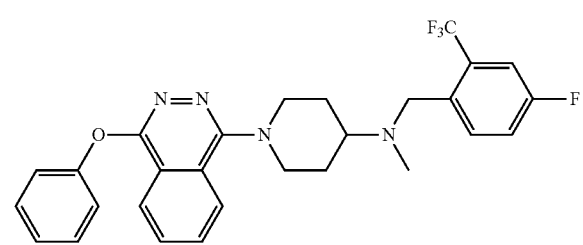
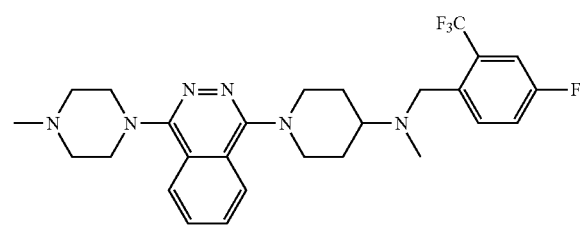
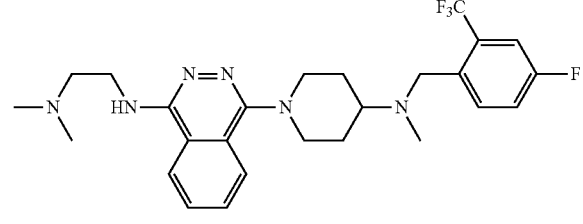
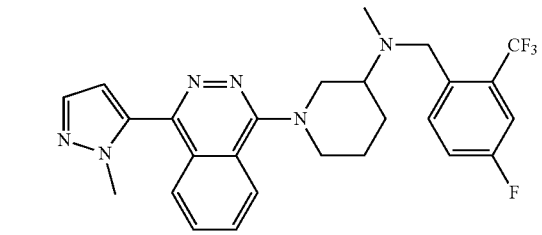
-continued
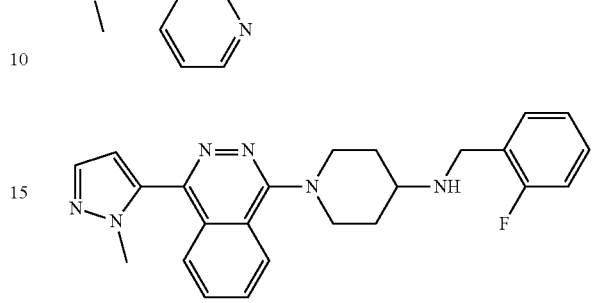
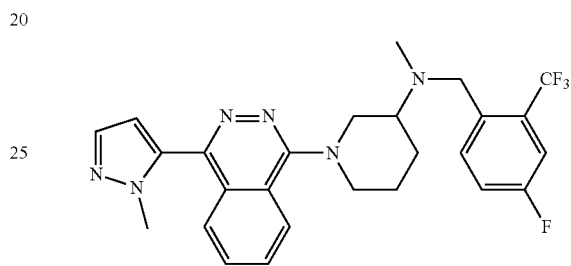
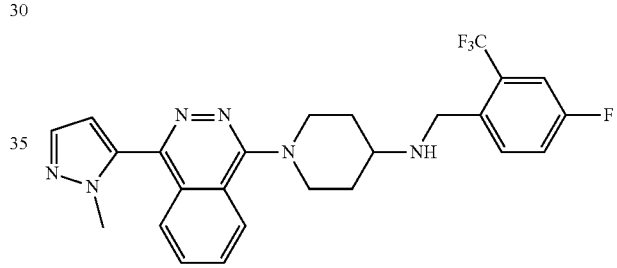
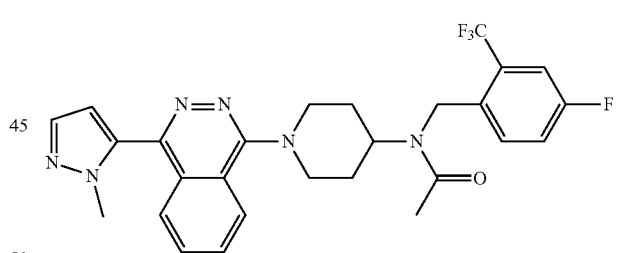
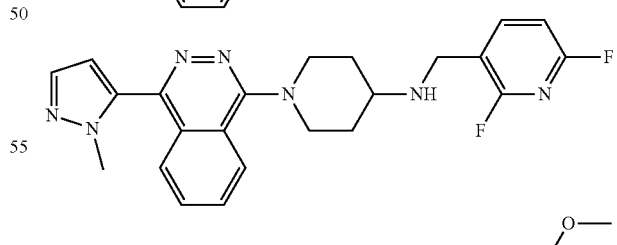

203
-continued
204
-continued
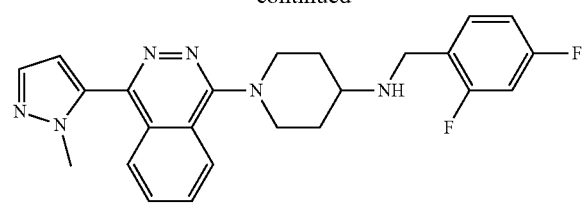
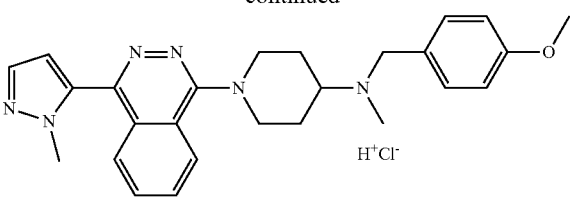

205
-continued
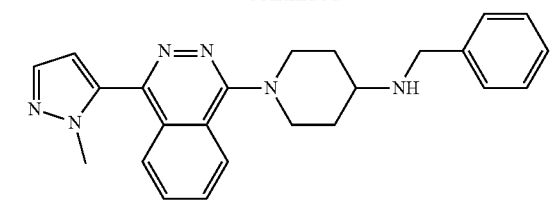
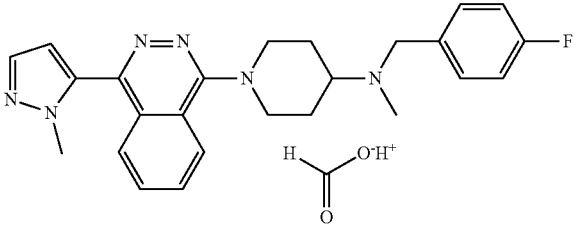
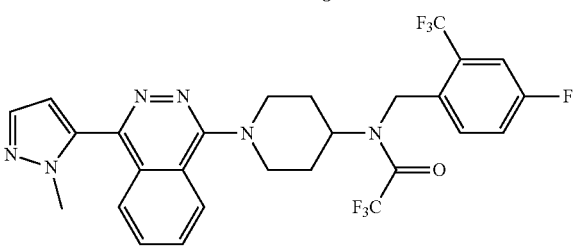
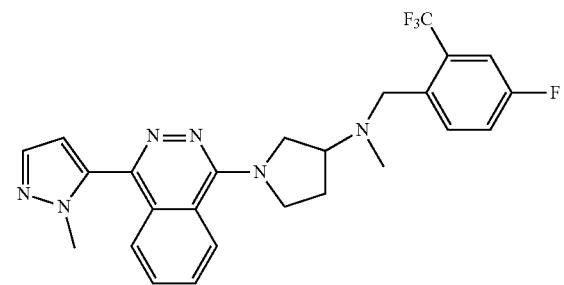 [SMILES: CN(Cc1ccc(F)cc1C(F)(F)F)C1CCN(c2nnc(-c3ccnn3C)c3ccccc23)C1]
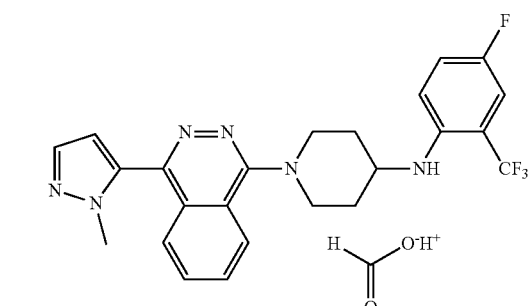
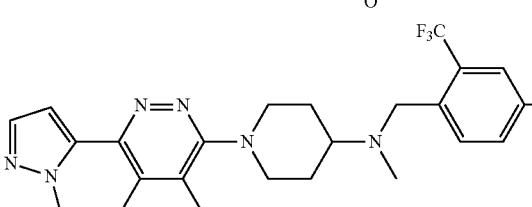
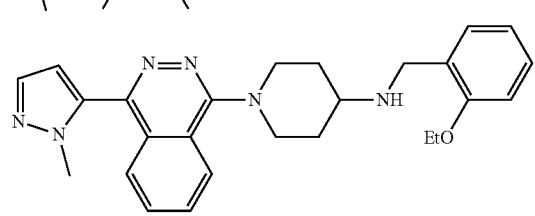
206
-continued
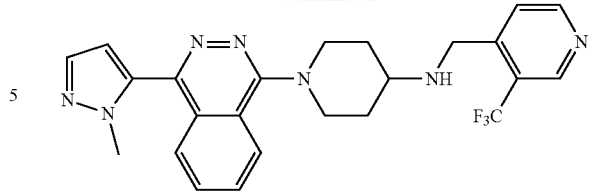
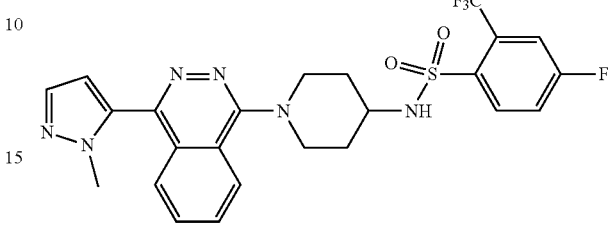
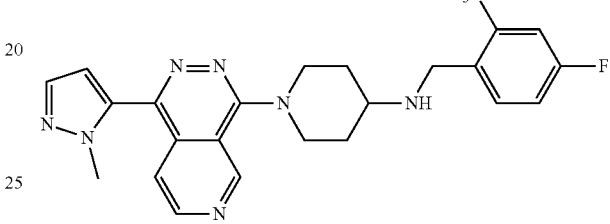
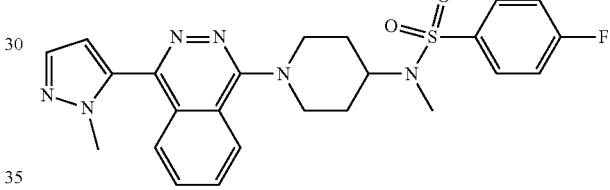
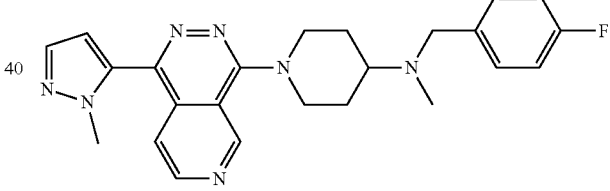
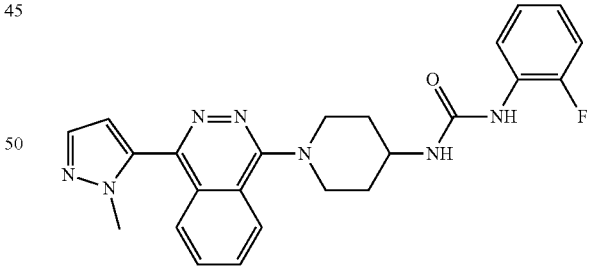
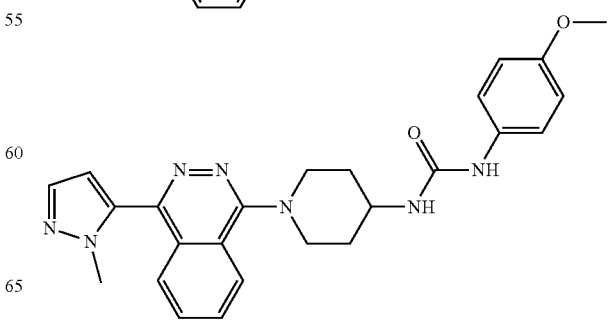

207
-continued
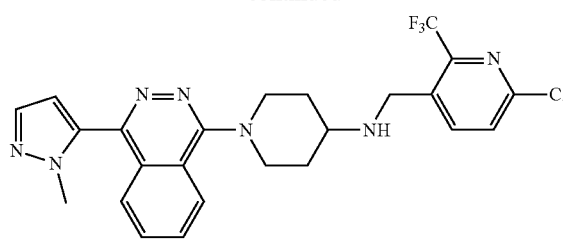
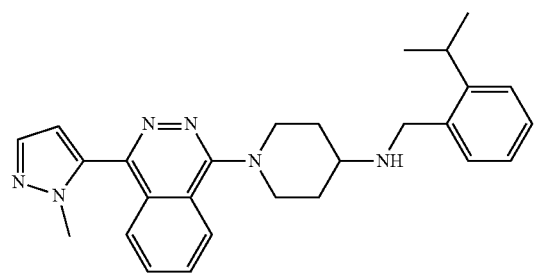
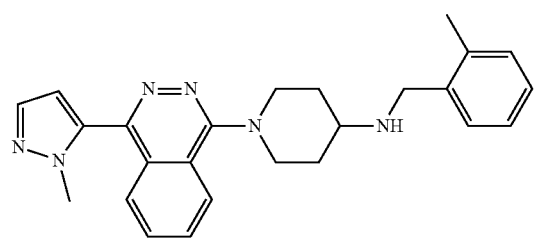
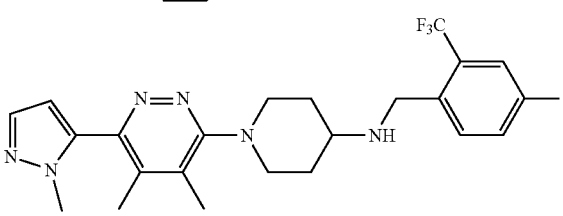
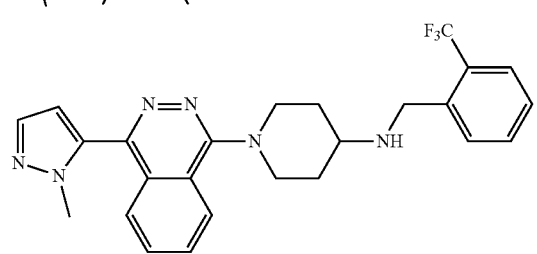
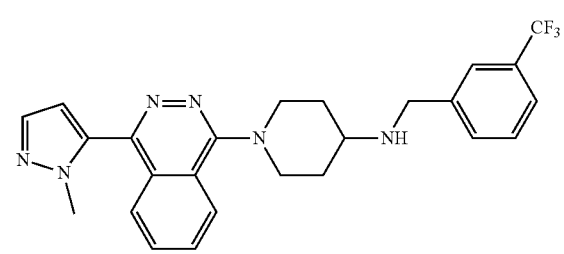
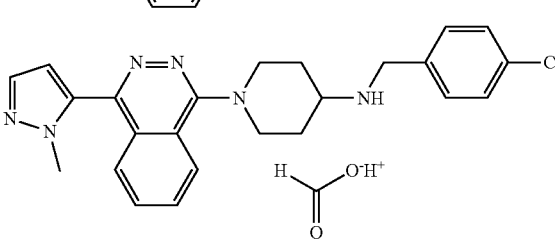
208
-continued
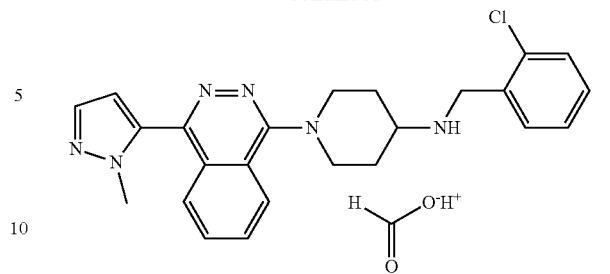
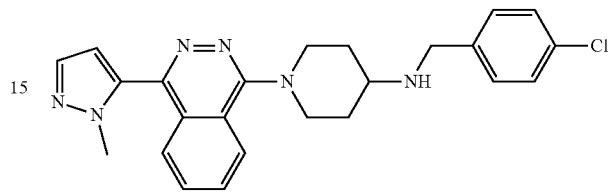
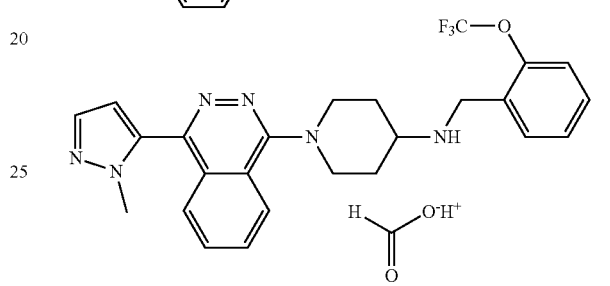
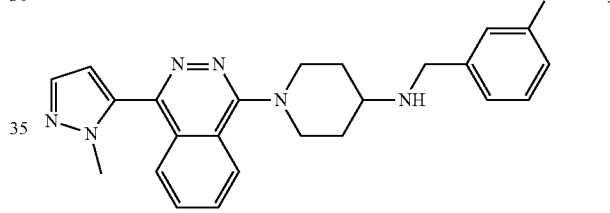
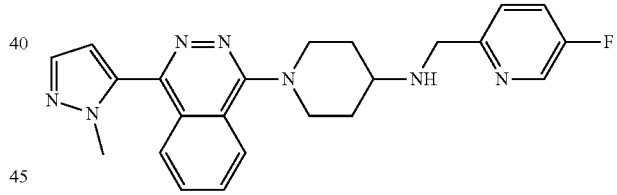
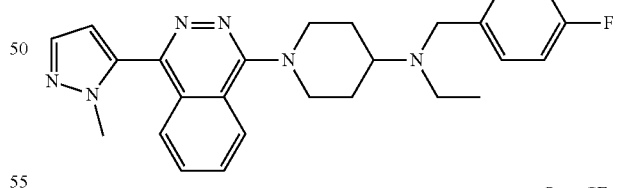
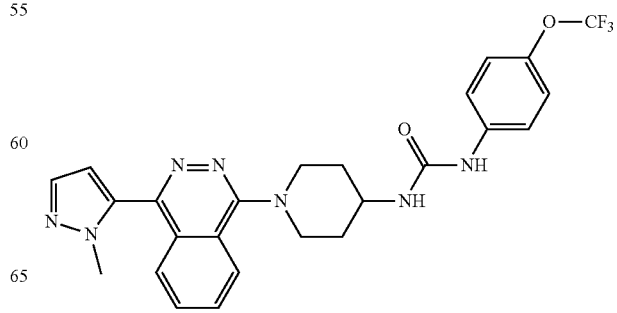

209
-continued
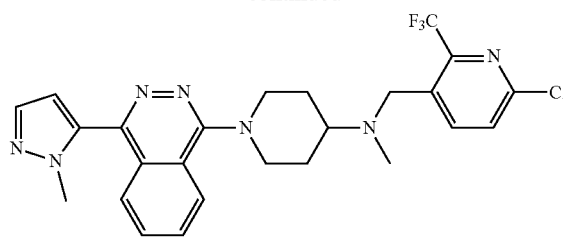
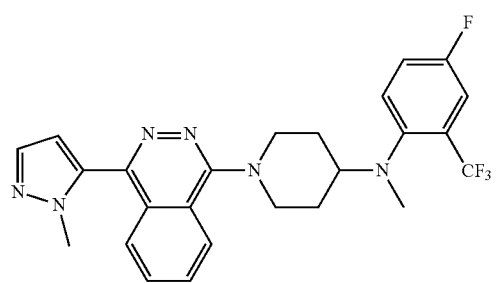
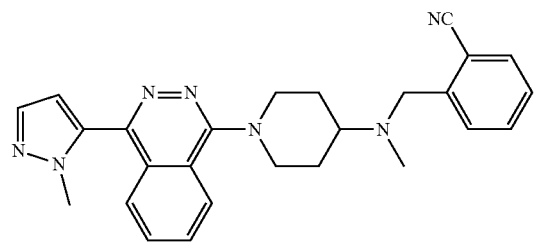
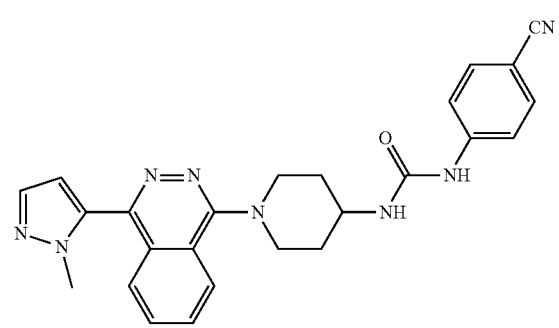
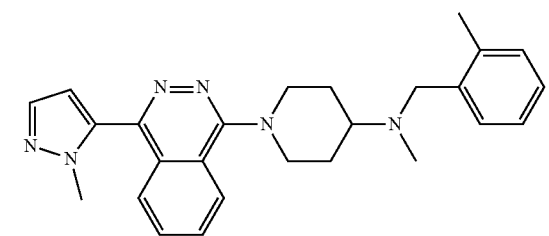
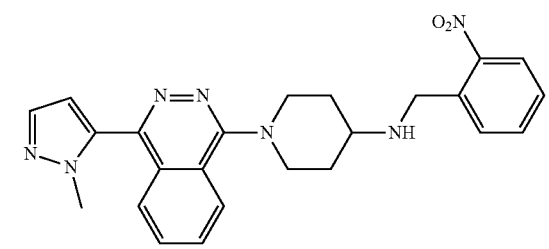
210
-continued
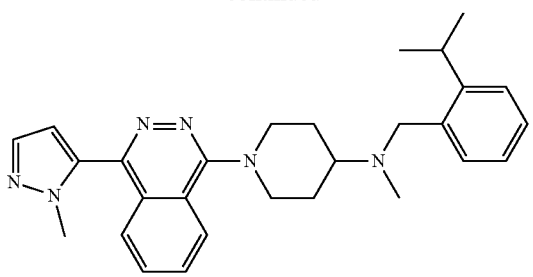
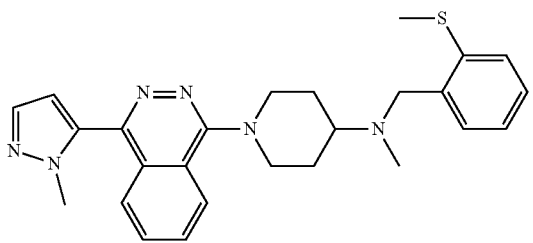
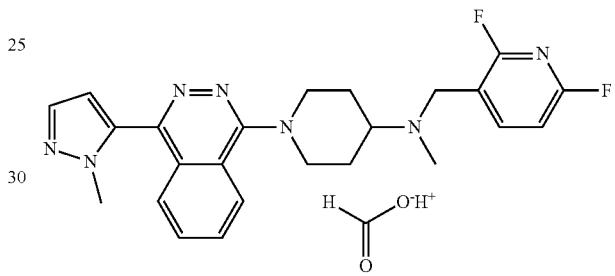
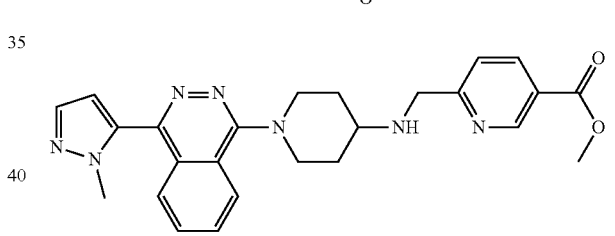
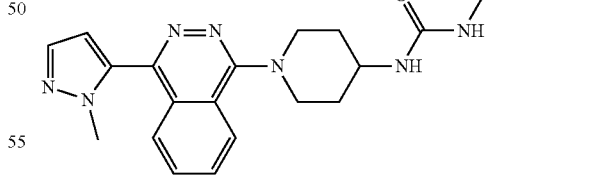
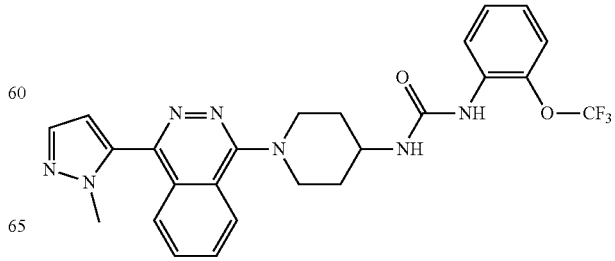

211
-continued
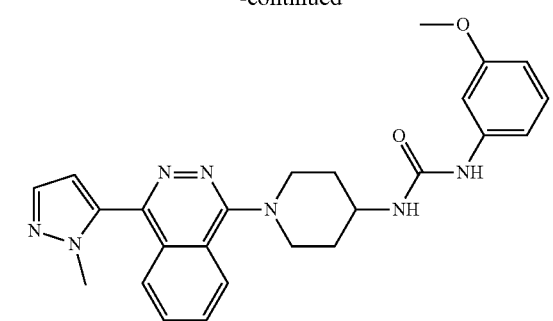
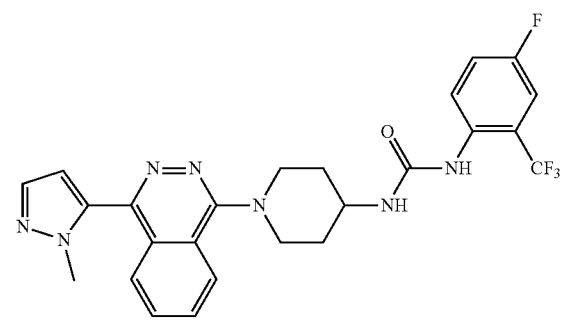
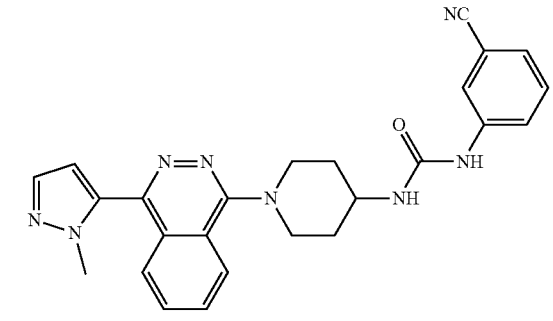
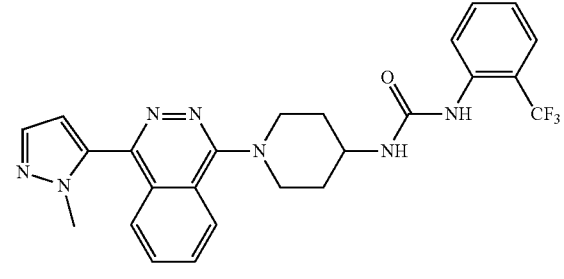
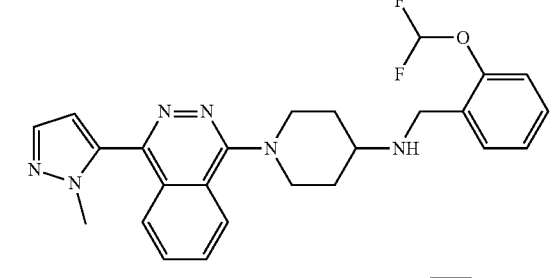
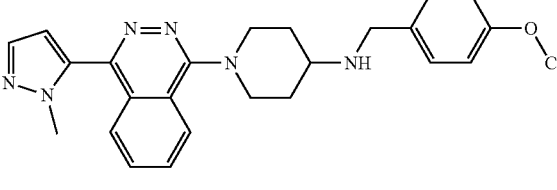
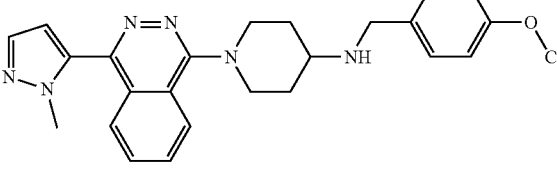
212
-continued
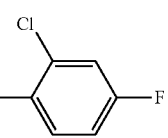
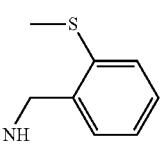
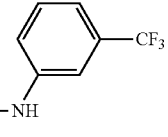
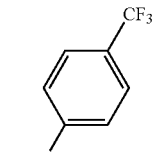
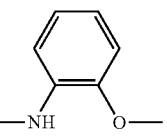
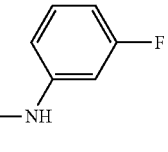

213
-continued
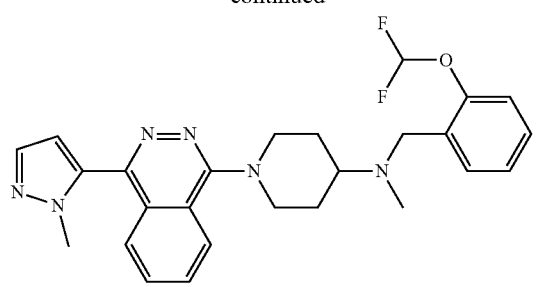
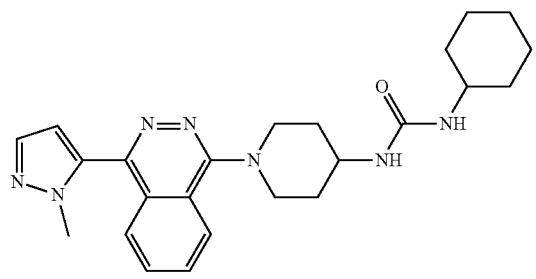
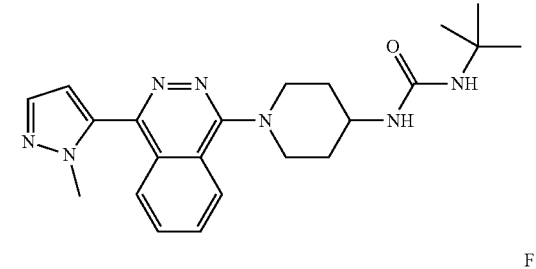
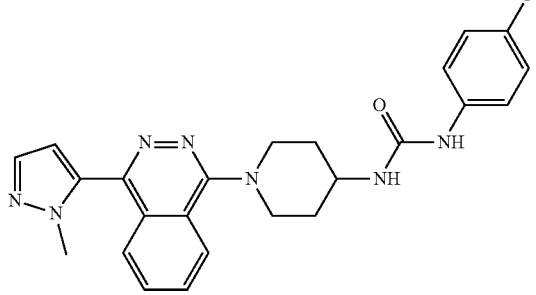
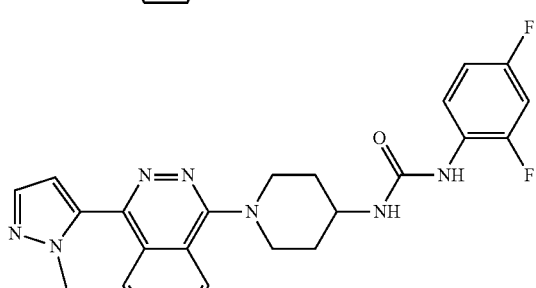
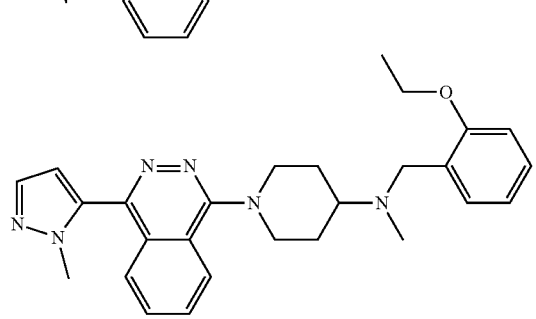
214
-continued
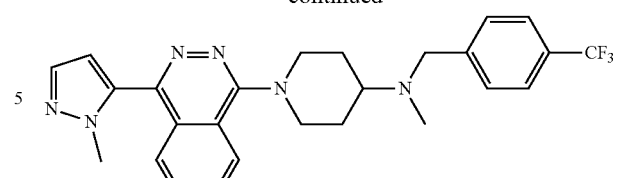
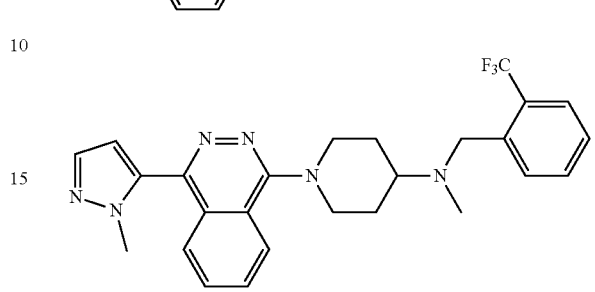
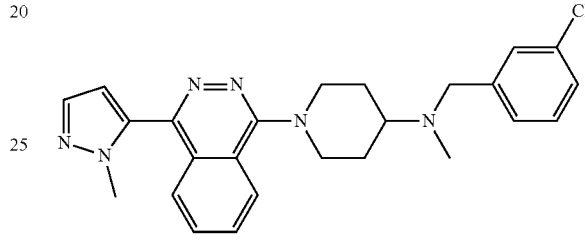
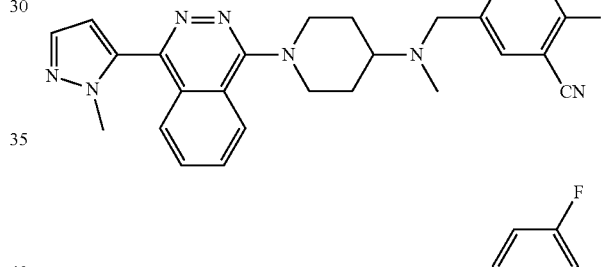
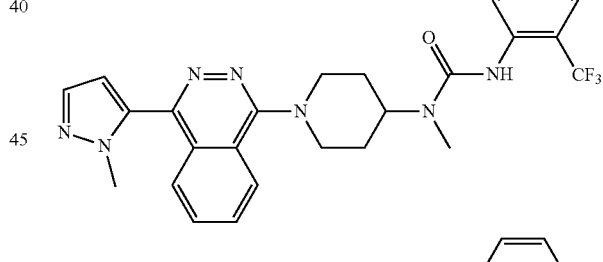
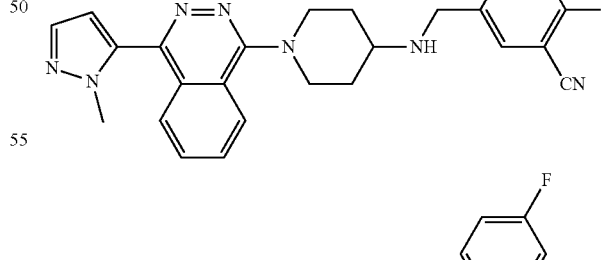

215
-continued
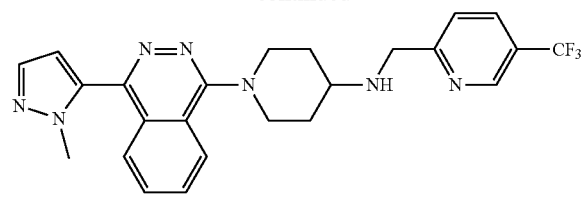
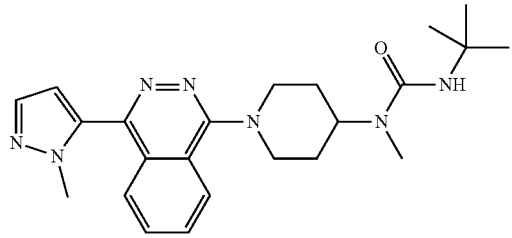
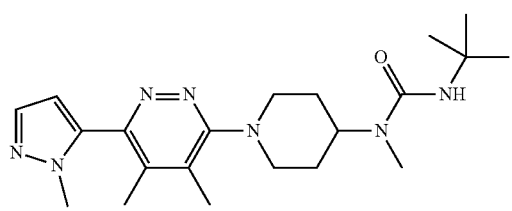
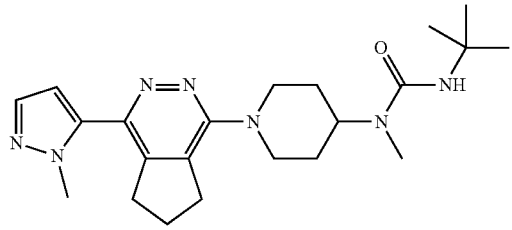
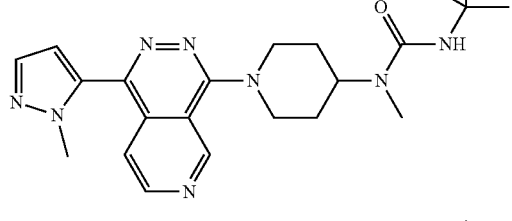
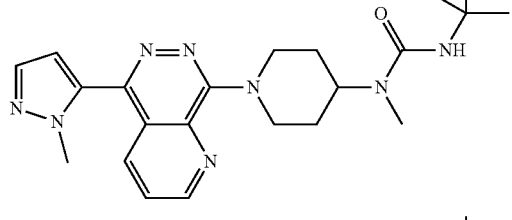
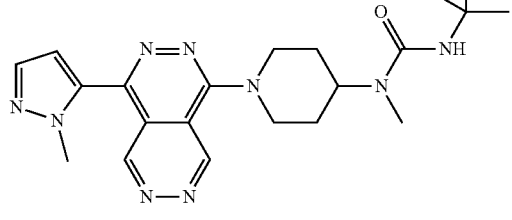
216
-continued
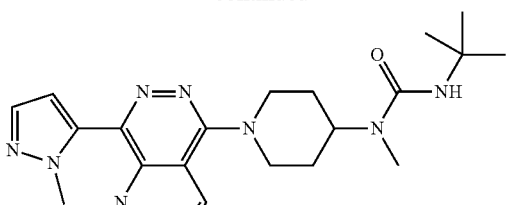
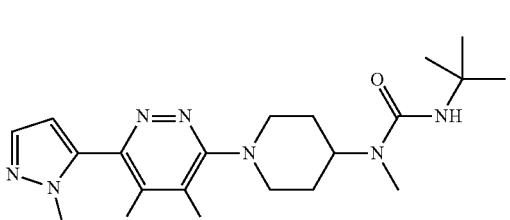
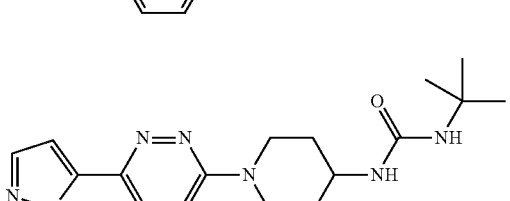
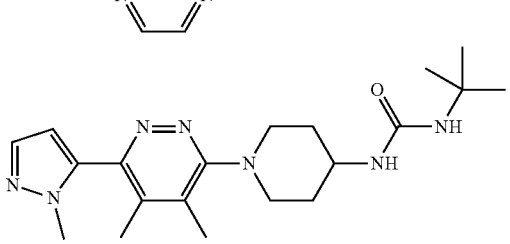
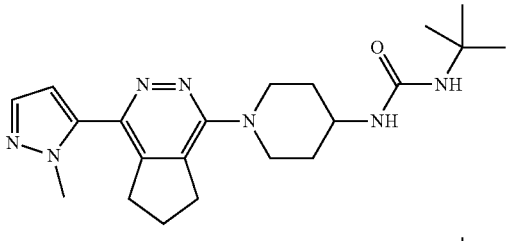
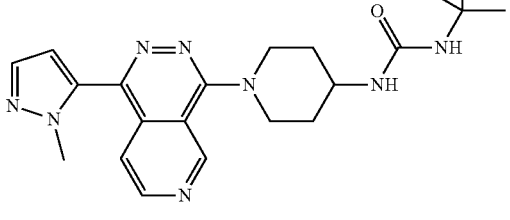
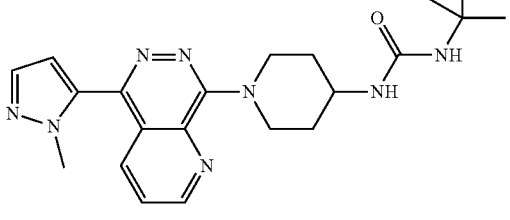

217
-continued
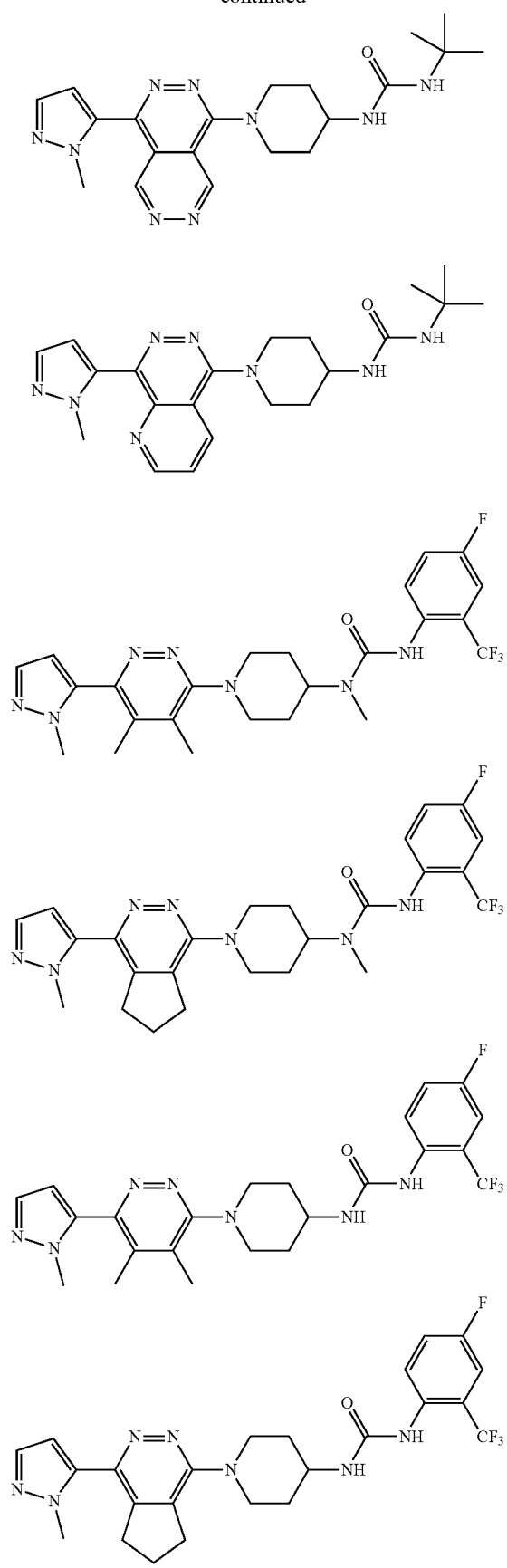
218
-continued
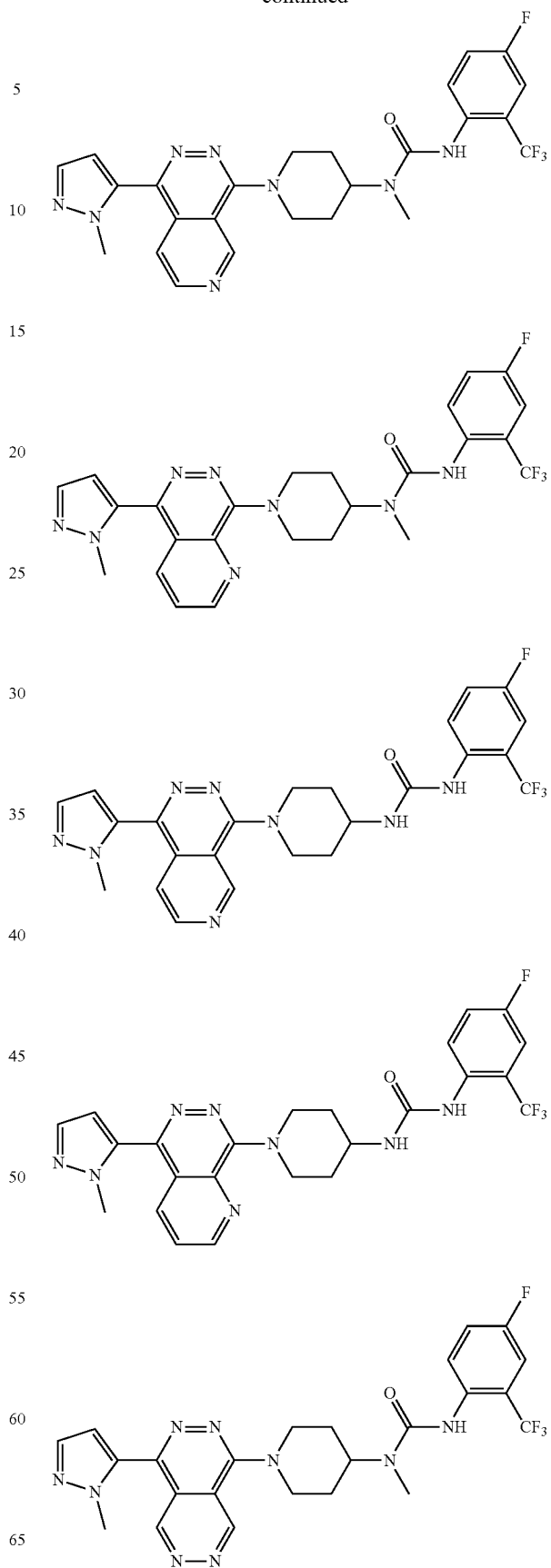

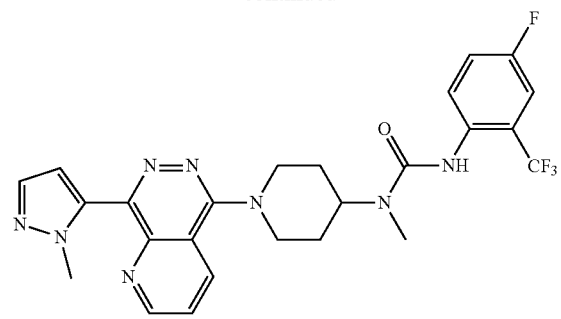
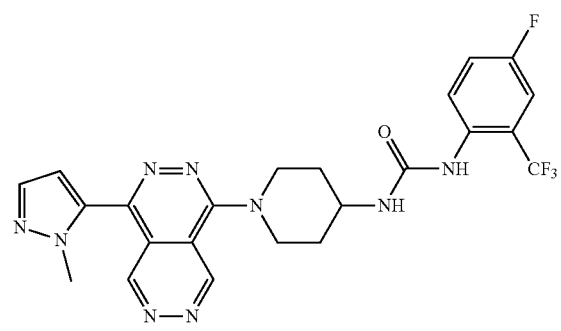
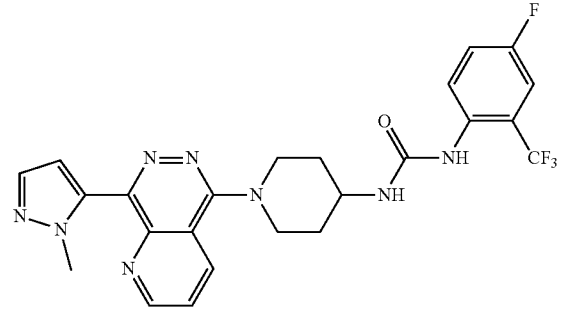
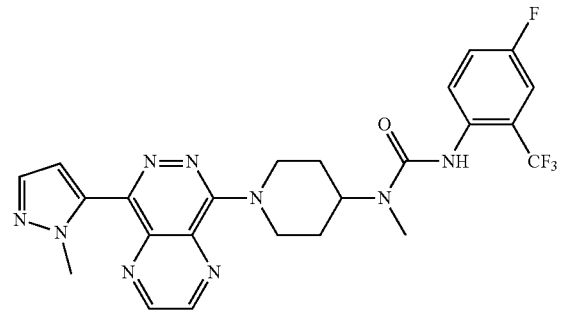
and
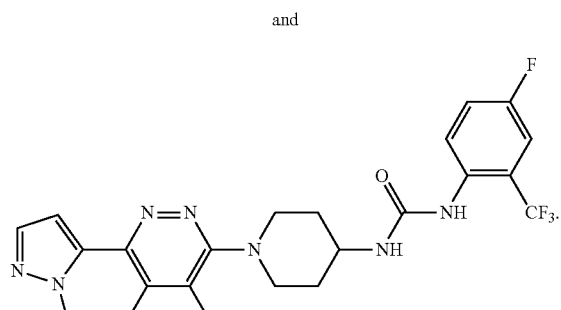
29. The compound of claim 1, wherein the compound of formula (Ia) is selected from the group consisting of:
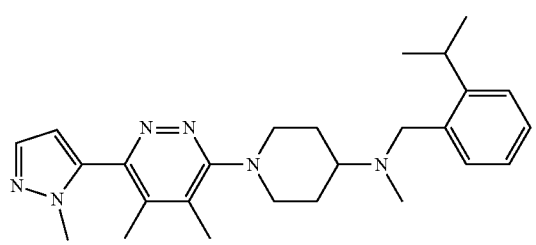
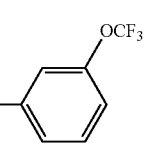
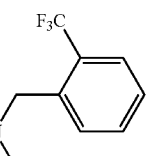
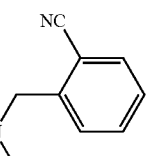
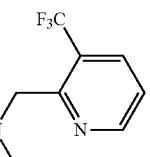
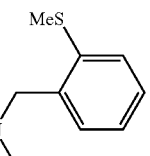
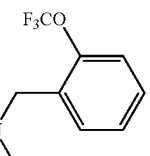

221
-continued
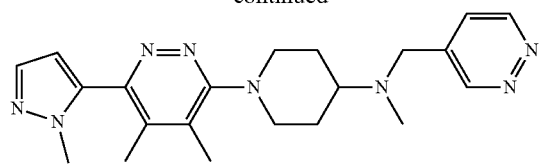
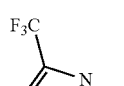
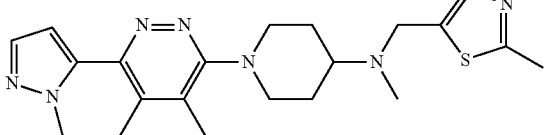
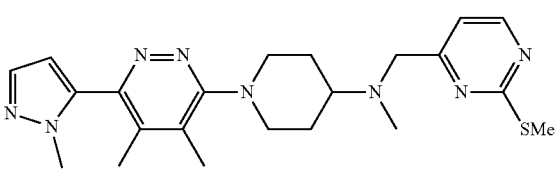
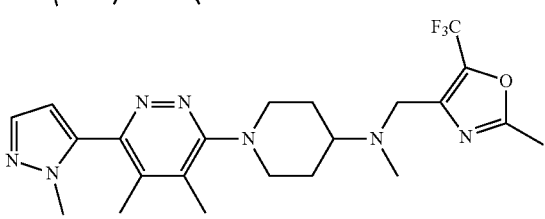
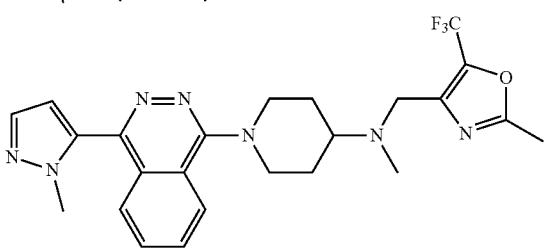
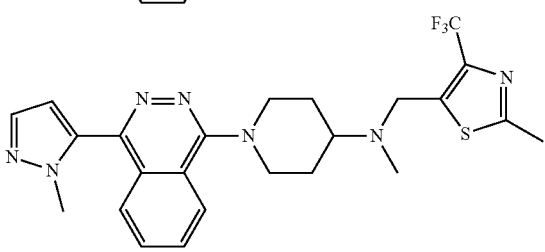
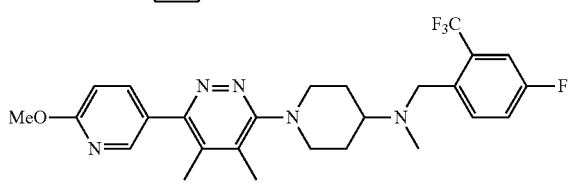
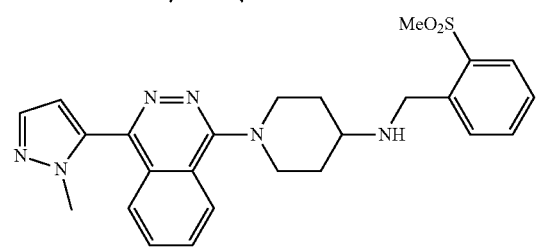
222
-continued
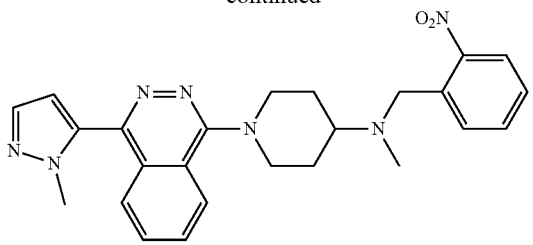
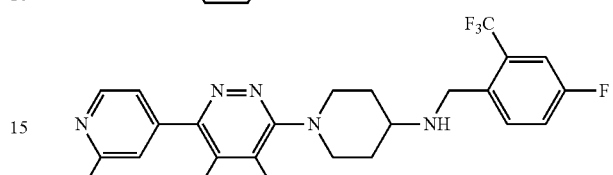
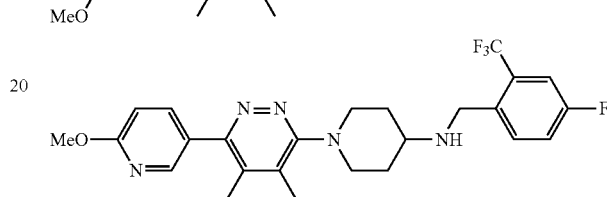
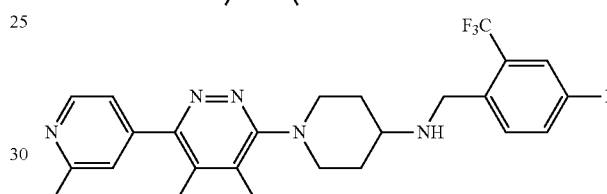
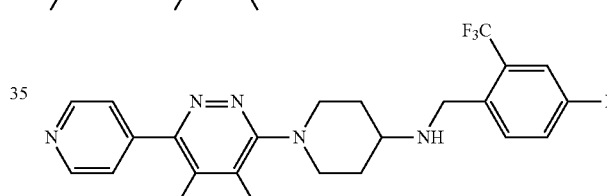
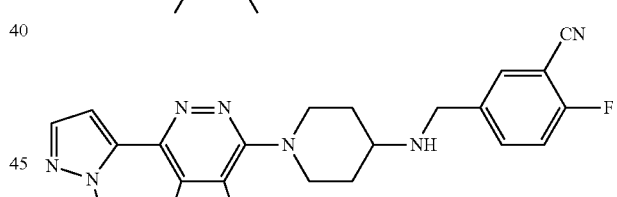
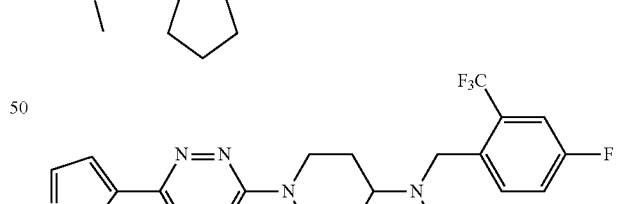
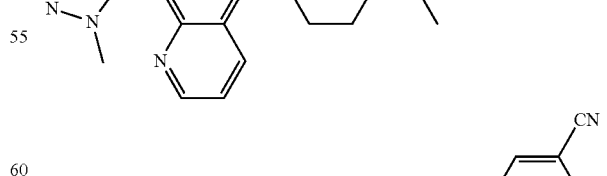
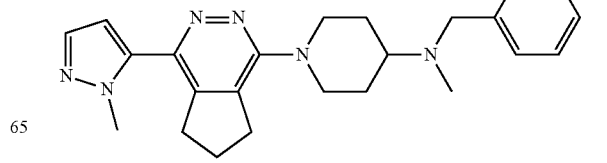

223
-continued
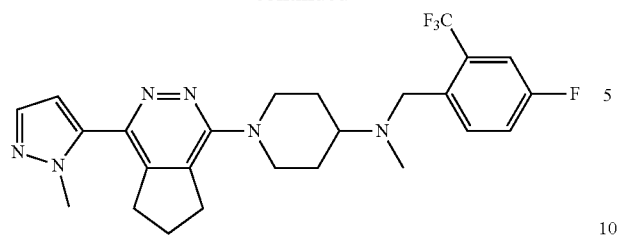
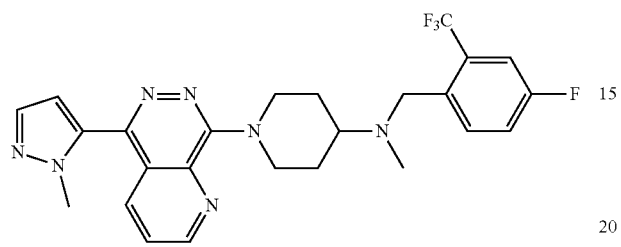
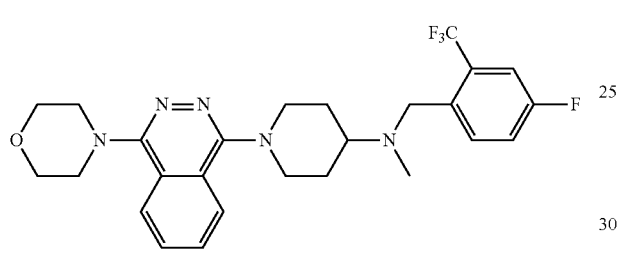
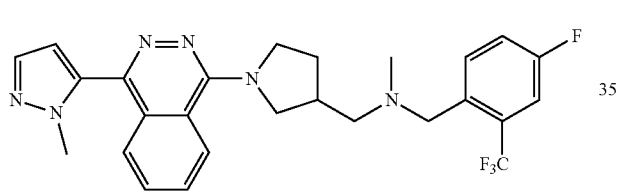
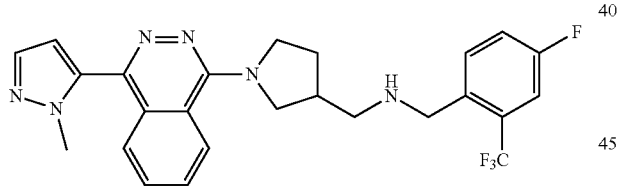
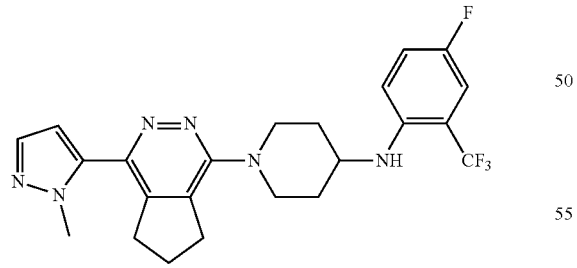
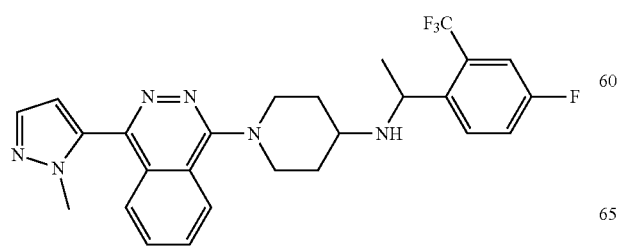
224
-continued
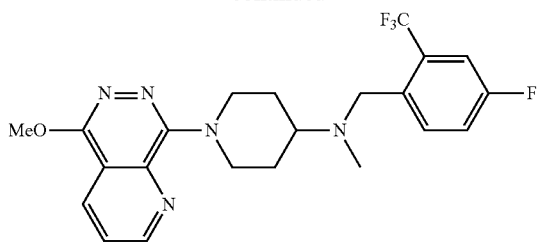
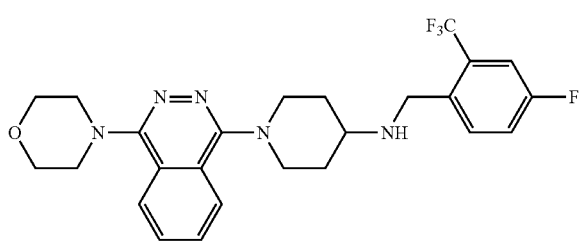
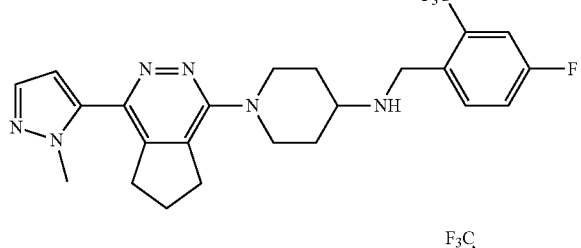
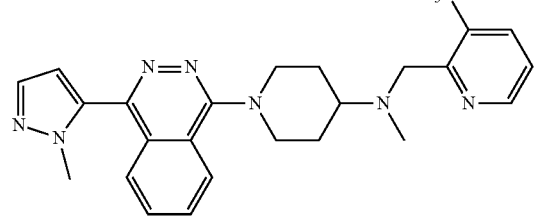
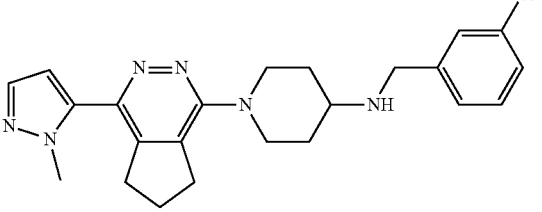
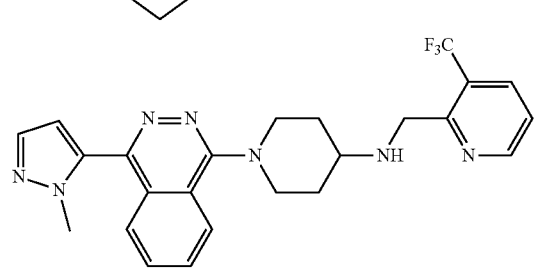
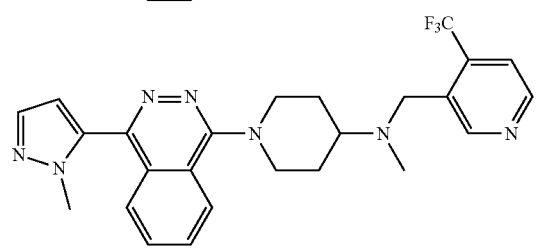

225
-continued
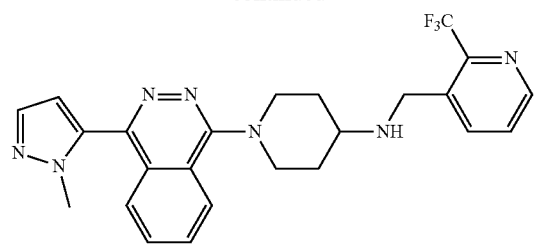
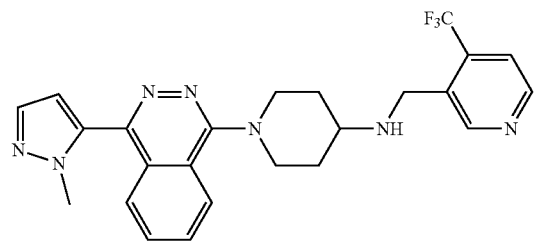
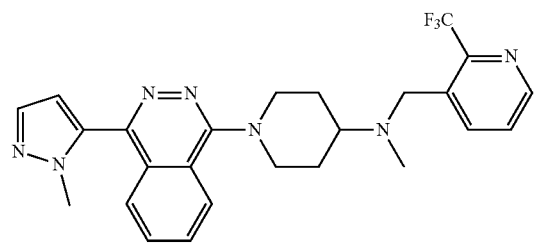
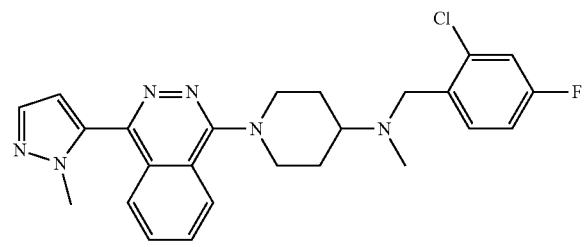
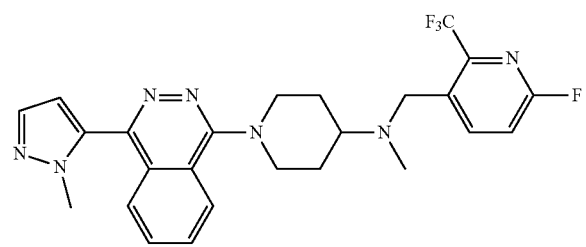
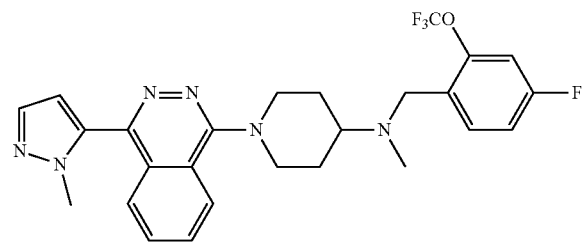
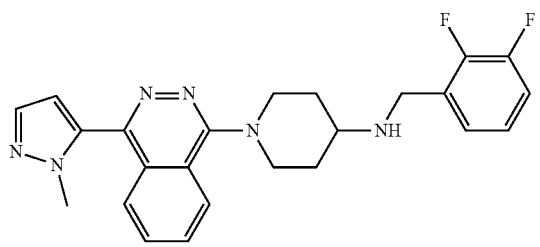
226
-continued
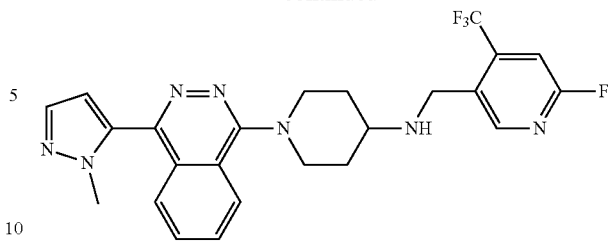
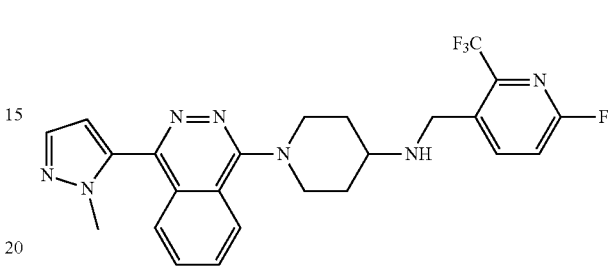
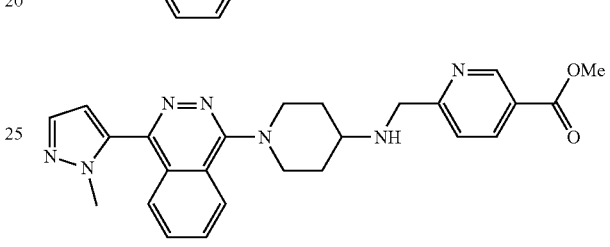
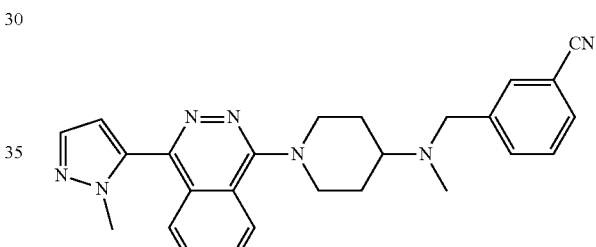
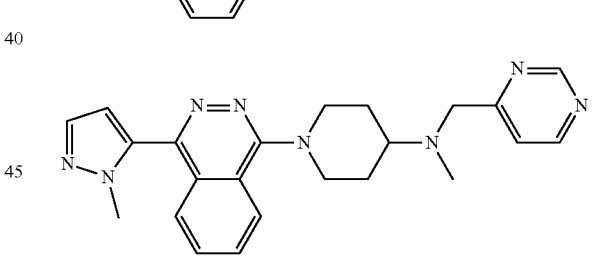
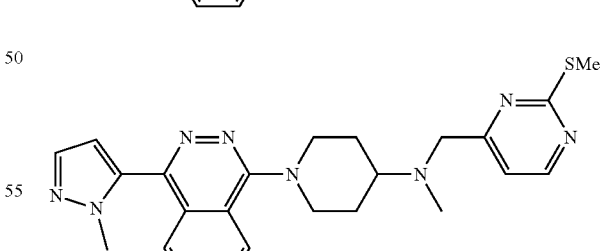
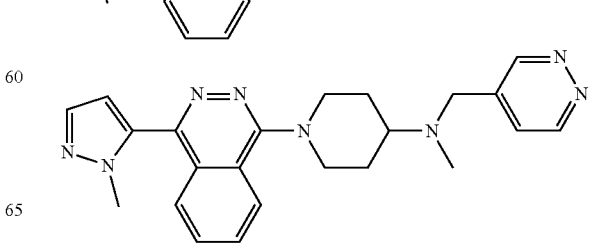

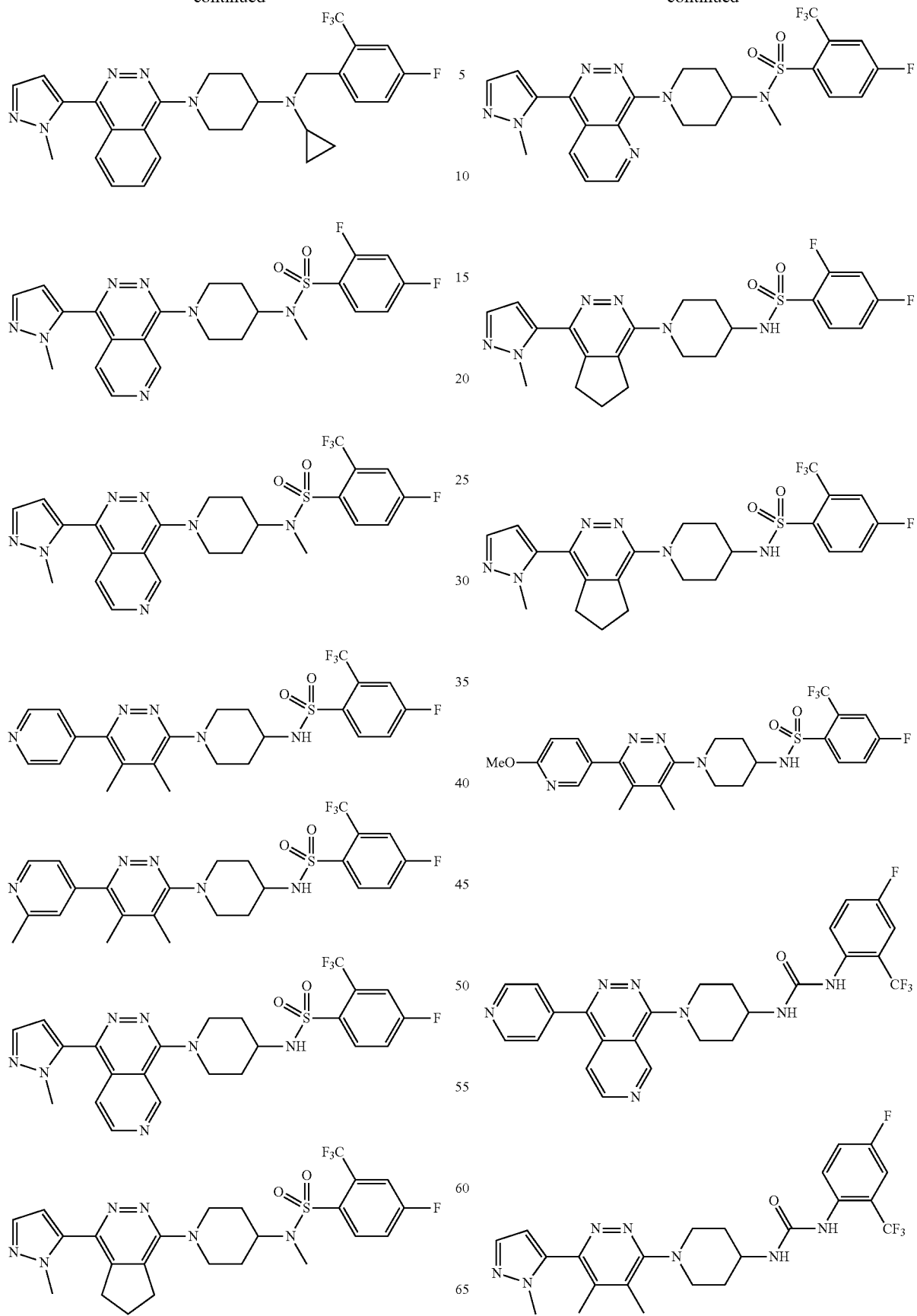

229
-continued
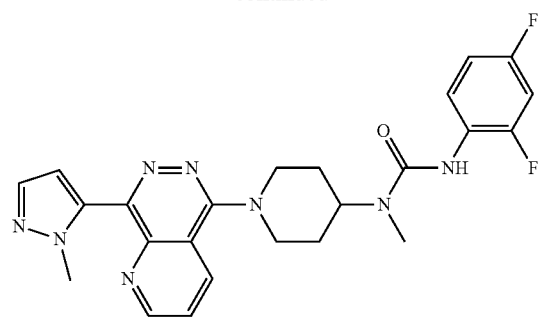
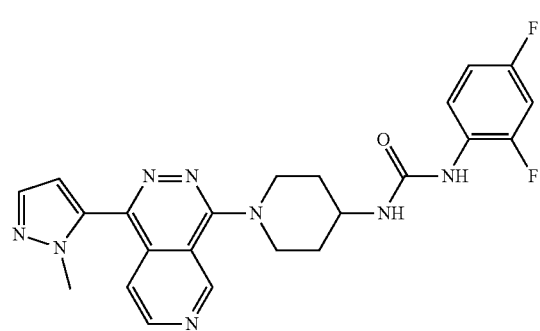
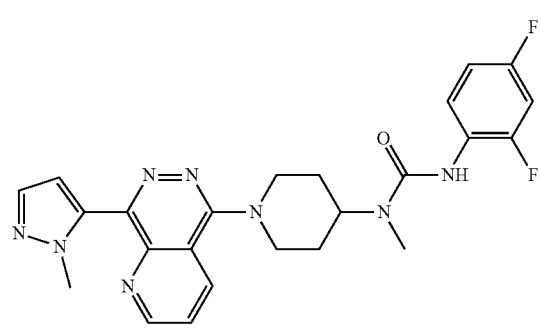
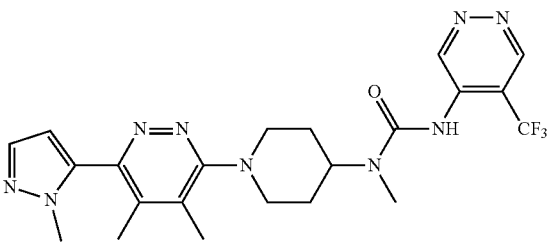
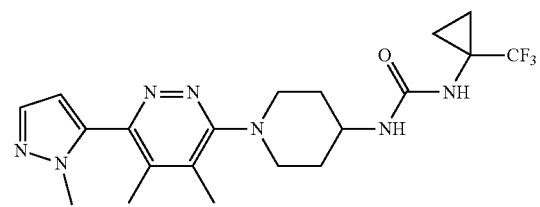
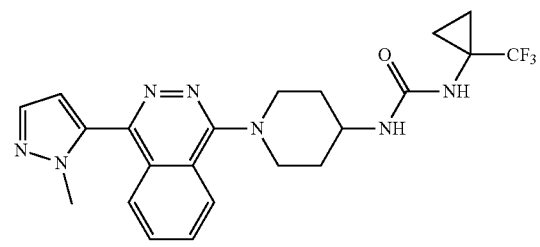
230
-continued
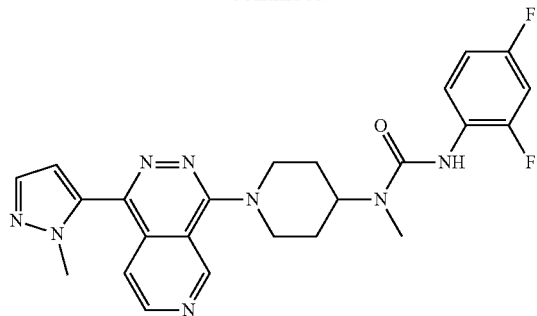
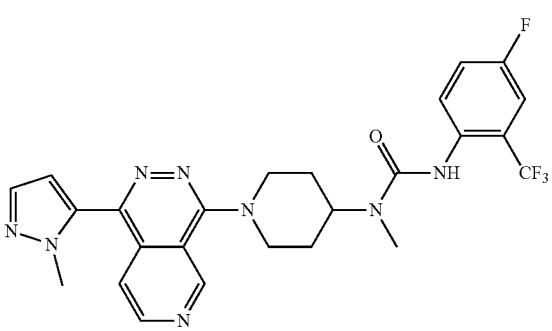
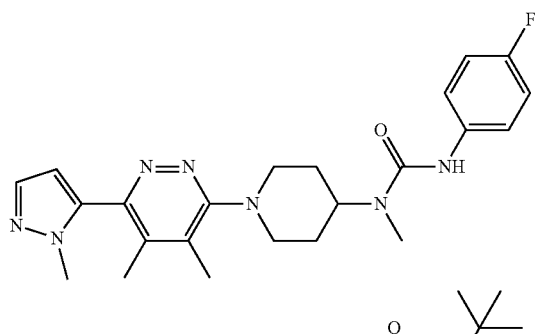
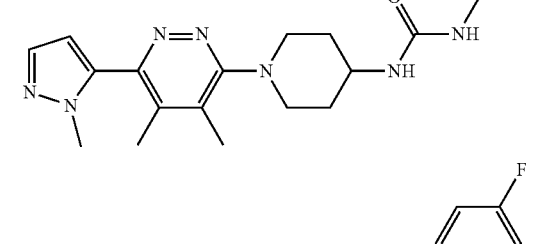
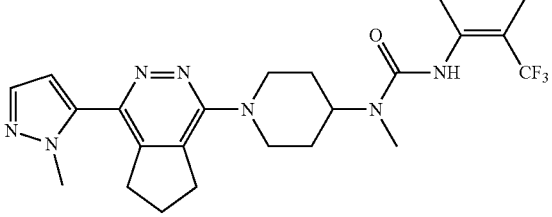
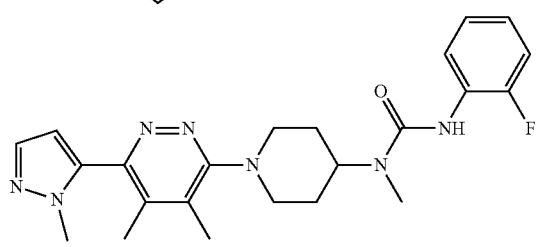

231
-continued

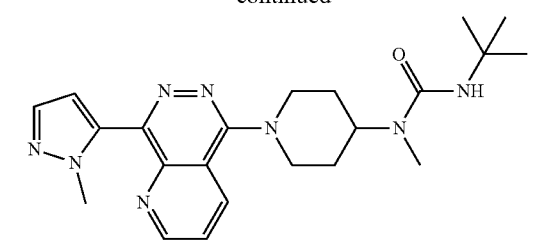
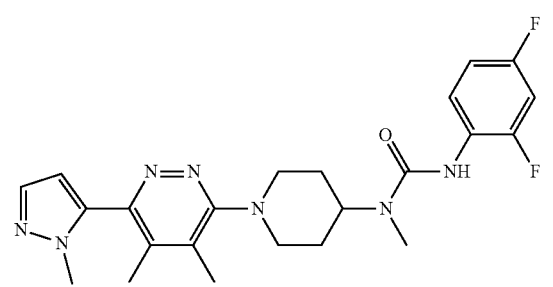
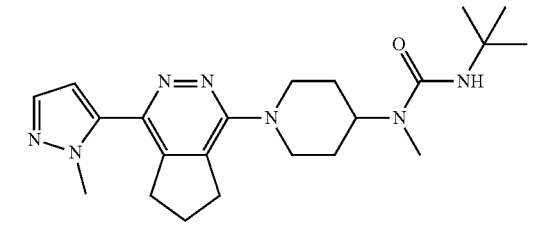
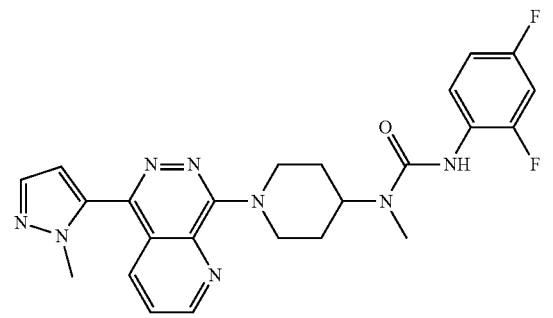
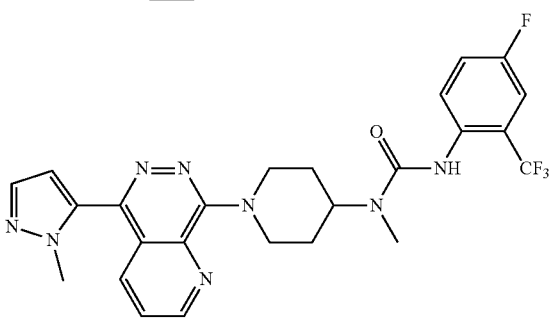
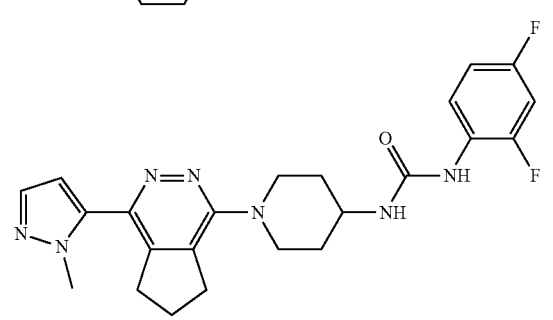

232
-continued

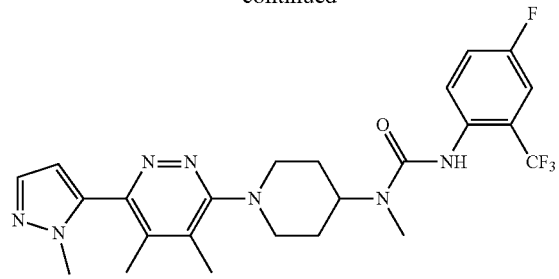
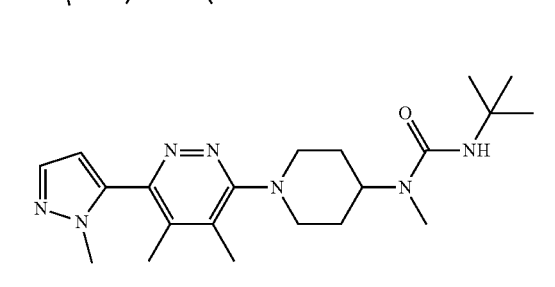
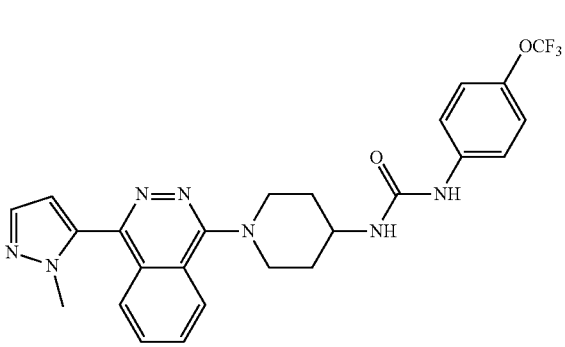
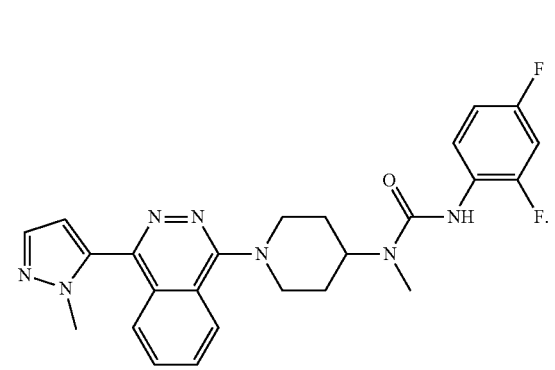

30. A pharmaceutical composition, wherein the composition comprises a compound of claim 1 and a pharmaceutically acceptable excipient.

31. A method of modulating the Hedgehog signalling pathway, wherein the method comprises administering a therapeutic amount of a compound of claim 1 to a patient in need thereof.

32. The method of treatment of claim 31, wherein the condition which is modulated by the Hedgehog signalling pathway is selected from the group consisting of: carcinoma, blastoma, leukemia and haematological malignancies.

33. The method of treatment of claim 31, wherein the condition is selected from the group consisting of: basal cell carcinoma, medulloblastoma, chondrosarcoma, small-cell lung cancer, non-small-cell lung cancer, multiple myeloma, esophagus cancer, breast cancer, prostate cancer, pancreatic cancer, acute leukemia, chronic leukemia, and ovarian cancer.

34. A method of inhibiting stem cell production, inhibiting stem cell renewal, and/or inhibiting and/or modulating stem cell differentiation, wherein the method comprises administering a therapeutic amount of a compound of claim 1 to a patient in need thereof.

35. A method of treatment of a condition selected from the group consisting of carcinoma, blastoma, and leukemia, comprising administering a therapeutically effective amount of a compound of claim 1 simultaneously, sequentially or separately with an additional anti-tumour agent to a patient in need thereof.

36. A compound of claim 1, wherein L is —C(O)NH— or —C(O)N(CH$_3$)—.

37. A compound of claim 1, wherein the compound of formula (Ia) is a compound according to formula (XIII) or a pharmaceutically acceptable salt or solvate thereof:

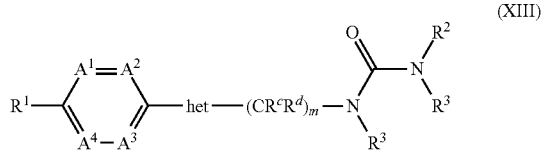
(XIII)

wherein

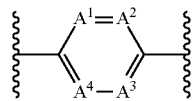

is selected from the group consisting of:

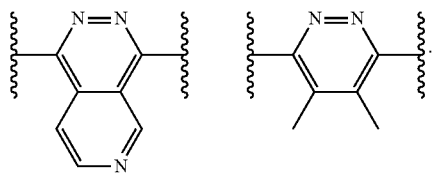

het is:

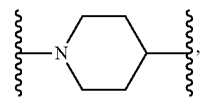

$R^1$ is substituted or unsubstituted pyrazolyl, $R^2$ is substituted or unsubstituted phenyl, toluenyl or pyridinyl, $R^3$ is H, methyl or —C(O)CF$_3$, $R^c$ and $R^d$ are independently selected from the group consisting of H, halo, —OR$^a$, $C_{1-4}$ alkyl, $C_{1-4}$ haloalkyl, $C_{1-4}$ acyl, $C_{3-7}$ cycloalkyl, and $C_{3-7}$ halocycloalkyl, and m is 0 or 1, wherein when a group is substituted, the group contains 1 to 5 substituents independently selected at each occurrence from the group consisting of: halo, —OR$^a$, —SR$^a$, —NR$^a$R$^b$, NO$_2$, —CN, acyl, $C_{1-6}$ alkyl, $C_{1-6}$ haloalkyl, $C_{3-8}$ cycloalkyl, —SO$_2$R$^a$, and SO$_3$R$^a$, —C(OR$^a$)R$^a$R$^b$, —C(O)R$^a$ and C(O)OR$^a$; and $R^a$ and $R^b$ are independently selected at each occurrence from the group consisting of: H, $C_{1-4}$ alkyl, $C_{1-4}$ haloalkyl, $C_{1-4}$ acyl, $C_{3-7}$ cycloalkyl, and $C_{3-7}$ halocycloalkyl.

* * * * *